(12) United States Patent
Maccoss et al.

(10) Patent No.: US 9,593,108 B2
(45) Date of Patent: *Mar. 14, 2017

(54) COMPOUNDS AND METHODS FOR ANTIVIRAL TREATMENT

(75) Inventors: Malcolm Maccoss, Seabrook Island, SC (US); F. George Njoroge, Warren, NJ (US); Amin Nomeir, Milford, NJ (US); Guangming Chen, Bridgewater, NJ (US); Gary Mitchell Karp, Princeton Junction, NJ (US); William Jospeh Lennox, Bedminster, NJ (US); Chunshi Li, East Brunswick, NJ (US); Christie Morrill, Green Brook, NJ (US); Steven D. Paget, Hillborough, NJ (US); Hongyu Ren, Dayton, NJ (US); Nanjing Zhang, Princeton, NJ (US); Xiaoyan Zhang, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/259,283

(22) PCT Filed: Apr. 5, 2010

(86) PCT No.: PCT/US2010/029928
§ 371 (c)(1),
(2), (4) Date: Dec. 9, 2011

(87) PCT Pub. No.: WO2010/117935
PCT Pub. Date: Oct. 14, 2010

(65) Prior Publication Data
US 2012/0135999 A1    May 31, 2012

Related U.S. Application Data

(60) Provisional application No. 61/166,883, filed on Apr. 6, 2009.

(51) Int. Cl.
| | |
|---|---|
| *C07D 487/04* | (2006.01) |
| *C07D 401/04* | (2006.01) |
| *C07D 401/14* | (2006.01) |
| *C07D 403/04* | (2006.01) |
| *C07D 403/14* | (2006.01) |
| *A61K 31/437* | (2006.01) |
| *A61K 31/506* | (2006.01) |
| *A61P 31/14* | (2006.01) |
| *C07D 471/04* | (2006.01) |

(52) U.S. Cl.
CPC .......... *C07D 471/04* (2013.01); *A61K 31/437* (2013.01); *A61K 31/506* (2013.01); *C07D 401/04* (2013.01); *C07D 401/14* (2013.01); *C07D 403/04* (2013.01); *C07D 403/14* (2013.01); *C07D 487/04* (2013.01)

(58) Field of Classification Search
CPC .. C07D 487/04; C07D 401/04; C07D 401/14; C07D 403/04; C07D 403/14; A61K 31/437; A61K 31/506
USPC .......................................... 546/113; 514/300
See application file for complete search history.

(56) References Cited

U.S. PATENT DOCUMENTS

| 5,502,187 A | 3/1996 | Ayer et al. |
|---|---|---|
| 2007/0299068 A1 | 12/2007 | Karp et al. |
| 2012/0087893 A1* | 4/2012 | Lahser et al. ............... 424/85.4 |

FOREIGN PATENT DOCUMENTS

| CN | 101103032 A | 1/2008 |
|---|---|---|
| EP | 1477489 A1 | 11/2004 |
| EP | 1829877 A1 | 9/2007 |
| WO | 9808845 A1 | 3/1998 |
| WO | 03010140 A2 | 2/2003 |
| WO | 2004087714 A1 | 10/2004 |
| WO | 2006112331 A1 | 10/2006 |
| WO | 2007071738 A1 | 6/2007 |
| WO | 2008132434 A2 | 11/2008 |

OTHER PUBLICATIONS

Vippagunta et al., Advanced Drug Delivery Reviews 48: 3-26, 2001.*
Chawla et. al.; CRIPS vol. 5, No. I, p. 9-12.*
Kwong, A.D. et al., Current Opinion in Pharmacology 2008, 8:522-531.*
Yin, Y.W. et al., Current Opinion in Structural Biology 2011, 21:83-91.*
Freshney et al.,Culture of Animal Cells, A Manual of Basic Technique, Alan R. Liss, Inc., 1983, New York, p. 4.*
Dermer et al., Bio/Technology, 1994, 12:320.*
International Search Report for PCT/US2010/029928 mailed May 19, 2010.
Written Opinion for PCT/US2010/029928 mailed May 19, 2010.
Xu et al., "Transition Metal Catalyzed Synthesis of 5-Azaindoles" Tetrahedron Letters 39(29): 5159-5162 (1998).

* cited by examiner

*Primary Examiner* — Venkataraman Balasubramanian
(74) *Attorney, Agent, or Firm* — Hoffmann & Baron, LLP

(57) ABSTRACT

The present invention is directed to compounds and forms and pharmaceutical compositions thereof useful for treating a viral infection, or for affecting viral activity by modulating viral replication.

15 Claims, No Drawings

COMPOUNDS AND METHODS FOR ANTIVIRAL TREATMENT

CROSS-REFERENCE TO RELATED APPLICATIONS

This application is the National Stage of International Application No. PCT/US2010/029928, filed Apr. 5, 2010 which claims benefit to provisional U.S. Ser. No. 61/166,883, filed Apr. 6, 2009, herein incorporated by reference.

This application is related to U.S. patent application Ser. No. 13/259,854, filed Sep. 23, 2011 (having 371(c) date Dec. 12, 2011), which is the National Stage of International Application No. PCT/US10/29930, filed Apr. 5, 2010, entitled "HCV Inhibitor and Therapeutic Agent Combinations."

GOVERNMENT SUPPORT

The present invention was not made with U.S. Government support.

STATEMENT OF JOINT RESEARCH AGREEMENT

The present invention was made by or on behalf of parties to a joint research agreement that was in effect on or before the date the invention was made, the present invention was made as a result of activities undertaken within the scope of the joint research agreement, and the application for patent of the present invention discloses the names of the parties to the joint research agreement.

FIELD OF THE INVENTION

The present invention is directed to compounds, pharmaceutical compositions, and methods of using such compounds or compositions thereof for treating a viral infection, or for affecting viral activity by modulating viral replication. More particularly, the present invention relates to azaindole compounds or compositions and methods for use thereof for treating or ameliorating Hepatitis C Virus (HCV) infection or disorders or symptoms associated therewith by inhibiting Hepatitis C viral replication.

BACKGROUND OF THE INVENTION

An estimated 170 million people worldwide are reported to be infected with the Hepatitis C virus, the causative agent of hepatitis C. Seventy to eighty percent of HCV infections lead to chronic liver infection, which in turn may result in severe liver disease, including liver fibrosis, cirrhosis, and hepatocellular carcinoma (see Saito I, et al., Hepatitis C virus infection is associated with the development of hepatocellular carcinoma, *Proc Natl Acad Sci USA,* 2003, 87:6547-6549).

Although the treatment outcome is variable among the six major HCV genotypes, only about one-half of all treated patients respond to therapy, suggesting that the virus encodes protein products that may directly or indirectly attenuate the antiviral action of interferon (IFN). IFNs are naturally produced in response to viral infection, and cellular exposure to IFN leads to the induced expression of a variety of IFN-stimulated genes (ISGs), many of which have an antiviral function. ISG action can limit virus replication at multiple points within the replicative cycle.

Compounds and methods for treating Hepatitis C have been disclosed in U.S. patent application Ser. No. 11/653,450, filed Jan. 16, 2007 (having corresponding International Application No. PCT/US2007/00996, filed Jan. 16, 2007), U.S. patent application Ser. No. 11/653,448, filed Jan. 16, 2007 (having corresponding International Application No. PCT/US2007/00923, filed Jan. 16, 2007), each of which are a continuation-in-part of U.S. patent application Ser. No. 11/331,180, filed Jan. 13, 2006, which is a continuation-in-part of U.S. patent application Ser. No. 11/180,961, filed Jul. 14, 2005 (having corresponding International Application No. PCT/US2005/024881, filed Jul. 14, 2005), each of which are incorporated herein by reference in their entirety and for all purposes.

United States Patent Publication 2006/0235028 discloses certain aryl and heteroaryl compounds as 11-beta-hydroxysteroid dehydrogenase type I inhibitors.

All other documents referred to herein are incorporated by reference into the present application as though fully set forth herein.

SUMMARY OF THE INVENTION

The present invention is directed to a compound of Formula (I):

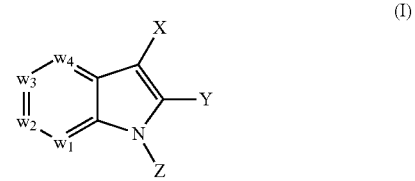

(I)

wherein $w_1$, $w_2$, $w_3$, $w_4$, X, Y and Z are as defined herein and forms and compositions thereof, and methods of using such compounds, forms or compositions thereof for treating a viral infection, or for affecting viral activity by modulating viral replication.

DETAILED DESCRIPTION OF THE INVENTION

The present invention is directed to a compound of Formula (I):

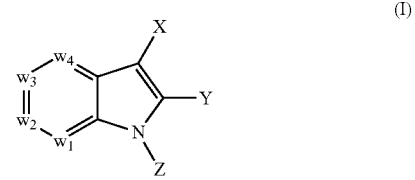

(I)

or a free acid, free base, salt, hydrate, solvate, clathrate, isotopologue, racemate, enantiomer, diastereomer, stereoisomer or polymorph form thereof, wherein $w_1$, $w_2$, $w_3$, $w_4$ are each selected from N or C—$R_1$, wherein N may be optionally substituted with an O atom to form an N-oxide and, wherein at least one and up to three of $w_1$, $w_2$, $w_3$ and $w_4$ are N and the remainder are C—$R_1$;

X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl;

Y is aryl, heterocyclyl, heteroaryl or heteroaryl-1-oxide each substituted with one substituent selected from —N($R_2$)—$SO_2$—$R_3$, —$SO_2$—N($R_4$)—$R_5$, —$SO_2$—$R_6$, —N(H)—$R_2$, —N($R_2$)—C(O)—N(H)—$R_4$ or —N($R_2$)—C(O)—$R_3$, wherein aryl, heterocyclyl or heteroaryl are each optionally substituted with one or two additional substituents independently selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl $C_{1-8}$alkyl-carbonyloxy or amino-sulfonyl;

$R_1$ is independently selected from hydrogen, halogen, hydroxy, cyano, nitro, $C_{1-8}$alkyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, (aryl-$C_{1-8}$alkyl)($C_{1-8}$alkyl)amino, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfonyl, $C_{1-8}$alkyl-sulfinyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_2$ is hydrogen or $C_{1-8}$alkyl, optionally substituted on $C_{1-8}$alkyl with one or more substituents each selected from halogen, hydroxy, cyano, $C_{1-8}$alkoxy, amino or $C_{1-8}$alkyl-amino;

$R_3$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

$R_4$ is hydrogen or $C_{1-8}$alkyl, optionally substituted on $C_{1-8}$alkyl with one or more substituents each selected from halogen, hydroxy, cyano or $C_{1-8}$alkoxy;

$R_5$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino; and $R_6$ is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, $C_{3-14}$cycloalkyl and heterocyclyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

Embodiments of the present invention include a compound of Formula (I) wherein $w_1$, $w_2$, $w_3$, $w_4$ are each selected from N or C—$R_1$, wherein at least one and up to three of $w_1$, $w_2$, $w_3$ and $w_4$ are N and the remainder are C—$R_1$;

X is hydrogen, cyano, amino-carbonyl or $C_{1-8}$alkyl-amino-carbonyl;

Y is aryl or heteroaryl each substituted with one substituent selected from —N($R_2$)—$SO_2$—$R_3$ or —$SO_2$—N($R_4$)—$R_5$;

Z is $C_{1-8}$alkyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino;

$R_1$ is independently selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy or heterocyclyloxy;

$R_2$ and $R_4$ are hydrogen or $C_{1-8}$alkyl;

$R_3$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl;

$R_5$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl; and $R_6$ is $C_{1-8}$alkyl, $C_{3-14}$cycloalkyl, aryl, heteroaryl or heterocyclyl, wherein $C_{3-14}$cycloalkyl and heterocyclyl are each optionally substituted with one or two substituents each selected from halogen or halo-$C_{1-8}$alkyl.

Embodiments of the present invention include a compound of Formula (I) wherein

X is cyano;

Z is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino;

$R_1$ is independently selected from hydrogen, halogen, cyano, $C_{1-8}$alkyl, halo-$C_{1-8}$alkyl, $C_{1-8}$alkoxy, halo-$C_{1-8}$alkoxy, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl or heterocyclyl-$C_{1-8}$alkoxy;

$R_2$ and $R_4$ are hydrogen; and $R_5$ is $C_{1-8}$alkyl, halo-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from $C_{1-8}$alkyl or halo-$C_{1-8}$alkyl.

Embodiments of the present invention include a compound of Formula (I) wherein

Y is phenyl, pyridinyl or pyrimidinyl each substituted with one substituent selected from —N($R_2$)—$SO_2$—$R_3$ or —$SO_2$—N($R_4$)—$R_5$;

Z is cyclobutyl, cyclopentyl or cyclopropyl-$C_{1-8}$alkyl;

$R_1$ is independently selected from hydrogen, chloro, fluoro, cyano, methyl, ethyl, methoxy, ethoxy, propoxy, isopropoxy, difluoromethoxy or cyclopropyl; and $R_5$ is isopropyl, tert-butyl, difluoroisopropyl, trifluoroisopropyl, trifluoro-tert-butyl, cyclopropyl, cyclobutyl or 1-cyclopropyl-ethyl, wherein each instance of cyclopropyl is optionally substituted with one or two substituents each selected from methyl or trifluoromethyl.

Embodiments of the present invention include a compound of Formula (I) wherein X is hydrogen, cyano, aminocarbonyl or $C_{1-8}$alkyl-amino-carbonyl.

Embodiments of the present invention include a compound of Formula (I) wherein X is cyano.

Embodiments of the present invention include a compound of Formula (I) wherein Y is aryl or heteroaryl each substituted with one substituent selected from —N($R_2$)—$SO_2$—$R_3$, —$SO_2$—N($R_4$)—$R_5$ or —$SO_2$—$R_6$.

Embodiments of the present invention include a compound of Formula (I) wherein Y is aryl or heteroaryl each substituted with one substituent selected from —N($R_2$)—$SO_2$—$R_3$ or —$SO_2$—N($R_4$)—$R_5$.

Embodiments of the present invention include a compound of Formula (I) wherein Y is phenyl, pyridinyl or pyrimidinyl each substituted with one substituent selected from —N($R_2$)—$SO_2$—$R_3$ or —$SO_2$—N($R_4$)—$R_5$.

Embodiments of the present invention include a compound of Formula (I) wherein Z is $C_{1-8}$alkyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino.

Embodiments of the present invention include a compound of Formula (I) wherein Z is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino.

Embodiments of the present invention include a compound of Formula (I) wherein Z is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl or heteroaryl-$C_{1-8}$alkyl.

Embodiments of the present invention include a compound of Formula (I) wherein Z is $C_{3-14}$cycloalkyl or $C_{3-14}$cycloalkyl-$C_{1-8}$alkyl.

Embodiments of the present invention include a compound of Formula (I) wherein Z is cyclobutyl, cyclopentyl or cyclopropyl-$C_{1-8}$alkyl.

Embodiments of the present invention include a compound of Formula (I) wherein $R_1$ is independently selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy or heterocyclyloxy.

Embodiments of the present invention include a compound of Formula (I) wherein $R_1$ is independently selected from hydrogen, halogen, cyano, $C_{1-8}$alkyl, halo-$C_{1-8}$alkyl, $C_{1-8}$alkoxy, halo-$C_{1-8}$alkoxy, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl or heterocyclyl-$C_{1-8}$alkoxy.

Embodiments of the present invention include a compound of Formula (I) wherein $R_1$ is independently selected from hydrogen, halogen, cyano, $C_{1-8}$alkyl, $C_{1-8}$alkoxy, halo-$C_{1-8}$alkoxy or $C_{3-14}$cycloalkyl;

Embodiments of the present invention include a compound of Formula (I) wherein $R_1$ is independently selected from hydrogen, chloro, fluoro, cyano, methyl, ethyl, methoxy, ethoxy, propoxy, isopropoxy, difluoromethoxy or cyclopropyl.

Embodiments of the present invention include a compound of Formula (I) wherein $R_2$ and $R_4$ are hydrogen or $C_{1-8}$alkyl.

Embodiments of the present invention include a compound of Formula (I) wherein $R_2$ and $R_4$ are hydrogen.

Embodiments of the present invention include a compound of Formula (I) wherein $R_3$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl.

Embodiments of the present invention include a compound of Formula (I) wherein $R_3$ is $C_{1-8}$alkyl, halo-$C_{1-8}$alkyl or $C_{3-14}$cycloalkyl.

Embodiments of the present invention include a compound of Formula (I) wherein $R_3$ is $C_{1-8}$alkyl.

Embodiments of the present invention include a compound of Formula (I) wherein $R_5$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl.

Embodiments of the present invention include a compound of Formula (I) wherein $R_5$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl.

Embodiments of the present invention include a compound of Formula (I) wherein $R_5$ is $C_{1-8}$alkyl, halo-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from $C_{1-8}$alkyl or halo-$C_{1-8}$alkyl.

Embodiments of the present invention include a compound of Formula (I) wherein $R_5$ is isopropyl, tert-butyl, difluoroisopropyl, trifluoroisopropyl, trifluoro-tert-butyl, cyclopropyl, cyclobutyl or 1-cyclopropyl-ethyl, wherein each instance of cyclopropyl is optionally substituted with one or two substituents each selected from methyl or trifluoromethyl.

Embodiments of the present invention include a compound of Formula (I) wherein $R_6$ is $C_{1-8}$alkyl, $C_{3-14}$cycloalkyl, aryl, heteroaryl or heterocyclyl, wherein $C_{3-14}$cycloalkyl and heterocyclyl are each optionally substituted with one or two substituents each selected from halogen or halo-$C_{1-8}$alkyl.

Embodiments of the present invention include a compound of Formula (I) wherein $R_6$ is $C_{1-8}$alkyl, $C_{3-14}$cycloalkyl, aryl, heteroaryl or heterocyclyl.

Embodiments of the present invention include a compound of Formula (I) and forms thereof having the structure selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a free acid, free base, salt, hydrate, solvate, clathrate, isotopologue, racemate, enantiomer, diastereomer, stereoisomer or polymorph form thereof:

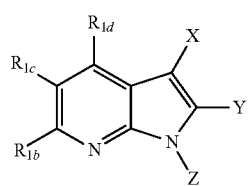

(Ia)

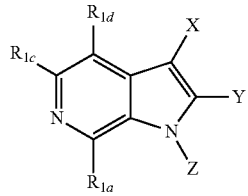

(Ib)

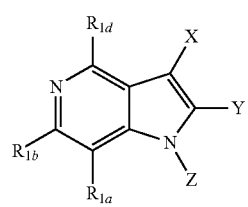

(Ic)

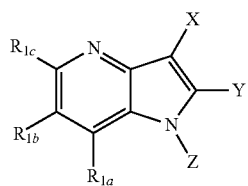

(Id)

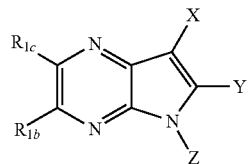

(Ie)

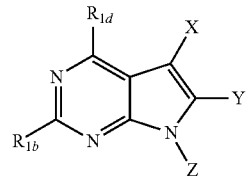

(If)

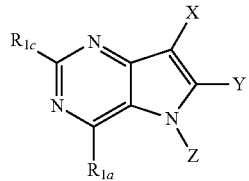

(Ig)

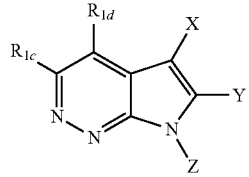

(Ih)

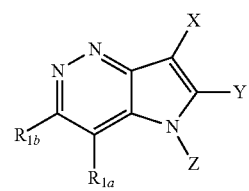

(Ii)

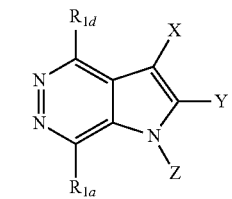

(Ij)

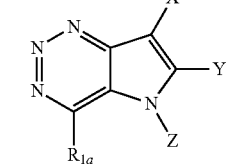

(Ik)

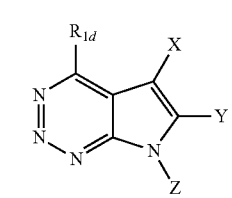

(Il)

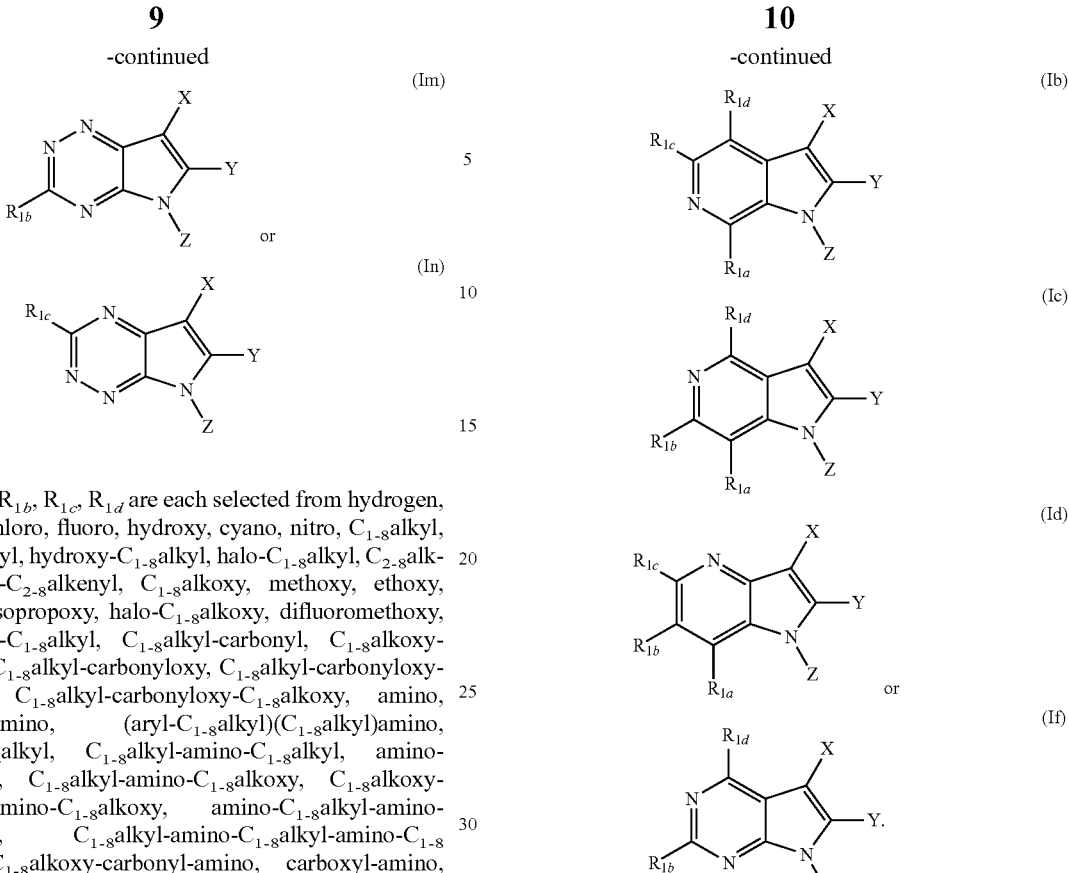

wherein $R_{1a}$, $R_{1b}$, $R_{1c}$, $R_{1d}$ are each selected from hydrogen, halogen, chloro, fluoro, hydroxy, cyano, nitro, $C_{1-8}$alkyl, methyl, ethyl, hydroxy-$C_{1-8}$alkyl, halo-$C_{1-8}$alkyl, $C_{2-8}$alkenyl, halo-$C_{2-8}$alkenyl, $C_{1-8}$alkoxy, methoxy, ethoxy, propoxy, isopropoxy, halo-$C_{1-8}$alkoxy, difluoromethoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, (aryl-$C_{1-8}$alkyl)($C_{1-8}$alkyl)amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkyl-sulfonyl-amino, $C_{1-8}$alkylthio, $C_{1-8}$alkyl-sulfonyl, $C_{1-8}$alkyl-sulfinyl, $C_{3-14}$cycloalkyl, cyclopropyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, and wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

and, all other variables are as previously defined.

Embodiments of the present invention include a compound of Formula (I) and forms thereof selected from Formula (Ia), Formula (Ib), Formula (Ic), Formula (Id) or Formula (If) or a free acid, free base, salt, hydrate, solvate, clathrate, isotopologue, racemate, enantiomer, diastereomer, stereoisomer or polymorph form thereof:

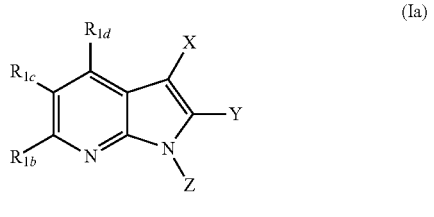

Embodiments of the present invention include a compound of Formula (I) and forms thereof selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) and forms thereof wherein $R_{1a}$, $R_{1b}$, $R_{1c}$, $R_{1d}$ are each independently selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy or heterocyclyloxy.

Embodiments of the present invention include a compound of Formula (I) and forms thereof selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) and forms thereof wherein $R_{1a}$, $R_{1b}$, $R_{1c}$, $R_{1d}$ are each independently selected from hydrogen, halogen, cyano, $C_{1-8}$alkyl, halo-$C_{1-8}$alkyl, $C_{1-8}$alkoxy, halo-$C_{1-8}$alkoxy, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl or heterocyclyl-$C_{1-8}$alkoxy.

Embodiments of the present invention include a compound of Formula (I) and forms thereof selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) and forms thereof wherein $R_{1a}$, $R_{1b}$, $R_{1c}$, $R_{1d}$ are each independently selected from hydrogen, halogen, cyano, $C_{1-8}$alkyl, $C_{1-8}$alkoxy, halo-$C_{1-8}$alkoxy or $C_{3-14}$cycloalkyl.

Embodiments of the present invention include a compound of Formula (I) and forms thereof selected from Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) and forms thereof wherein $R_{1a}$, $R_{1b}$, $R_{1c}$, $R_{1d}$ are each independently selected from hydrogen, chloro, fluoro, cyano, methyl, ethyl, methoxy, ethoxy, propoxy, isopropoxy, difluoromethoxy or cyclopropyl.

Embodiments of the present invention include a compound of Formula (I) and forms thereof, wherein the isotopologue is deuterium.

In one embodiment of the present invention, a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a free acid, free base, salt, hydrate, solvate, clathrate, isotopologue, racemate, enantiomer, diastereomer, stereoisomer or polymorph form thereof is selected from:

1

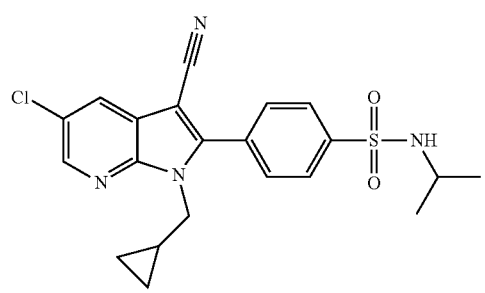

2

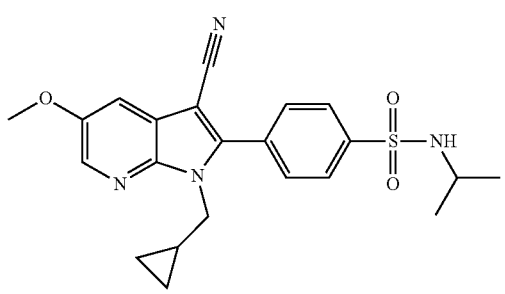

3

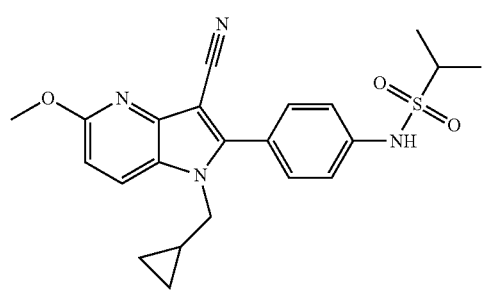

-continued

4

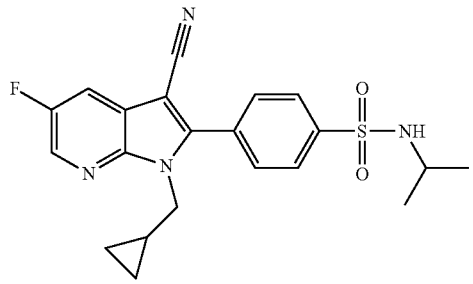

5

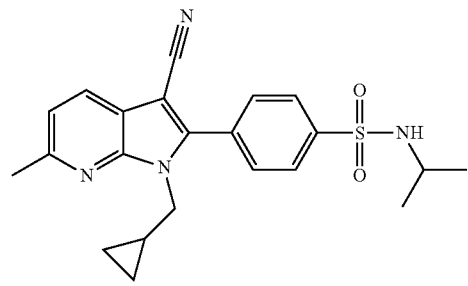

6

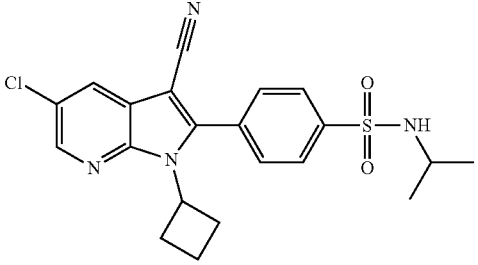

7

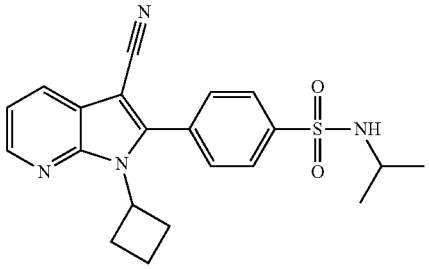

8

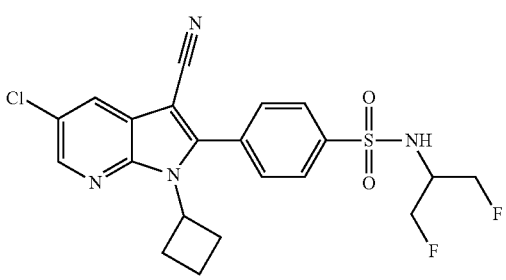

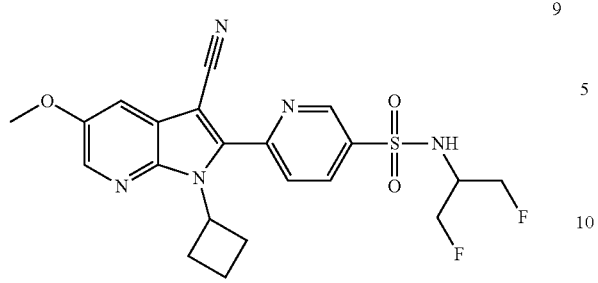
9
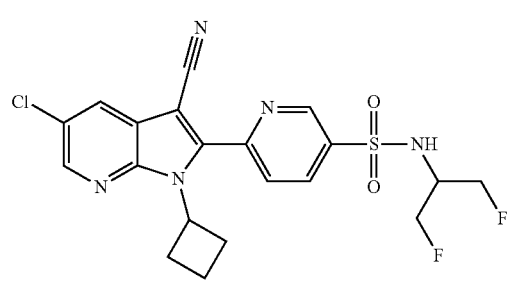
14
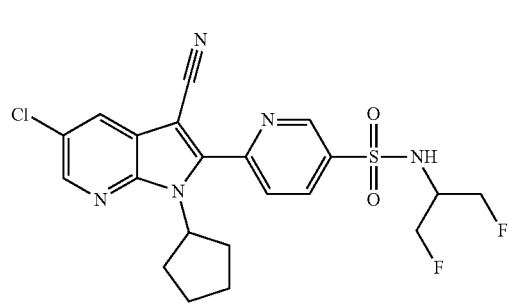
10
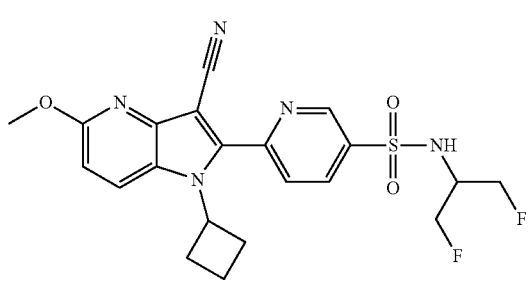
15
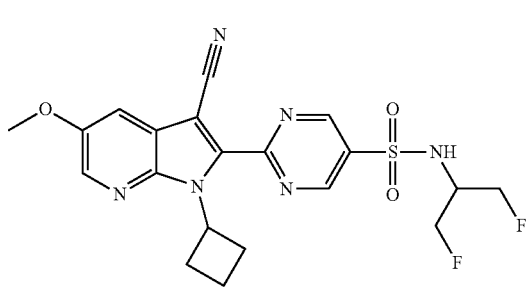
11
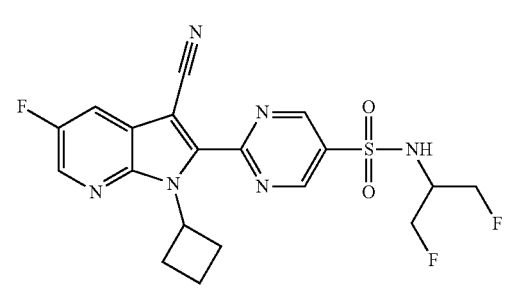
16
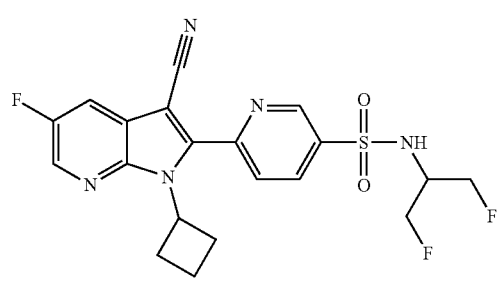
12
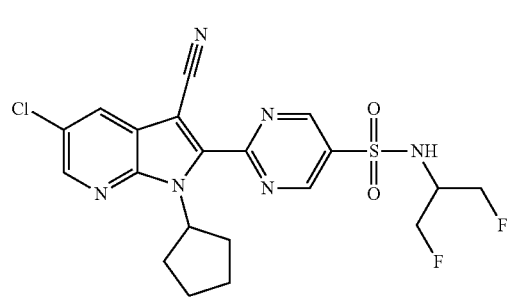
17
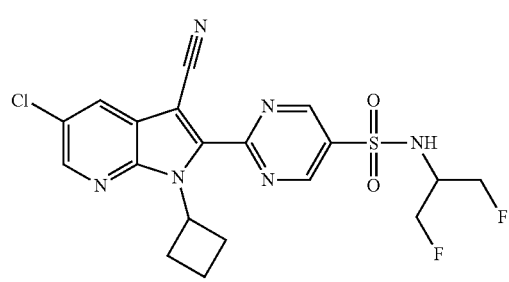
13
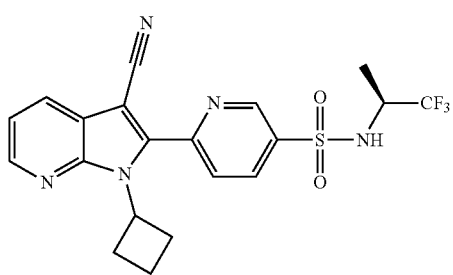
18

19
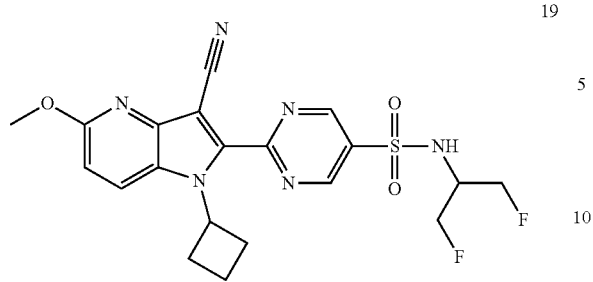
20
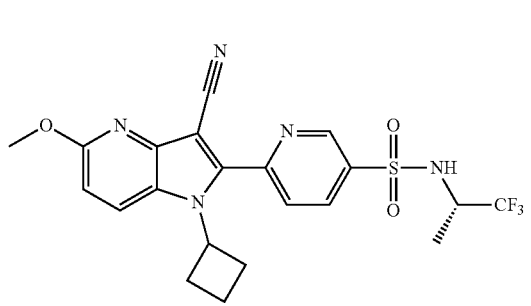
21
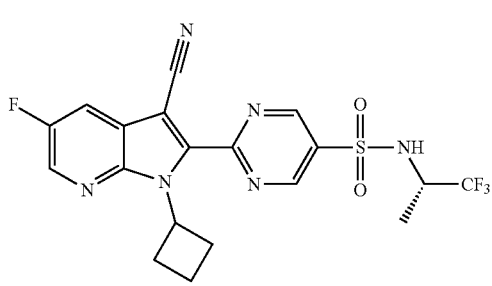
22
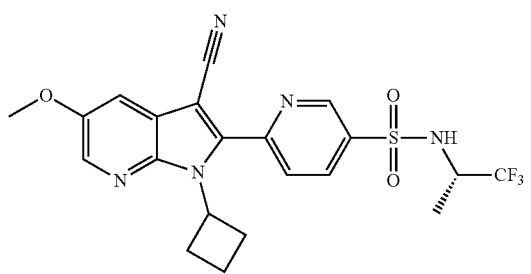
23
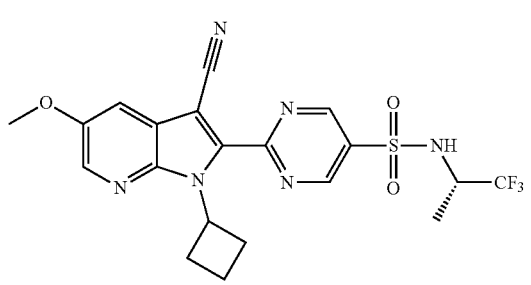
24
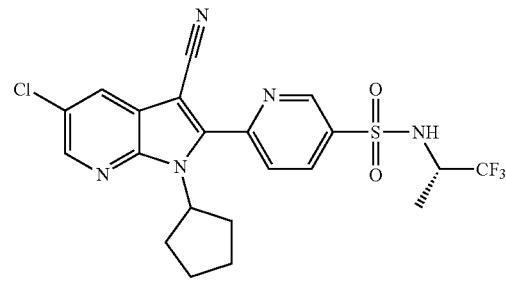
25
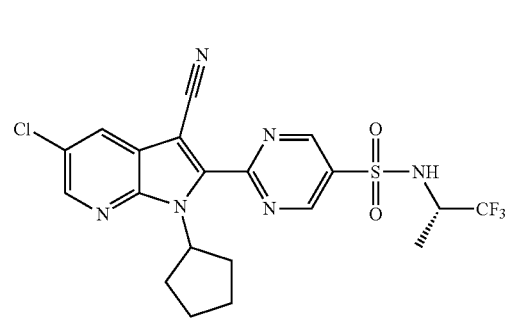
26
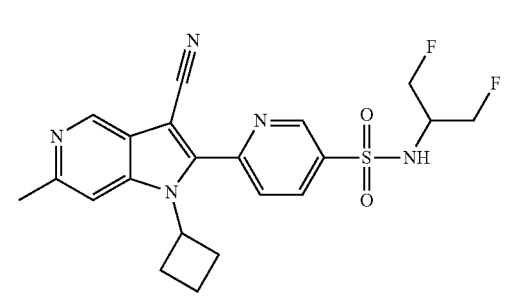
27
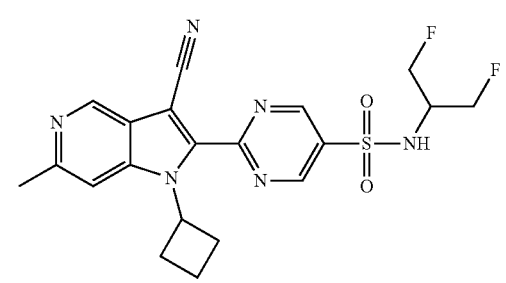
28
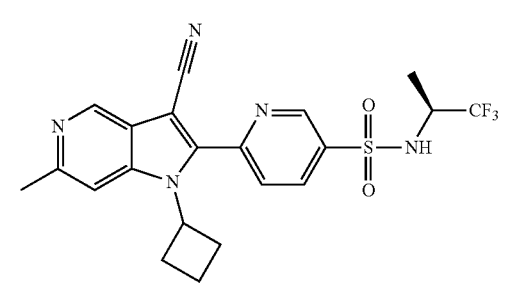

29
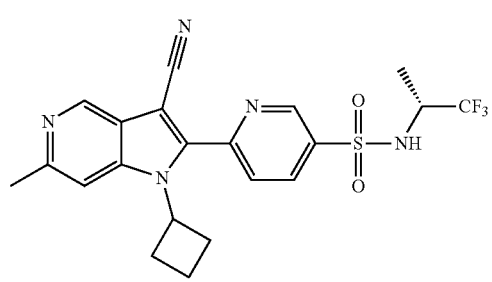
30
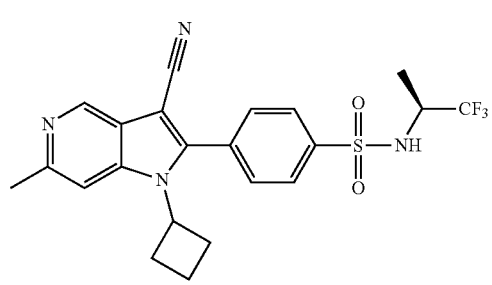
31
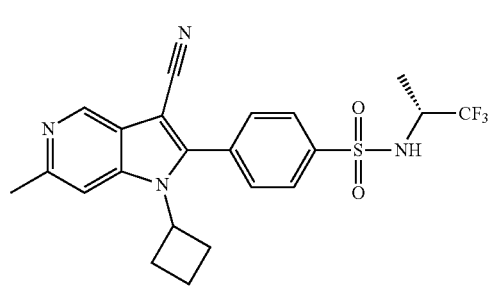
32
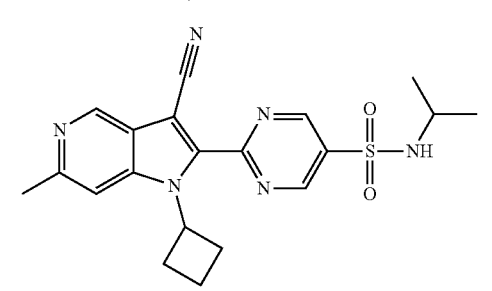
33
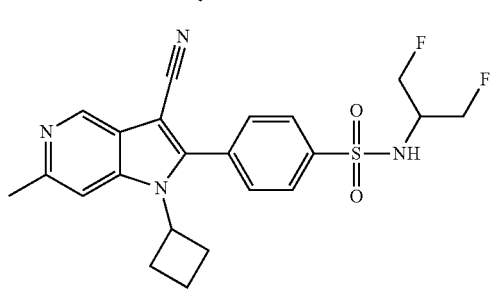
34
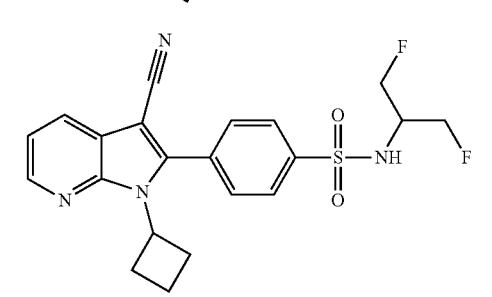
35
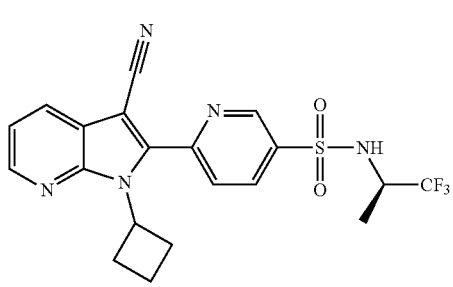
36
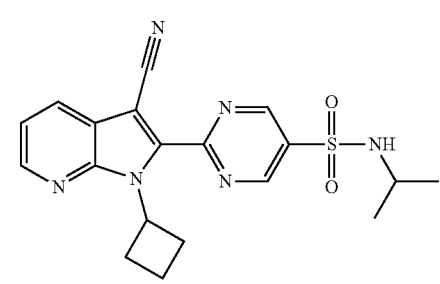
37
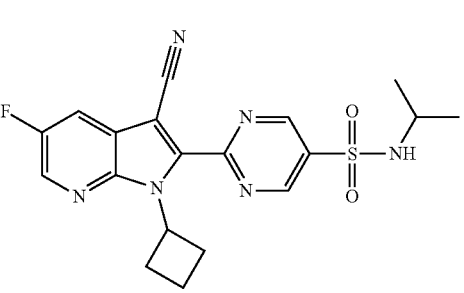
38
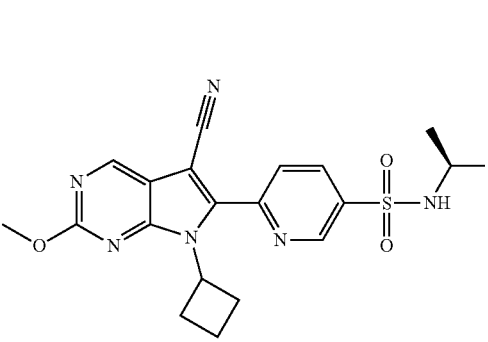
39
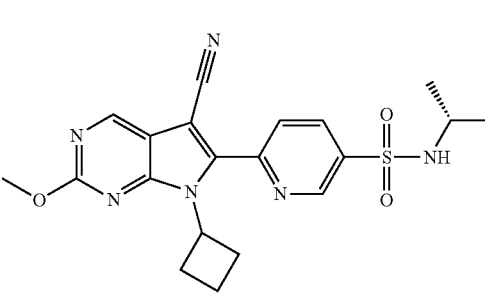

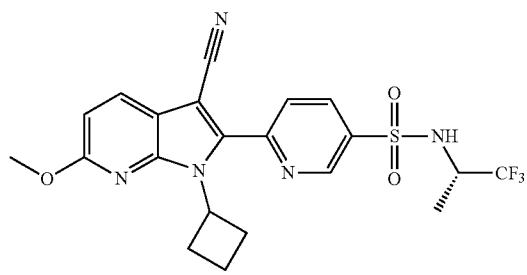
40
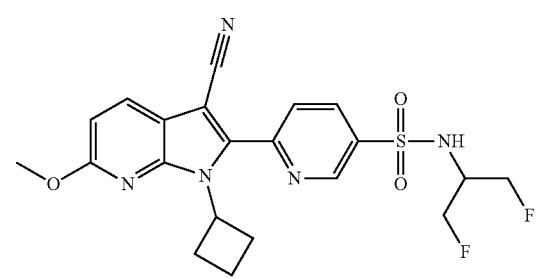
41
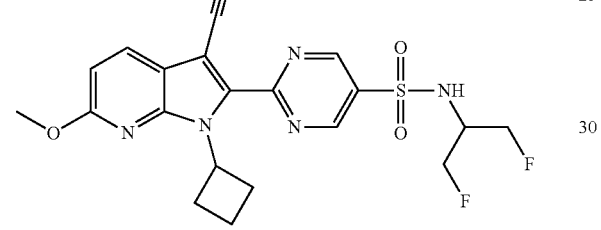
42
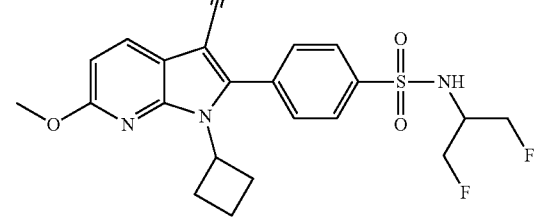
43
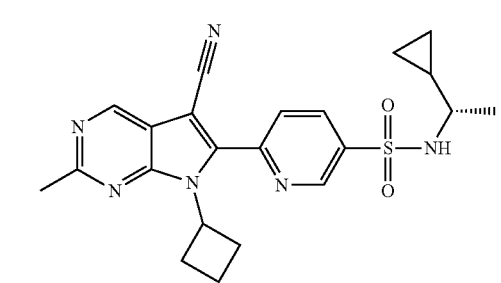
44
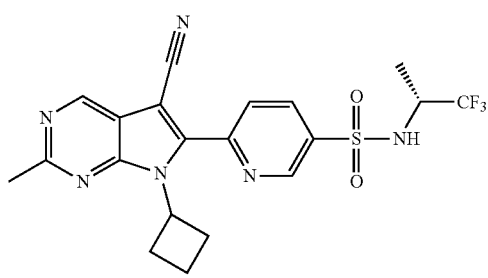
46
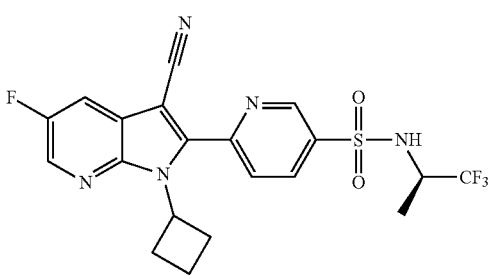
47
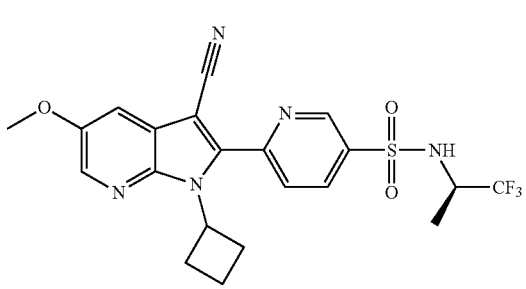
48
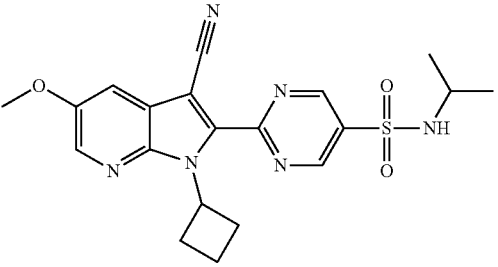
49
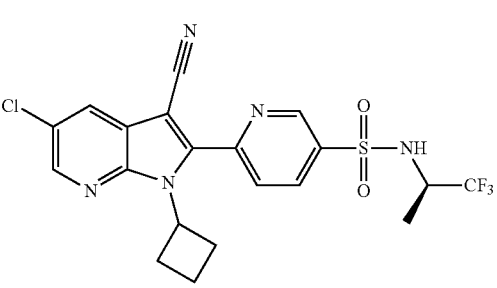
50

51
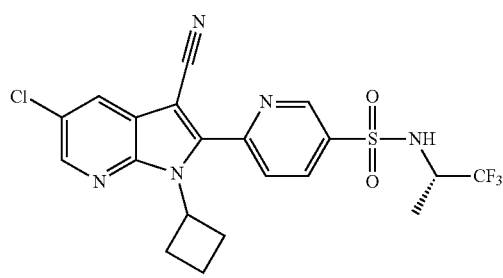
52
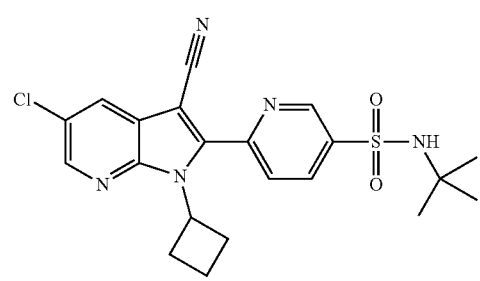
53
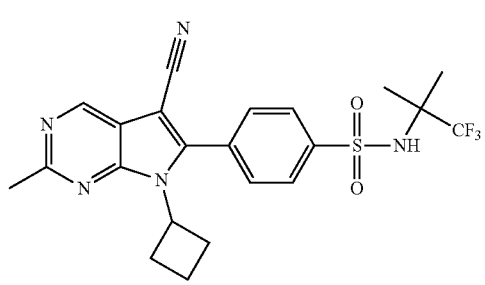
54
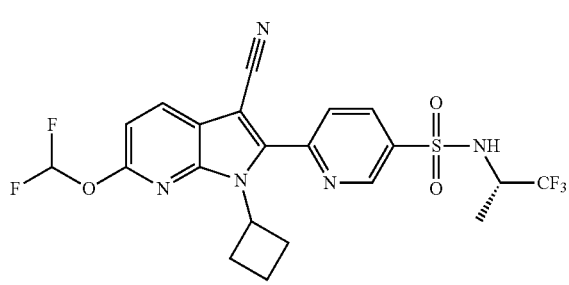
55
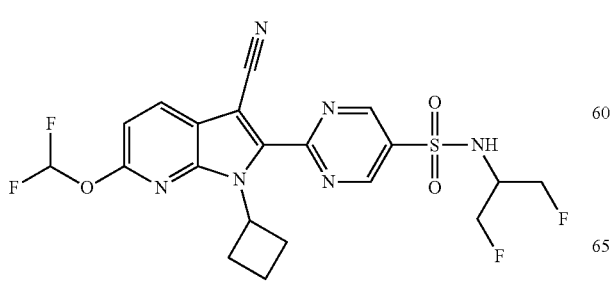
56
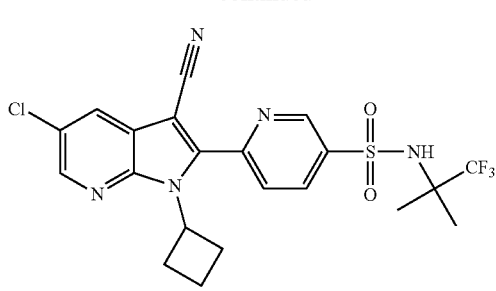
57
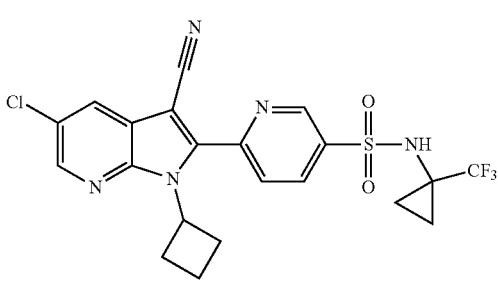
58
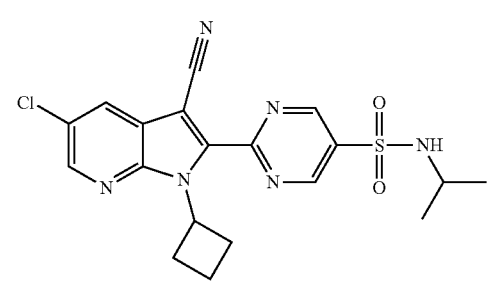
59
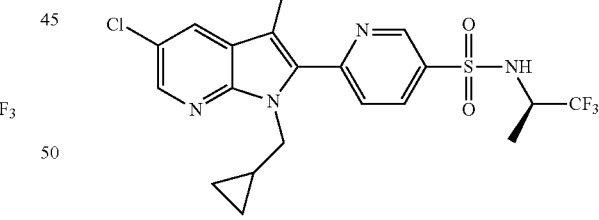
60
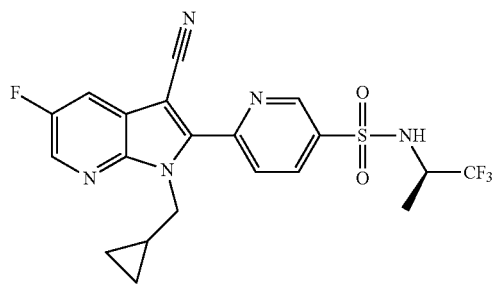

-continued
61
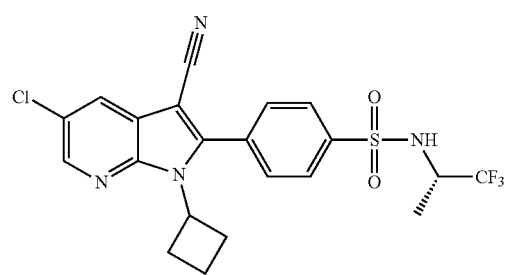
62
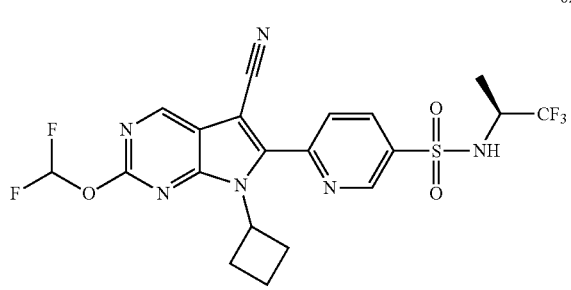
63
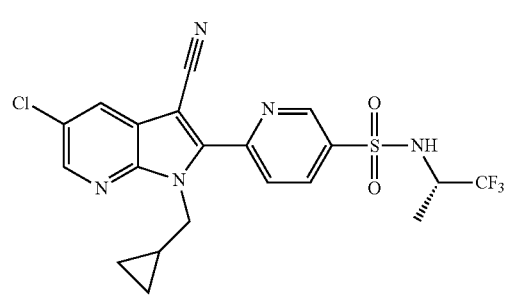
64
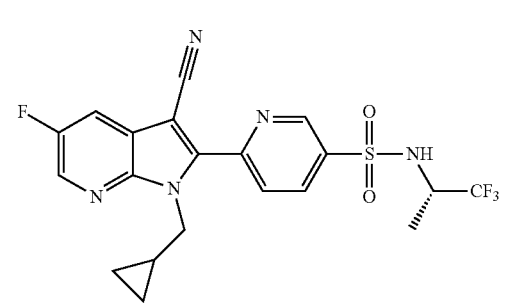
65
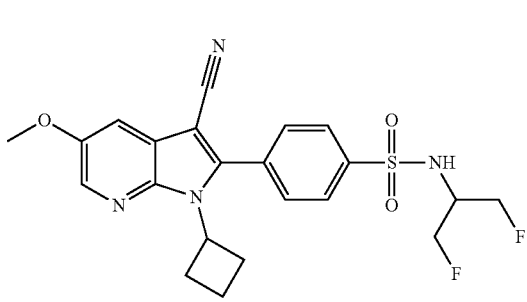
-continued
66
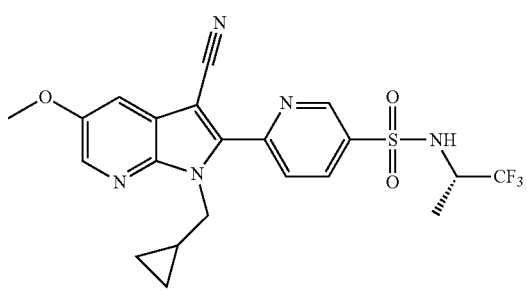
67
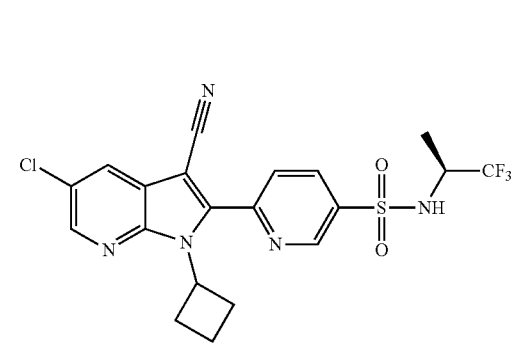
68
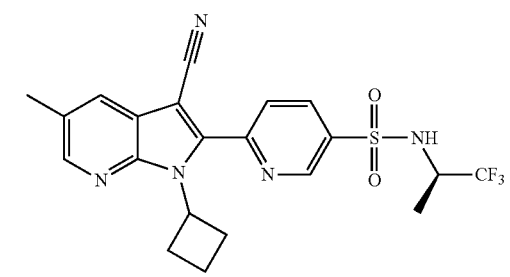
69
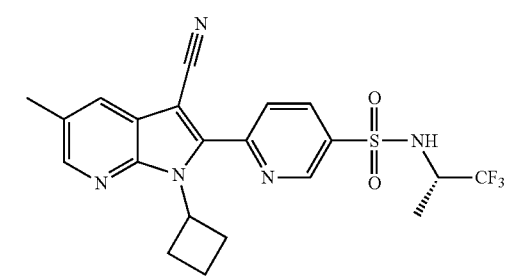
70
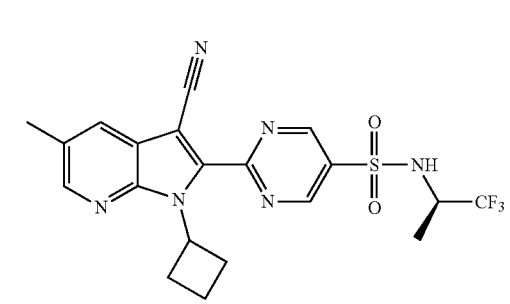

-continued
71
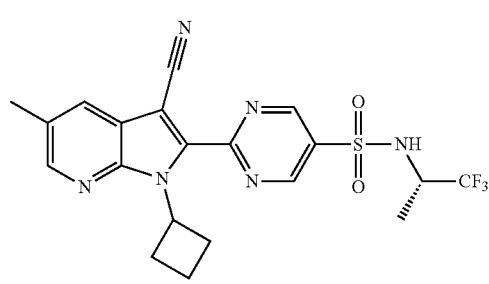
72
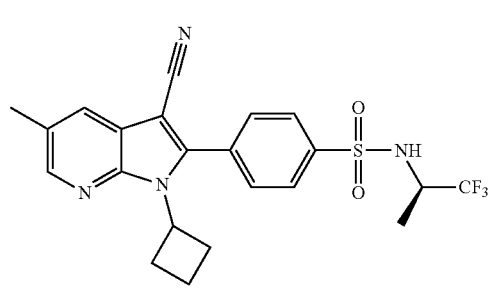
73
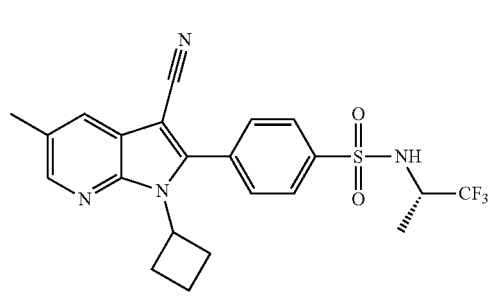
74
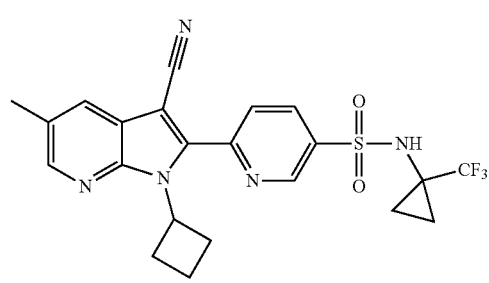
75
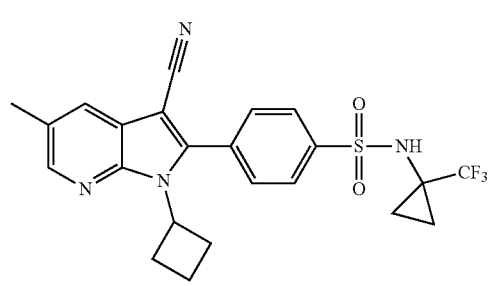
-continued
76
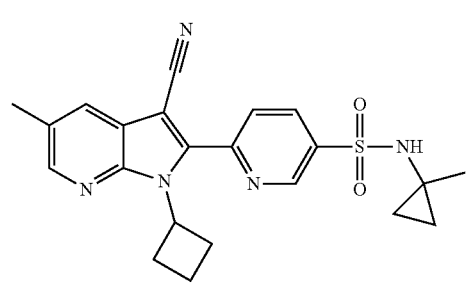
77
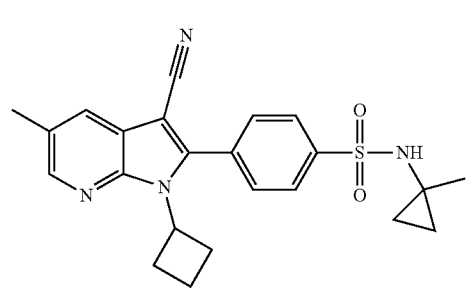
78
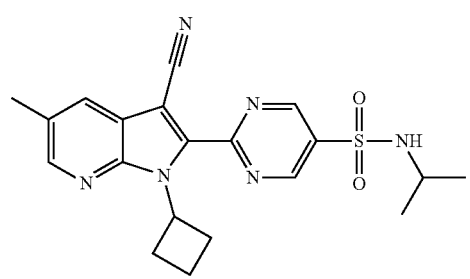
79
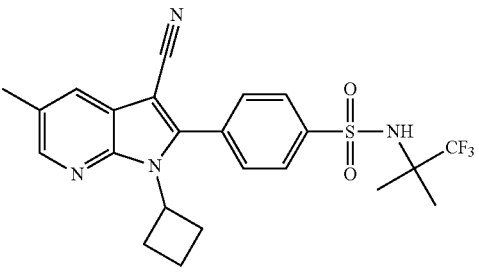
80
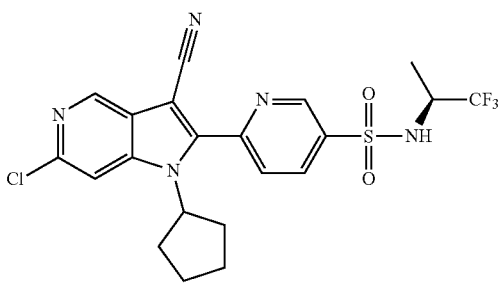

-continued
81
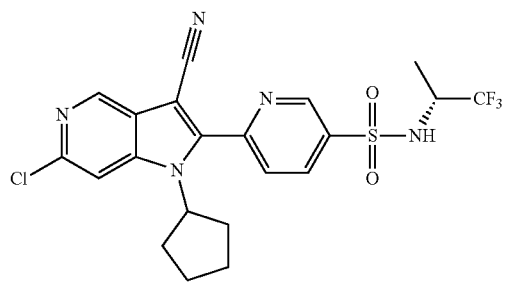
82
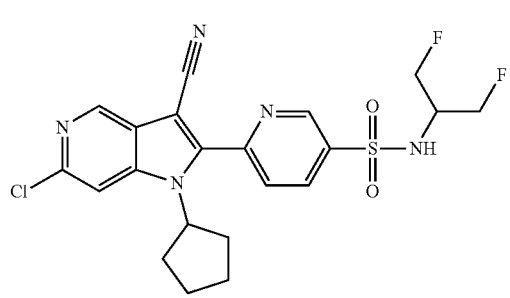
83
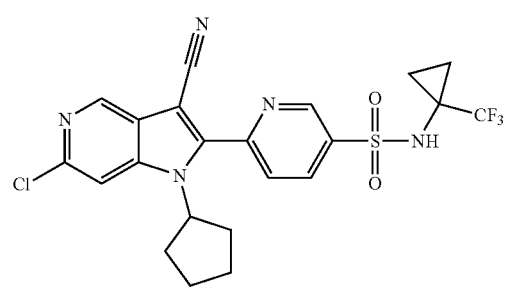
84
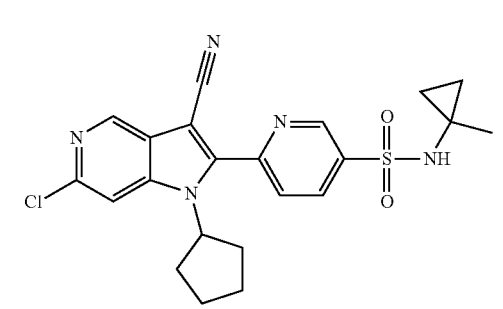
85
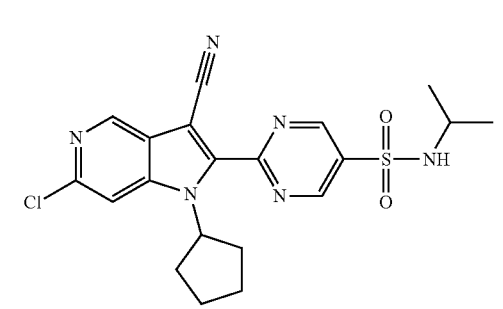
-continued
86
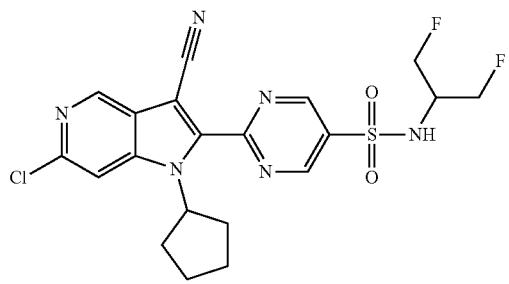
87
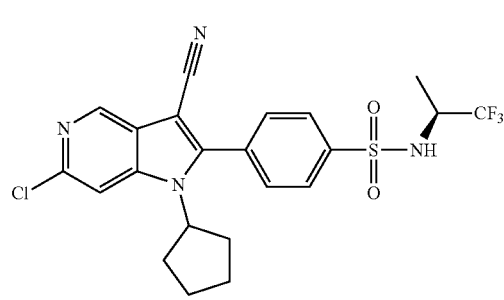
88
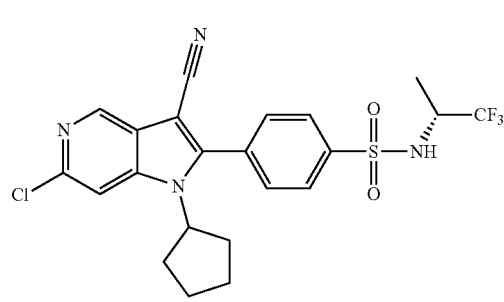
89
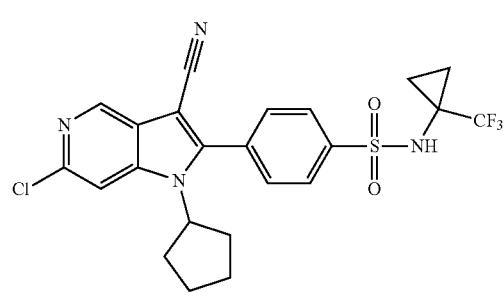
90
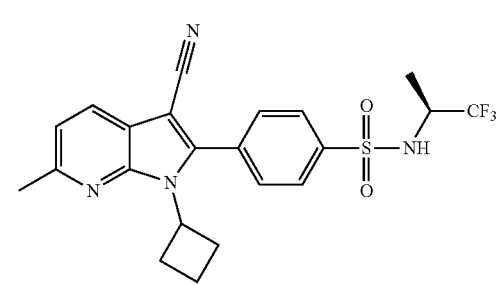

91
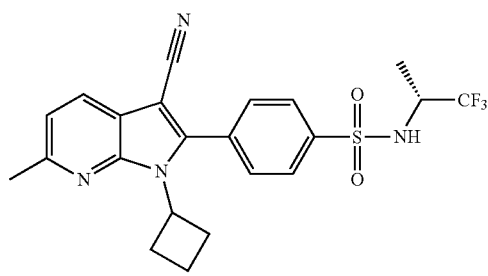
92
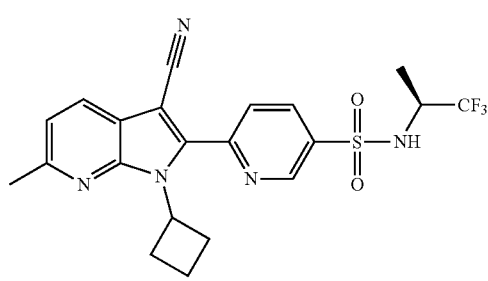
93
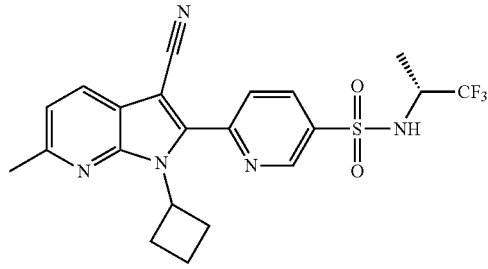
94
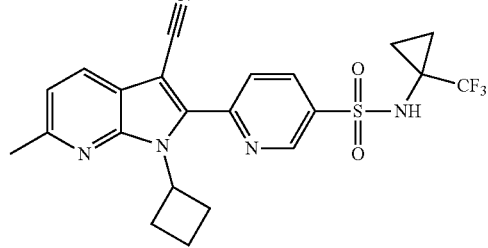
95
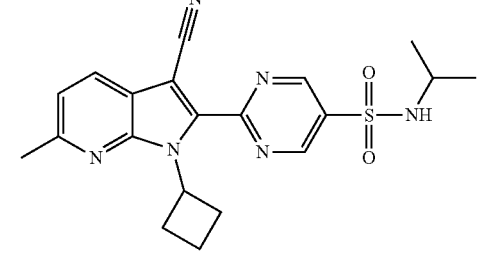
96
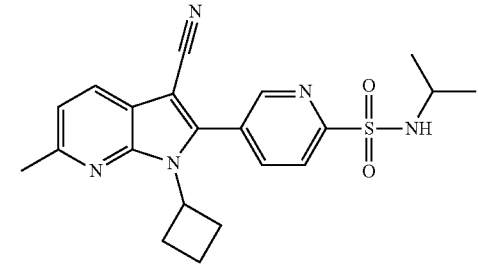
97
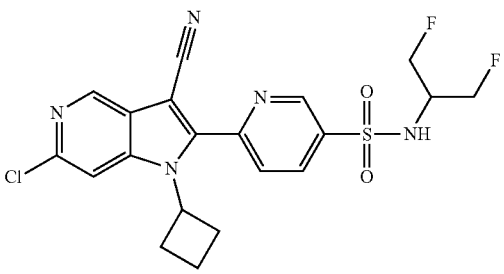
98
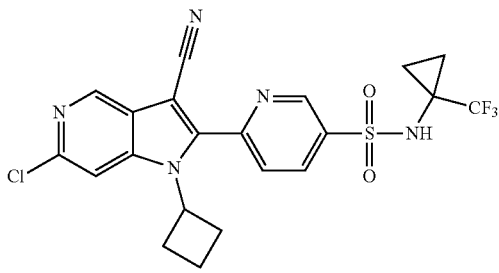
99
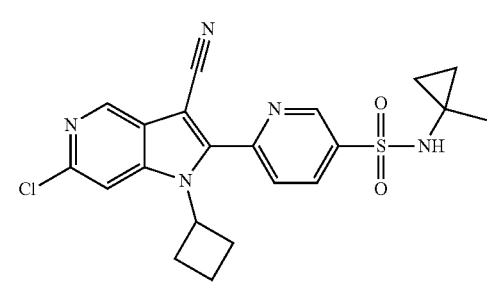
100
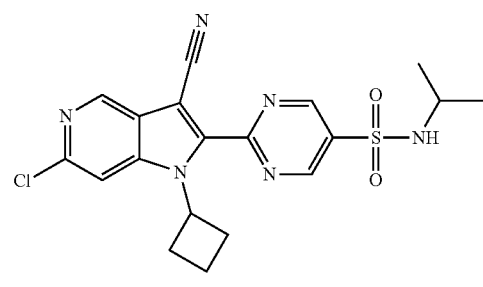
101
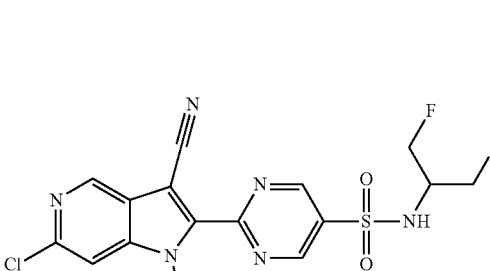
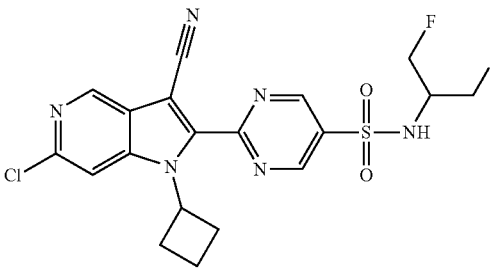

102
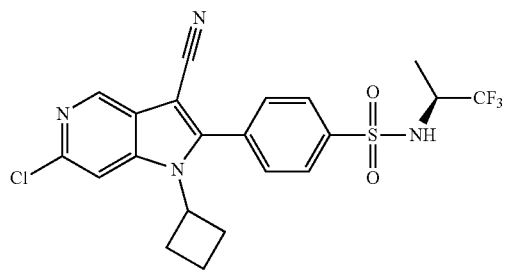
103
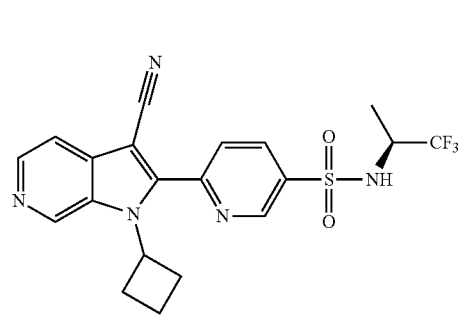
104
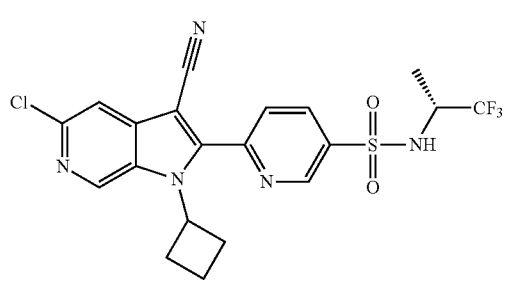
105
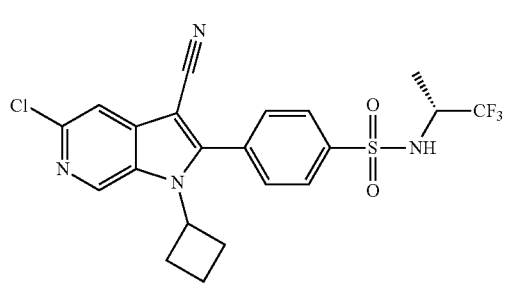
106
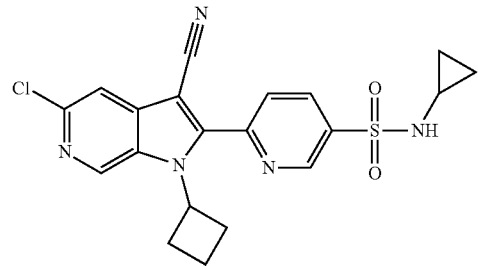
107
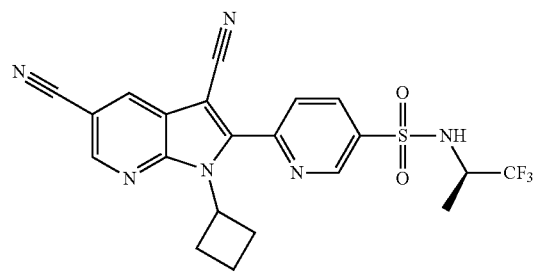
108
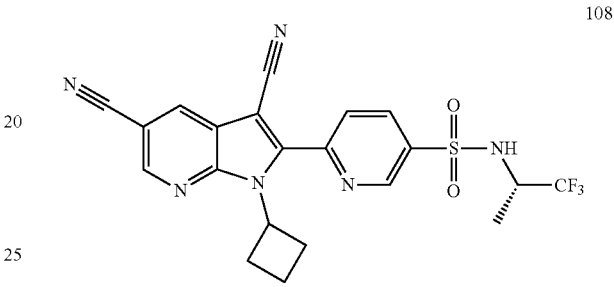
109
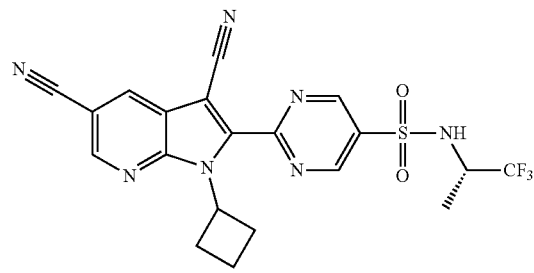
110
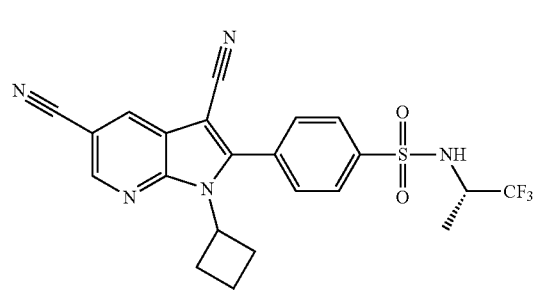
111
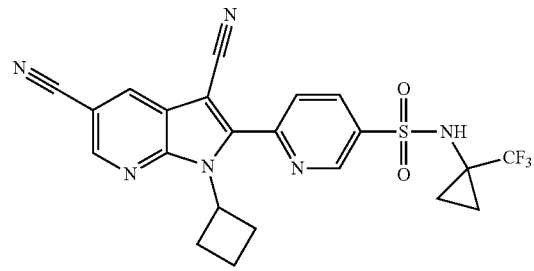

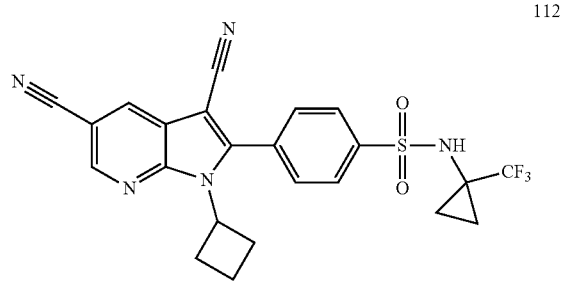
112
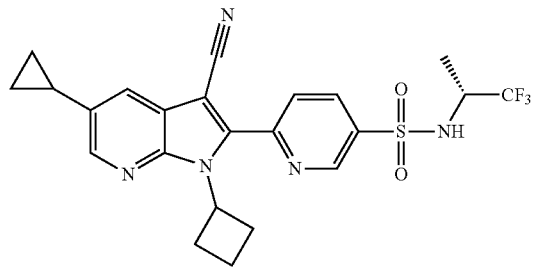
117
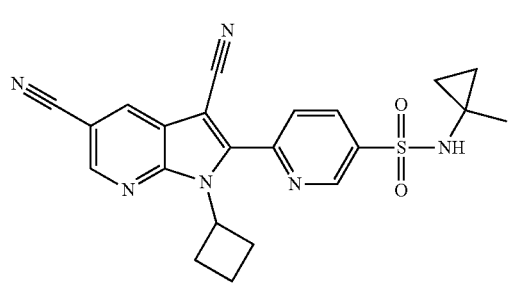
113
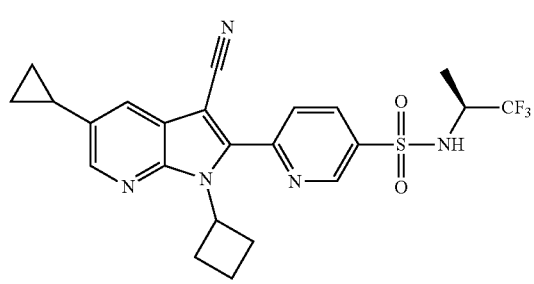
118
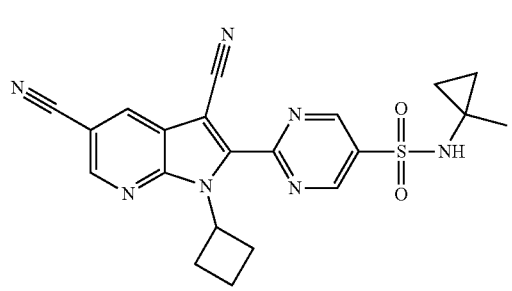
114
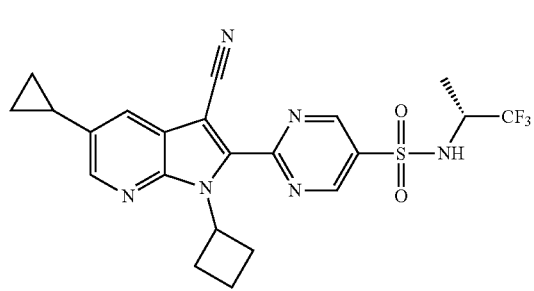
119
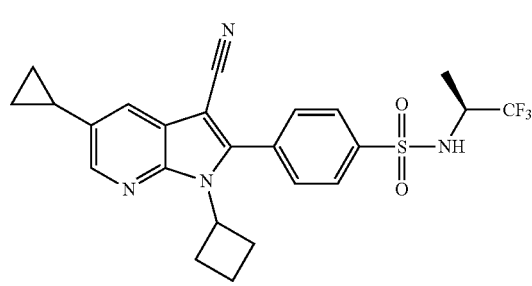
115
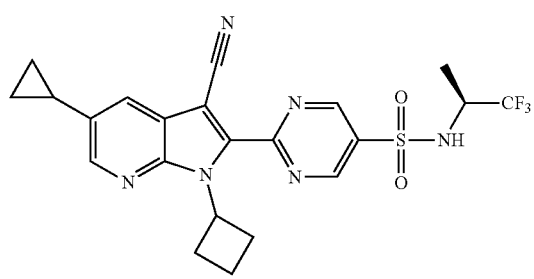
120
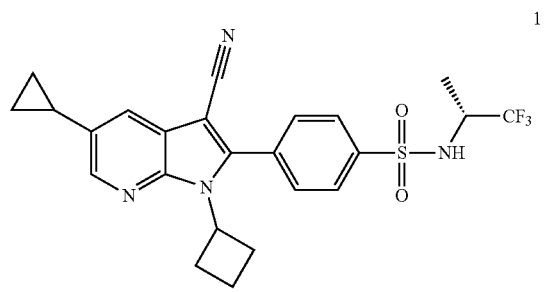
116
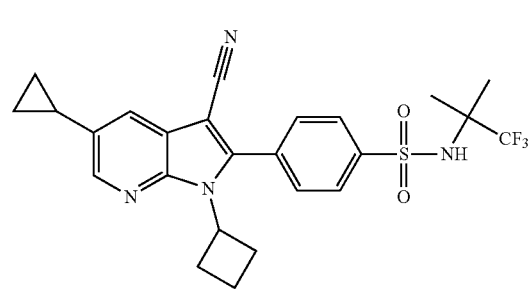
121

-continued
122
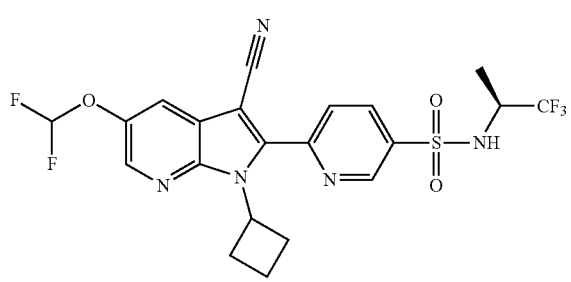
123
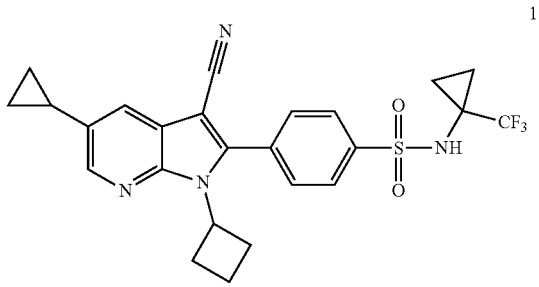
124
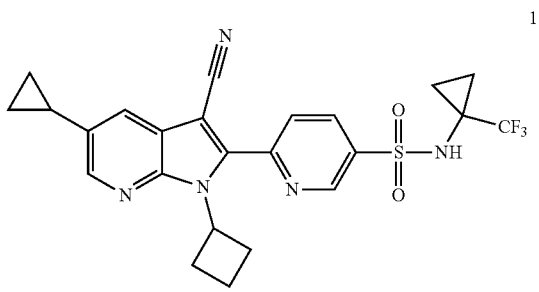
125
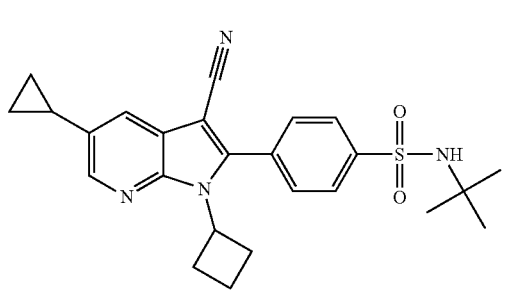
126
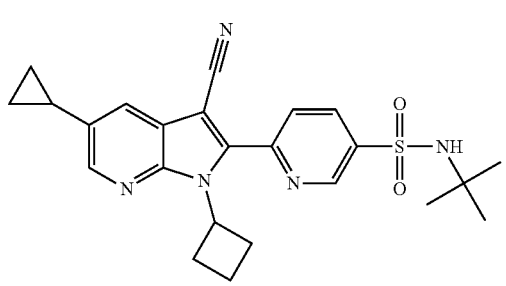
-continued
127
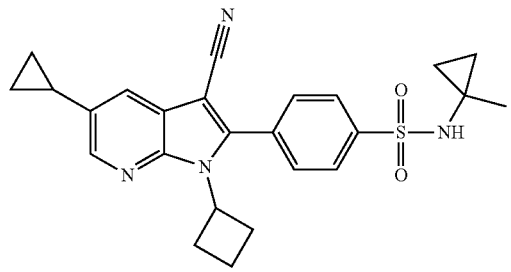
128
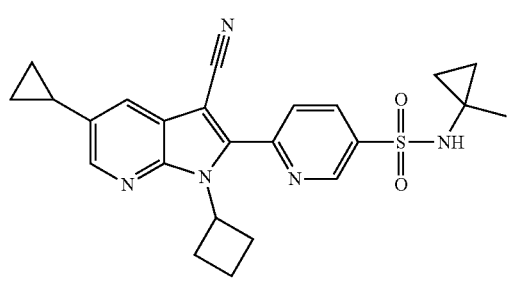
129
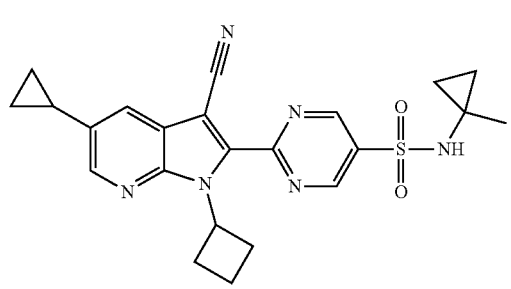
130
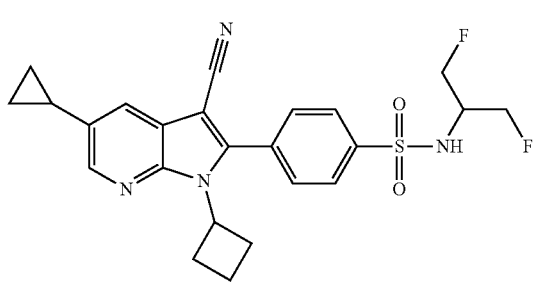
131
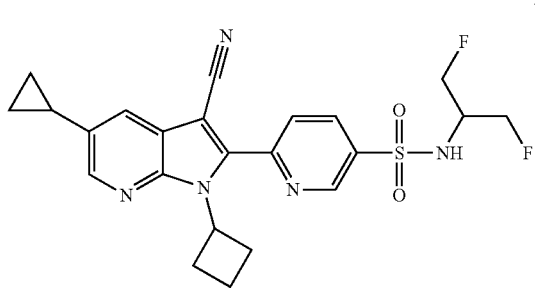

132
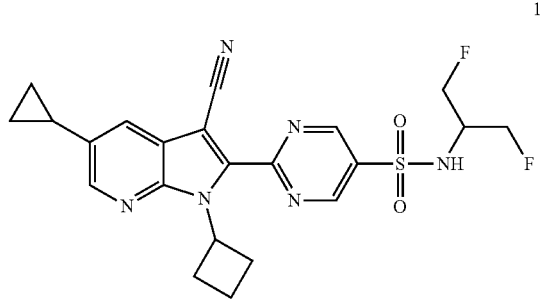
133
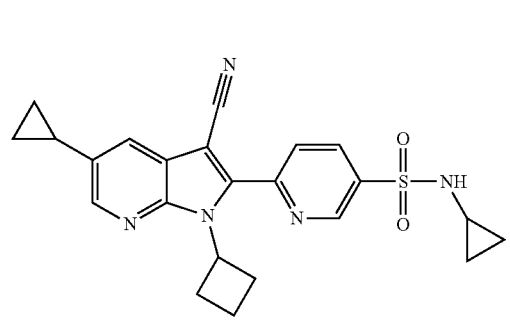
134
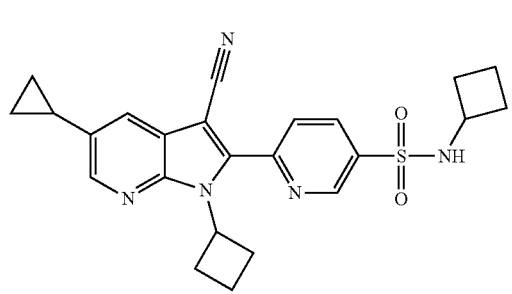
135
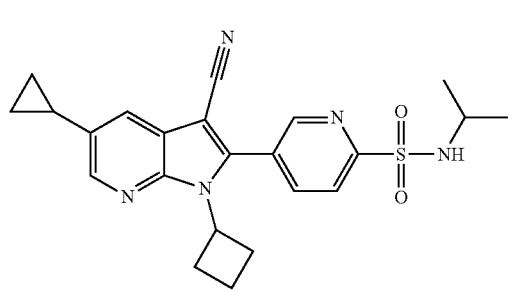
136
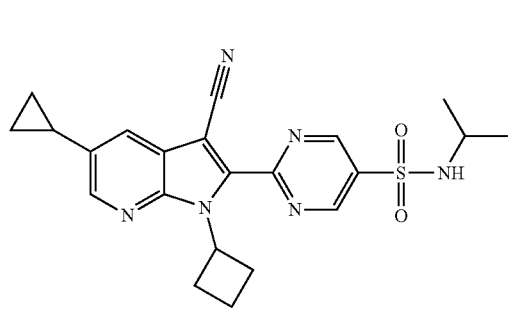
137
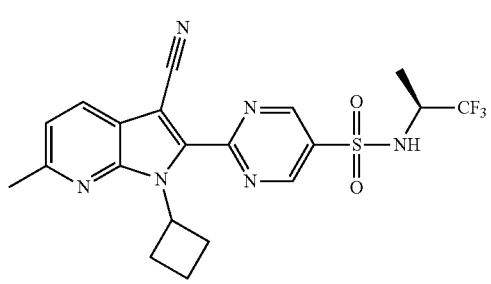
138
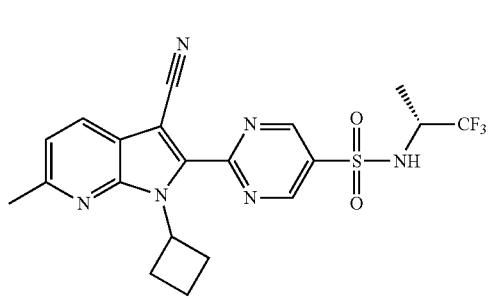
139
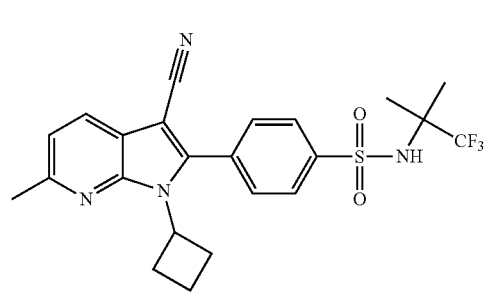
140
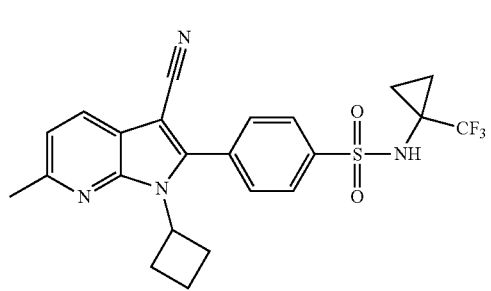
141
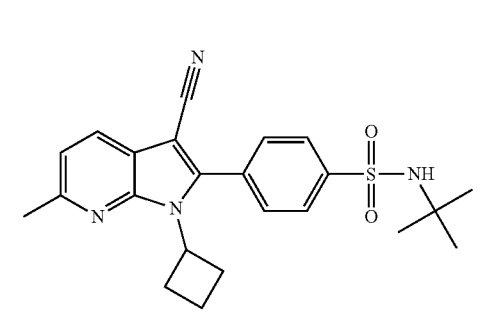

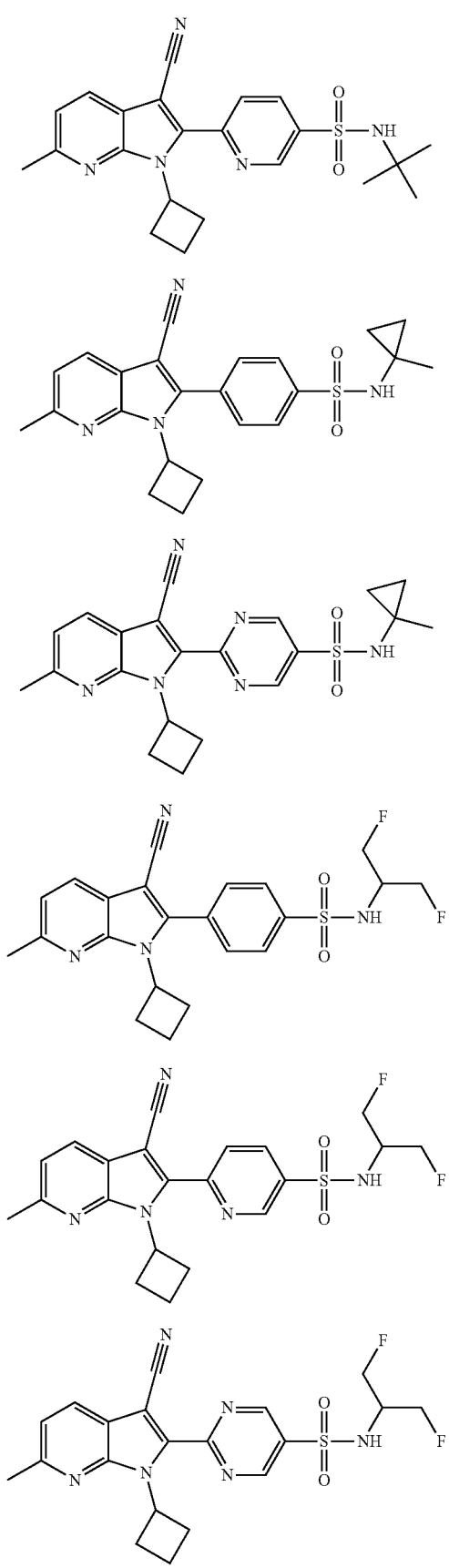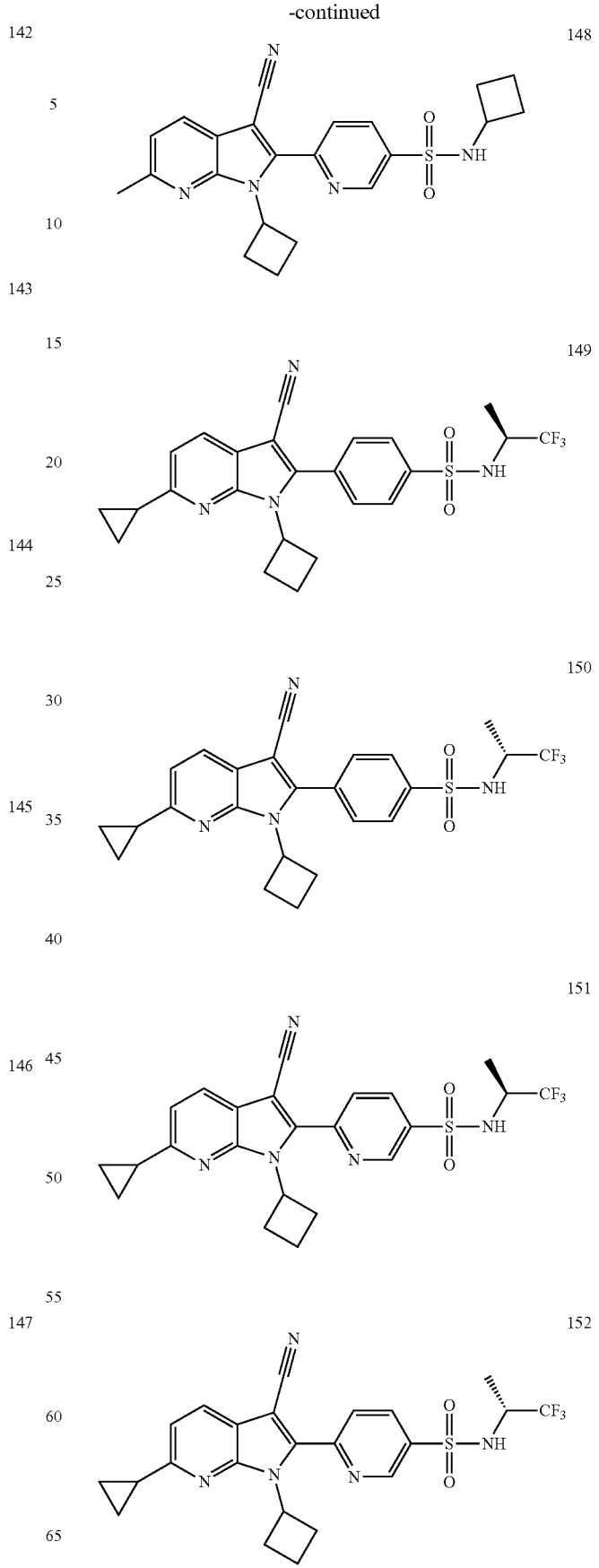

153
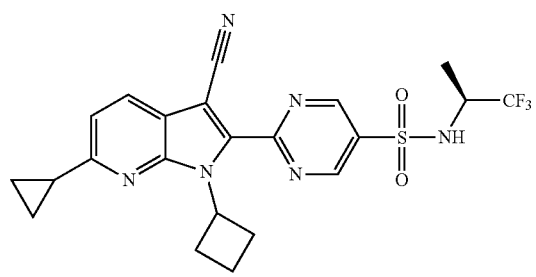
154
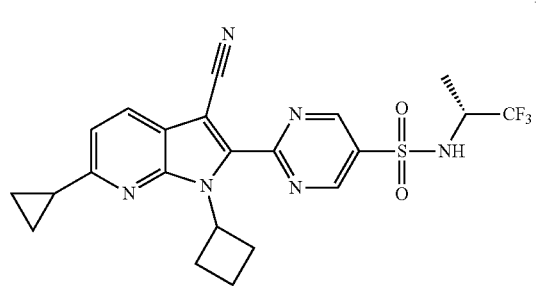
155
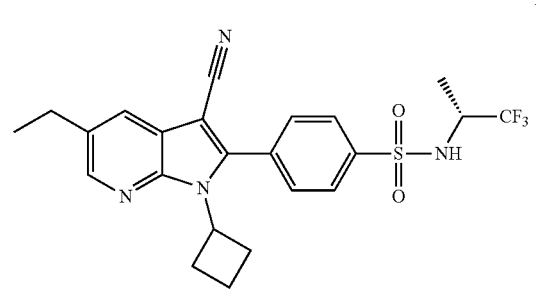
156
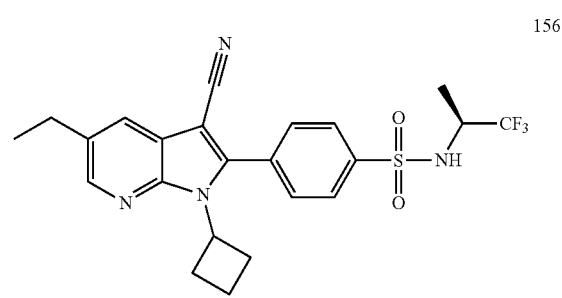
157
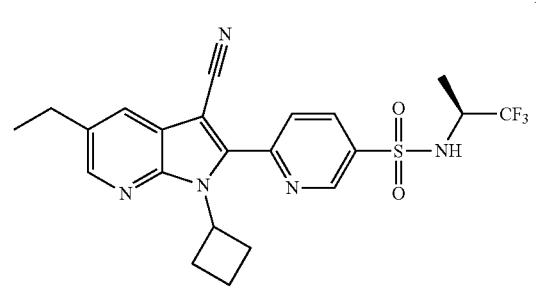
158
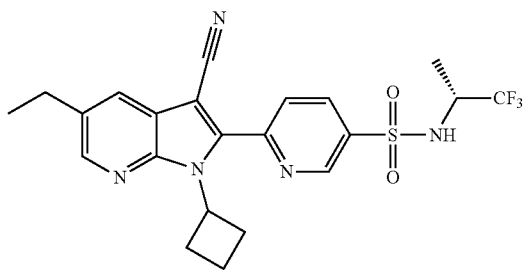
159
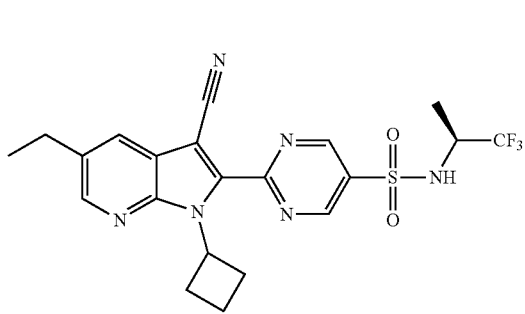
160
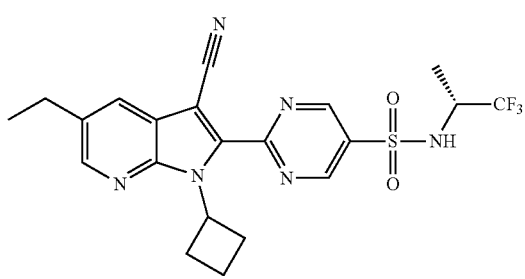
161
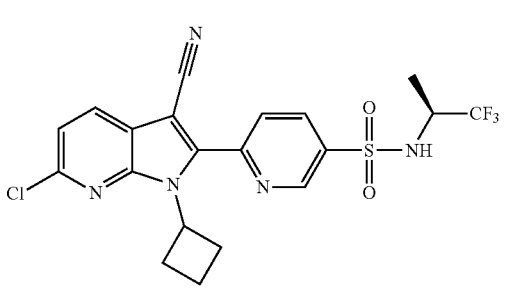
162
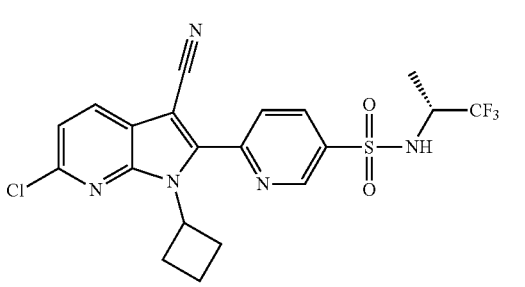

163
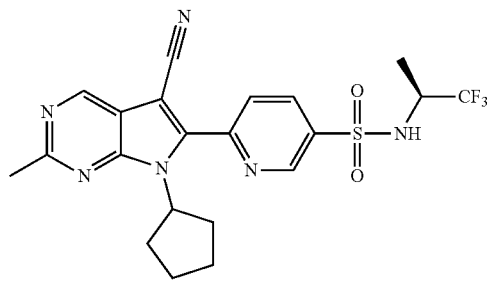
164
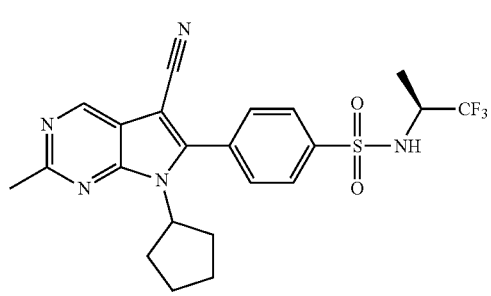
165
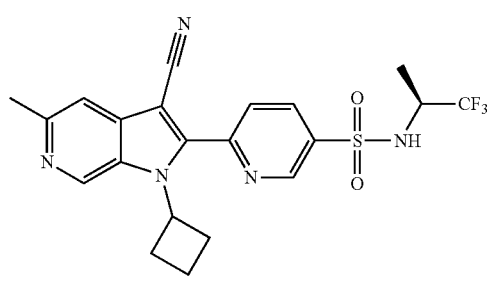
166
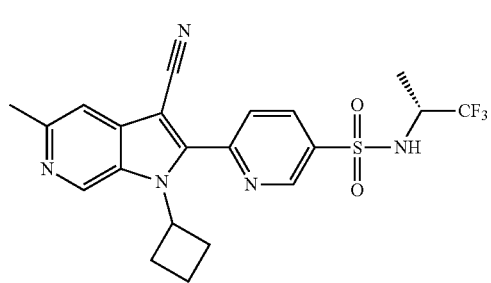
167
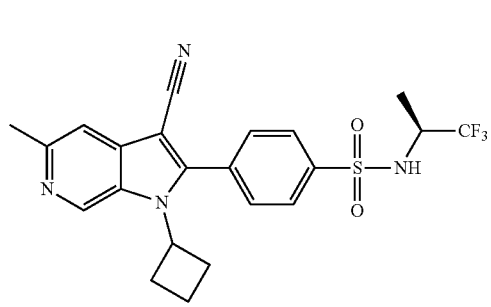
168
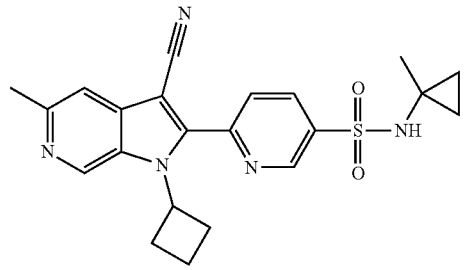
169
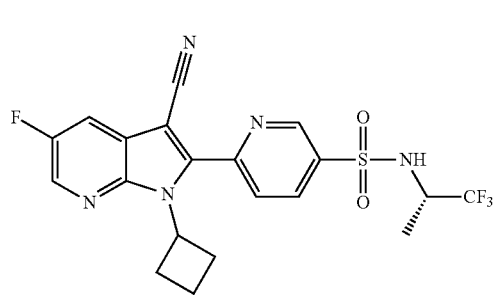
170
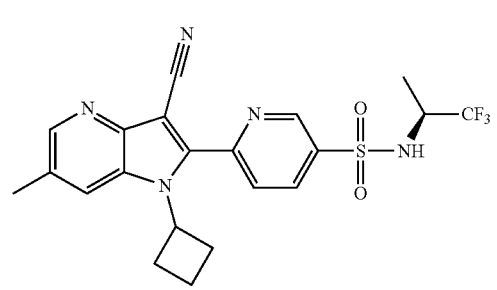
171
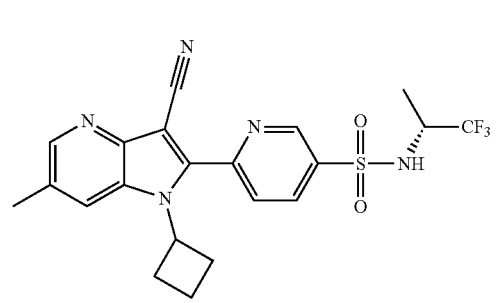
172
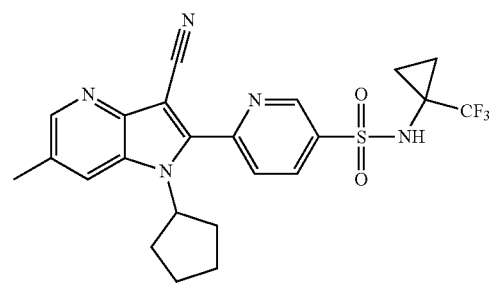

45
-continued
173
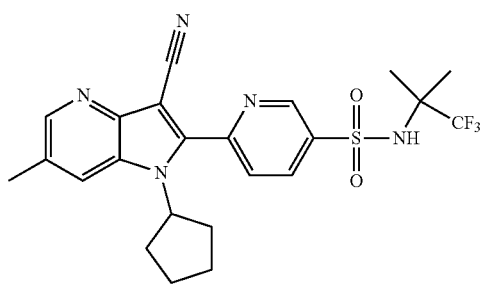
174
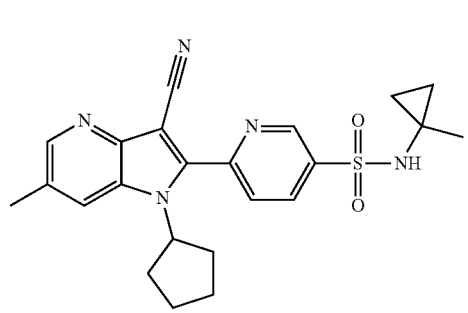
175
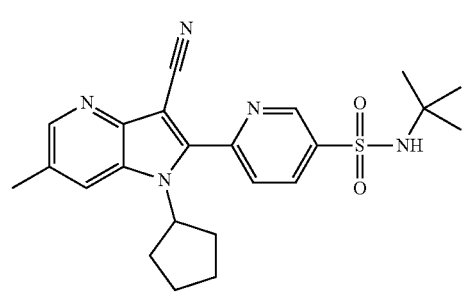
176
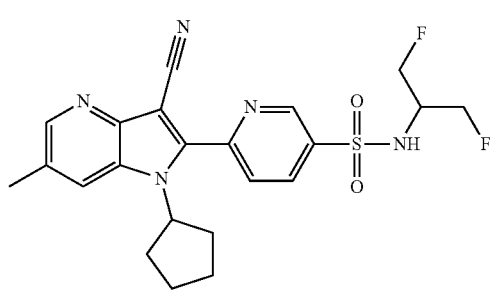
177
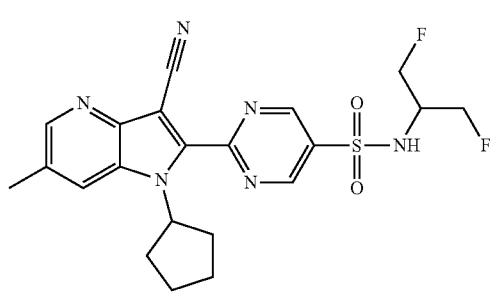
46
-continued
178
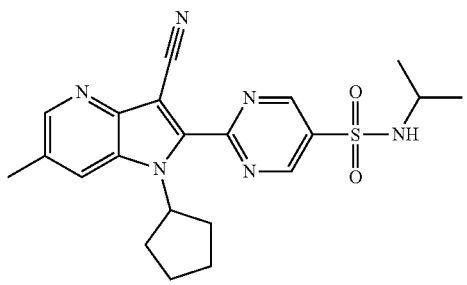
179
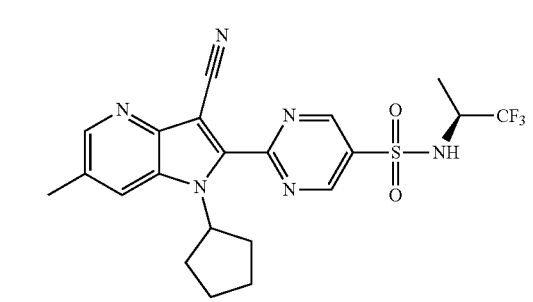
180
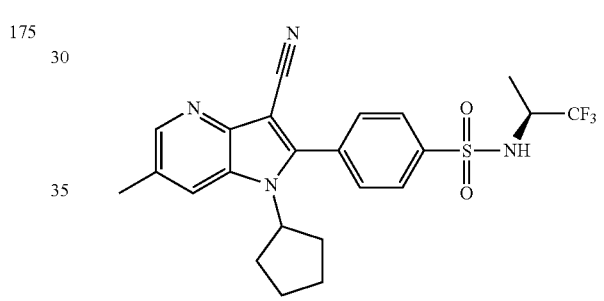
181
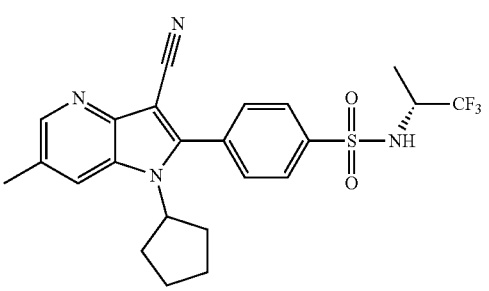
182
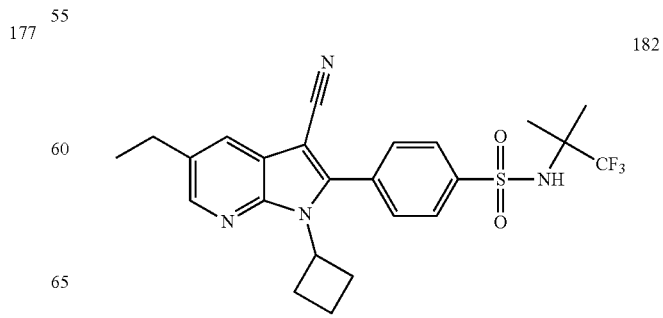

-continued
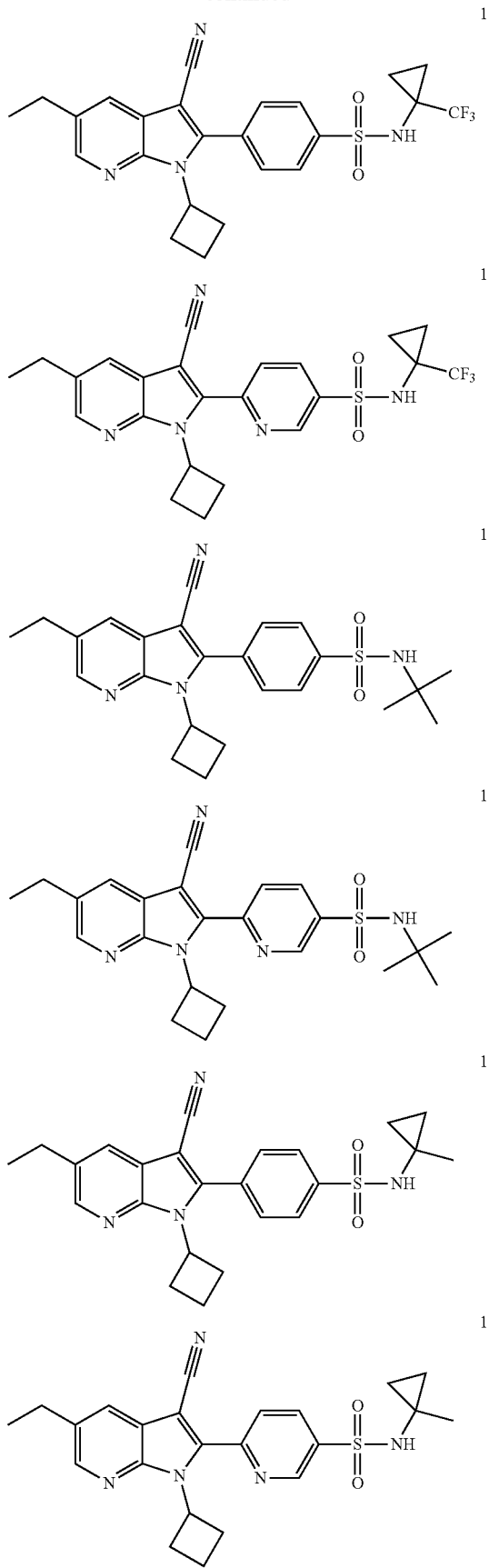
-continued
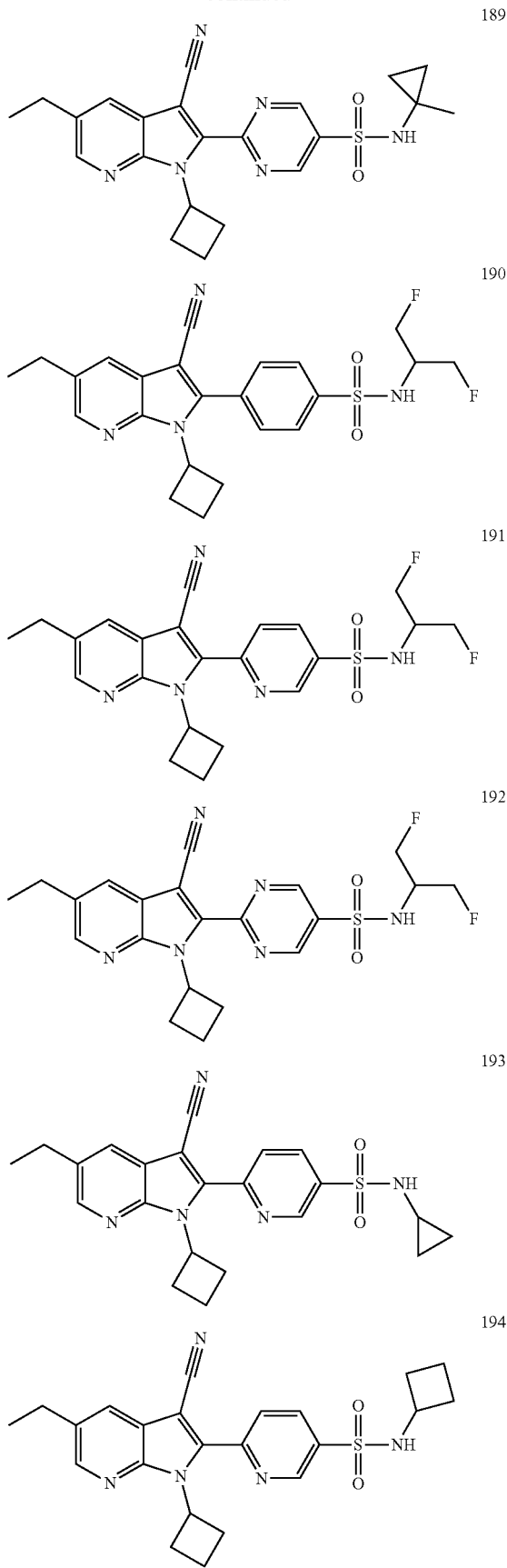

195
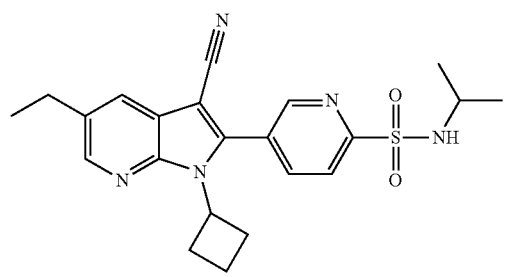
196
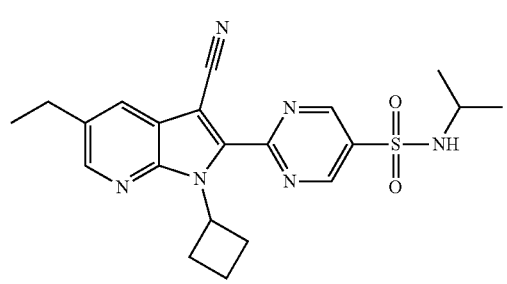
197
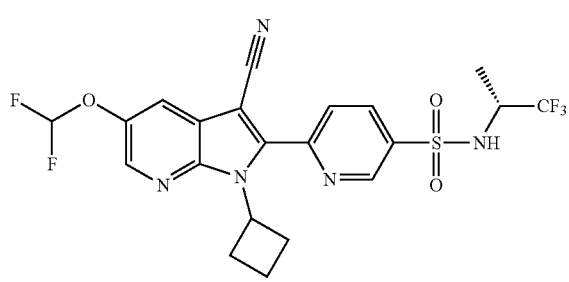
198
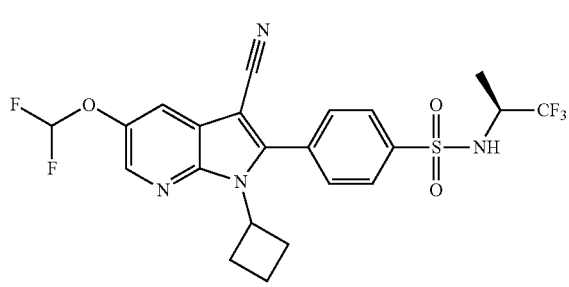
199
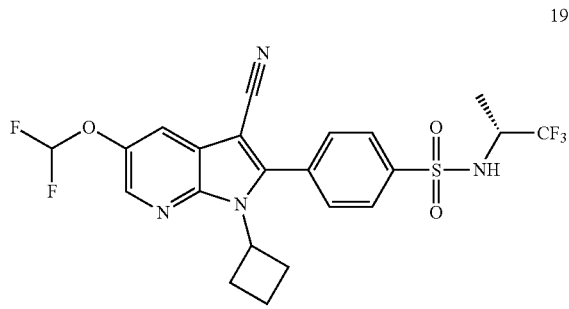
200
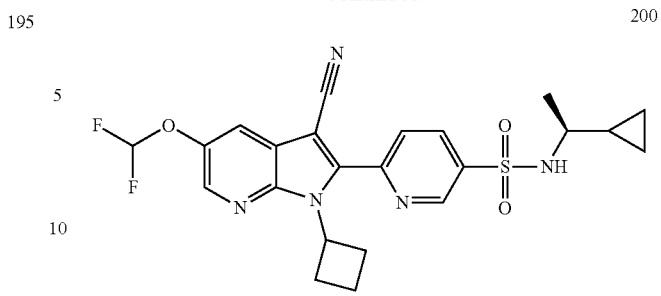
201
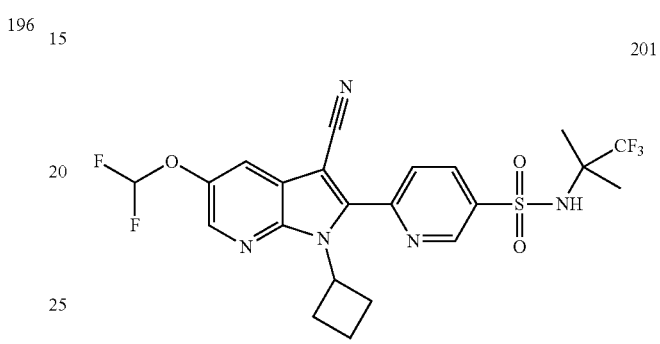
202
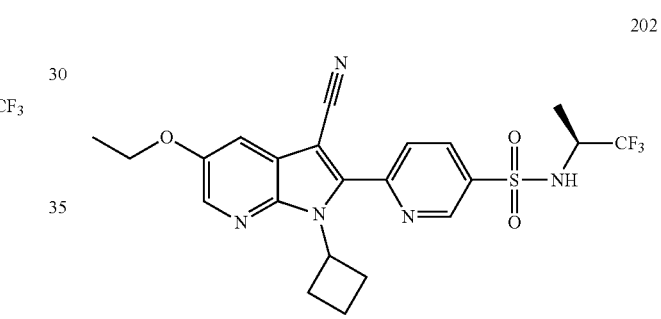
203
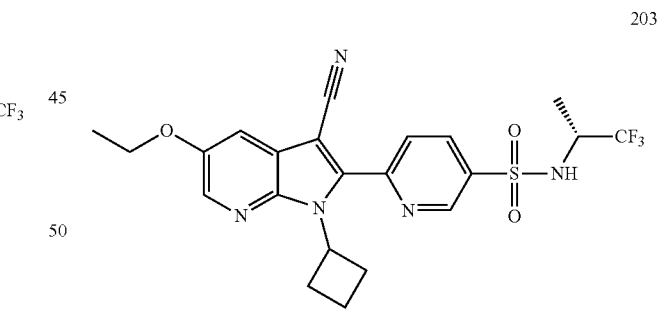
204
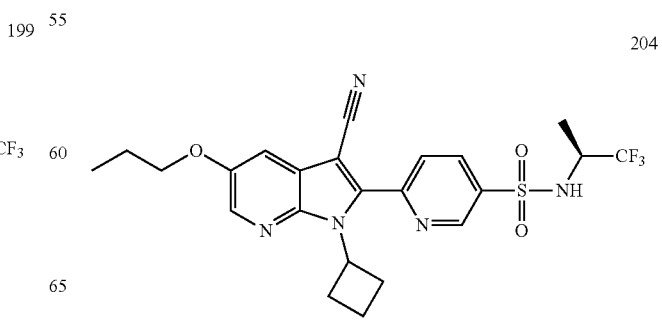

-continued
205
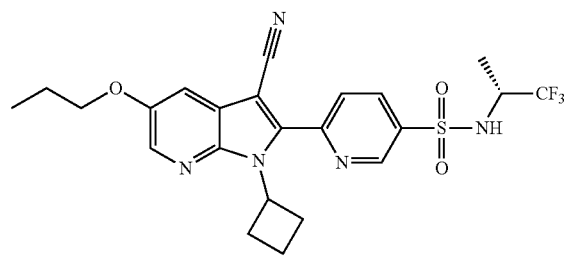
206
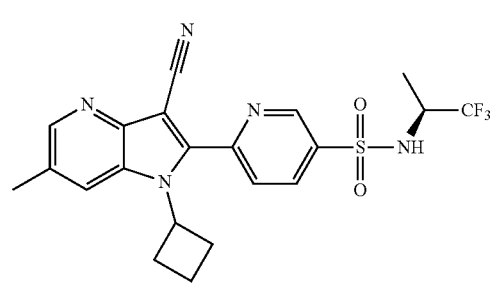
207
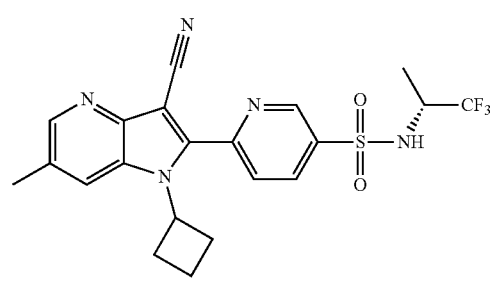
208
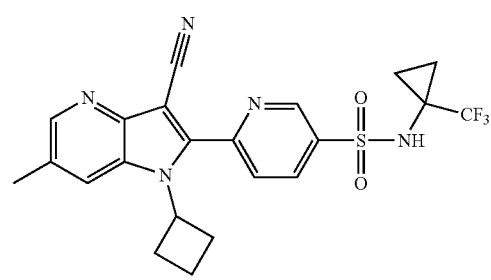
209
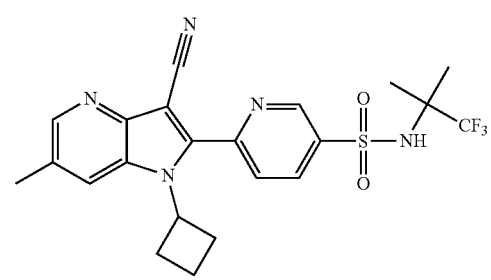
-continued
210
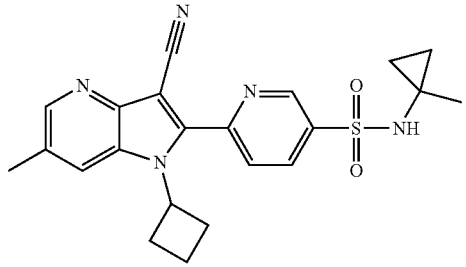
211
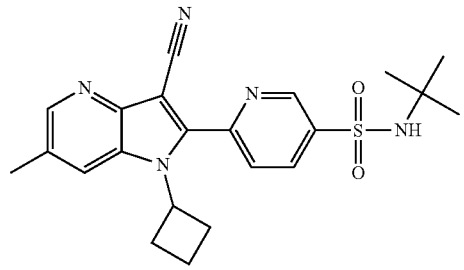
212
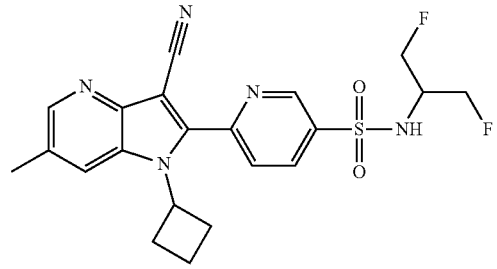
213
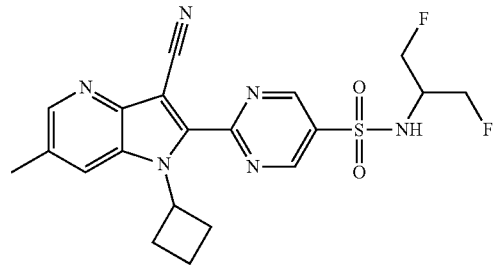
214
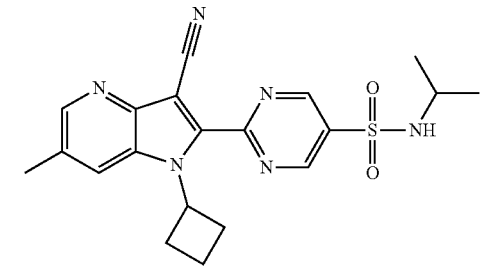
215
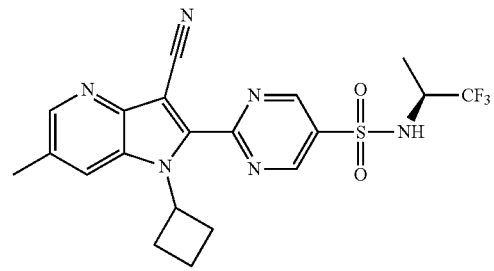

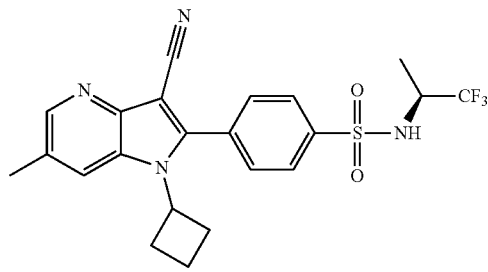
216
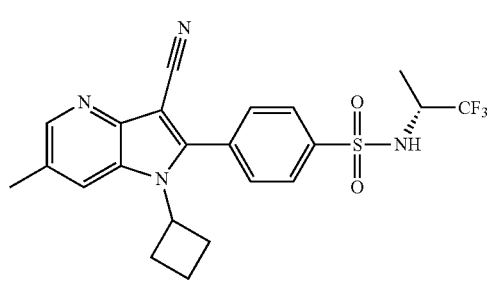
217
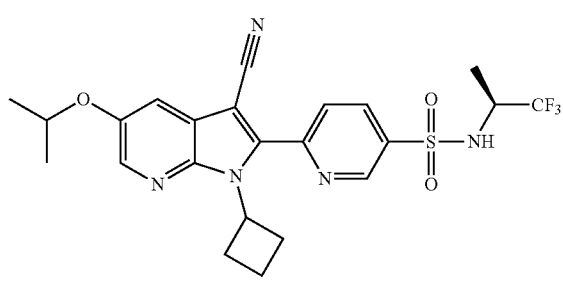
218
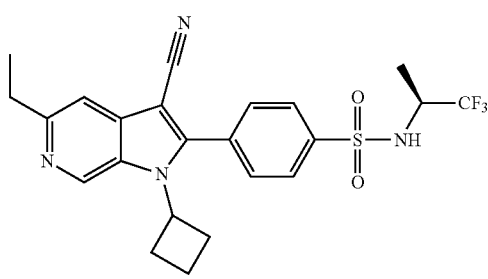
219
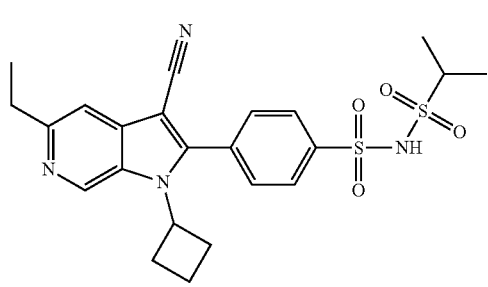
220
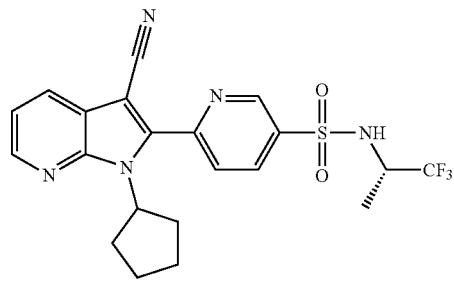
221
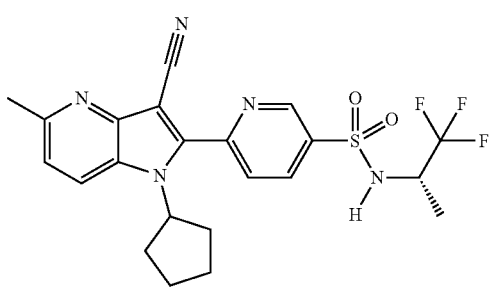
222
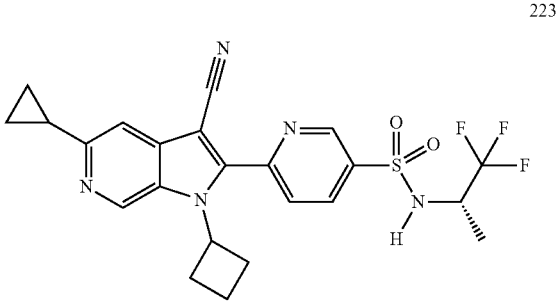
223
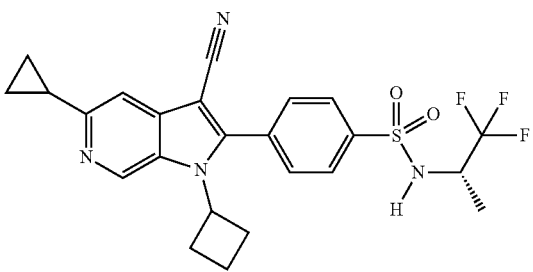
224
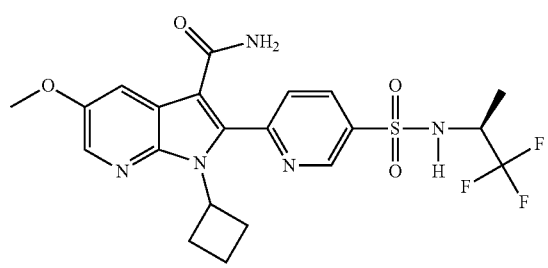
226

-continued
227
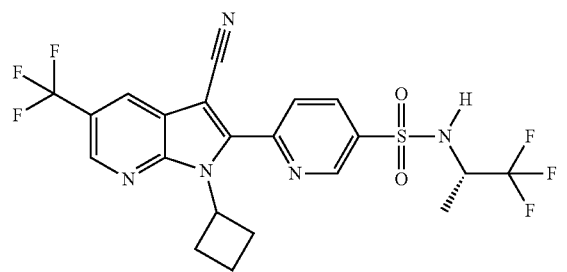
228
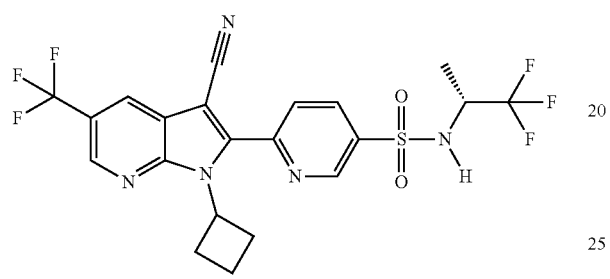
229
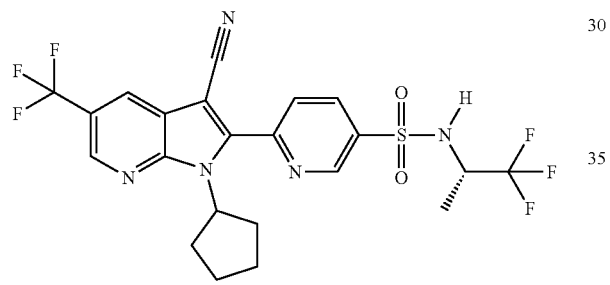
230
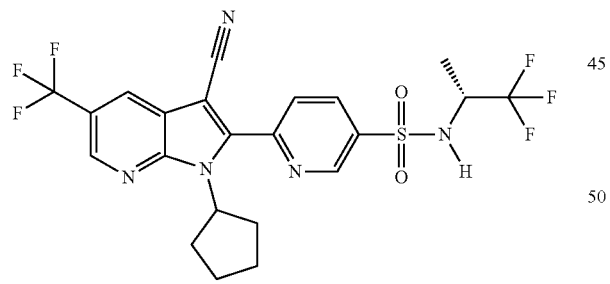
232
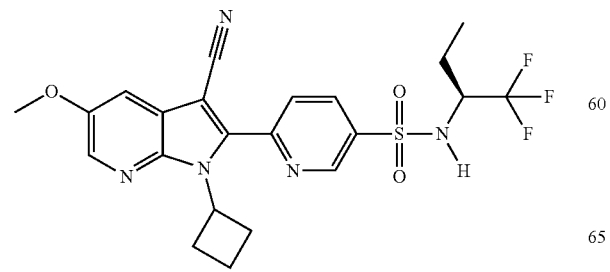
-continued
233
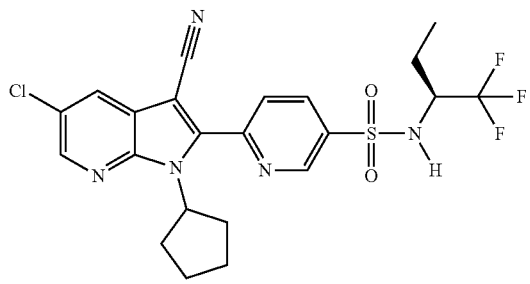
234
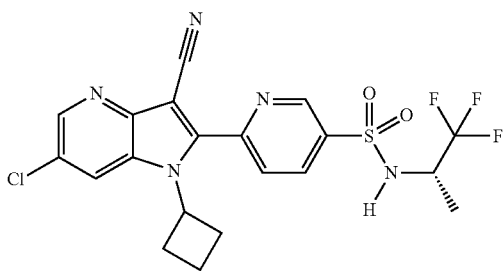
235
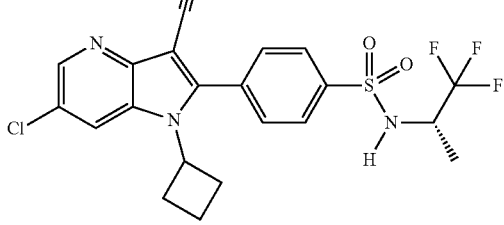
236
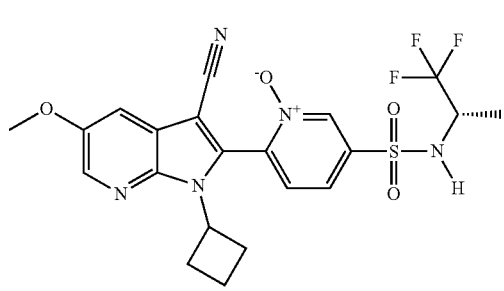
237
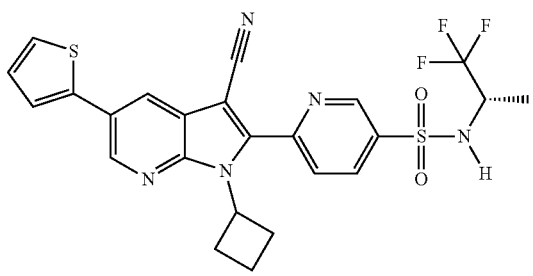

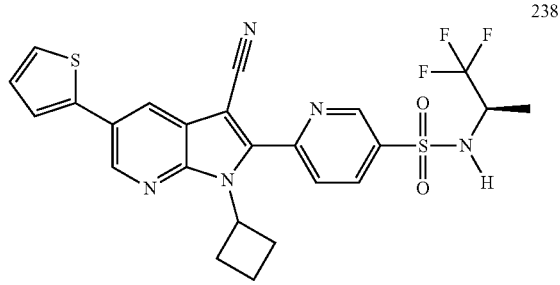 238
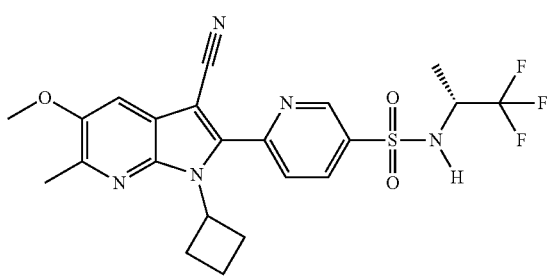 243
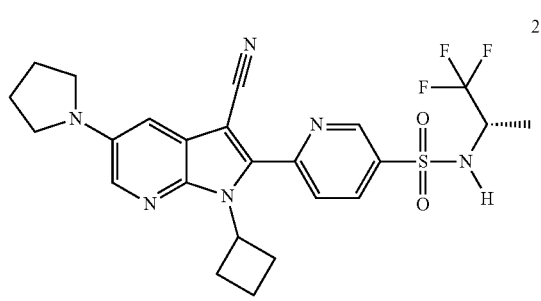 239
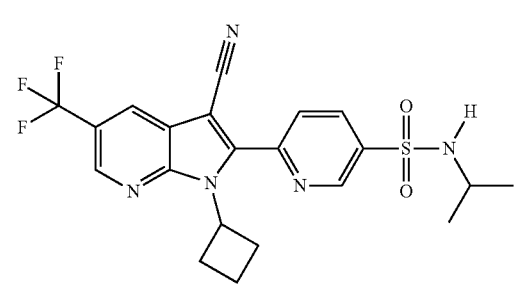 244
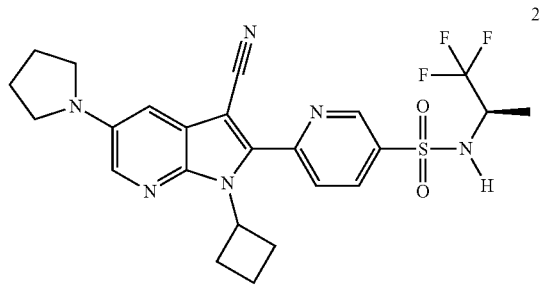 240
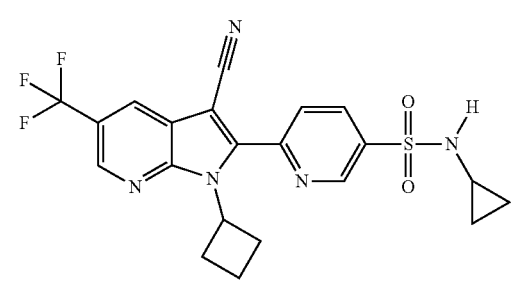 245
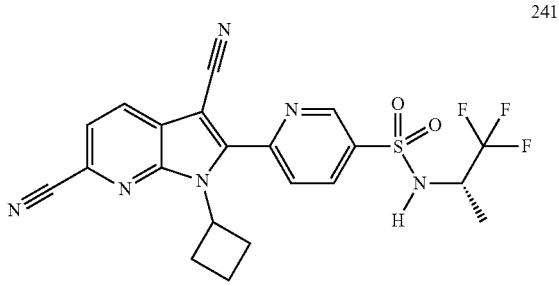 241
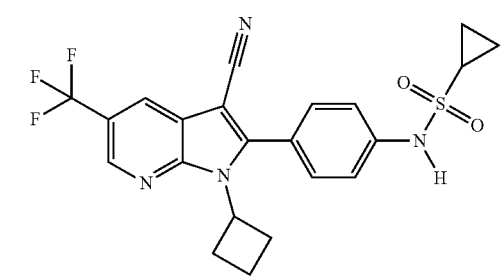 246
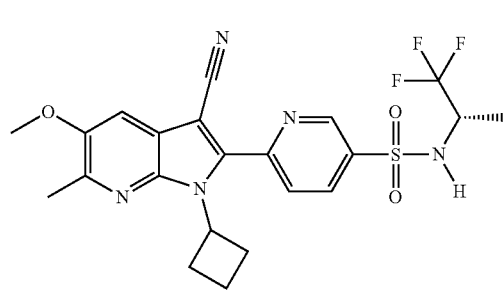 242
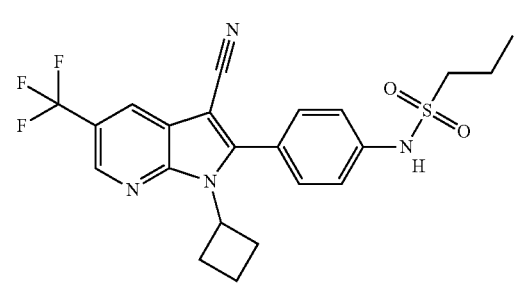 247

248
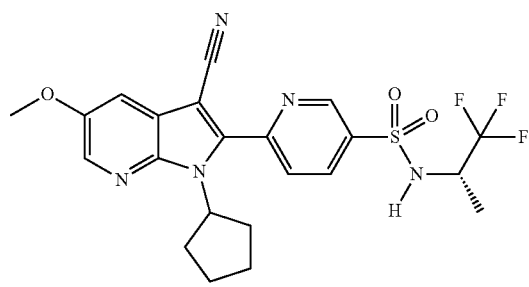
249
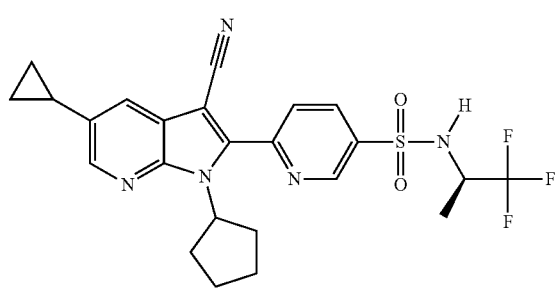
250
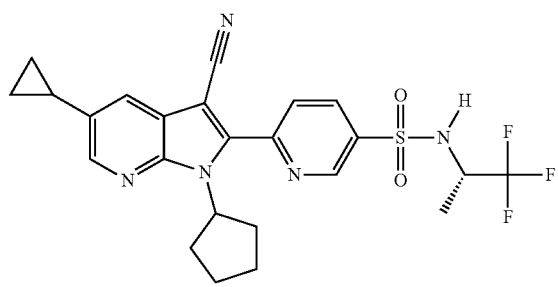
251
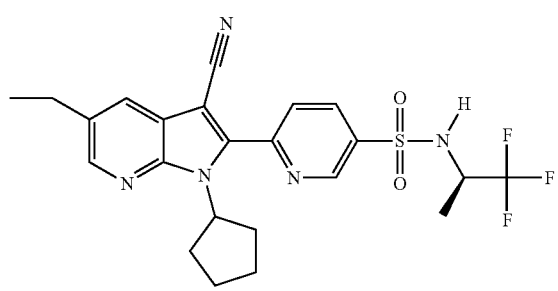
252
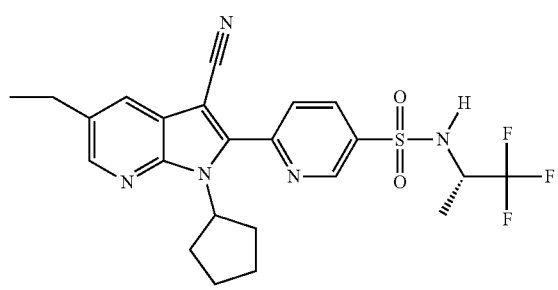
253
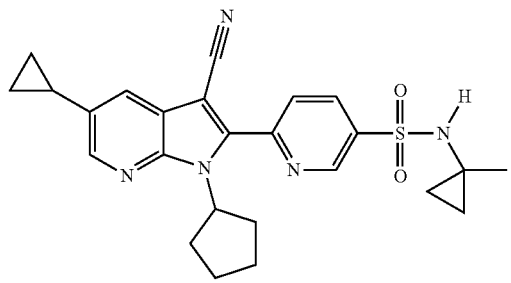
254
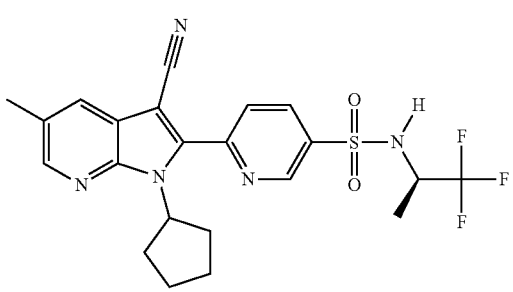
255
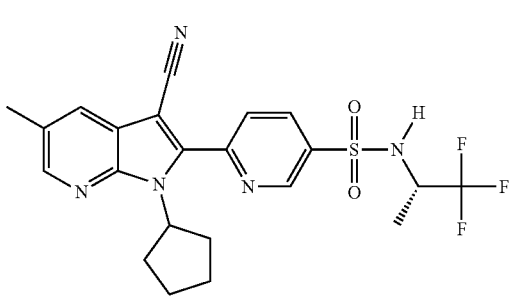
256
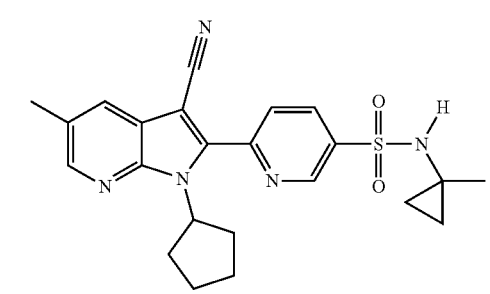
257
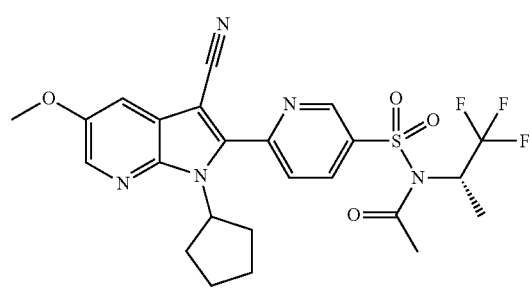

258 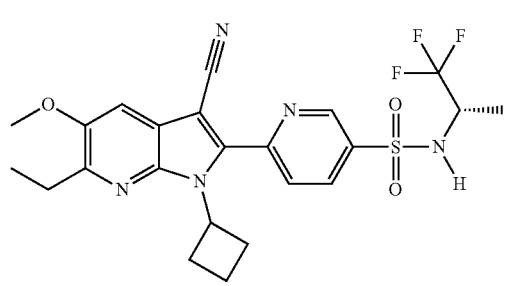
263 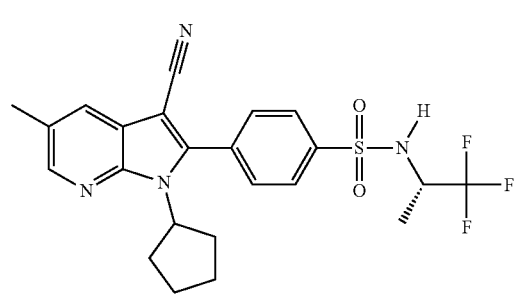
259 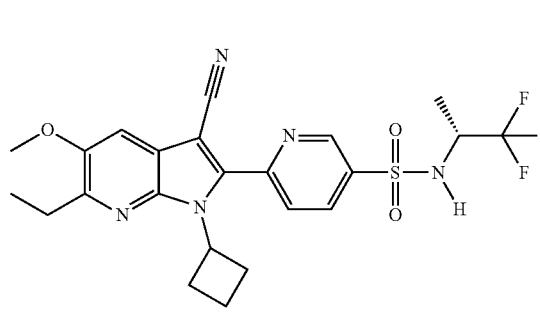
264 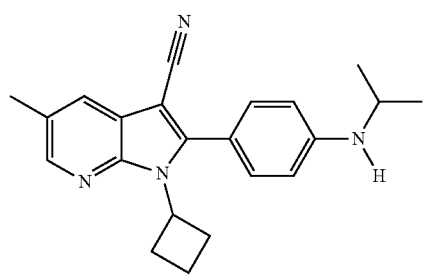
260 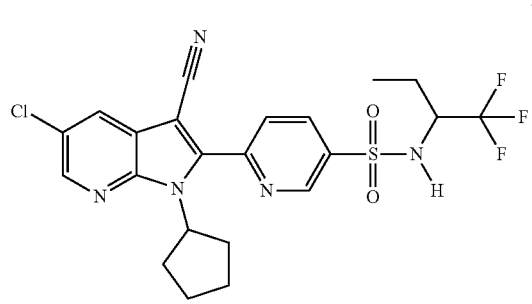
265 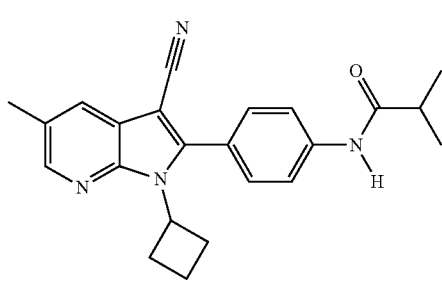
261 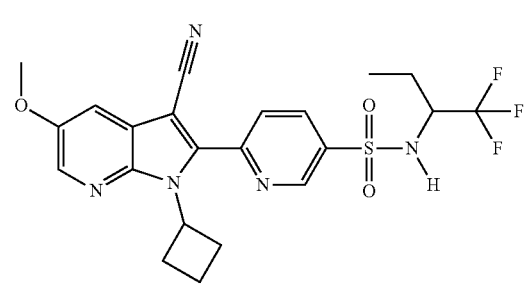
266 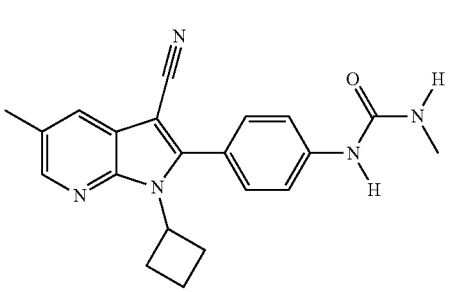
262 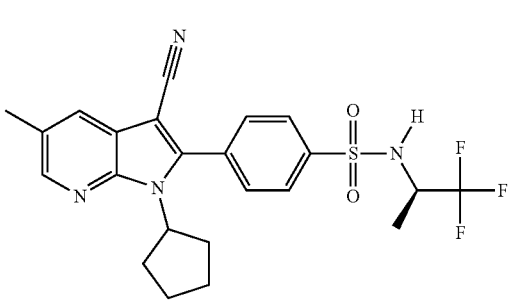
267 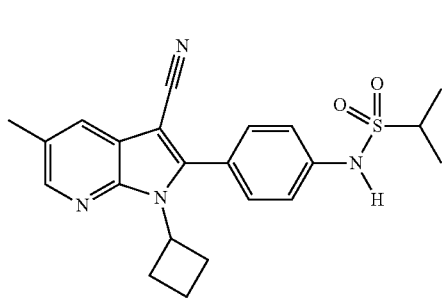

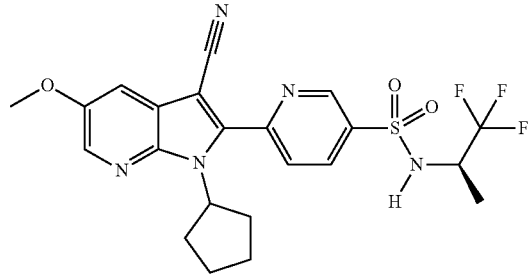
268
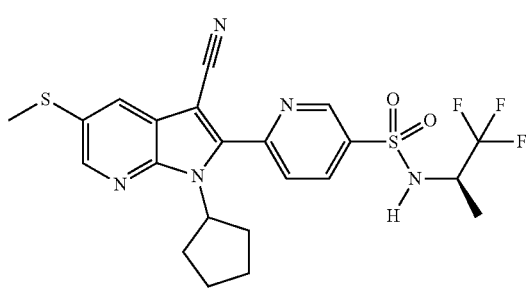
273
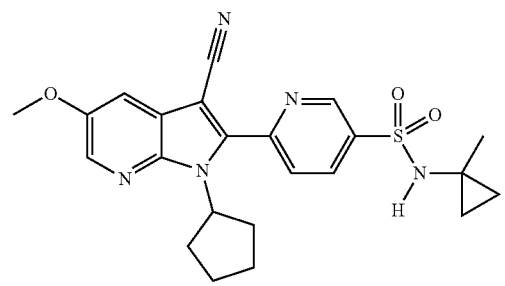
269
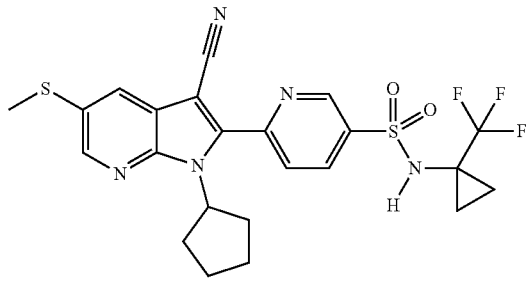
274
270
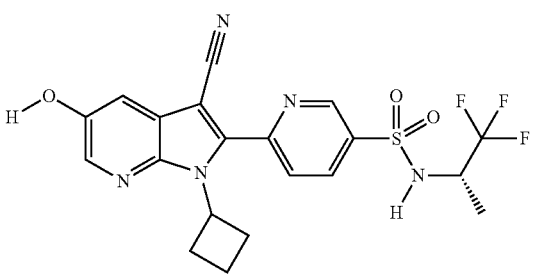
275
271
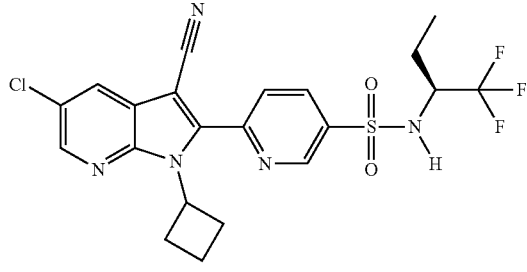
276
272
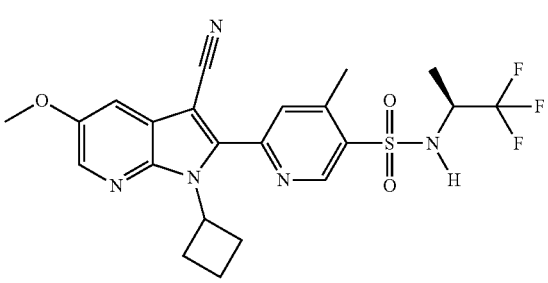
277

278 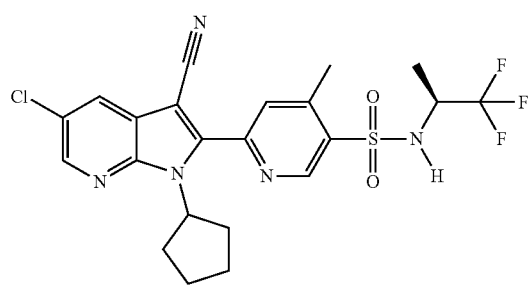
279 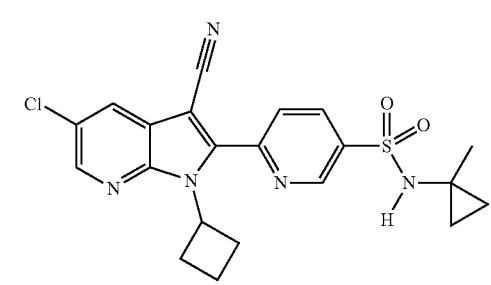
280 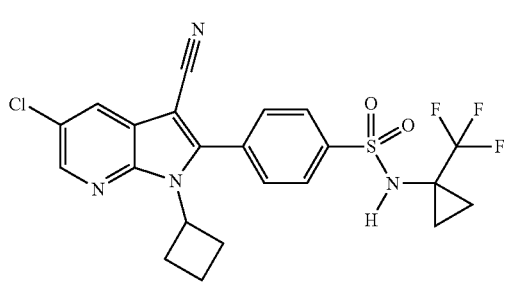
281 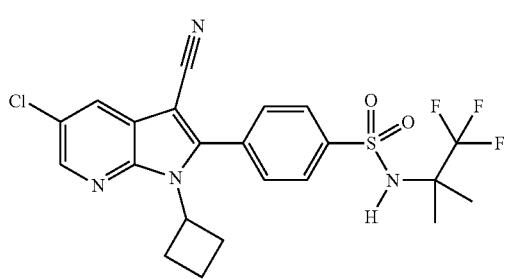
283 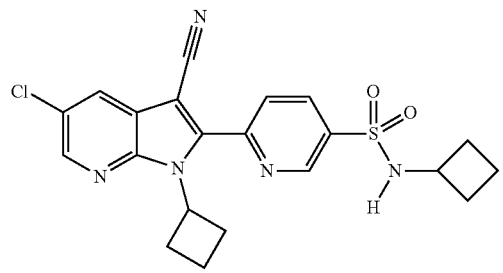
284 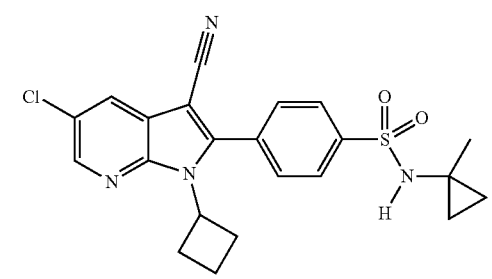
285 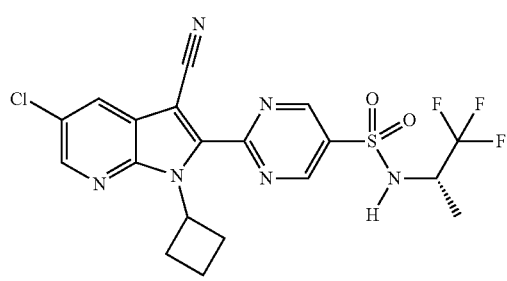
286 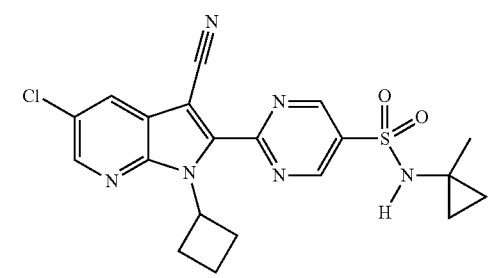
287 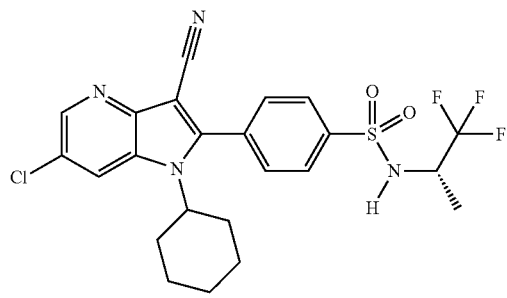

288 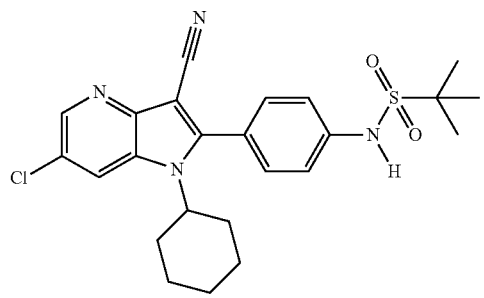
289 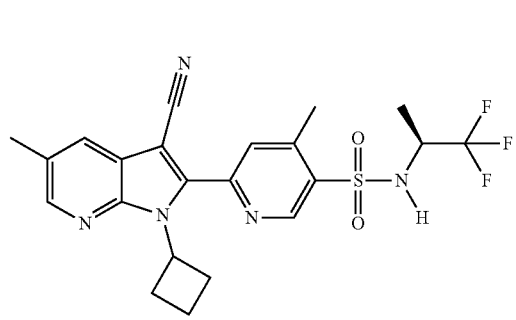
290 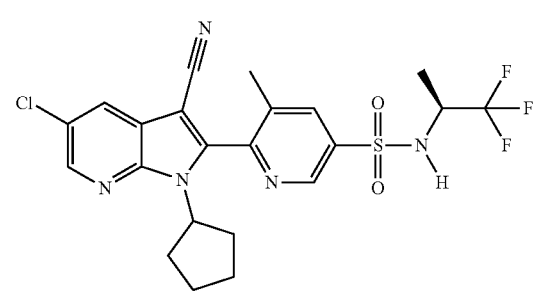
291 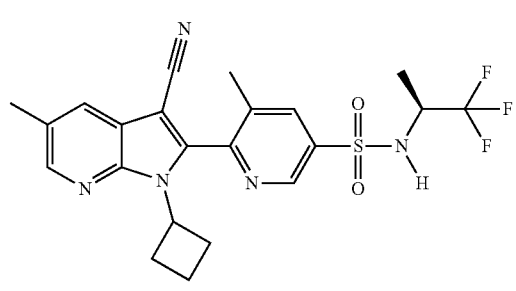
292 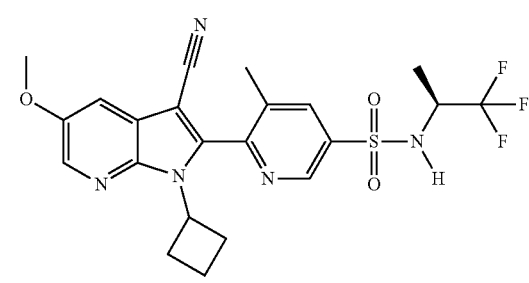
293 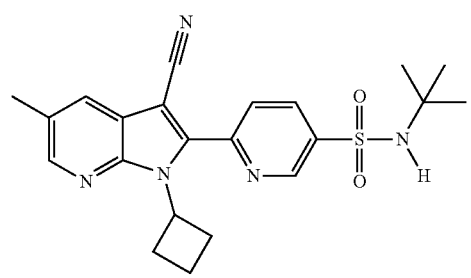
294 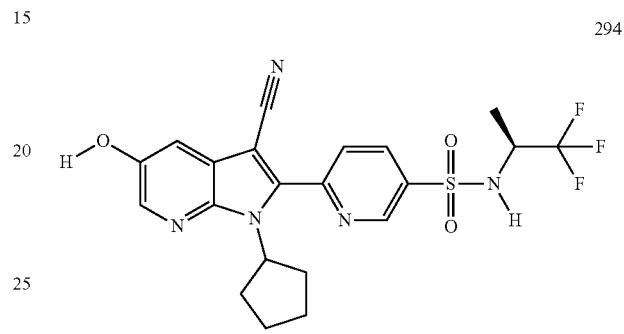
295 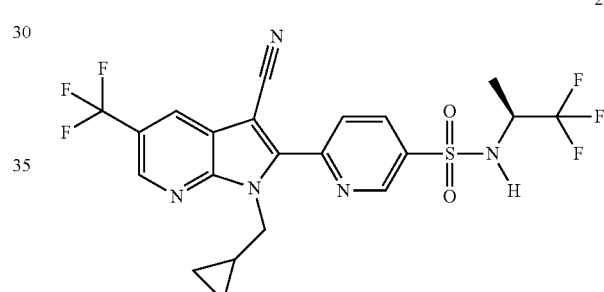
296 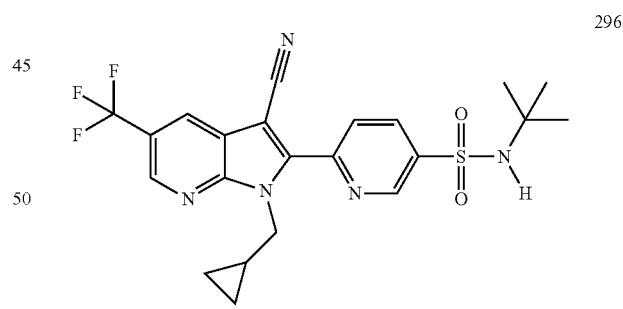
297 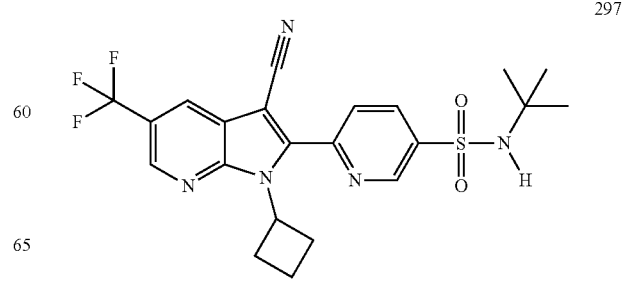

298
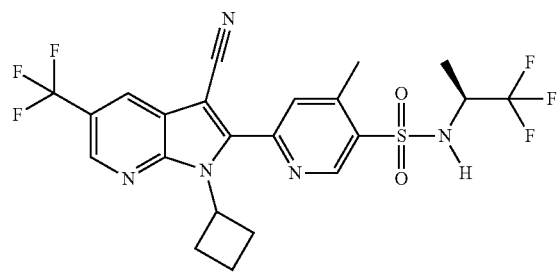
299
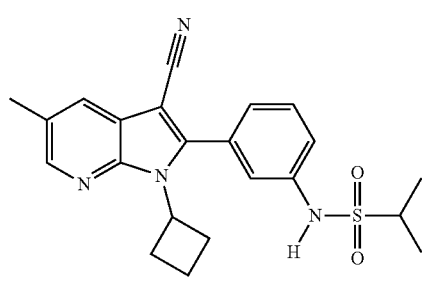
300
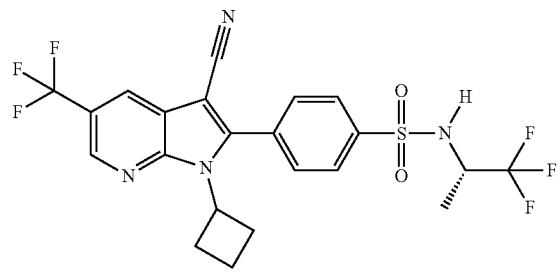
301
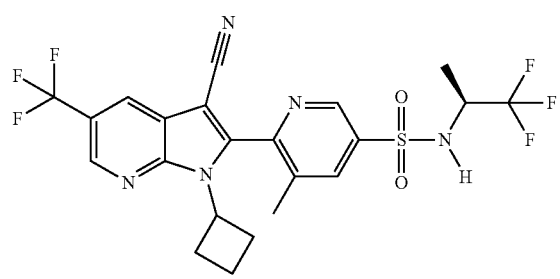
302
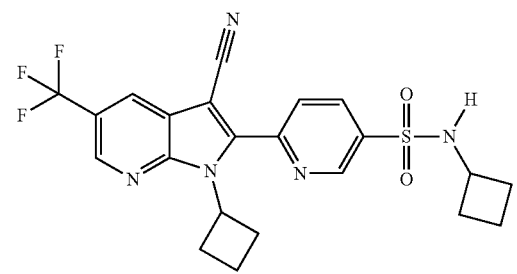
303
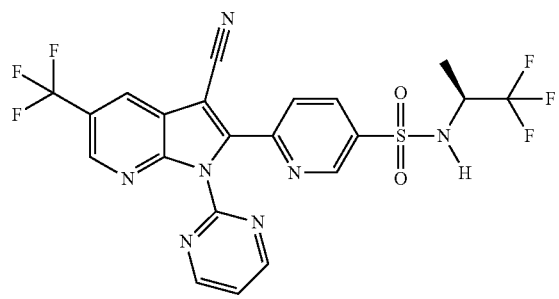
304
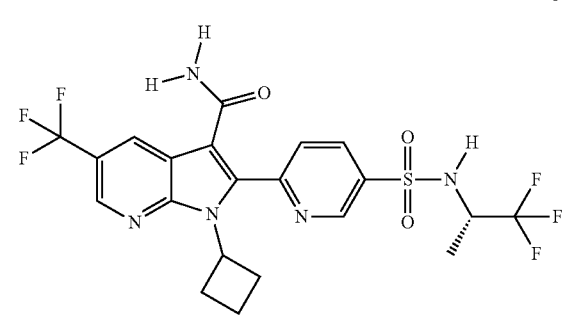
305
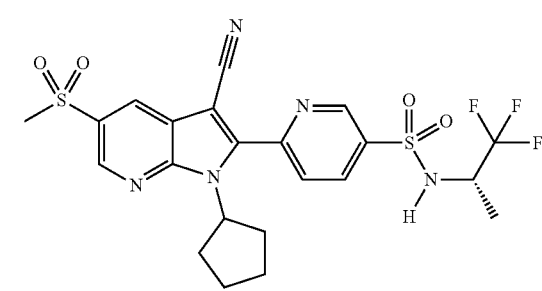
306
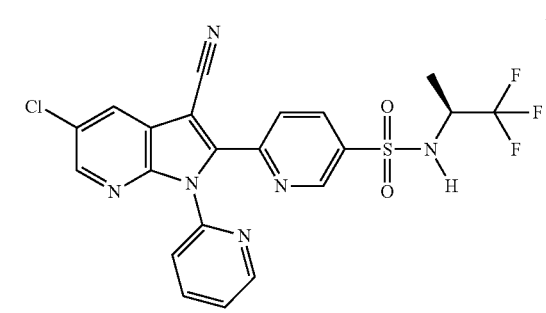
307
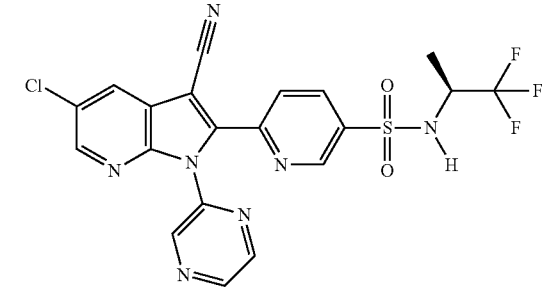

308 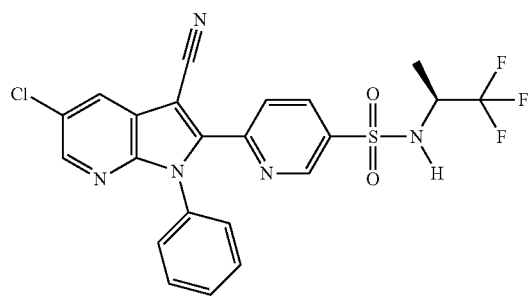
309 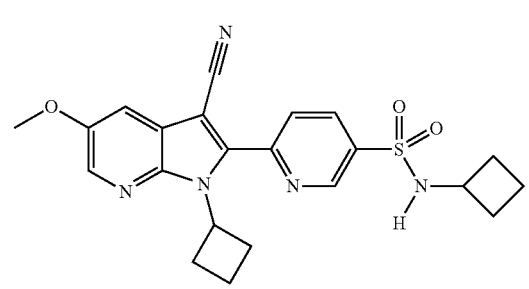
310 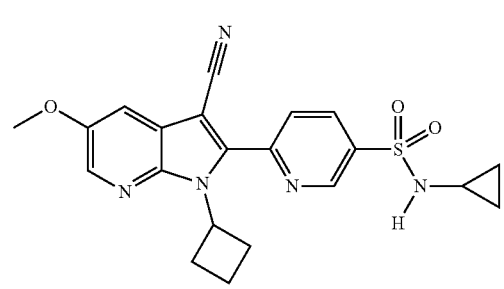
311 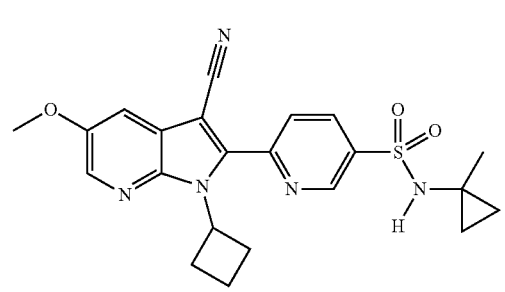
312 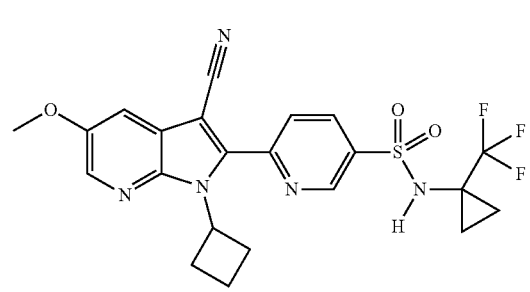
313 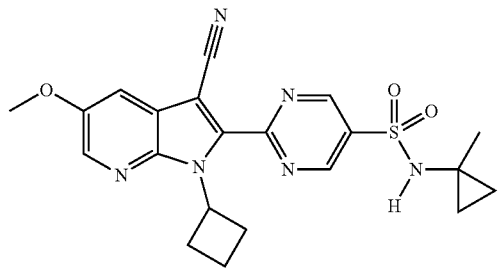
314 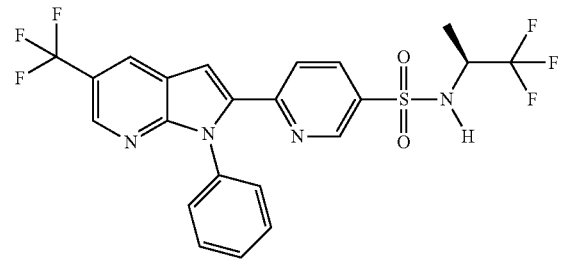
315 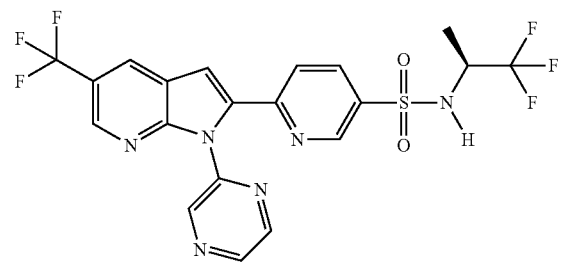
316 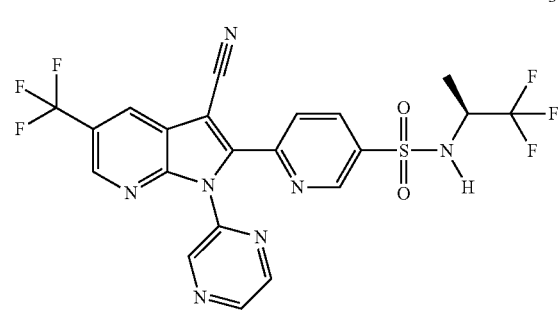
317 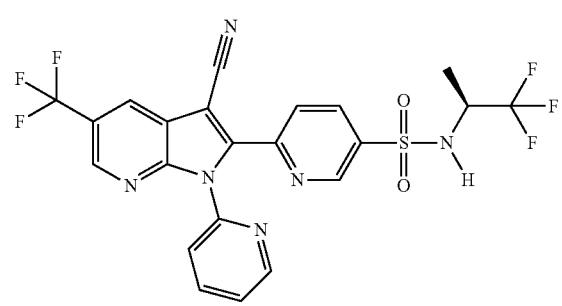

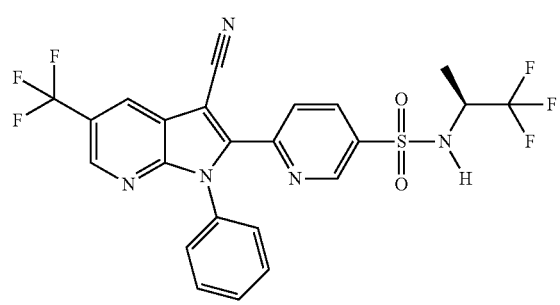
318
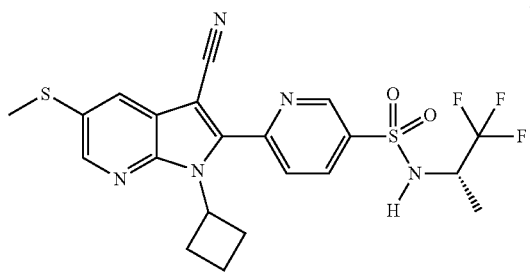
323
319
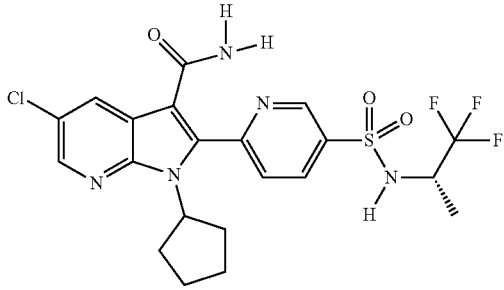
324
320
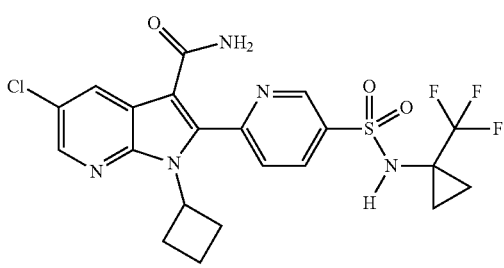
325
321
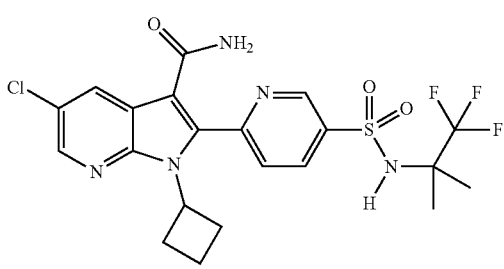
326
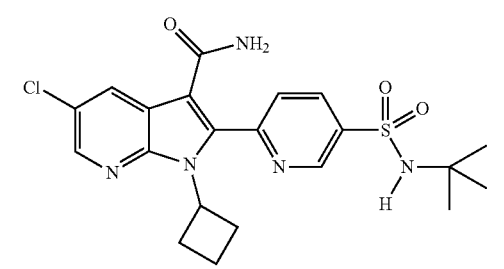
327
322
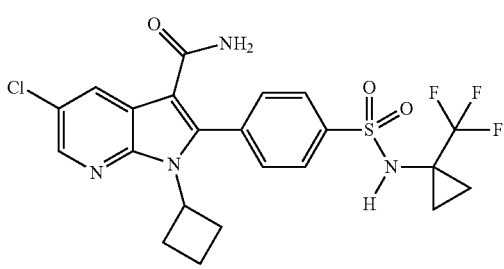
328

75
-continued
329
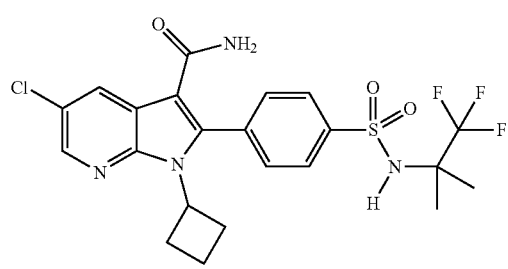
330
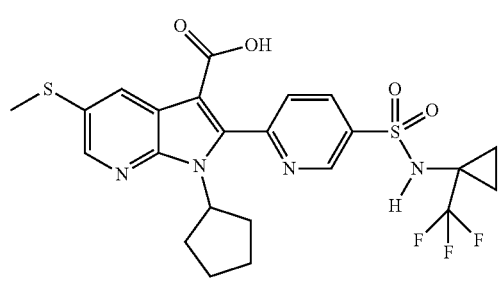
331
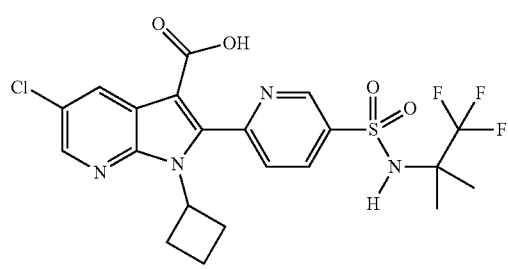
332
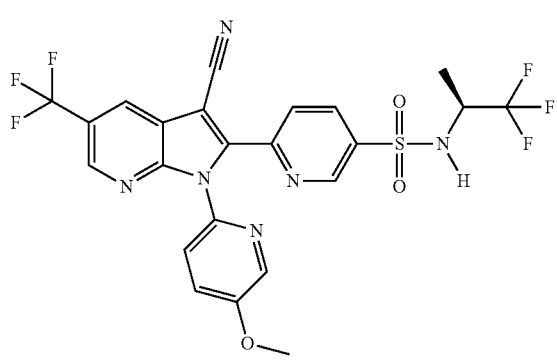
333
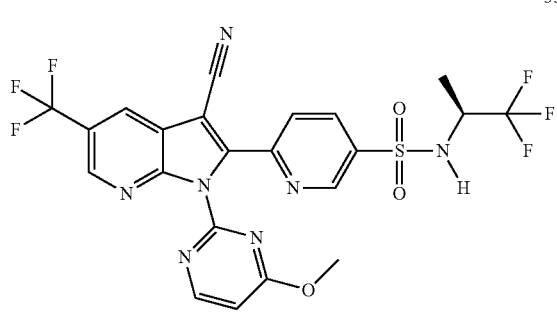
76
-continued
334
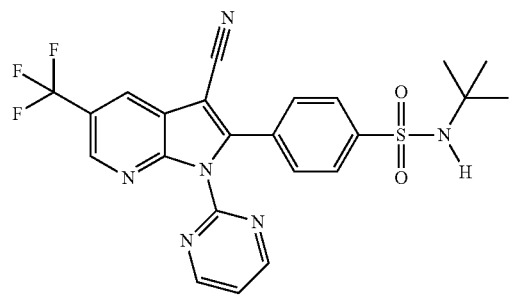
335
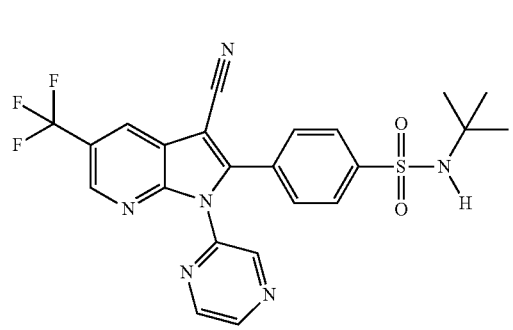
336
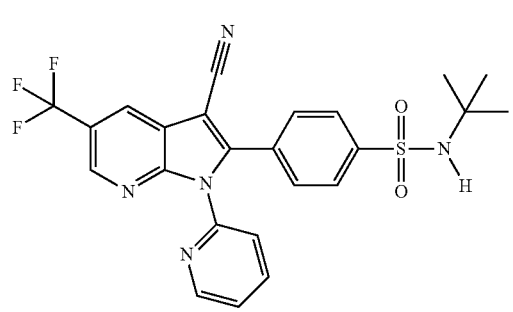
337
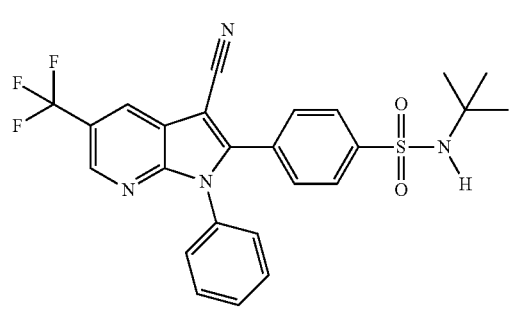
338
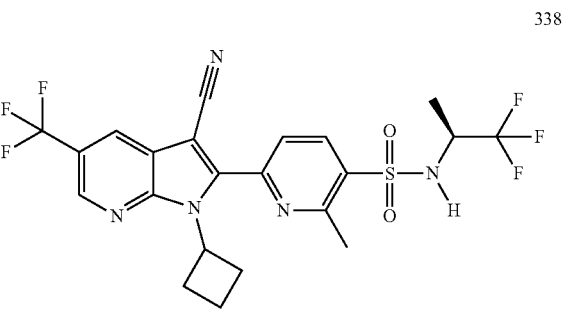

339
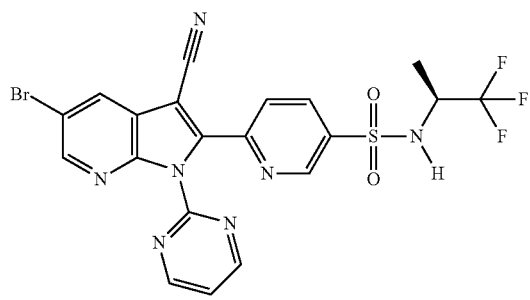
340
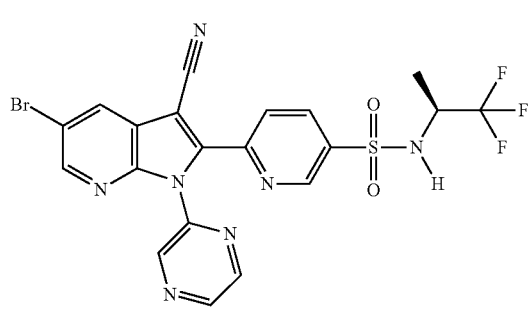
341
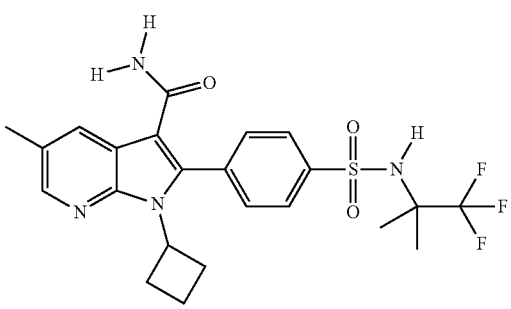
342
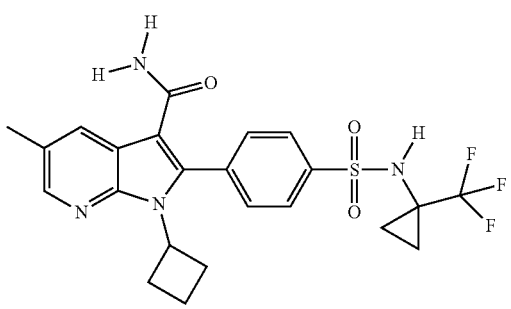
343
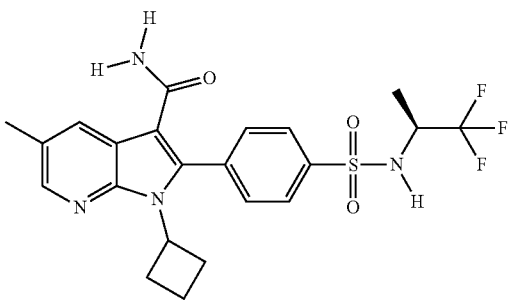
344
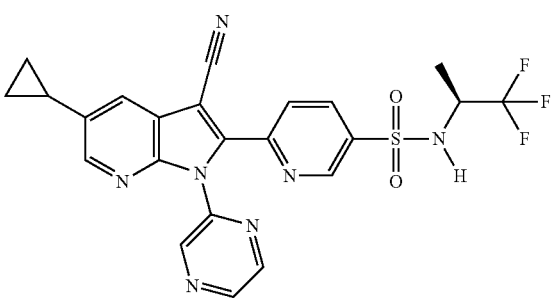
345
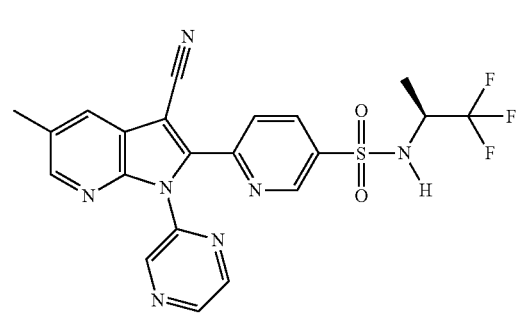
346
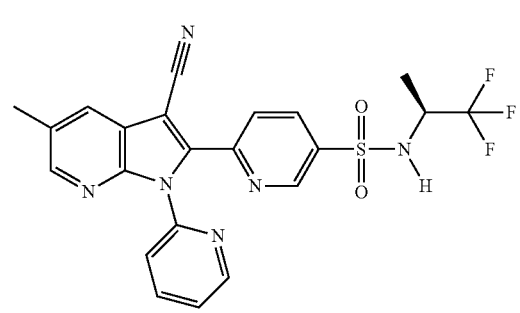
347
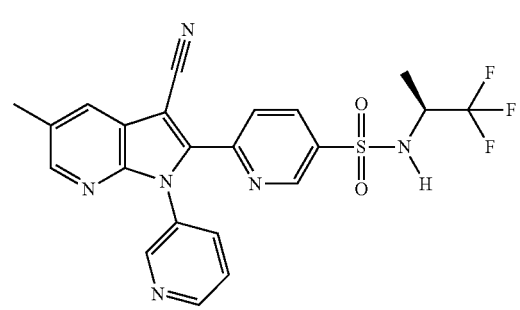
348
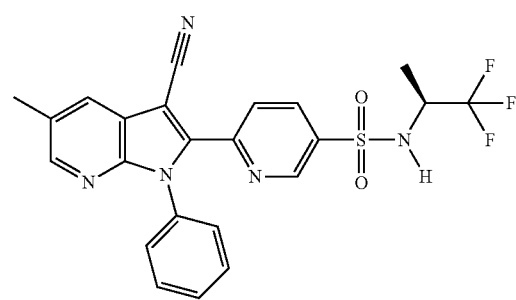

349
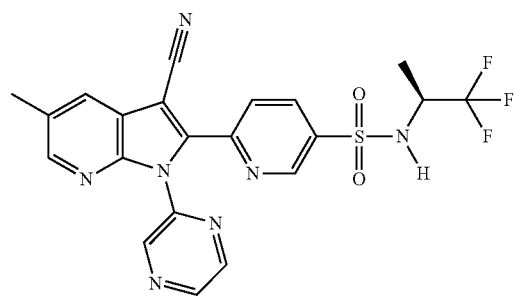
350
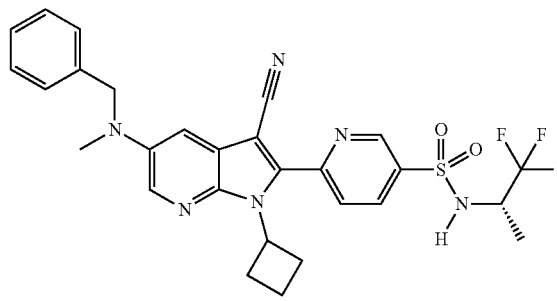
351
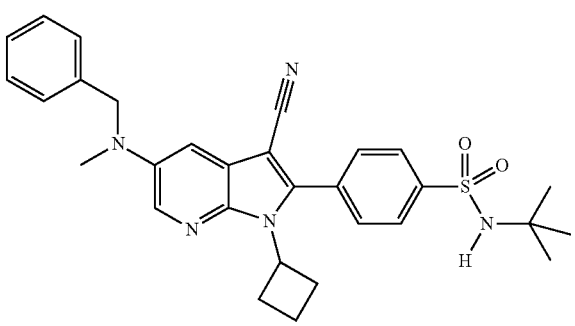
352
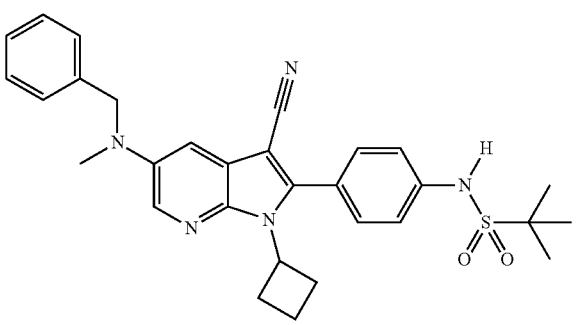
353
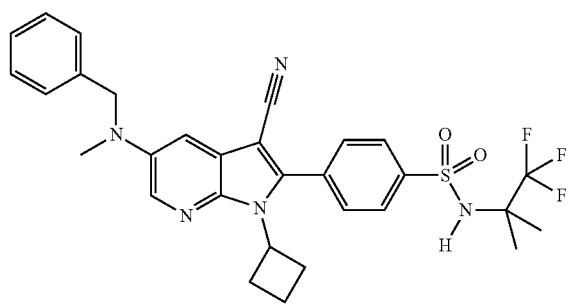
354
355
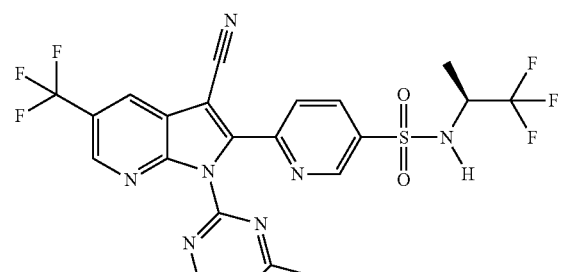
356
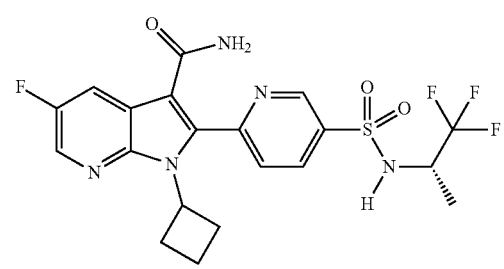
357
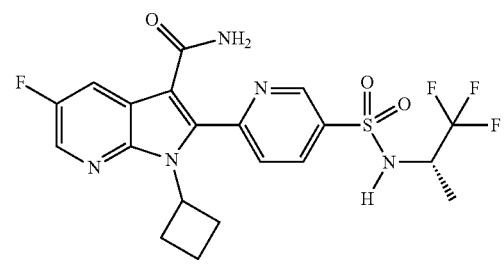
358
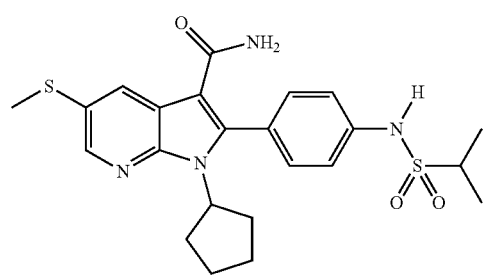

359
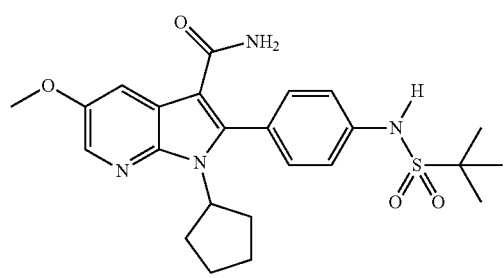
360
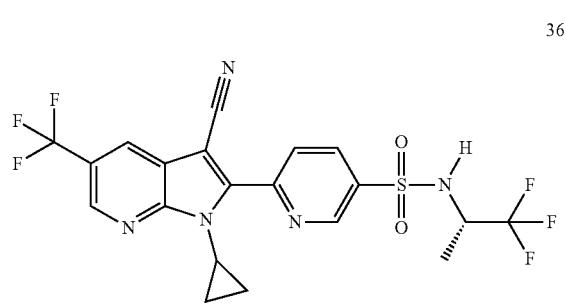
361
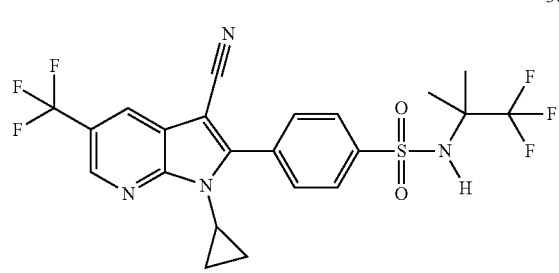
362
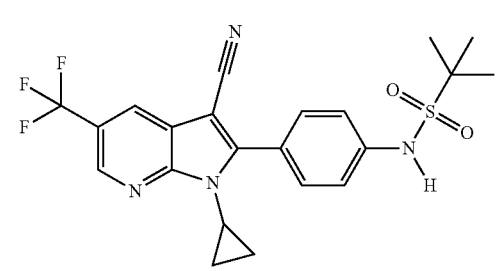
363
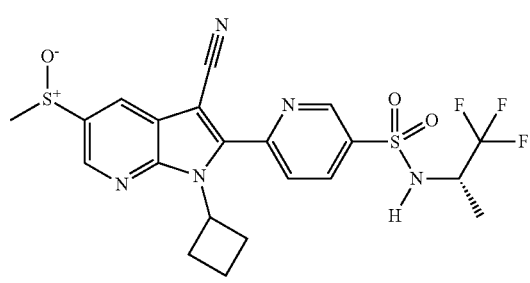
364
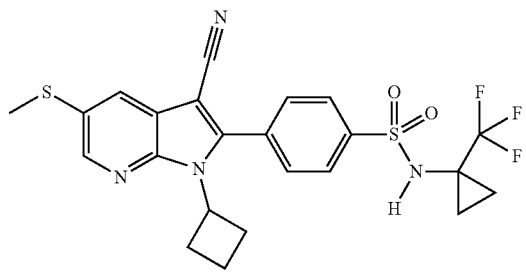
365
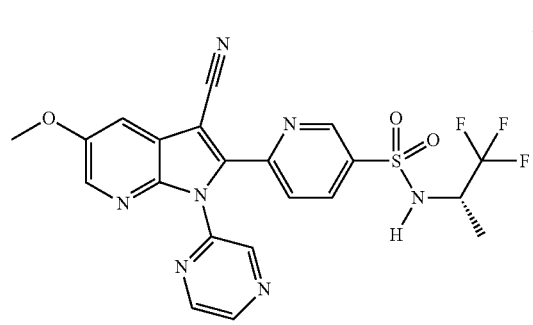
366
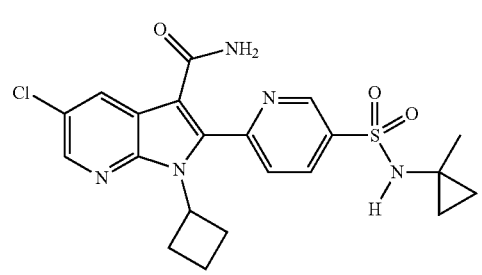
367
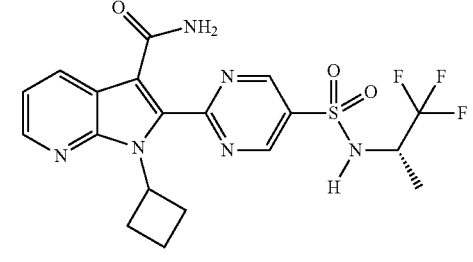
368
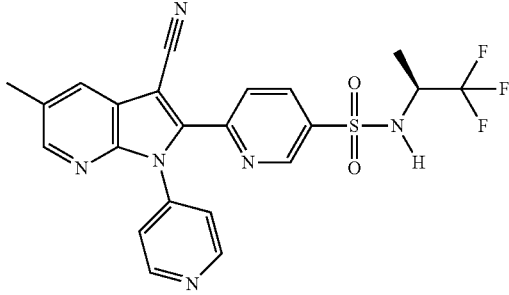

369
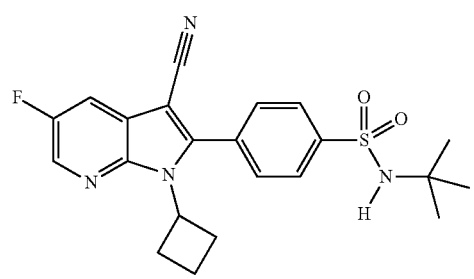
370
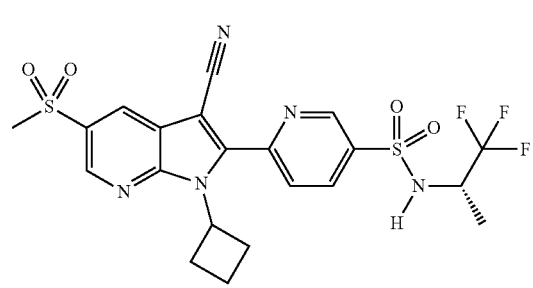
371
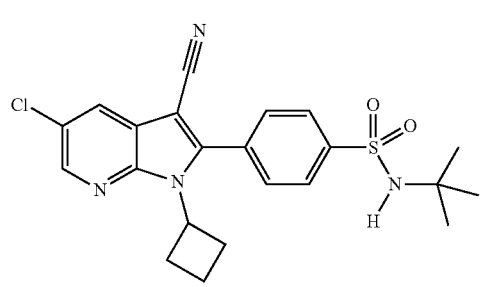
372
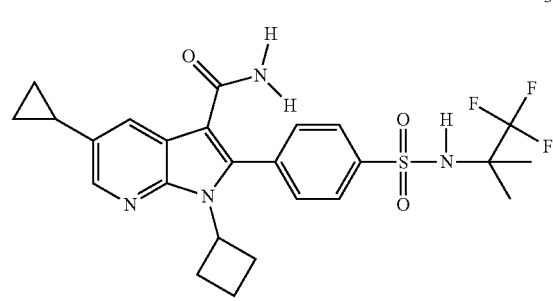
373
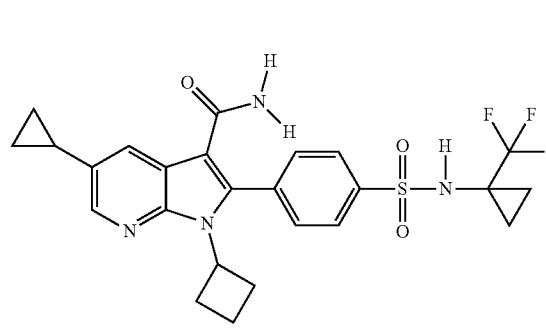
374
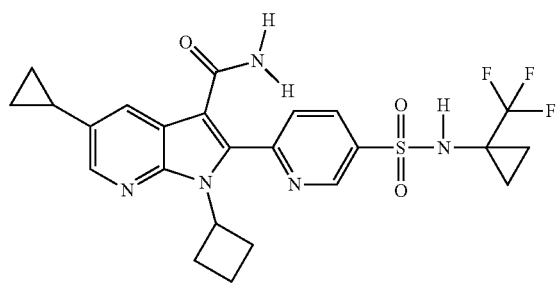
375
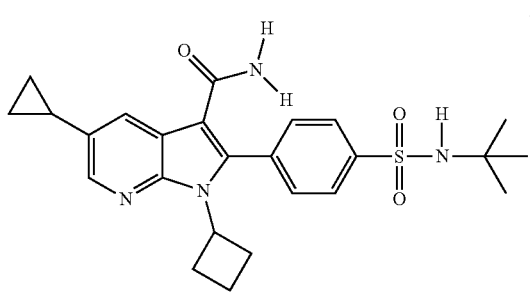
376
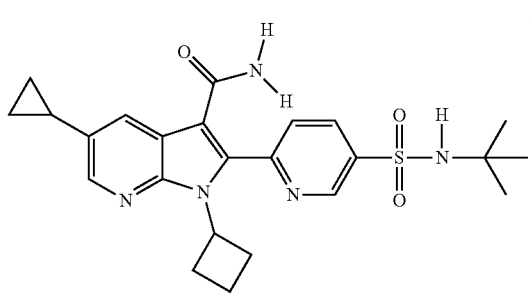
377
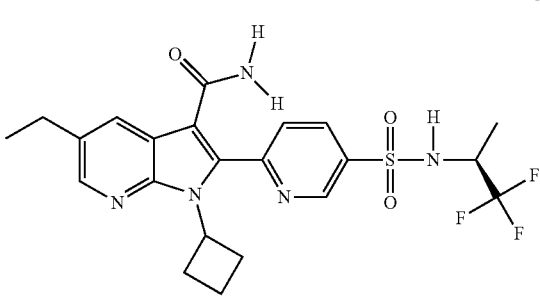
378
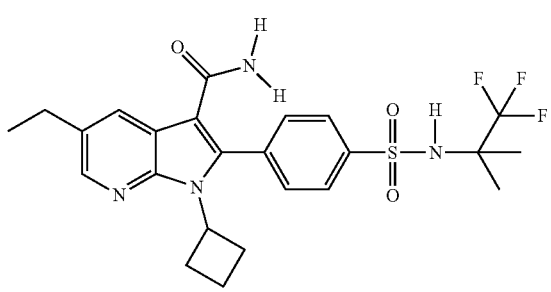

-continued
379
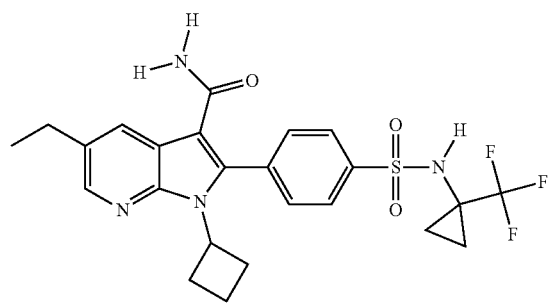
380
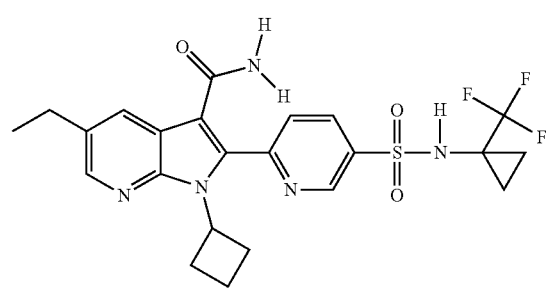
381
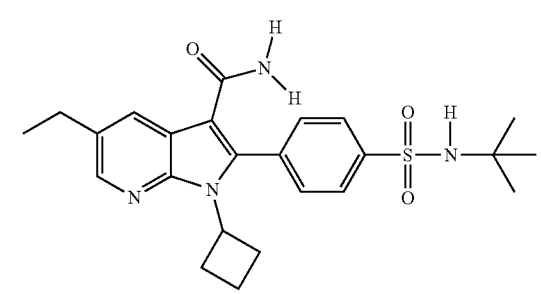
382
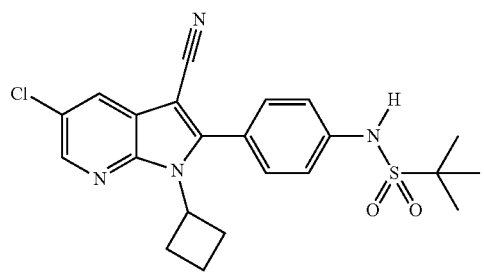
383
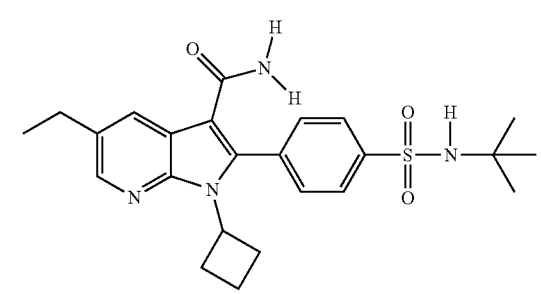
-continued
384
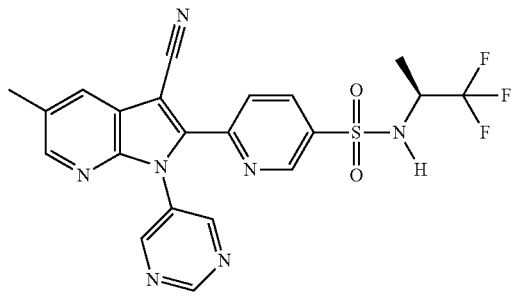
385
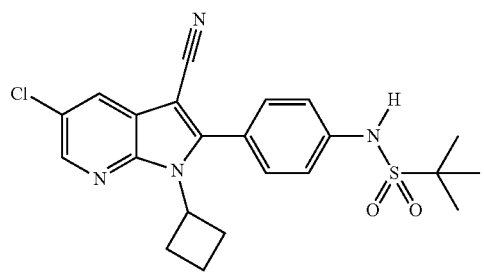
386
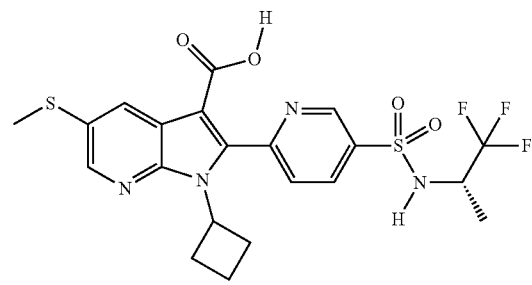
387
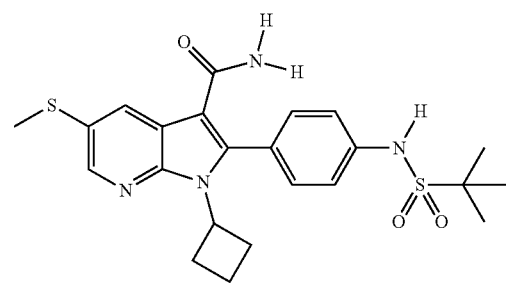
388
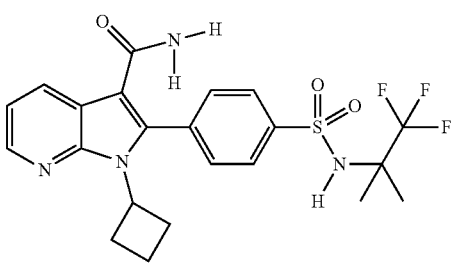

389
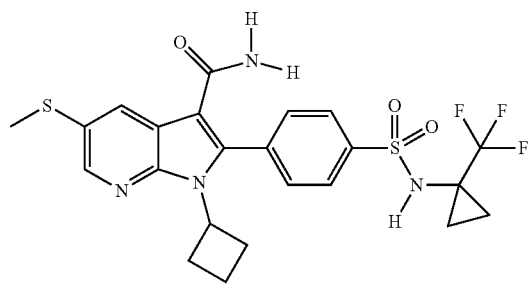
390
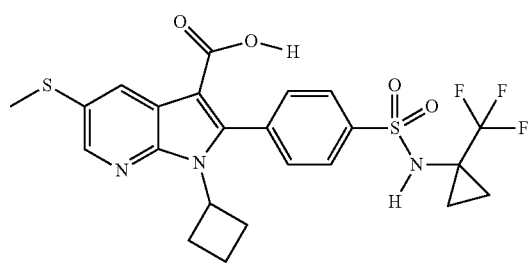
391
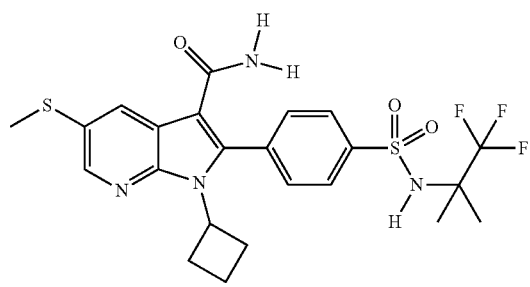
392
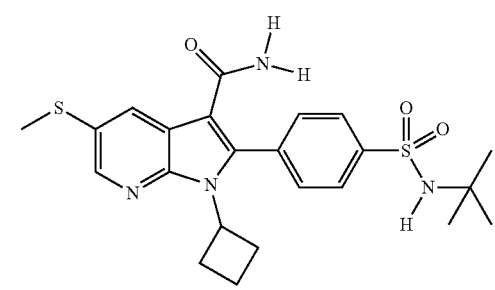
393
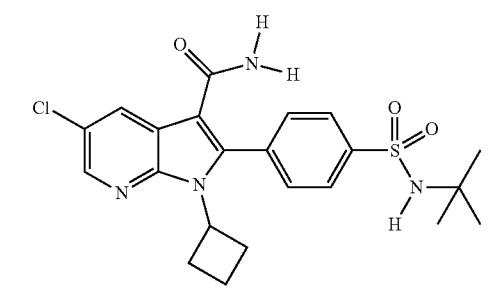
394
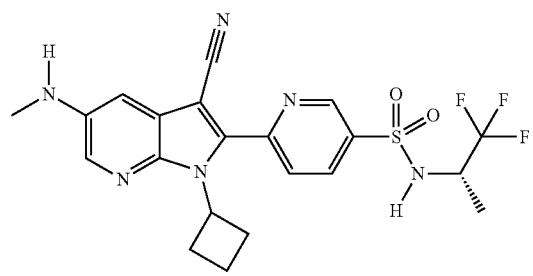
395
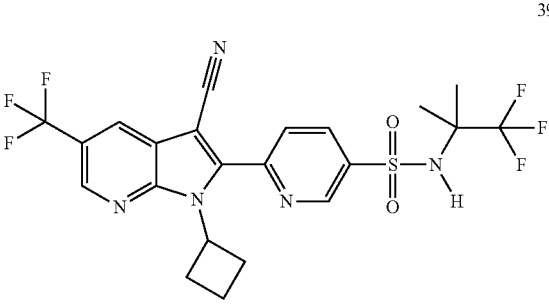
396
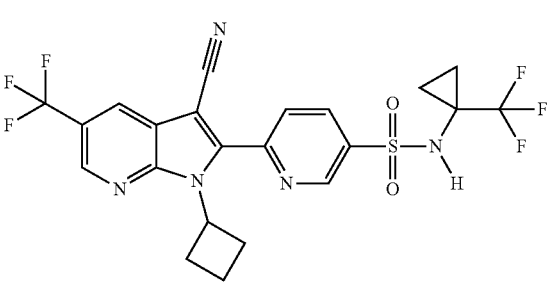
397
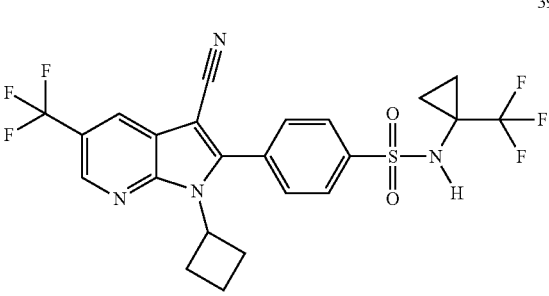
398
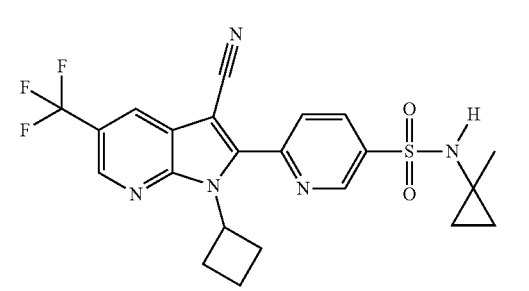

-continued

409
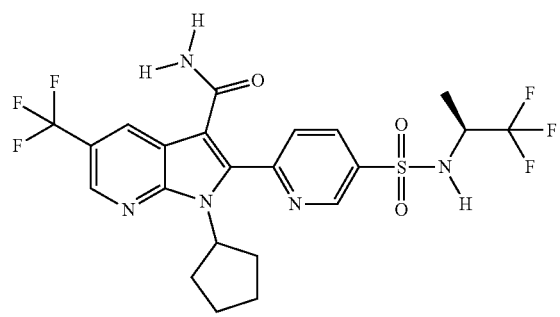
410
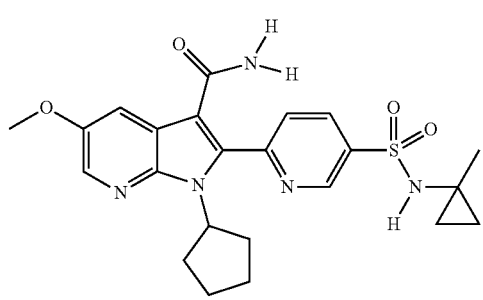
411
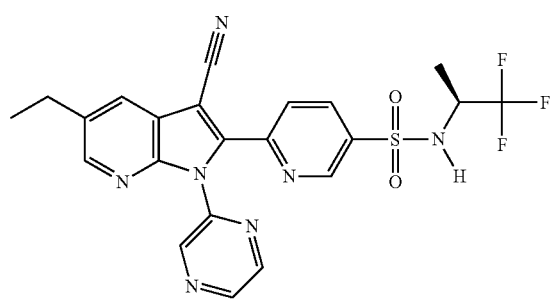
412
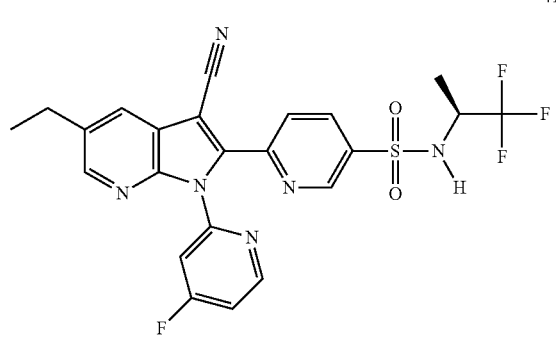
413
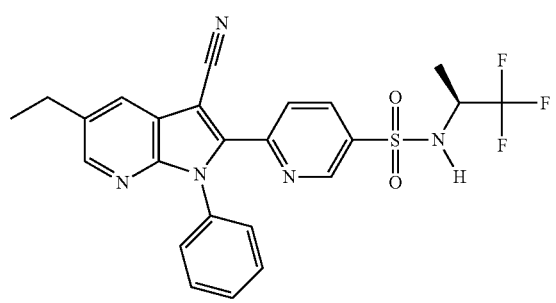
414
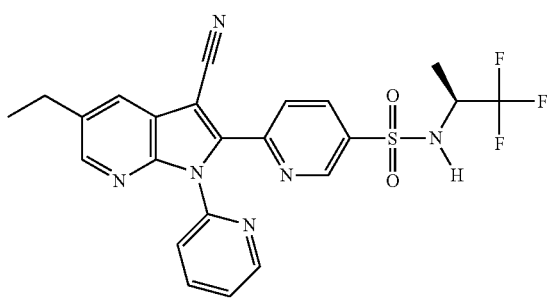
415
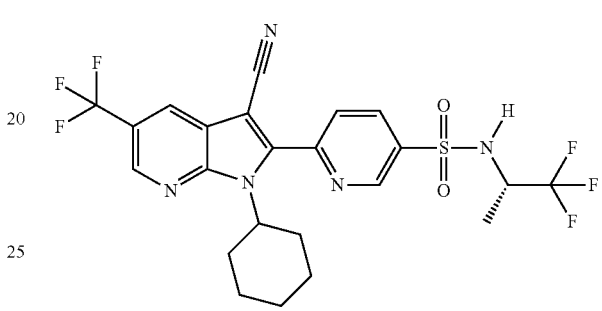
416
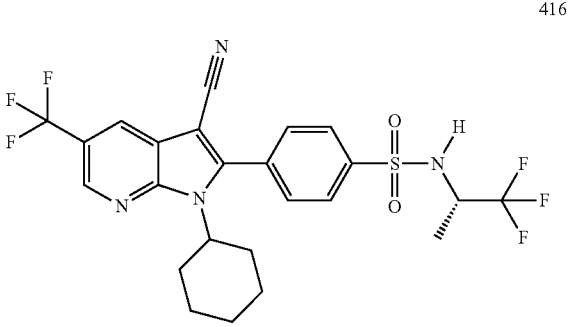
417
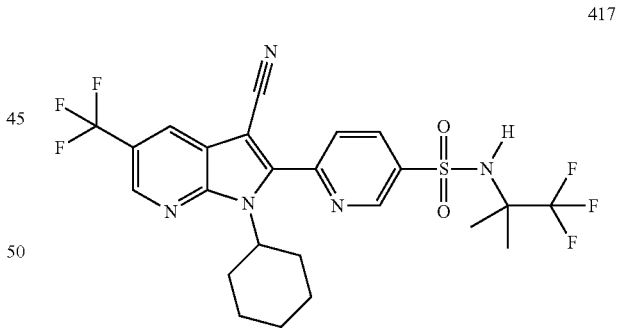
418
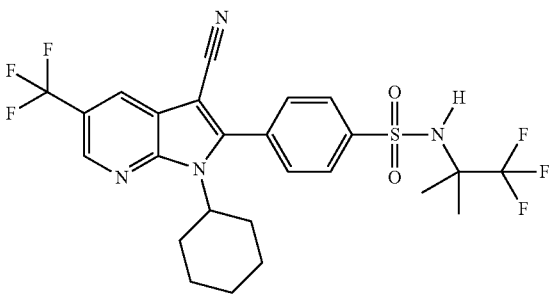

419 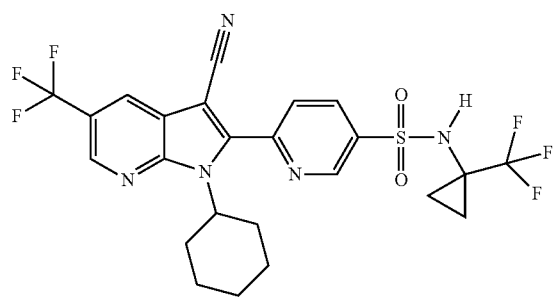
420 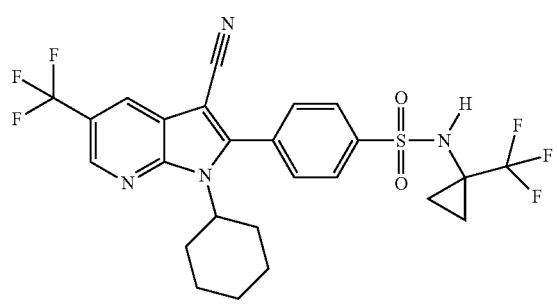
421 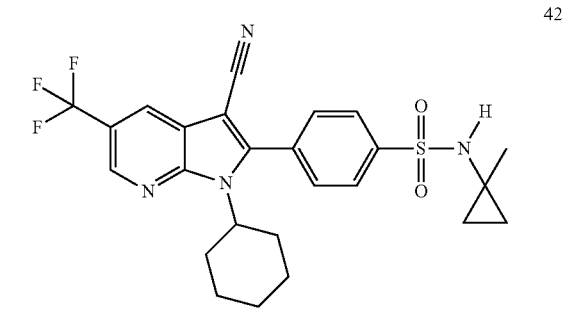
422 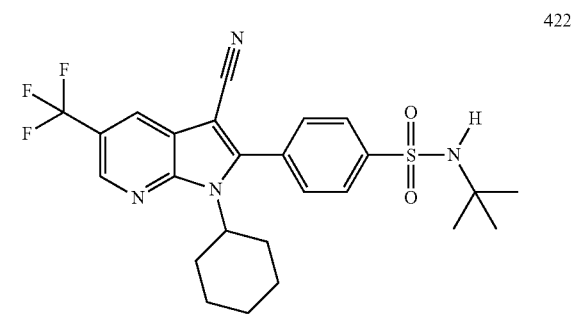
423 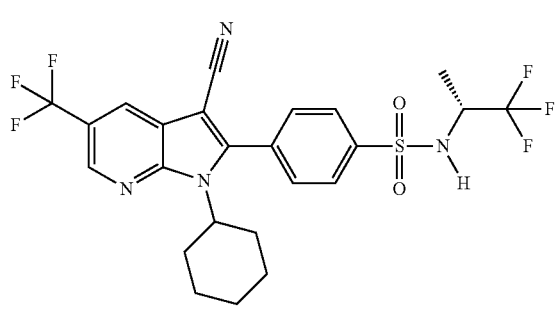
424 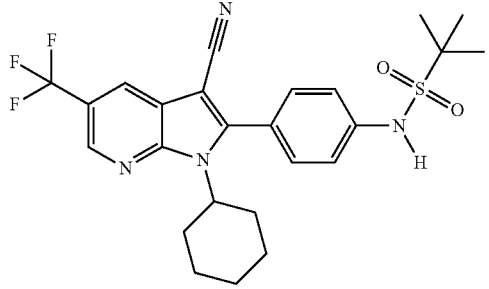
425 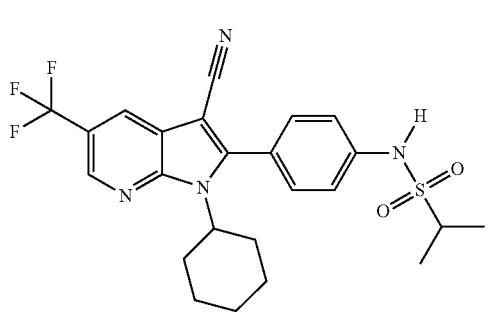
426 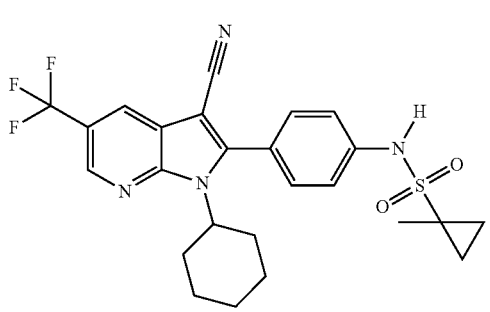
427 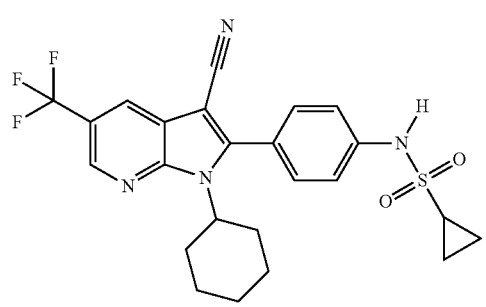
428 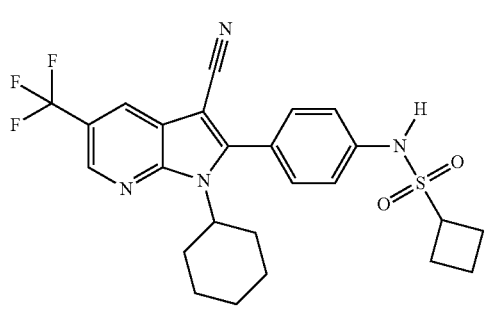

95
-continued
429
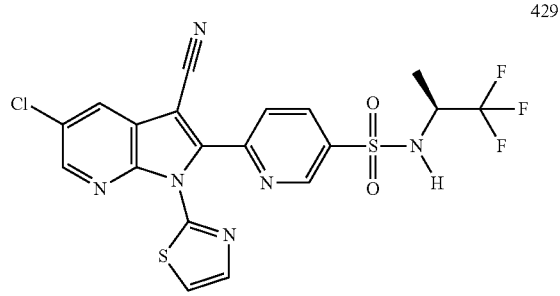
430
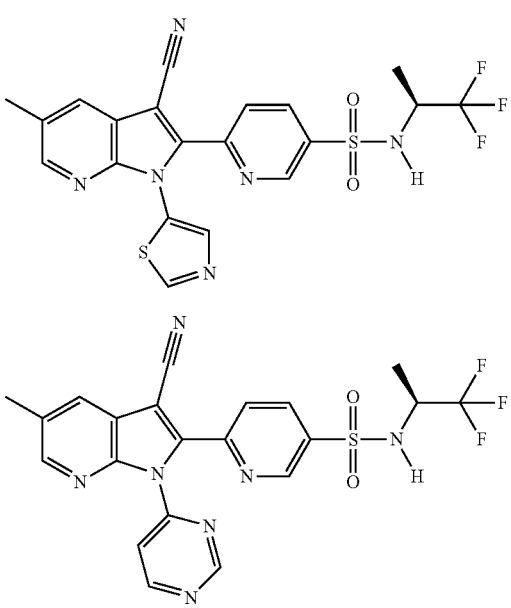
431
432
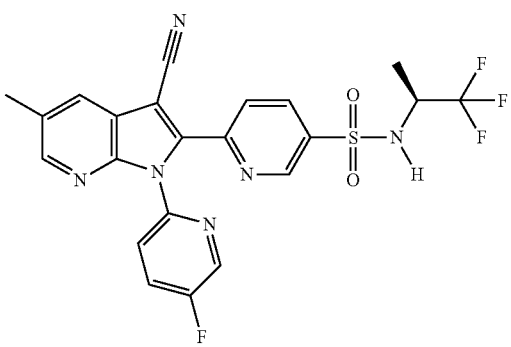
433
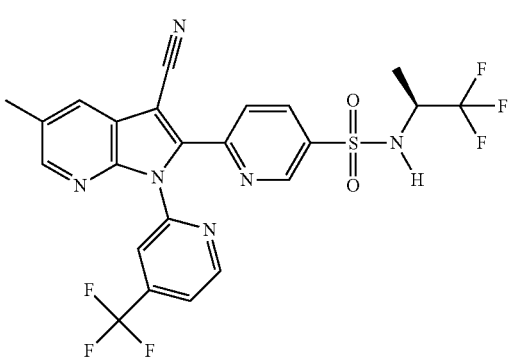
96
-continued
434
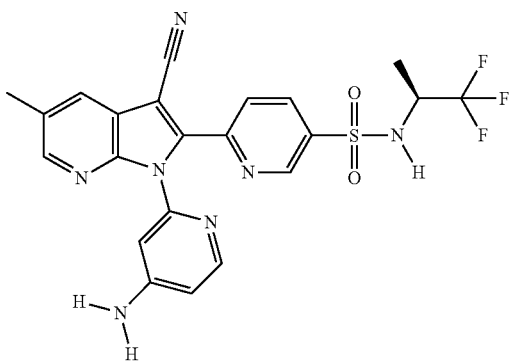
435
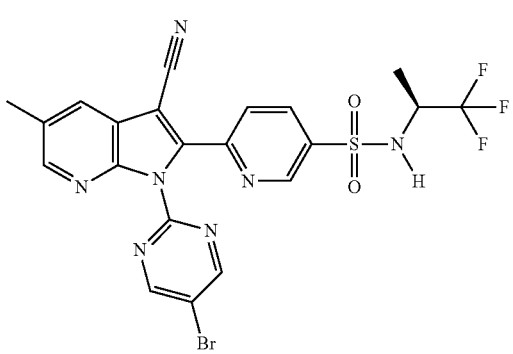
436
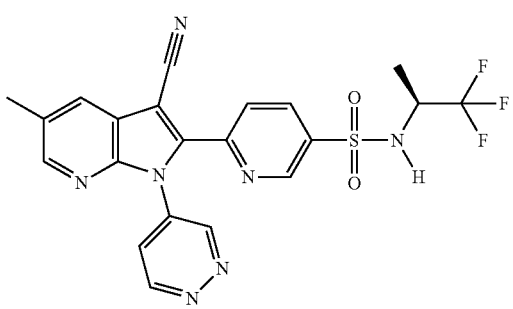
437
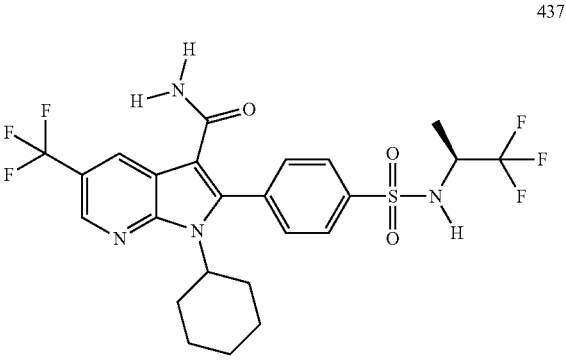

97
-continued
438
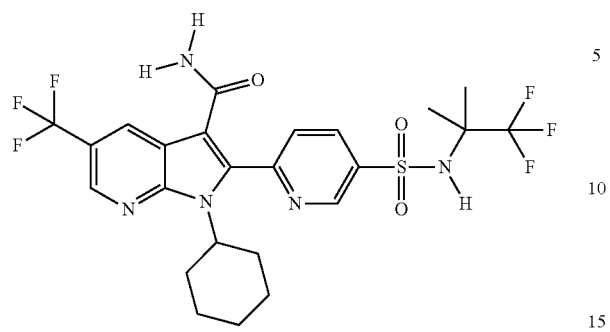
439
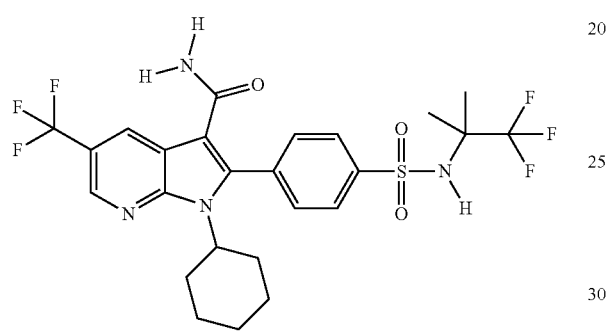
440
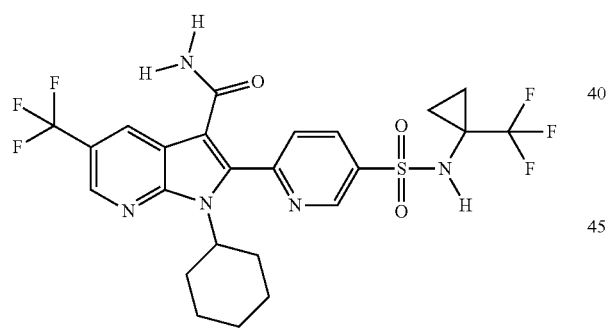
441
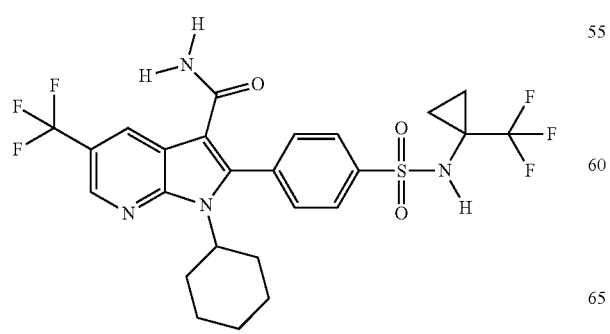
98
-continued
442
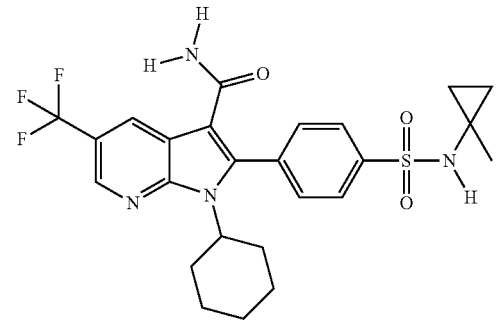
443
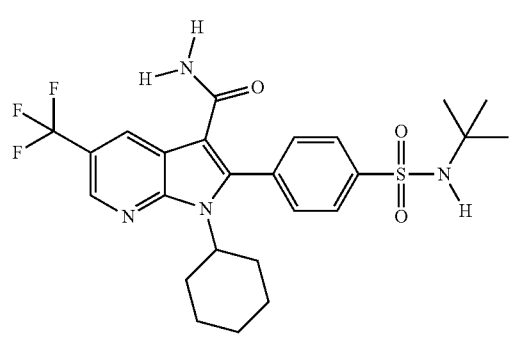
444
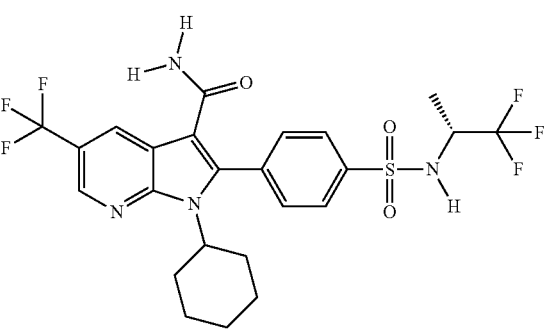
445
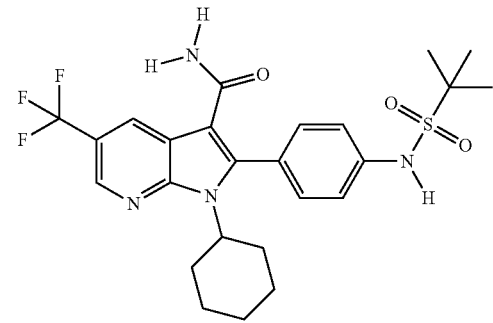

446 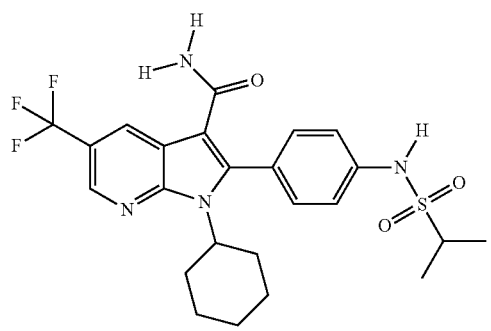
447 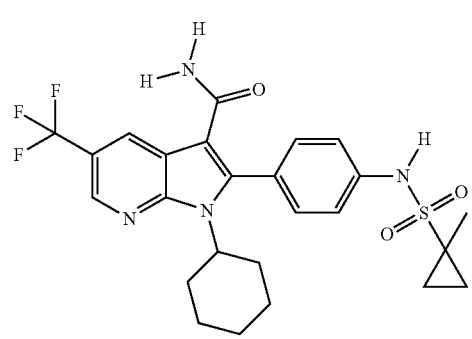
448 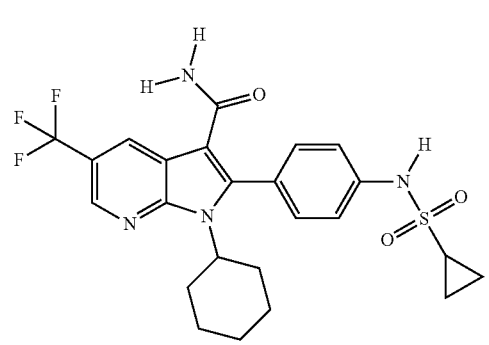
449 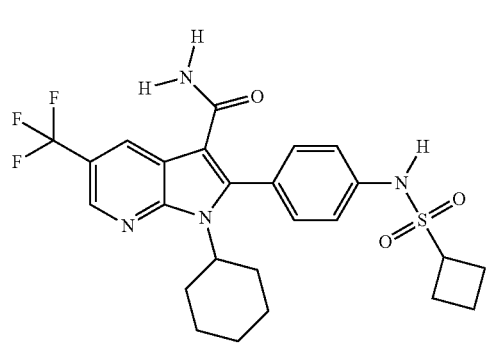
450 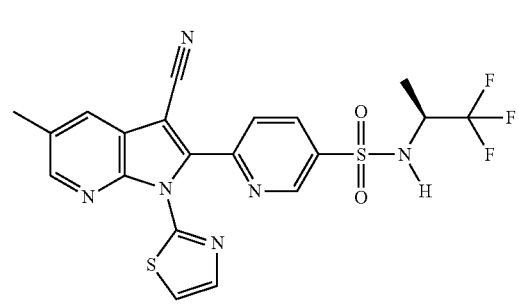
451 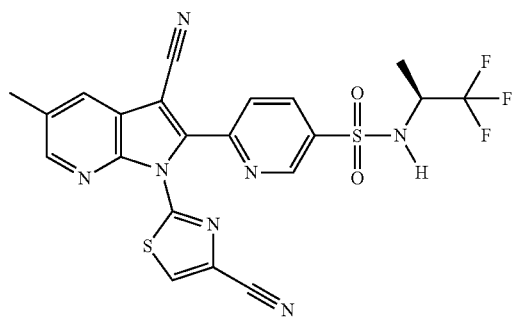
452 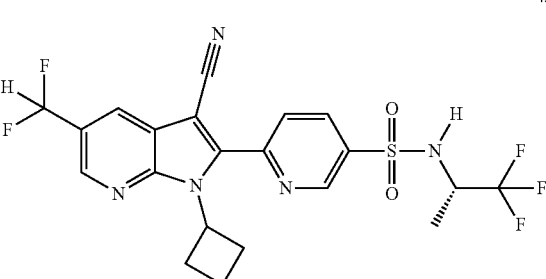
453 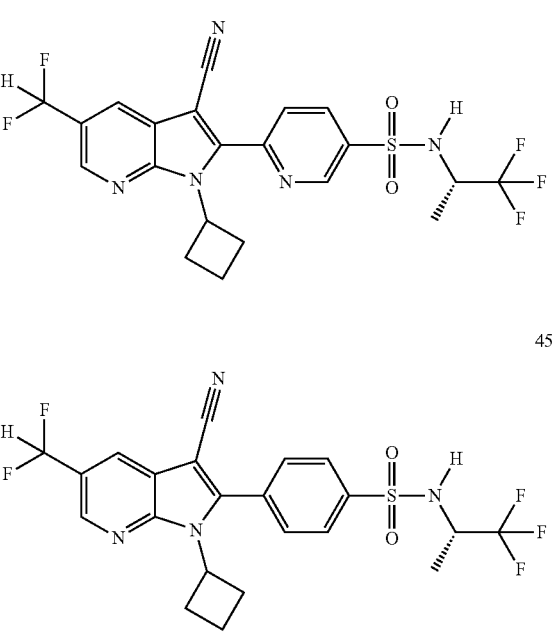
454 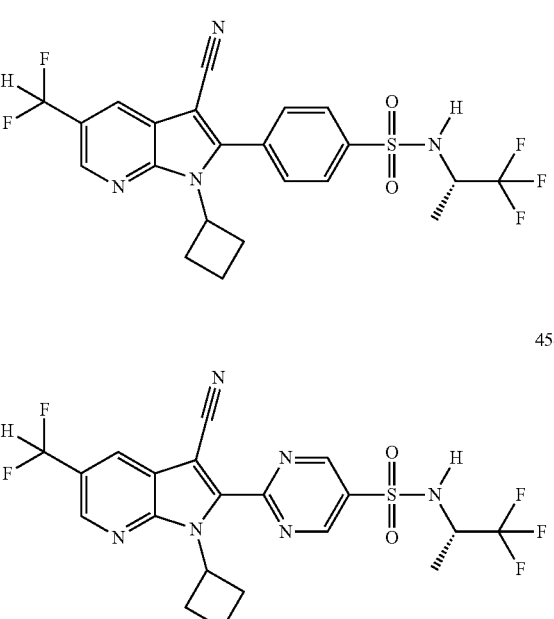
455 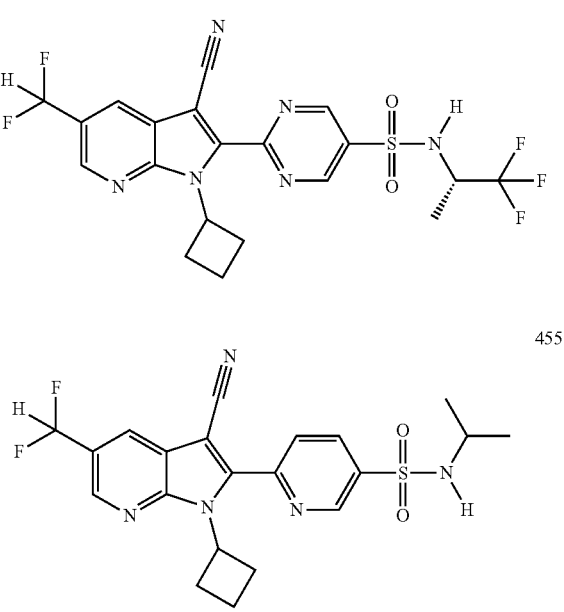

| 456 | 461 |
| 457 | 462 |
| 458 | 463 |
| 459 | 464 |
| 460 | 465 |

466 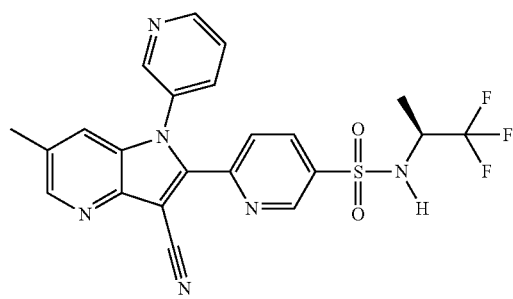
467 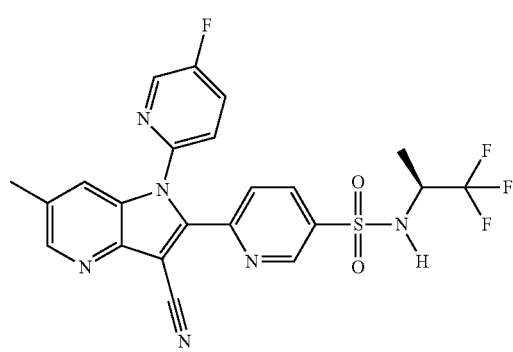
468 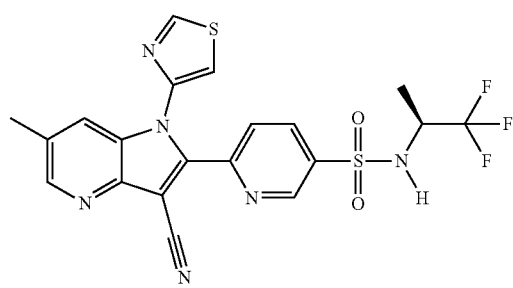
469 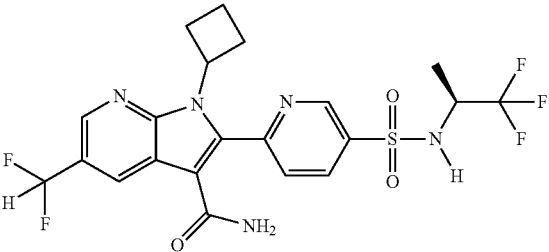
470 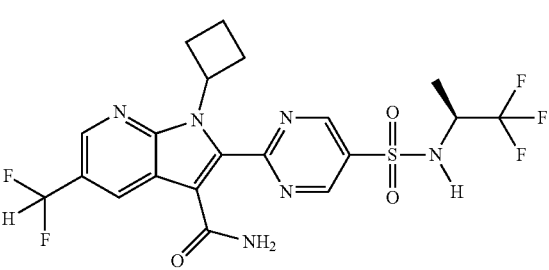
471 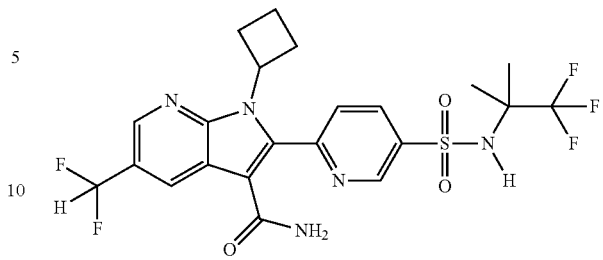
472 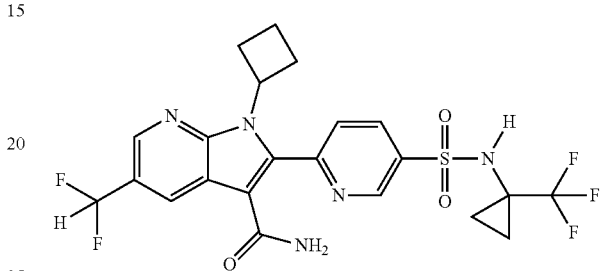
473 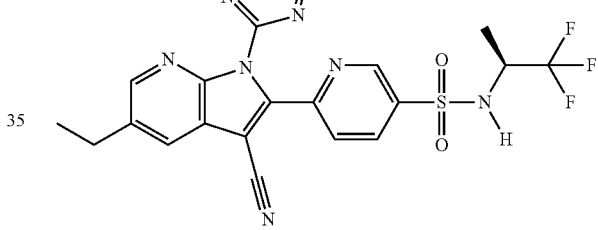
474 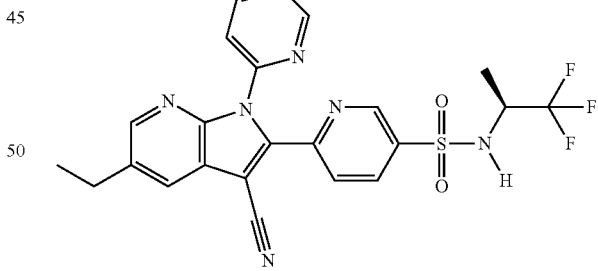
475 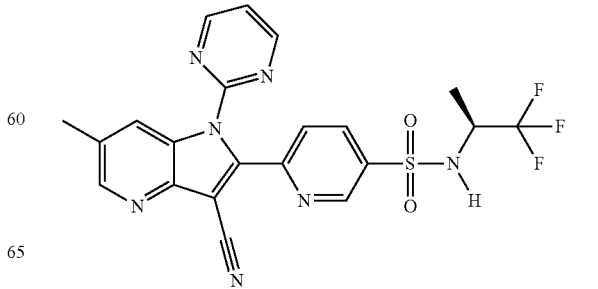

476
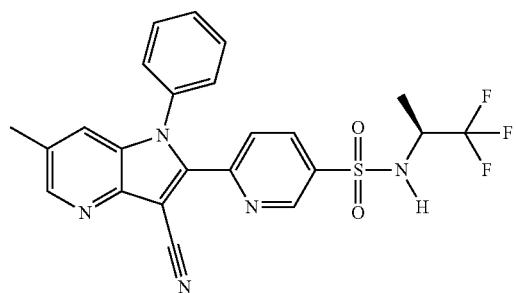
477
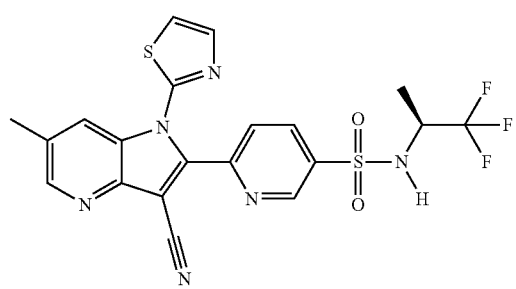
478
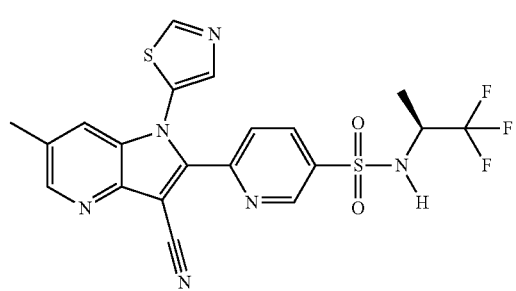
479
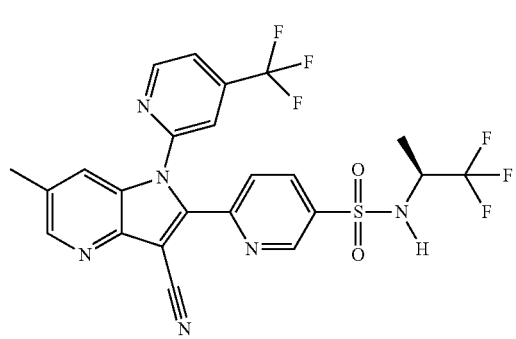
480
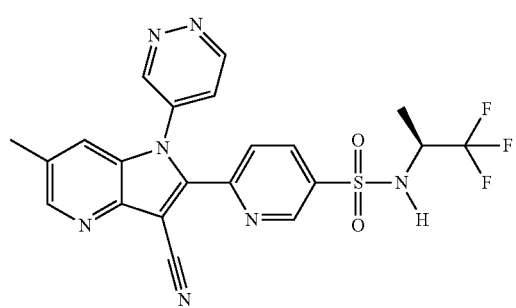
481
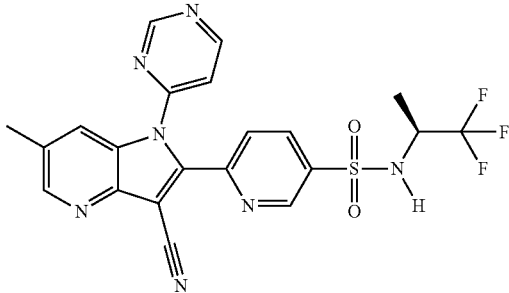
482
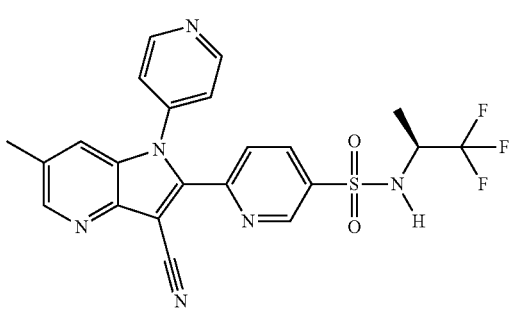
483
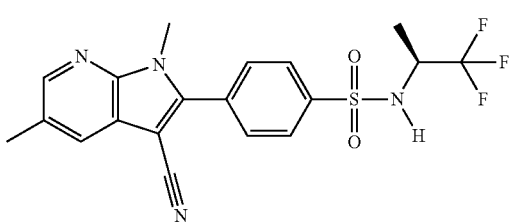
484
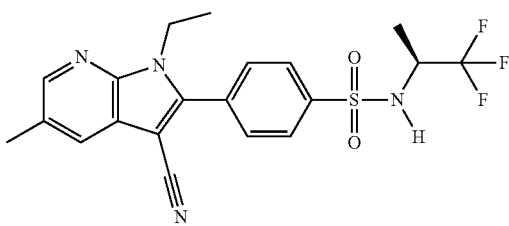
485
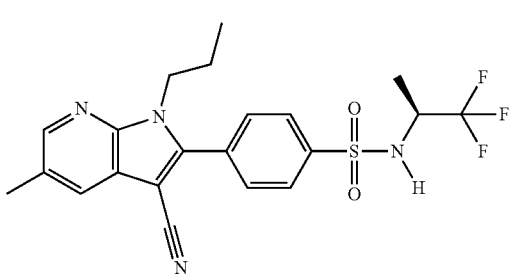
486
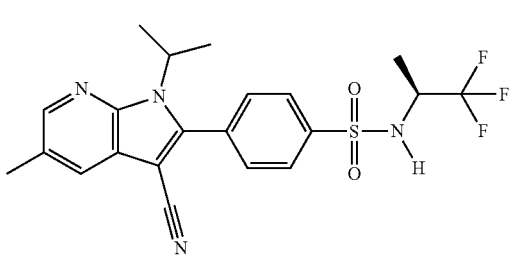

107
-continued
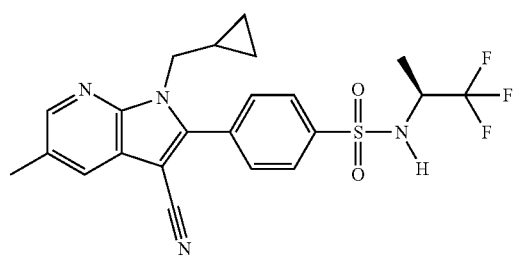
487
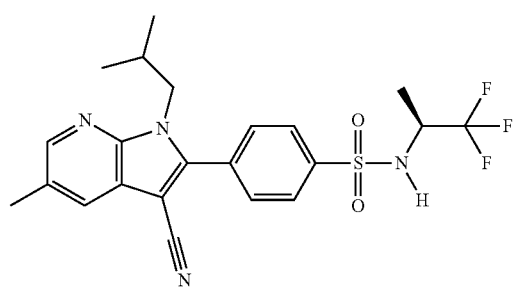
488
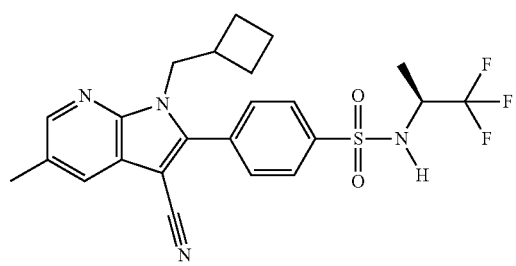
489
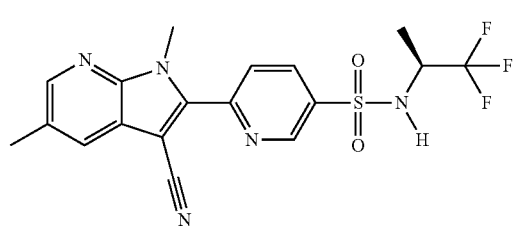
490
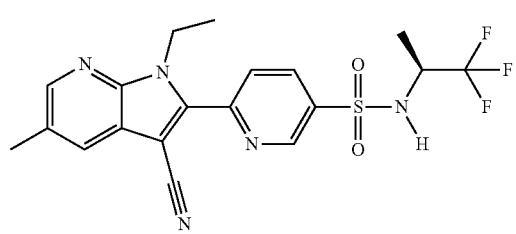
491
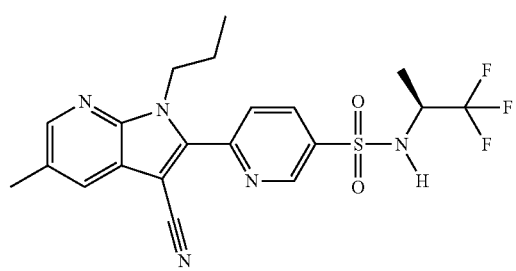
492
108
-continued
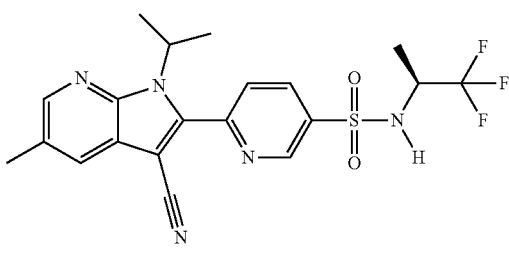
493
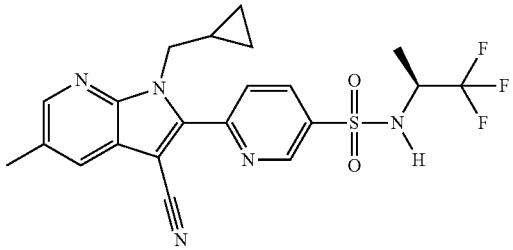
494
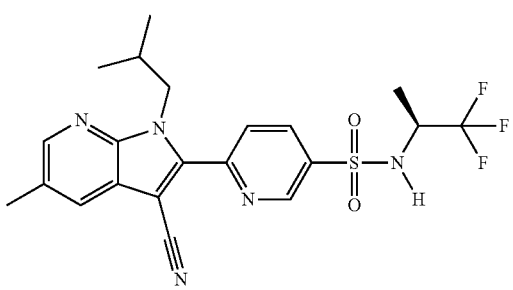
495
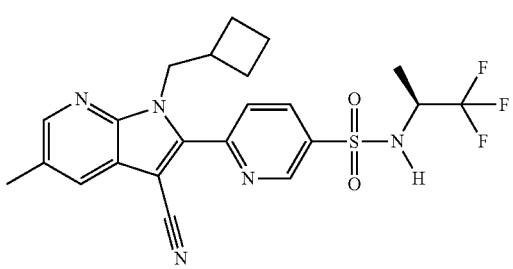
496
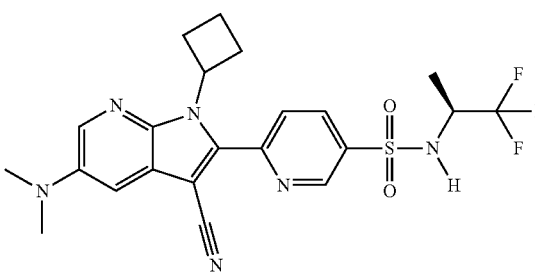
497
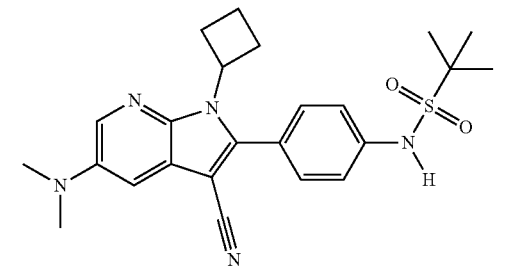
498

499 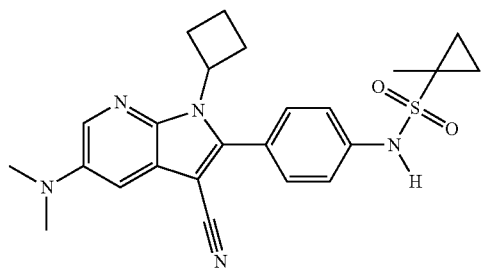
500 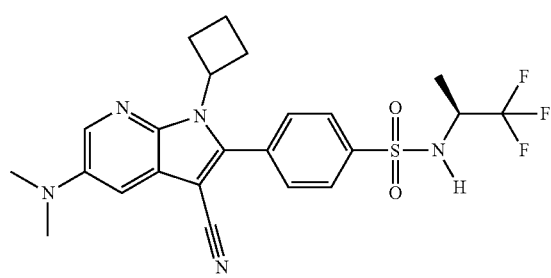
501 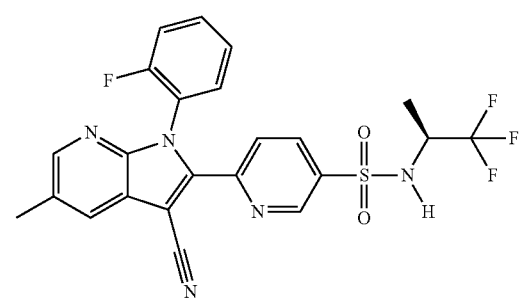
502 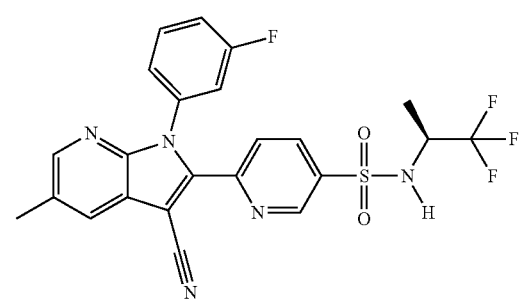
503 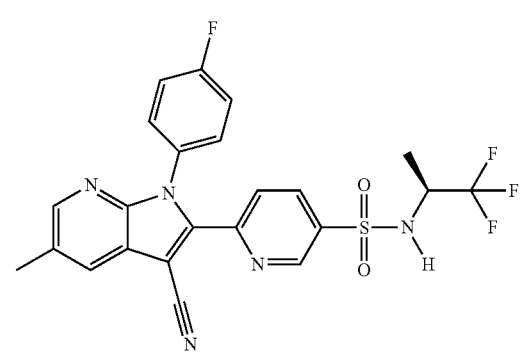
504 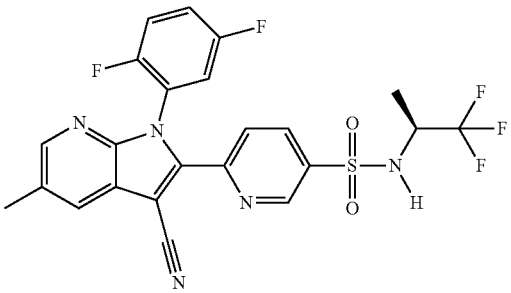
505 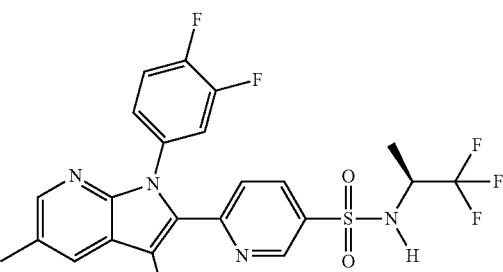
506 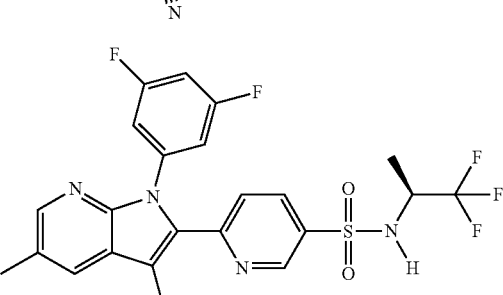
507 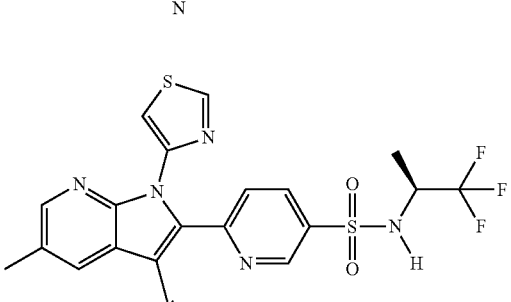
508 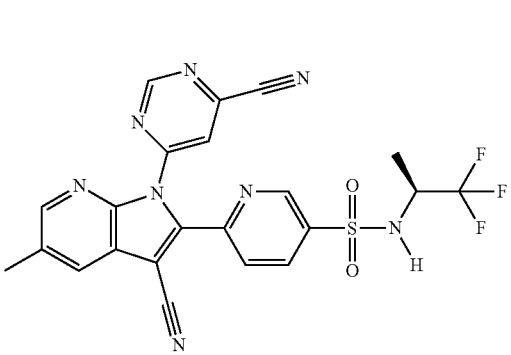

509
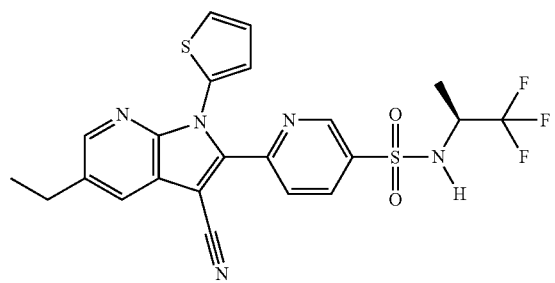
514
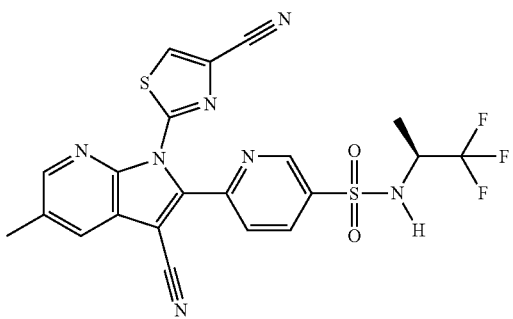
510
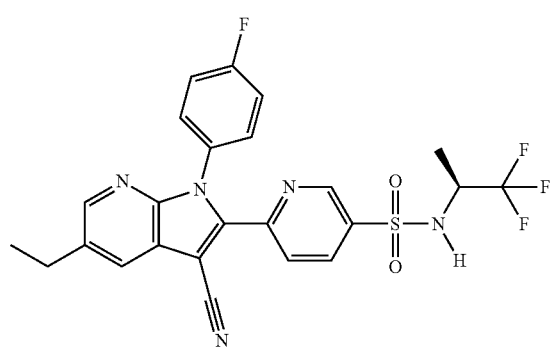
515
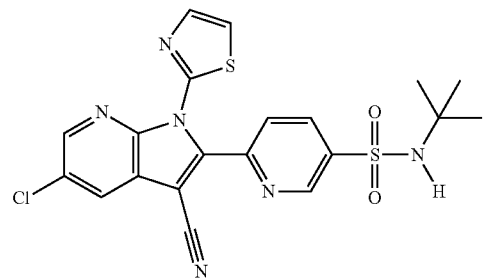
511
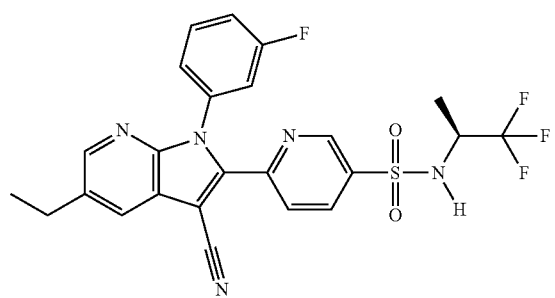
516
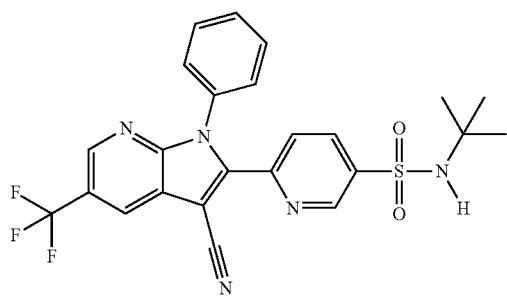
512
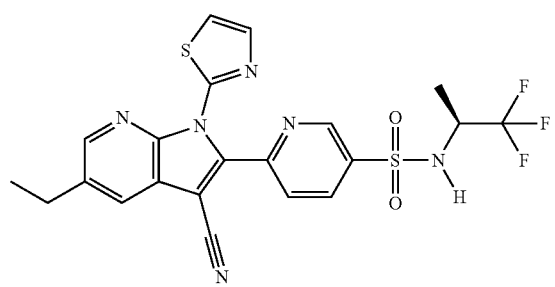
517
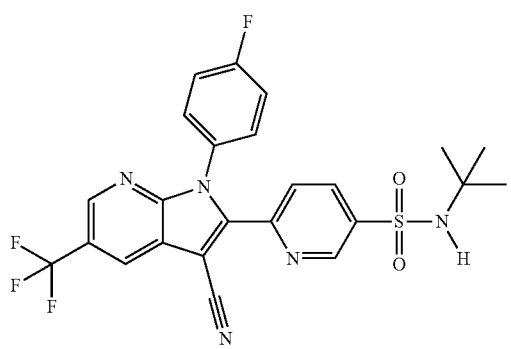
513
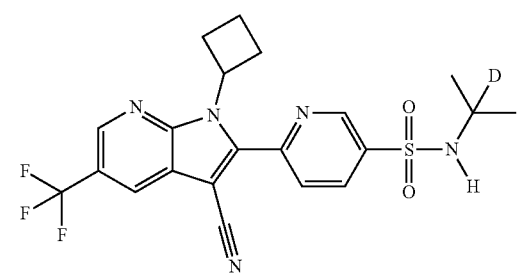
518
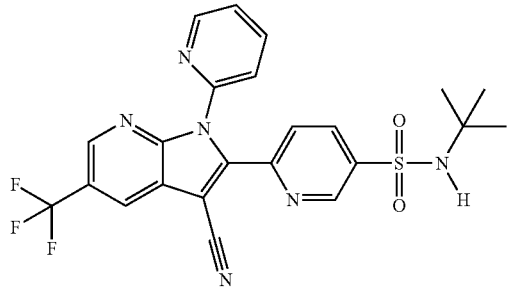

519

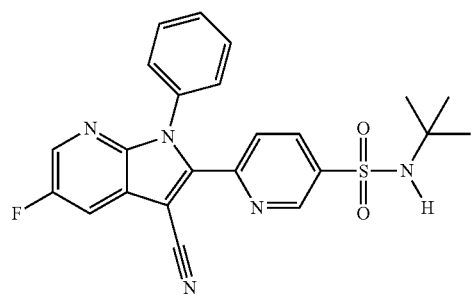

520

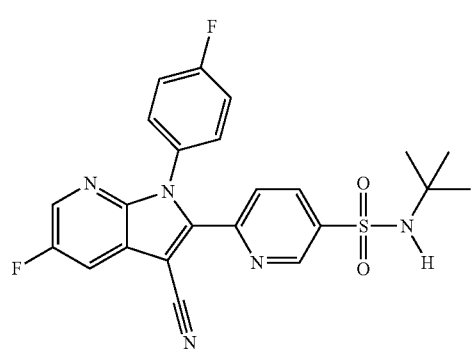

521

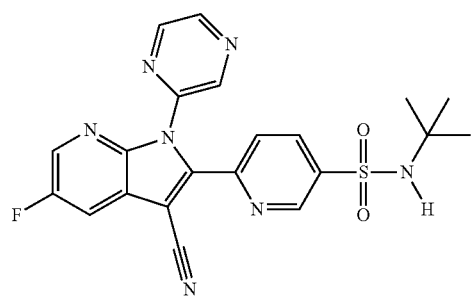

522

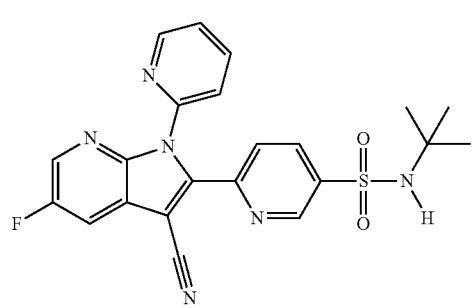

523

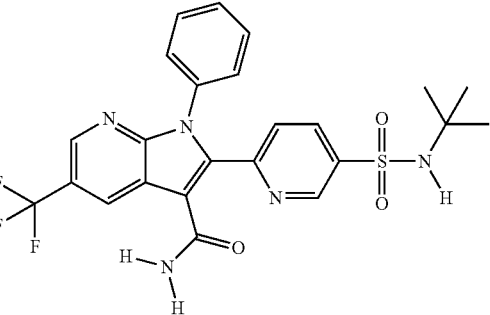

524

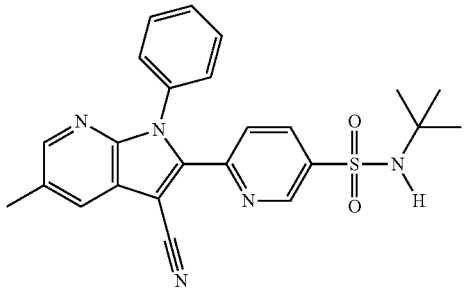

525

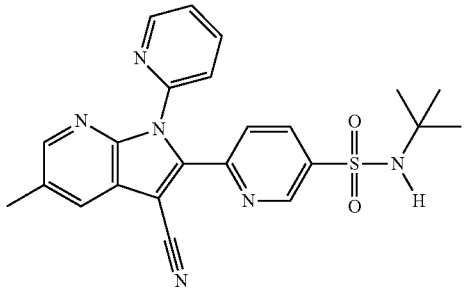

526

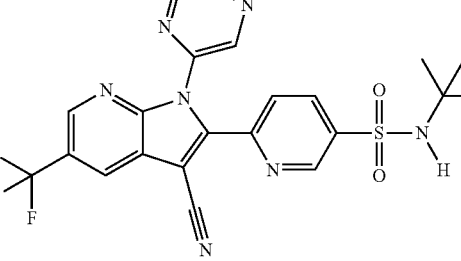

527

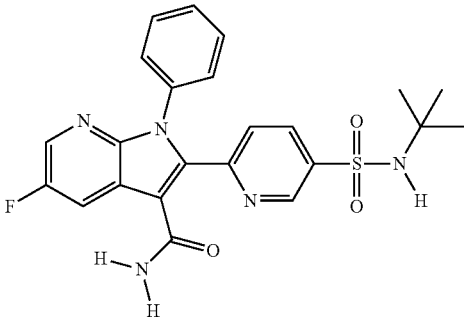

In another embodiment of the present invention, a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a free acid, free base, salt, hydrate, solvate, clathrate, isotopologue, racemate, enantiomer, diastereomer, stereoisomer or polymorph form thereof is selected from:

| Cpd | Name |
|---|---|
| 1 | 4-[5-chloro-3-cyano-1-(cyclopropylmethyl)-1H-pyrrolo[2,3-b]pyridin-2-yl]-N-(propan-2-yl)benzenesulfonamide, |
| 2 | 4-[3-cyano-1-(cyclopropylmethyl)-5-methoxy-1H-pyrrolo[2,3-b]pyridin-2-yl]-N-(propan-2-yl)benzenesulfonamide, |

| Cpd | Name |
|---|---|
| 3 | N-{4-[3-cyano-1-(cyclopropylmethyl)-5-methoxy-1H-pyrrolo[3,2-b]pyridin-2-yl]phenyl}propane-2-sulfonamide, |
| 4 | 4-[3-cyano-1-(cyclopropylmethyl)-5-fluoro-1H-pyrrolo[2,3-b]pyridin-2-yl]-N-(propan-2-yl)benzenesulfonamide, |
| 5 | 4-[3-cyano-1-(cyclopropylmethyl)-6-methyl-1H-pyrrolo[2,3-b]pyridin-2-yl]-N-(propan-2-yl)benzenesulfonamide, |
| 6 | 4-(5-chloro-3-cyano-1-cyclobutyl-1H-pyrrolo[2,3-b]pyridin-2-yl)-N-(propan-2-yl)benzenesulfonamide, |
| 7 | 4-(3-cyano-1-cyclobutyl-1H-pyrrolo[2,3-b]pyridin-2-yl)-N-(propan-2-yl)benzenesulfonamide, |
| 8 | 4-(5-chloro-3-cyano-1-cyclobutyl-1H-pyrrolo[2,3-b]pyridin-2-yl)-N-(1,3-difluoropropan-2-yl)benzenesulfonamide, |
| 9 | 6-(3-cyano-1-cyclobutyl-5-methoxy-1H-pyrrolo[2,3-b]pyridin-2-yl)-N-(1,3-difluoropropan-2-yl)pyridine-3-sulfonamide, |
| 10 | 6-(5-chloro-3-cyano-1-cyclopentyl-1H-pyrrolo[2,3-b]pyridin-2-yl)-N-(1,3-difluoropropan-2-yl)pyridine-3-sulfonamide, |
| 11 | 2-(3-cyano-1-cyclobutyl-5-methoxy-1H-pyrrolo[2,3-b]pyridin-2-yl)-N-(1,3-difluoropropan-2-yl)pyrimidine-5-sulfonamide, |
| 12 | 6-(3-cyano-1-cyclobutyl-5-fluoro-1H-pyrrolo[2,3-b]pyridin-2-yl)-N-(1,3-difluoropropan-2-yl)pyridine-3-sulfonamide, |
| 13 | 2-(5-chloro-3-cyano-1-cyclobutyl-1H-pyrrolo[2,3-b]pyridin-2-yl)-N-(1,3-difluoropropan-2-yl)pyrimidine-5-sulfonamide, |
| 14 | 6-(5-chloro-3-cyano-1-cyclobutyl-1H-pyrrolo[2,3-b]pyridin-2-yl)-N-(1,3-difluoropropan-2-yl)pyridine-3-sulfonamide, |
| 15 | 6-(3-cyano-1-cyclobutyl-5-methoxy-1H-pyrrolo[3,2-b]pyridin-2-yl)-N-(1,3-difluoropropan-2-yl)pyridine-3-sulfonamide, |
| 16 | 2-(3-cyano-1-cyclobutyl-5-fluoro-1H-pyrrolo[2,3-b]pyridin-2-yl)-N-(1,3-difluoropropan-2-yl)pyrimidine-5-sulfonamide, |
| 17 | 2-(5-chloro-3-cyano-1-cyclopentyl-1H-pyrrolo[2,3-b]pyridin-2-yl)-N-(1,3-difluoropropan-2-yl)pyrimidine-5-sulfonamide, |
| 18 | 6-(3-cyano-1-cyclobutyl-1H-pyrrolo[2,3-b]pyridin-2-yl)-N-[(2S)-1,1,1-trifluoropropan-2-yl]pyridine-3-sulfonamide, |
| 19 | 2-(3-cyano-1-cyclobutyl-5-methoxy-1H-pyrrolo[3,2-b]pyridin-2-yl)-N-(1,3-difluoropropan-2-yl)pyrimidine-5-sulfonamide, |
| 20 | 6-(3-cyano-1-cyclobutyl-5-methoxy-1H-pyrrolo[3,2-b]pyridin-2-yl)-N-[(2S)-1,1,1-trifluoropropan-2-yl]pyridine-3-sulfonamide, |
| 21 | 2-(3-cyano-1-cyclobutyl-5-fluoro-1H-pyrrolo[2,3-b]pyridin-2-yl)-N-[(2S)-1,1,1-trifluoropropan-2-yl]pyrimidine-5-sulfonamide, |
| 22 | 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide, |
| 23 | 2-(3-cyano-1-cyclobutyl-5-methoxy-1H-pyrrolo[2,3-b]pyridin-2-yl)-N-[(2S)-1,1,1-trifluoropropan-2-yl]pyrimidine-5-sulfonamide, |
| 24 | 6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide, |
| 25 | 2-(5-chloro-3-cyano-1-cyclopentyl-1H-pyrrolo[2,3-b]pyridin-2-yl)-N-[(2S)-1,1,1-trifluoropropan-2-yl]pyrimidine-5-sulfonamide, |
| 26 | 6-(3-cyano-1-cyclobutyl-6-methyl-1H-pyrrolo[3,2-c]pyridin-2-yl)-N-(1,3-difluoropropan-2-yl)pyridine-3-sulfonamide, |
| 27 | 2-(3-cyano-1-cyclobutyl-6-methyl-1H-pyrrolo[3,2-c]pyridin-2-yl)-N-(1,3-difluoropropan-2-yl)pyrimidine-5-sulfonamide, |
| 28 | 6-(3-cyano-1-cyclobutyl-6-methyl-1H-pyrrolo[3,2-c]pyridin-2-yl)-N-[(2S)-1,1,1-trifluoropropan-2-yl]pyridine-3-sulfonamide, |
| 29 | 6-(3-cyano-1-cyclobutyl-6-methyl-1H-pyrrolo[3,2-c]pyridin-2-yl)-N-[(2R)-1,1,1-trifluoropropan-2-yl]pyridine-3-sulfonamide, |
| 30 | 4-(3-cyano-1-cyclobutyl-6-methyl-1H-pyrrolo[3,2-c]pyridin-2-yl)-N-[(2S)-1,1,1-trifluoropropan-2-yl]benzenesulfonamide, |
| 31 | 4-(3-cyano-1-cyclobutyl-6-methyl-1H-pyrrolo[3,2-c]pyridin-2-yl)-N-[(2R)-1,1,1-trifluoropropan-2-yl]benzenesulfonamide, |
| 32 | 2-(3-cyano-1-cyclobutyl-6-methyl-1H-pyrrolo[3,2-c]pyridin-2-yl)-N-(propan-2-yl)pyrimidine-5-sulfonamide, |
| 33 | 4-(3-cyano-1-cyclobutyl-6-methyl-1H-pyrrolo[3,2-c]pyridin-2-yl)-N-(1,3-difluoropropan-2-yl)benzenesulfonamide, |
| 34 | 4-(3-cyano-1-cyclobutyl-1H-pyrrolo[2,3-b]pyridin-2-yl)-N-(1,3-difluoropropan-2-yl)benzenesulfonamide, |
| 35 | 6-(3-cyano-1-cyclobutyl-1H-pyrrolo[2,3-b]pyridin-2-yl)-N-[(2R)-1,1,1-trifluoropropan-2-yl]pyridine-3-sulfonamide, |
| 36 | 2-(3-cyano-1-cyclobutyl-1H-pyrrolo[2,3-b]pyridin-2-yl)-N-(propan-2-yl)pyrimidine-5-sulfonamide, |
| 37 | 2-(3-cyano-1-cyclobutyl-5-fluoro-1H-pyrrolo[2,3-b]pyridin-2-yl)-N-(propan-2-yl)pyrimidine-5-sulfonamide, |
| 38 | 6-(5-cyano-7-cyclobutyl-2-methoxy-7H-pyrrolo[2,3-d]pyrimidin-6-yl)-N-[(2S)-1,1,1-trifluoropropan-2-yl]pyridine-3-sulfonamide, |
| 39 | 6-(5-cyano-7-cyclobutyl-2-methoxy-7H-pyrrolo[2,3-d]pyrimidin-6-yl)-N-[(2R)-1,1,1-trifluoropropan-2-yl]pyridine-3-sulfonamide, |
| 40 | 6-(3-cyano-1-cyclobutyl-6-methoxy-1H-pyrrolo[2,3-b]pyridin-2-yl)-N-[(2S)-1,1,1-trifluoropropan-2-yl]pyridine-3-sulfonamide, |
| 41 | 6-(3-cyano-1-cyclobutyl-6-methoxy-1H-pyrrolo[2,3-b]pyridin-2-yl)-N-(1,3-difluoropropan-2-yl)pyridine-3-sulfonamide, |
| 42 | 2-(3-cyano-1-cyclobutyl-6-methoxy-1H-pyrrolo[2,3-b]pyridin-2-yl)-N-(1,3-difluoropropan-2-yl)pyrimidine-5-sulfonamide, |
| 43 | 4-(3-cyano-1-cyclobutyl-6-methoxy-1H-pyrrolo[2,3-b]pyridin-2-yl)-N-(1,3-difluoropropan-2-yl)benzenesulfonamide, |
| 44 | N-tert-butyl-4-(3-cyano-1-cyclobutyl-6-methoxy-1H-pyrrolo[2,3-b]pyridin-2-yl)benzenesulfonamide, |
| 45 | 6-(5-cyano-7-cyclobutyl-2-methyl-7H-pyrrolo[2,3-d]pyrimidin-6-yl)-N-[(1S)-1-cyclopropylethyl]pyridine-3-sulfonamide, |
| 46 | 6-(5-cyano-7-cyclobutyl-2-methyl-7H-pyrrolo[2,3-d]pyrimidin-6-yl)-N-[(2R)-1,1,1-trifluoropropan-2-yl]pyridine-3-sulfonamide, |
| 47 | 6-(3-cyano-1-cyclobutyl-5-fluoro-1H-pyrrolo[2,3-b]pyridin-2-yl)-N-[(2R)-1,1,1-trifluoropropan-2-yl]pyridine-3-sulfonamide, |
| 48 | 6-(3-cyano-1-cyclobutyl-5-methoxy-1H-pyrrolo[2,3-b]pyridin-2-yl)-N-[(2R)-1,1,1-trifluoropropan-2-yl]pyridine-3-sulfonamide, |
| 49 | 2-(3-cyano-1-cyclobutyl-5-methoxy-1H-pyrrolo[2,3-b]pyridin-2-yl)-N-(propan-2-yl)pyrimidine-5-sulfonamide, |
| 50 | 6-(5-chloro-3-cyano-1-cyclobutyl-1H-pyrrolo[2,3-b]pyridin-2-yl)-N-[(2R)-1,1,1-trifluoropropan-2-yl]pyridine-3-sulfonamide, |
| 51 | 6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide, |
| 52 | N-tert-butyl-6-(5-chloro-3-cyano-1-cyclobutyl-1H-pyrrolo[2,3-b]pyridin-2-yl)pyridine-3-sulfonamide, |
| 53 | 4-(5-cyano-7-cyclobutyl-2-methyl-7H-pyrrolo[2,3-d]pyrimidin-6-yl)-N-(1,1,1-trifluoro-2-methylpropan-2-yl)benzenesulfonamide, |
| 54 | 6-[3-cyano-1-cyclobutyl-6-(difluoromethoxy)-1H-pyrrolo[2,3-b]pyridin-2-yl]-N-[(2S)-1,1,1-trifluoropropan-2-yl]pyridine-3-sulfonamide, |
| 55 | 2-[3-cyano-1-cyclobutyl-6-(difluoromethoxy)-1H-pyrrolo[2,3-b]pyridin-2-yl]-N-(1,3-difluoropropan-2-yl)pyrimidine-5-sulfonamide, |
| 56 | 6-(5-chloro-3-cyano-1-cyclobutyl-1H-pyrrolo[2,3-b]pyridin-2-yl)-N-(1,1,1-trifluoro-2-methylpropan-2-yl)pyridine-3-sulfonamide, |
| 57 | 6-(5-chloro-3-cyano-1-cyclobutyl-1H-pyrrolo[2,3-b]pyridin-2-yl)-N-[1-(trifluoromethyl)cyclopropyl]pyridine-3-sulfonamide, |
| 58 | 2-(5-chloro-3-cyano-1-cyclobutyl-1H-pyrrolo[2,3-b]pyridin-2-yl)-N-(propan-2-yl)pyrimidine-5-sulfonamide, |
| 59 | 6-[5-chloro-3-cyano-1-(cyclopropylmethyl)-1H-pyrrolo[2,3-b]pyridin-2-yl]-N-[(2R)-1,1,1-trifluoropropan-2-yl]pyridine-3-sulfonamide, |
| 60 | 6-[3-cyano-1-(cyclopropylmethyl)-5-fluoro-1H-pyrrolo[2,3-b]pyridin-2-yl]-N-[(2R)-1,1,1-trifluoropropan-2-yl]pyridine-3-sulfonamide, |
| 61 | 4-(5-chloro-3-cyano-1-cyclobutyl-1H-pyrrolo[2,3-b]pyridin-2-yl)-N-[(2S)-1,1,1-trifluoropropan-2-yl]benzenesulfonamide, |
| 62 | 6-[5-cyano-7-cyclobutyl-2-(difluoromethoxy)-7H-pyrrolo[2,3-d]pyrimidin-6-yl]-N-[(2S)-1,1,1-trifluoropropan-2-yl]pyridine-3-sulfonamide, |
| 63 | 6-[5-chloro-3-cyano-1-(cyclopropylmethyl)-1H-pyrrolo[2,3-b]pyridin-2-yl]-N-[(2S)-1,1,1-trifluoropropan-2-yl]pyridine-3-sulfonamide, |
| 64 | 6-[3-cyano-1-(cyclopropylmethyl)-5-fluoro-1H-pyrrolo[2,3-b]pyridin-2-yl]-N-[(2S)-1,1,1-trifluoropropan-2-yl]pyridine-3-sulfonamide, |
| 65 | 4-(3-cyano-1-cyclobutyl-5-methoxy-1H-pyrrolo[2,3-b]pyridin-2-yl)-N-(1,3-difluoropropan-2-yl)benzenesulfonamide, |
| 66 | 6-[3-cyano-1-(cyclopropylmethyl)-5-methoxy-1H-pyrrolo[2,3-b]pyridin-2-yl]-N-[(2S)-1,1,1-trifluoropropan-2-yl]pyridine-3-sulfonamide, |
| 67 | 6-(5-chloro-3-cyano-1-cyclobutyl-1H-pyrrolo[2,3-c]pyridin-2-yl)-N-[(2S)-1,1,1-trifluoropropan-2-yl]pyridine-3-sulfonamide, |
| 68 | 6-(3-cyano-1-cyclobutyl-5-methyl-1H-pyrrolo[2,3-b]pyridin-2-yl)-N-[(2R)-1,1,1-trifluoropropan-2-yl]pyridine-3-sulfonamide, |
| 69 | 6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide, |
| 70 | 2-(3-cyano-1-cyclobutyl-5-methyl-1H-pyrrolo[2,3-b]pyridin-2-yl)-N-[(2R)-1,1,1-trifluoropropan-2-yl]pyrimidine-5-sulfonamide, |
| 71 | 2-(3-cyano-1-cyclobutyl-5-methyl-1H-pyrrolo[2,3-b]pyridin-2-yl)-N-[(2S)-1,1,1-trifluoropropan-2-yl]pyrimidine-5-sulfonamide, |
| 72 | 4-(3-cyano-1-cyclobutyl-5-methyl-1H-pyrrolo[2,3-b]pyridin-2-yl)-N-[(2R)-1,1,1-trifluoropropan-2-yl]benzenesulfonamide, |

-continued

| Cpd | Name |
|---|---|
| 73 | 4-(3-cyano-1-cyclobutyl-5-methyl-1H-pyrrolo[2,3-b]pyridin-2-yl)-N-[(2S)-1,1,1-trifluoropropan-2-yl]benzenesulfonamide, |
| 74 | 6-(3-cyano-1-cyclobutyl-5-methyl-1H-pyrrolo[2,3-b]pyridin-2-yl)-N-[1-(trifluoromethyl)cyclopropyl]pyridine-3-sulfonamide, |
| 75 | 4-(3-cyano-1-cyclobutyl-5-methyl-1H-pyrrolo[2,3-b]pyridin-2-yl)-N-[1-(trifluoromethyl)cyclopropyl]benzenesulfonamide, |
| 76 | 6-(3-cyano-1-cyclobutyl-5-methyl-1H-pyrrolo[2,3-b]pyridin-2-yl)-N-(1-methylcyclopropyl)pyridine-3-sulfonamide, |
| 77 | 4-(3-cyano-1-cyclobutyl-5-methyl-1H-pyrrolo[2,3-b]pyridin-2-yl)-N-(1-methylcyclopropyl)benzenesulfonamide, |
| 78 | 2-(3-cyano-1-cyclobutyl-5-methyl-1H-pyrrolo[2,3-b]pyridin-2-yl)-N-(propan-2-yl)pyrimidine-5-sulfonamide, |
| 79 | 4-(3-cyano-1-cyclobutyl-5-methyl-1H-pyrrolo[2,3-b]pyridin-2-yl)-N-(1,1,1-trifluoro-2-methylpropan-2-yl)benzenesulfonamide, |
| 80 | 6-(6-chloro-3-cyano-1-cyclopentyl-1H-pyrrolo[3,2-c]pyridin-2-yl)-N-[(2S)-1,1,1-trifluoropropan-2-yl]pyridine-3-sulfonamide, |
| 81 | 6-(6-chloro-3-cyano-1-cyclopentyl-1H-pyrrolo[3,2-c]pyridin-2-yl)-N-[(2R)-1,1,1-trifluoropropan-2-yl]pyridine-3-sulfonamide, |
| 82 | 6-(6-chloro-3-cyano-1-cyclopentyl-1H-pyrrolo[3,2-c]pyridin-2-yl)-N-(1,3-difluoropropan-2-yl)pyridine-3-sulfonamide, |
| 83 | 6-(6-chloro-3-cyano-1-cyclopentyl-1H-pyrrolo[3,2-c]pyridin-2-yl)-N-[1-(trifluoromethyl)cyclopropyl]pyridine-3-sulfonamide, |
| 84 | 6-(6-chloro-3-cyano-1-cyclopentyl-1H-pyrrolo[3,2-c]pyridin-2-yl)-N-(1-methylcyclopropyl)pyridine-3-sulfonamide, |
| 85 | 2-(6-chloro-3-cyano-1-cyclopentyl-1H-pyrrolo[3,2-c]pyridin-2-yl)-N-(propan-2-yl)pyrimidine-5-sulfonamide, |
| 86 | 2-(6-chloro-3-cyano-1-cyclopentyl-1H-pyrrolo[3,2-c]pyridin-2-yl)-N-(1,3-difluoropropan-2-yl)pyrimidine-5-sulfonamide, |
| 87 | 4-(6-chloro-3-cyano-1-cyclopentyl-1H-pyrrolo[3,2-c]pyridin-2-yl)-N-[(2S)-1,1,1-trifluoropropan-2-yl]benzenesulfonamide, |
| 88 | 4-(6-chloro-3-cyano-1-cyclopentyl-1H-pyrrolo[3,2-c]pyridin-2-yl)-N-[(2R)-1,1,1-trifluoropropan-2-yl]benzenesulfonamide, |
| 89 | 4-(6-chloro-3-cyano-1-cyclopentyl-1H-pyrrolo[3,2-c]pyridin-2-yl)-N-[1-(trifluoromethyl)cyclopropyl]benzenesulfonamide, |
| 90 | 4-(3-cyano-1-cyclobutyl-6-methyl-1H-pyrrolo[2,3-b]pyridin-2-yl)-N-[(2S)-1,1,1-trifluoropropan-2-yl]benzenesulfonamide, |
| 91 | 4-(3-cyano-1-cyclobutyl-6-methyl-1H-pyrrolo[2,3-b]pyridin-2-yl)-N-[(2R)-1,1,1-trifluoropropan-2-yl]benzenesulfonamide, |
| 92 | 6-(3-cyano-1-cyclobutyl-6-methyl-1H-pyrrolo[2,3-b]pyridin-2-yl)-N-[(2S)-1,1,1-trifluoropropan-2-yl]pyridine-3-sulfonamide, |
| 93 | 6-(3-cyano-1-cyclobutyl-6-methyl-1H-pyrrolo[2,3-b]pyridin-2-yl)-N-[(2R)-1,1,1-trifluoropropan-2-yl]pyridine-3-sulfonamide, |
| 94 | 6-(3-cyano-1-cyclobutyl-6-methyl-1H-pyrrolo[2,3-b]pyridin-2-yl)-N-[1-(trifluoromethyl)cyclopropyl]pyridine-3-sulfonamide, |
| 95 | 2-(3-cyano-1-cyclobutyl-6-methyl-1H-pyrrolo[2,3-b]pyridin-2-yl)-N-(propan-2-yl)pyrimidine-5-sulfonamide, |
| 96 | 5-(3-cyano-1-cyclobutyl-6-methyl-1H-pyrrolo[2,3-b]pyridin-2-yl)-N-(propan-2-yl)pyridine-2-sulfonamide, |
| 97 | 6-(6-chloro-3-cyano-1-cyclobutyl-1H-pyrrolo[3,2-c]pyridin-2-yl)-N-(1,3-difluoropropan-2-yl)pyridine-3-sulfonamide, |
| 98 | 6-(6-chloro-3-cyano-1-cyclobutyl-1H-pyrrolo[3,2-c]pyridin-2-yl)-N-[1-(trifluoromethyl)cyclopropyl]pyridine-3-sulfonamide, |
| 99 | 6-(6-chloro-3-cyano-1-cyclobutyl-1H-pyrrolo[3,2-c]pyridin-2-yl)-N-(1-methylcyclopropyl)pyridine-3-sulfonamide, |
| 100 | 2-(6-chloro-3-cyano-1-cyclobutyl-1H-pyrrolo[3,2-c]pyridin-2-yl)-N-(propan-2-yl)pyrimidine-5-sulfonamide, |
| 101 | 2-(6-chloro-3-cyano-1-cyclobutyl-1H-pyrrolo[3,2-c]pyridin-2-yl)-N-(1,3-difluoropropan-2-yl)pyrimidine-5-sulfonamide, |
| 102 | 4-(6-chloro-3-cyano-1-cyclobutyl-1H-pyrrolo[3,2-c]pyridin-2-yl)-N-[(2S)-1,1,1-trifluoropropan-2-yl]benzenesulfonamide, |
| 103 | 6-(3-cyano-1-cyclobutyl-1H-pyrrolo[2,3-c]pyridin-2-yl)-N-[(2S)-1,1,1-trifluoropropan-2-yl]pyridine-3-sulfonamide, |
| 104 | 6-(5-chloro-3-cyano-1-cyclobutyl-1H-pyrrolo[2,3-b]pyridin-2-yl)-N-[(2R)-1,1,1-trifluoropropan-2-yl]pyridine-3-sulfonamide, |
| 105 | 4-(5-chloro-3-cyano-1-cyclobutyl-1H-pyrrolo[2,3-b]pyridin-2-yl)-N-[(2R)-1,1,1-trifluoropropan-2-yl]benzenesulfonamide, |
| 106 | 6-(5-chloro-3-cyano-1-cyclobutyl-1H-pyrrolo[2,3-b]pyridin-2-yl)-N-cyclopropylpyridine-3-sulfonamide, |
| 107 | 6-(3,5-dicyano-1-cyclobutyl-1H-pyrrolo[2,3-b]pyridin-2-yl)-N-[(2R)-1,1,1-trifluoropropan-2-yl]pyridine-3-sulfonamide, |
| 108 | 6-(3,5-dicyano-1-cyclobutyl-1H-pyrrolo[2,3-b]pyridin-2-yl)-N-[(2S)-1,1,1-trifluoropropan-2-yl]pyridine-3-sulfonamide, |
| 109 | 2-(3,5-dicyano-1-cyclobutyl-1H-pyrrolo[2,3-b]pyridin-2-yl)-N-[(2S)-1,1,1-trifluoropropan-2-yl]pyrimidine-5-sulfonamide, |
| 110 | 4-(3,5-dicyano-1-cyclobutyl-1H-pyrrolo[2,3-b]pyridin-2-yl)-N-[(2S)-1,1,1-trifluoropropan-2-yl]benzenesulfonamide, |
| 111 | 6-(3,5-dicyano-1-cyclobutyl-1H-pyrrolo[2,3-b]pyridin-2-yl)-N-[1-(trifluoromethyl)cyclopropyl]pyridine-3-sulfonamide, |
| 112 | 4-(3,5-dicyano-1-cyclobutyl-1H-pyrrolo[2,3-b]pyridin-2-yl)-N-[1-(trifluoromethyl)cyclopropyl]benzenesulfonamide, |
| 113 | 6-(3,5-dicyano-1-cyclobutyl-1H-pyrrolo[2,3-b]pyridin-2-yl)-N-(1-methylcyclopropyl)pyridine-3-sulfonamide, |
| 114 | 2-(3,5-dicyano-1-cyclobutyl-1H-pyrrolo[2,3-b]pyridin-2-yl)-N-(1-methylcyclopropyl)pyrimidine-5-sulfonamide, |
| 115 | 4-(3-cyano-1-cyclobutyl-5-cyclopropyl-1H-pyrrolo[2,3-b]pyridin-2-yl)-N-[(2S)-1,1,1-trifluoropropan-2-yl]benzenesulfonamide, |
| 116 | 4-(3-cyano-1-cyclobutyl-5-cyclopropyl-1H-pyrrolo[2,3-b]pyridin-2-yl)-N-[(2R)-1,1,1-trifluoropropan-2-yl]benzenesulfonamide, |
| 117 | 6-(3-cyano-1-cyclobutyl-5-cyclopropyl-1H-pyrrolo[2,3-b]pyridin-2-yl)-N-[(2S)-1,1,1-trifluoropropan-2-yl]pyridine-3-sulfonamide, |
| 118 | 6-(3-cyano-1-cyclobutyl-5-cyclopropyl-1H-pyrrolo[2,3-b]pyridin-2-yl)-N-[(2R)-1,1,1-trifluoropropan-2-yl]pyridine-3-sulfonamide, |
| 119 | 2-(3-cyano-1-cyclobutyl-5-cyclopropyl-1H-pyrrolo[2,3-b]pyridin-2-yl)-N-[(2S)-1,1,1-trifluoropropan-2-yl]pyrimidine-5-sulfonamide, |
| 120 | 2-(3-cyano-1-cyclobutyl-5-cyclopropyl-1H-pyrrolo[2,3-b]pyridin-2-yl)-N-[(2R)-1,1,1-trifluoropropan-2-yl]pyrimidine-5-sulfonamide, |
| 121 | 4-(3-cyano-1-cyclobutyl-5-cyclopropyl-1H-pyrrolo[2,3-b]pyridin-2-yl)-N-(1,1,1-trifluoro-2-methylpropan-2-yl)benzenesulfonamide, |
| 122 | 6-[3-cyano-1-cyclobutyl-5-(difluoromethoxy)-1H-pyrrolo[2,3-b]pyridin-2-yl]-N-[(2S)-1,1,1-trifluoropropan-2-yl]pyridine-3-sulfonamide, |
| 123 | 4-(3-cyano-1-cyclobutyl-5-cyclopropyl-1H-pyrrolo[2,3-b]pyridin-2-yl)-N-[1-(trifluoromethyl)cyclopropyl]benzenesulfonamide, |
| 124 | 6-(3-cyano-1-cyclobutyl-5-cyclopropyl-1H-pyrrolo[2,3-b]pyridin-2-yl)-N-[1-(trifluoromethyl)cyclopropyl]pyridine-3-sulfonamide, |
| 125 | N-tert-butyl-4-(3-cyano-1-cyclobutyl-5-cyclopropyl-1H-pyrrolo[2,3-b]pyridin-2-yl)benzenesulfonamide, |
| 126 | N-tert-butyl-6-(3-cyano-1-cyclobutyl-5-cyclopropyl-1H-pyrrolo[2,3-b]pyridin-2-yl)pyridine-3-sulfonamide, |
| 127 | 4-(3-cyano-1-cyclobutyl-5-cyclopropyl-1H-pyrrolo[2,3-b]pyridin-2-yl)-N-(1-methylcyclopropyl)benzenesulfonamide, |
| 128 | 6-(3-cyano-1-cyclobutyl-5-cyclopropyl-1H-pyrrolo[2,3-b]pyridin-2-yl)-N-(1-methylcyclopropyl)pyridine-3-sulfonamide, |
| 129 | 2-(3-cyano-1-cyclobutyl-5-cyclopropyl-1H-pyrrolo[2,3-b]pyridin-2-yl)-N-(1-methylcyclopropyl)pyrimidine-5-sulfonamide, |
| 130 | 4-(3-cyano-1-cyclobutyl-5-cyclopropyl-1H-pyrrolo[2,3-b]pyridin-2-yl)-N-(1,3-difluoropropan-2-yl)benzenesulfonamide, |
| 131 | 6-(3-cyano-1-cyclobutyl-5-cyclopropyl-1H-pyrrolo[2,3-b]pyridin-2-yl)-N-(1,3-difluoropropan-2-yl)pyridine-3-sulfonamide, |
| 132 | 2-(3-cyano-1-cyclobutyl-5-cyclopropyl-1H-pyrrolo[2,3-b]pyridin-2-yl)-N-(1,3-difluoropropan-2-yl)pyrimidine-5-sulfonamide, |
| 133 | 6-(3-cyano-1-cyclobutyl-5-cyclopropyl-1H-pyrrolo[2,3-b]pyridin-2-yl)-N-cyclopropylpyridine-3-sulfonamide, |
| 134 | 6-(3-cyano-1-cyclobutyl-5-cyclopropyl-1H-pyrrolo[2,3-b]pyridin-2-yl)-N-cyclobutylpyridine-3-sulfonamide, |
| 135 | 5-(3-cyano-1-cyclobutyl-5-cyclopropyl-1H-pyrrolo[2,3-b]pyridin-2-yl)-N-(propan-2-yl)pyridine-2-sulfonamide, |
| 136 | 2-(3-cyano-1-cyclobutyl-5-cyclopropyl-1H-pyrrolo[2,3-b]pyridin-2-yl)-N-(propan-2-yl)pyrimidine-5-sulfonamide, |
| 137 | 2-(3-cyano-1-cyclobutyl-6-methyl-1H-pyrrolo[2,3-b]pyridin-2-yl)-N-[(2S)-1,1,1-trifluoropropan-2-yl]pyrimidine-5-sulfonamide, |
| 138 | 2-(3-cyano-1-cyclobutyl-6-methyl-1H-pyrrolo[2,3-b]pyridin-2-yl)-N-[(2R)-1,1,1-trifluoropropan-2-yl]pyrimidine-5-sulfonamide, |
| 139 | 4-(3-cyano-1-cyclobutyl-6-methyl-1H-pyrrolo[2,3-b]pyridin-2-yl)-N-(1,1,1-trifluoro-2-methylpropan-2-yl)benzenesulfonamide, |
| 140 | 4-(3-cyano-1-cyclobutyl-6-methyl-1H-pyrrolo[2,3-b]pyridin-2-yl)-N-[1-(trifluoromethyl)cyclopropyl]benzenesulfonamide, |
| 141 | N-tert-butyl-4-(3-cyano-1-cyclobutyl-6-methyl-1H-pyrrolo[2,3-b]pyridin-2-yl)benzenesulfonamide, |
| 142 | N-tert-butyl-6-(3-cyano-1-cyclobutyl-6-methyl-1H-pyrrolo[2,3-b]pyridin-2-yl)pyridine-3-sulfonamide, |
| 143 | 4-(3-cyano-1-cyclobutyl-6-methyl-1H-pyrrolo[2,3-b]pyridin-2-yl)-N-(1-methylcyclopropyl)benzenesulfonamide, |
| 144 | 2-(3-cyano-1-cyclobutyl-6-methyl-1H-pyrrolo[2,3-b]pyridin-2-yl)-N-(1-methylcyclopropyl)pyrimidine-5-sulfonamide, |
| 145 | 4-(3-cyano-1-cyclobutyl-6-methyl-1H-pyrrolo[2,3-b]pyridin-2-yl)-N-(1,3-difluoropropan-2-yl)benzenesulfonamide, |
| 146 | 6-(3-cyano-1-cyclobutyl-6-methyl-1H-pyrrolo[2,3-b]pyridin-2-yl)-N-(1,3-difluoropropan-2-yl)pyridine-3-sulfonamide, |
| 147 | 2-(3-cyano-1-cyclobutyl-6-methyl-1H-pyrrolo[2,3-b]pyridin-2-yl)-N-(1,3-difluoropropan-2-yl)pyrimidine-5-sulfonamide, |

| Cpd | Name |
|---|---|
| 148 | 6-(3-cyano-1-cyclobutyl-6-methyl-1H-pyrrolo[2,3-b]pyridin-2-yl)-N-cyclobutylpyridine-3-sulfonamide, |
| 149 | 4-(3-cyano-1-cyclobutyl-6-cyclopropyl-1H-pyrrolo[2,3-b]pyridin-2-yl)-N-[(2S)-1,1,1-trifluoropropan-2-yl]benzenesulfonamide, |
| 150 | 4-(3-cyano-1-cyclobutyl-6-cyclopropyl-1H-pyrrolo[2,3-b]pyridin-2-yl)-N-[(2R)-1,1,1-trifluoropropan-2-yl]benzenesulfonamide, |
| 151 | 6-(3-cyano-1-cyclobutyl-6-cyclopropyl-1H-pyrrolo[2,3-b]pyridin-2-yl)-N-[(2S)-1,1,1-trifluoropropan-2-yl]pyridine-3-sulfonamide, |
| 152 | 6-(3-cyano-1-cyclobutyl-6-cyclopropyl-1H-pyrrolo[2,3-b]pyridin-2-yl)-N-[(2R)-1,1,1-trifluoropropan-2-yl]pyridine-3-sulfonamide, |
| 153 | 2-(3-cyano-1-cyclobutyl-6-cyclopropyl-1H-pyrrolo[2,3-b]pyridin-2-yl)-N-[(2S)-1,1,1-trifluoropropan-2-yl]pyrimidine-5-sulfonamide, |
| 154 | 2-(3-cyano-1-cyclobutyl-6-cyclopropyl-1H-pyrrolo[2,3-b]pyridin-2-yl)-N-[(2R)-1,1,1-trifluoropropan-2-yl]pyrimidine-5-sulfonamide, |
| 155 | 4-(3-cyano-1-cyclobutyl-5-ethyl-1H-pyrrolo[2,3-b]pyridin-2-yl)-N-[(2S)-1,1,1-trifluoropropan-2-yl]benzenesulfonamide, |
| 156 | 4-(3-cyano-1-cyclobutyl-5-ethyl-1H-pyrrolo[2,3-b]pyridin-2-yl)-N-[(2R)-1,1,1-trifluoropropan-2-yl]benzenesulfonamide, |
| 157 | 6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide, |
| 158 | 6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide, |
| 159 | 2-(3-cyano-1-cyclobutyl-5-ethyl-1H-pyrrolo[2,3-b]pyridin-2-yl)-N-[(2S)-1,1,1-trifluoropropan-2-yl]pyrimidine-5-sulfonamide, |
| 160 | 2-(3-cyano-1-cyclobutyl-5-ethyl-1H-pyrrolo[2,3-b]pyridin-2-yl)-N-[(2R)-1,1,1-trifluoropropan-2-yl]pyrimidine-5-sulfonamide, |
| 161 | 6-(6-chloro-3-cyano-1-cyclobutyl-1H-pyrrolo[2,3-b]pyridin-2-yl)-N-[(2S)-1,1,1-trifluoropropan-2-yl]pyridine-3-sulfonamide, |
| 162 | 6-(6-chloro-3-cyano-1-cyclobutyl-1H-pyrrolo[2,3-b]pyridin-2-yl)-N-[(2R)-1,1,1-trifluoropropan-2-yl]pyridine-3-sulfonamide, |
| 163 | 6-(5-cyano-7-cyclopentyl-2-methyl-7H-pyrrolo[2,3-d]pyrimidin-6-yl)-N-[(2S)-1,1,1-trifluoropropan-2-yl]pyridine-3-sulfonamide, |
| 164 | 4-(5-cyano-7-cyclopentyl-2-methyl-7H-pyrrolo[2,3-d]pyrimidin-6-yl)-N-[(2S)-1,1,1-trifluoropropan-2-yl]benzenesulfonamide, |
| 165 | 6-(3-cyano-1-cyclobutyl-5-methyl-1H-pyrrolo[2,3-c]pyridin-2-yl)-N-[(2S)-1,1,1-trifluoropropan-2-yl]pyridine-3-sulfonamide, |
| 166 | 6-(3-cyano-1-cyclobutyl-5-methyl-1H-pyrrolo[2,3-c]pyridin-2-yl)-N-[(2R)-1,1,1-trifluoropropan-2-yl]pyridine-3-sulfonamide, |
| 167 | 4-(3-cyano-1-cyclobutyl-5-methyl-1H-pyrrolo[2,3-c]pyridin-2-yl)-N-[(2S)-1,1,1-trifluoropropan-2-yl]benzenesulfonamide, |
| 168 | 6-(3-cyano-1-cyclobutyl-5-methyl-1H-pyrrolo[2,3-c]pyridine-2-yl)-N-(1-methylcyclopropyl)pyridine-3-sulfonamide, |
| 169 | 6-(3-cyano-1-cyclobutyl-5-fluoro-1H-pyrrolo[2,3-b]pyridin-2-yl)-N-[(2S)-1,1,1-trifluoropropan-2-yl]pyridine-3-sulfonamide, |
| 170 | 6-(3-cyano-1-cyclopentyl-6-methyl-1H-pyrrolo[3,2-b]pyridin-2-yl)-N-[(2S)-1,1,1-trifluoropropan-2-yl]pyridine-3-sulfonamide, |
| 171 | 6-(3-cyano-1-cyclopentyl-6-methyl-1H-pyrrolo[3,2-b]pyridin-2-yl)-N-[(2R)-1,1,1-trifluoropropan-2-yl]pyridine-3-sulfonamide, |
| 172 | 6-(3-cyano-1-cyclopentyl-6-methyl-1H-pyrrolo[3,2-b]pyridin-2-yl)-N-[1-(trifluoromethyl)cyclopropyl]pyridine-3-sulfonamide, |
| 173 | 6-(3-cyano-1-cyclopentyl-6-methyl-1H-pyrrolo[3,2-b]pyridin-2-yl)-N-(1,1,1-trifluoro-2-methylpropan-2-yl)pyridine-3-sulfonamide, |
| 174 | 6-(3-cyano-1-cyclopentyl-6-methyl-1H-pyrrolo[3,2-b]pyridin-2-yl)-N-(1-methylcyclopropyl)pyridine-3-sulfonamide, |
| 175 | N-tert-butyl-6-(3-cyano-1-cyclopentyl-6-methyl-1H-pyrrolo[3,2-b]pyridin-2-yl)pyridine-3-sulfonamide, |
| 176 | 6-(3-cyano-1-cyclopentyl-6-methyl-1H-pyrrolo[3,2-b]pyridin-2-yl)-N-(1,3-difluoropropan-2-yl)pyridine-3-sulfonamide, |
| 177 | 2-(3-cyano-1-cyclopentyl-6-methyl-1H-pyrrolo[3,2-b]pyridin-2-yl)-N-(1,3-difluoropropan-2-yl)pyrimidine-5-sulfonamide, |
| 178 | 2-(3-cyano-1-cyclopentyl-6-methyl-1H-pyrrolo[3,2-b]pyridin-2-yl)-N-(propan-2-yl)pyrimidine-5-sulfonamide, |
| 179 | 2-(3-cyano-1-cyclopentyl-6-methyl-1H-pyrrolo[3,2-b]pyridin-2-yl)-N-[(2S)-1,1,1-trifluoropropan-2-yl]pyrimidine-5-sulfonamide, |
| 180 | 4-(3-cyano-1-cyclopentyl-6-methyl-1H-pyrrolo[3,2-b]pyridin-2-yl)-N-[(2S)-1,1,1-trifluoropropan-2-yl]benzenesulfonamide, |
| 181 | 4-(3-cyano-1-cyclopentyl-6-methyl-1H-pyrrolo[3,2-b]pyridin-2-yl)-N-[(2R)-1,1,1-trifluoropropan-2-yl]benzenesulfonamide, |
| 182 | 4-(3-cyano-1-cyclobutyl-5-ethyl-1H-pyrrolo[2,3-b]pyridin-2-yl)-N-(1,1,1-trifluoro-2-methylpropan-2-yl)benzenesulfonamide, |
| 183 | 4-(3-cyano-1-cyclobutyl-5-ethyl-1H-pyrrolo[2,3-b]pyridin-2-yl)-N-[1-(trifluoromethyl)cyclopropyl]benzenesulfonamide, |
| 184 | 6-(3-cyano-1-cyclobutyl-5-ethyl-1H-pyrrolo[2,3-b]pyridin-2-yl)-N-[1-(trifluoromethyl)cyclopropyl]pyridine-3-sulfonamide, |
| 185 | N-tert-butyl-4-(3-cyano-1-cyclobutyl-5-ethyl-1H-pyrrolo[2,3-b]pyridin-2-yl)benzenesulfonamide, |
| 186 | N-tert-butyl-6-(3-cyano-1-cyclobutyl-5-ethyl-1H-pyrrolo[2,3-b]pyridin-2-yl)pyridine-3-sulfonamide, |
| 187 | 4-(3-cyano-1-cyclobutyl-5-ethyl-1H-pyrrolo[2,3-b]pyridin-2-yl)-N-(1-methylcyclopropyl)benzenesulfonamide, |
| 188 | 6-(3-cyano-1-cyclobutyl-5-ethyl-1H-pyrrolo[2,3-b]pyridin-2-yl)-N-(1-methylcyclopropyl)pyridine-3-sulfonamide, |
| 189 | 2-(3-cyano-1-cyclobutyl-5-ethyl-1H-pyrrolo[2,3-b]pyridin-2-yl)-N-(1-methylcyclopropyl)pyrimidine-5-sulfonamide, |
| 190 | 4-(3-cyano-1-cyclobutyl-5-ethyl-1H-pyrrolo[2,3-b]pyridin-2-yl)-N-(1,3-difluoropropan-2-yl)benzenesulfonamide, |
| 191 | 6-(3-cyano-1-cyclobutyl-5-ethyl-1H-pyrrolo[2,3-b]pyridin-2-yl)-N-(1,3-difluoropropan-2-yl)pyridine-3-sulfonamide, |
| 192 | 2-(3-cyano-1-cyclobutyl-5-ethyl-1H-pyrrolo[2,3-b]pyridin-2-yl)-N-(1,3-difluoropropan-2-yl)pyrimidine-5-sulfonamide, |
| 193 | 6-(3-cyano-1-cyclobutyl-5-ethyl-1H-pyrrolo[2,3-b]pyridin-2-yl)-N-cyclopropylpyridine-3-sulfonamide, |
| 194 | 6-(3-cyano-1-cyclobutyl-5-ethyl-1H-pyrrolo[2,3-b]pyridin-2-yl)-N-cyclobutylpyridine-3-sulfonamide, |
| 195 | 5-(3-cyano-1-cyclobutyl-5-ethyl-1H-pyrrolo[2,3-b]pyridin-2-yl)-N-(propan-2-yl)pyridine-2-sulfonamide, |
| 196 | 2-(3-cyano-1-cyclobutyl-5-ethyl-1H-pyrrolo[2,3-b]pyridin-2-yl)-N-(propan-2-yl)pyrimidine-5-sulfonamide, |
| 197 | 6-[3-cyano-1-cyclobutyl-5-(difluoromethoxy)-1H-pyrrolo[2,3-b]pyridin-2-yl]-N-[(2R)-1,1,1-trifluoropropan-2-yl]pyridine-3-sulfonamide, |
| 198 | 4-[3-cyano-1-cyclobutyl-5-(difluoromethoxy)-1H-pyrrolo[2,3-b]pyridin-2-yl]-N-[(2S)-1,1,1-trifluoropropan-2-yl]benzenesulfonamide, |
| 199 | 4-[3-cyano-1-cyclobutyl-5-(difluoromethoxy)-1H-pyrrolo[2,3-b]pyridin-2-yl]-N-[(2R)-1,1,1-trifluoropropan-2-yl]benzenesulfonamide, |
| 200 | 6-[3-cyano-1-cyclobutyl-5-(difluoromethoxy)-1H-pyrrolo[2,3-b]pyridin-2-yl]-N-[(1S)-1-cyclopropylethyl]pyridine-3-sulfonamide, |
| 201 | 6-[3-cyano-1-cyclobutyl-5-(difluoromethoxy)-1H-pyrrolo[2,3-b]pyridin-2-yl]-N-(1,1,1-trifluoro-2-methylpropan-2-yl)pyridine-3-sulfonamide, |
| 202 | 6-(3-cyano-1-cyclobutyl-5-ethoxy-1H-pyrrolo[2,3-b]pyridin-2-yl)-N-[(2S)-1,1,1-trifluoropropan-2-yl]pyridine-3-sulfonamide, |
| 203 | 6-(3-cyano-1-cyclobutyl-5-ethoxy-1H-pyrrolo[2,3-b]pyridin-2-yl)-N-[(2R)-1,1,1-trifluoropropan-2-yl]pyridine-3-sulfonamide, |
| 204 | 6-(3-cyano-1-cyclobutyl-5-propoxy-1H-pyrrolo[2,3-b]pyridin-2-yl)-N-[(2S)-1,1,1-trifluoropropan-2-yl]pyridine-3-sulfonamide, |
| 205 | 6-(3-cyano-1-cyclobutyl-5-propoxy-1H-pyrrolo[2,3-b]pyridin-2-yl)-N-[(2R)-1,1,1-trifluoropropan-2-yl]pyridine-3-sulfonamide, |
| 206 | 6-(3-cyano-1-cyclobutyl-6-methyl-1H-pyrrolo[3,2-b]pyridin-2-yl)-N-[(2S)-1,1,1-trifluoropropan-2-yl]pyridine-3-sulfonamide, |
| 207 | 6-(3-cyano-1-cyclobutyl-6-methyl-1H-pyrrolo[3,2-b]pyridin-2-yl)-N-[(2R)-1,1,1-trifluoropropan-2-yl]pyridine-3-sulfonamide, |
| 208 | 6-(3-cyano-1-cyclobutyl-6-methyl-1H-pyrrolo[3,2-b]pyridin-2-yl)-N-[1-(trifluoromethyl)cyclopropyl]pyridine-3-sulfonamide, |
| 209 | 6-(3-cyano-1-cyclobutyl-6-methyl-1H-pyrrolo[3,2-b]pyridin-2-yl)-N-(1,1,1-trifluoro-2-methylpropan-2-yl)pyridine-3-sulfonamide, |
| 210 | 6-(3-cyano-1-cyclobutyl-6-methyl-1H-pyrrolo[3,2-b]pyridin-2-yl)-N-(1-methylcyclopropyl)pyridine-3-sulfonamide, |
| 211 | N-tert-butyl-6-(3-cyano-1-cyclobutyl-6-methyl-1H-pyrrolo[3,2-b]pyridin-2-yl)pyridine-3-sulfonamide, |

-continued

| Cpd | Name |
|---|---|
| 212 | 6-(3-cyano-1-cyclobutyl-6-methyl-1H-pyrrolo[3,2-b]pyridin-2-yl)-N-(1,3-difluoropropan-2-yl)pyridine-3-sulfonamide, |
| 213 | 2-(3-cyano-1-cyclobutyl-6-methyl-1H-pyrrolo[3,2-b]pyridin-2-yl)-N-(1,3-difluoropropan-2-yl)pyrimidine-5-sulfonamide, |
| 214 | 2-(3-cyano-1-cyclobutyl-6-methyl-1H-pyrrolo[3,2-b]pyridin-2-yl)-N-(propan-2-yl)pyrimidine-5-sulfonamide, |
| 215 | 2-(3-cyano-1-cyclobutyl-6-methyl-1H-pyrrolo[3,2-b]pyridin-2-yl)-N-[(2S)-1,1,1-trifluoropropan-2-yl]pyrimidine-5-sulfonamide, |
| 216 | 4-(3-cyano-1-cyclobutyl-6-methyl-1H-pyrrolo[3,2-b]pyridin-2-yl)-N-[(2S)-1,1,1-trifluoropropan-2-yl]benzenesulfonamide, |
| 217 | 4-(3-cyano-1-cyclobutyl-6-methyl-1H-pyrrolo[3,2-b]pyridin-2-yl)-N-[(2R)-1,1,1-trifluoropropan-2-yl]benzenesulfonamide, |
| 218 | 6-[3-cyano-1-cyclobutyl-5-(propan-2-yloxy)-1H-pyrrolo[2,3-b]pyridin-2-yl]-N-[(2S)-1,1,1-trifluoropropan-2-yl]pyridine-3-sulfonamide, |
| 219 | 4-(3-cyano-1-cyclobutyl-5-ethyl-1H-pyrrolo[2,3-c]pyridin-2-yl)-N-[(2S)-1,1,1-trifluoropropan-2-yl]benzenesulfonamide, |
| 220 | N-[4-(3-cyano-1-cyclobutyl-5-ethyl-1H-pyrrolo[2,3-c]pyridin-2-yl)phenyl]propane-2-sulfonamide, |
| 221 | 6-(3-cyano-1-cyclopentyl-1H-pyrrolo[2,3-b]pyridin-2-yl)-N-[(2S)-1,1,1-trifluoropropan-2-yl]pyridine-3-sulfonamide, |
| 222 | 6-(3-cyano-1-cyclopentyl-5-methyl-1H-pyrrolo[3,2-b]pyridin-2-yl)-N-[(2S)-1,1,1-trifluoropropan-2-yl]pyridine-3-sulfonamide, |
| 223 | 6-(3-cyano-1-cyclobutyl-5-cyclopropyl-1H-pyrrolo[2,3-c]pyridin-2-yl)-N-[(2S)-1,1,1-trifluoropropan-2-yl]pyridine-3-sulfonamide, |
| 224 | 4-(3-cyano-1-cyclobutyl-5-cyclopropyl-1H-pyrrolo[2,3-c]pyridin-2-yl)-N-[(2S)-1,1,1-trifluoropropan-2-yl]benzenesulfonamide, |
| 226 | 1-cyclobutyl-5-methoxy-2-(5-{[(2S)-1,1,1-trifluoropropan-2-yl]sulfamoyl}pyridin-2-yl)-1H-pyrrolo[2,3-b]pyridine-3-carboxamide, |
| 227 | 6-[3-cyano-1-cyclobutyl-5-(trifluoromethyl)-1H-pyrrolo[2,3-b]pyridin-2-yl]-N-[(2S)-1,1,1-trifluoropropan-2-yl]pyridine-3-sulfonamide, |
| 228 | 6-[3-cyano-1-cyclobutyl-5-(trifluoromethyl)-1H-pyrrolo[2,3-b]pyridin-2-yl]-N-[(2R)-1,1,1-trifluoropropan-2-yl]pyridine-3-sulfonamide, |
| 229 | 6-[3-cyano-1-cyclopentyl-5-(trifluoromethyl)-1H-pyrrolo[2,3-b]pyridin-2-yl]-N-[(2S)-1,1,1-trifluoropropan-2-yl]pyridine-3-sulfonamide, |
| 230 | 6-[3-cyano-1-cyclobutyl-5-(trifluoromethyl)-1H-pyrrolo[2,3-b]pyridin-2-yl]-N-[(2R)-1,1,1-trifluoropropan-2-yl]pyridine-3-sulfonamide, |
| 232 | 6-(3-cyano-1-cyclobutyl-5-methoxy-1H-pyrrolo[2,3-b]pyridin-2-yl)-N-[(2S)-1,1,1-trifluorobutan-2-yl]pyridine-3-sulfonamide, |
| 233 | 6-(5-chloro-3-cyano-1-cyclopentyl-1H-pyrrolo[2,3-b]pyridin-2-yl)-N-[(2S)-1,1,1-trifluorobutan-2-yl]pyridine-3-sulfonamide, |
| 234 | 6-(6-chloro-3-cyano-1-cyclobutyl-1H-pyrrolo[3,2-b]pyridin-2-yl)-N-[(2S)-1,1,1-trifluoropropan-2-yl]pyridine-3-sulfonamide, |
| 235 | 4-(6-chloro-3-cyano-1-cyclobutyl-1H-pyrrolo[3,2-b]pyridin-2-yl)-N-[(2S)-1,1,1-trifluoropropan-2-yl]benzenesulfonamide, |
| 236 | 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide 1-oxide, |
| 237 | 6-[3-cyano-1-cyclobutyl-5-(thiophen-2-yl)-1H-pyrrolo[2,3-b]pyridin-2-yl]-N-[(2S)-1,1,1-trifluoropropan-2-yl]pyridine-3-sulfonamide, |
| 238 | 6-[3-cyano-1-cyclobutyl-5-(thiophen-2-yl)-1H-pyrrolo[2,3-b]pyridin-2-yl]-N-[(2R)-1,1,1-trifluoropropan-2-yl]pyridine-3-sulfonamide, |
| 239 | 6-[3-cyano-1-cyclopentyl-5-(pyrrolidin-1-yl)-1H-pyrrolo[2,3-b]pyridin-2-yl]-N-[(2S)-1,1,1-trifluoropropan-2-yl]pyridine-3-sulfonamide, |
| 240 | 6-[3-cyano-1-cyclobutyl-5-(pyrrolidin-1-yl)-1H-pyrrolo[2,3-b]pyridin-2-yl]-N-[(2R)-1,1,1-trifluoropropan-2-yl]pyridine-3-sulfonamide, |
| 241 | 6-(3,6-dicyano-1-cyclobutyl-1H-pyrrolo[2,3-b]pyridin-2-yl)-N-[(2S)-1,1,1-trifluoropropan-2-yl]pyridine-3-sulfonamide, |
| 242 | 6-(3-cyano-1-cyclobutyl-5-methoxy-6-methyl-1H-pyrrolo[2,3-b]pyridin-2-yl)-N-[(2S)-1,1,1-trifluoropropan-2-yl]pyridine-3-sulfonamide, |
| 243 | 6-(3-cyano-1-cyclobutyl-5-methoxy-6-methyl-1H-pyrrolo[2,3-b]pyridin-2-yl)-N-[(2R)-1,1,1-trifluoropropan-2-yl]pyridine-3-sulfonamide, |
| 244 | 6-[3-cyano-1-cyclobutyl-5-(trifluoromethyl)-1H-pyrrolo[2,3-b]pyridin-2-yl]-N-(propan-2-yl)pyridine-3-sulfonamide, |
| 245 | 6-[3-cyano-1-cyclobutyl-5-(trifluoromethyl)-1H-pyrrolo[2,3-b]pyridin-2-yl]-N-cyclopropylpyridine-3-sulfonamide, |
| 246 | N-{4-[3-cyano-1-cyclobutyl-5-(trifluoromethyl)-1H-pyrrolo[2,3-b]pyridin-2-yl]phenyl}cyclopropanesulfonamide, |
| 247 | N-{4-[3-cyano-1-cyclobutyl-5-(trifluoromethyl)-1H-pyrrolo[2,3-b]pyridin-2-yl]phenyl}propane-1-sulfonamide, |
| 248 | 6-(3-cyano-1-cyclopentyl-5-methoxy-1H-pyrrolo[2,3-b]pyridin-2-yl)-N-[(2S)-1,1,1-trifluoropropan-2-yl]pyridine-3-sulfonamide, |
| 249 | 6-(3-cyano-1-cyclobutyl-5-cyclopropyl-1H-pyrrolo[2,3-b]pyridin-2-yl)-N-[(2R)-1,1,1-trifluoropropan-2-yl]pyridine-3-sulfonamide, |
| 250 | 6-(3-cyano-1-cyclobutyl-5-cyclopropyl-1H-pyrrolo[2,3-b]pyridin-2-yl)-N-[(2S)-1,1,1-trifluoropropan-2-yl]pyridine-3-sulfonamide, |
| 251 | 6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide, |
| 252 | 6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide, |
| 253 | 6-(3-cyano-1-cyclopentyl-5-cyclopropyl-1H-pyrrolo[2,3-b]pyridin-2-yl)-N-(1-methylcyclopropyl)pyridine-3-sulfonamide, |
| 254 | 6-(3-cyano-1-cyclopentyl-5-methyl-1H-pyrrolo[2,3-b]pyridin-2-yl)-N-[(2R)-1,1,1-trifluoropropan-2-yl]pyridine-3-sulfonamide, |
| 255 | 6-(3-cyano-1-cyclopentyl-5-methyl-1H-pyrrolo[2,3-b]pyridin-2-yl)-N-[(2S)-1,1,1-trifluoropropan-2-yl]pyridine-3-sulfonamide, |
| 256 | 6-(3-cyano-1-cyclopentyl-5-methyl-1H-pyrrolo[2,3-b]pyridin-2-yl)-N-(1-methylcyclopropyl)pyridine-3-sulfonamide, |
| 257 | N-{[6-(3-cyano-1-cyclopentyl-5-methoxy-1H-pyrrolo[2,3-b]pyridin-2-yl)pyridin-3-yl]sulfonyl}-N-[(2S)-1,1,1-trifluoropropan-2-yl]acetamide, |
| 258 | 6-(3-cyano-1-cyclobutyl-6-ethyl-5-methoxy-1H-pyrrolo[2,3-b]pyridin-2-yl)-N-[(2S)-1,1,1-trifluoropropan-2-yl]pyridine-3-sulfonamide, |
| 259 | 6-(3-cyano-1-cyclobutyl-6-ethyl-5-methoxy-1H-pyrrolo[2,3-b]pyridin-2-yl)-N-[(2R)-1,1,1-trifluoropropan-2-yl]pyridine-3-sulfonamide, |
| 260 | 6-(5-chloro-3-cyano-1-cyclopentyl-1H-pyrrolo[2,3-b]pyridin-2-yl)-N-(1,1,1-trifluorobutan-2-yl)pyridine-3-sulfonamide, |
| 261 | 6-(3-cyano-1-cyclobutyl-5-methoxy-1H-pyrrolo[2,3-b]pyridin-2-yl)-N-(1,1,1-trifluorobutan-2-yl)pyridine-3-sulfonamide, |
| 262 | 4-(3-cyano-1-cyclopentyl-5-methyl-1H-pyrrolo[2,3-b]pyridin-2-yl)-N-[(2R)-1,1,1-trifluoropropan-2-yl]benzenesulfonamide |
| 263 | 4-(3-cyano-1-cyclopentyl-5-methyl-1H-pyrrolo[2,3-b]pyridin-2-yl)-N-[(2S)-1,1,1-trifluoropropan-2-yl]benzenesulfonamide, |
| 264 | 1-cyclobutyl-5-methyl-2-[4-(propan-2-ylamino)phenyl]-1H-pyrrolo[2,3-b]pyridine-3-carbonitrile, |
| 265 | N-[4-(3-cyano-1-cyclobutyl-5-methyl-1H-pyrrolo[2,3-b]pyridin-2-yl)phenyl]-2-methylpropanamide, |
| 266 | 1-[4-(3-cyano-1-cyclobutyl-5-methyl-1H-pyrrolo[2,3-b]pyridin-2-yl)phenyl]-3-propan-2-ylurea, |
| 267 | N-[4-(3-cyano-1-cyclobutyl-5-methyl-1H-pyrrolo[2,3-b]pyridin-2-yl)phenyl]propane-2-sulfonamide, |
| 268 | 6-(3-cyano-1-cyclopentyl-5-methoxy-1H-pyrrolo[2,3-b]pyridin-2-yl)-N-[(2R)-1,1,1-trifluoropropan-2-yl]pyridine-3-sulfonamide |
| 269 | 6-(3-cyano-1-cyclopentyl-5-methoxy-1H-pyrrolo[2,3-b]pyridin-2-yl)-N-(1-methylcyclopropyl)pyridine-3-sulfonamide, |
| 270 | 6-[5-chloro-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide, |
| 271 | N-tert-butyl-6-(3-cyano-1-cyclobutyl-5-methoxy-1H-pyrrolo[2,3-b]pyridin-2-yl)pyridine-3-sulfonamide, |
| 272 | 6-[3-cyano-1-cyclopentyl-5-(methylsulfanyl)-1H-pyrrolo[2,3-b]pyridin-2-yl]-N-[(2S)-1,1,1-trifluoropropan-2-yl]pyridine-3-sulfonamide, |
| 273 | 6-[3-cyano-1-cyclopentyl-5-(methylsulfanyl)-1H-pyrrolo[2,3-b]pyridin-2-yl]-N-[(2R)-1,1,1-trifluoropropan-2-yl]pyridine-3-sulfonamide |
| 274 | 6-[3-cyano-1-cyclopentyl-5-(methylsulfanyl)-1H-pyrrolo[2,3-b]pyridin-2-yl]-N-[1-(trifluoromethyl)cyclopropyl]pyridine-3-sulfonamide, |
| 275 | 6-(3-cyano-1-cyclobutyl-5-hydroxy-1H-pyrrolo[2,3-b]pyridin-2-yl)-N-[(2S)-1,1,1-trifluoropropan-2-yl]pyridine-3-sulfonamide, |
| 276 | 6-(5-chloro-3-cyano-1-cyclobutyl-1H-pyrrolo[2,3-b]pyridin-2-yl)-N-[(2S)-1,1,1-trifluorobutan-2-yl]pyridine-3-sulfonamide, |
| 277 | 6-(3-cyano-1-cyclobutyl-5-methoxy-1H-pyrrolo[2,3-b]pyridin-2-yl)-4-methyl-N-[(2S)-1,1,1-trifluoropropan-2-yl]pyridine-3-sulfonamide, |
| 278 | 6-(5-chloro-3-cyano-1-cyclopentyl-1H-pyrrolo[2,3-b]pyridin-2-yl)-4-methyl-N-[(2S)-1,1,1-trifluoropropan-2-yl]pyridine-3-sulfonamide, |
| 279 | 6-(3-cyano-1-cyclobutyl-5-methyl-1H-pyrrolo[2,3-b]pyridin-2-yl)-N-[(2S)-1,1,1-trifluorobutan-2-yl]pyridine-3-sulfonamide, |

| Cpd | Name |
|---|---|
| 280 | 6-(5-chloro-3-cyano-1-cyclobutyl-1H-pyrrolo[2,3-b]pyridin-2-yl)-N-(1-methylcyclopropyl)pyridine-3-sulfonamide, |
| 281 | 4-(5-cyclobutyl-3-cyano-1-cyclobutyl-1H-pyrrolo[2,3-b]pyridin-2-yl)-N-[1-(trifluoromethyl)cyclopropyl]benzenesulfonamide, |
| 282 | 4-(5-chloro-3-cyano-1-cyclobutyl-1H-pyrrolo[2,3-b]pyridin-2-yl)-N-(1,1,1-trifluoro-2-methylpropan-2-yl)benzenesulfonamide, |
| 283 | 6-(5-chloro-3-cyano-1-cyclobutyl-1H-pyrrolo[2,3-b]pyridin-2-yl)-N-cyclobutylpyridine-3-sulfonamide, |
| 284 | 4-(5-chloro-3-cyano-1-cyclobutyl-1H-pyrrolo[2,3-b]pyridin-2-yl)-N-(1-methylcyclopropyl)benzenesulfonamide, |
| 285 | 2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide, |
| 286 | 2-(5-chloro-3-cyano-1-cyclobutyl-1H-pyrrolo[2,3-b]pyridin-2-yl)-N-(1-methylcyclopropyl)pyrimidine-5-sulfonamide |
| 287 | 4-(6-chloro-3-cyano-1-cyclohexyl-1H-pyrrolo[3,2-b]pyridin-2-yl)-N-[(2S)-1,1,1-trifluoropropan-2-yl]benzenesulfonamide, |
| 288 | N-[4-(6-chloro-3-cyano-1-cyclohexyl-1H-pyrrolo[3,2-b]pyridin-2-yl)phenyl]-2-methylpropane-2-sulfonamide, |
| 289 | 6-(3-cyano-1-cyclobutyl-5-methyl-1H-pyrrolo[2,3-b]pyridin-2-yl)-4-methyl-N-[(2S)-1,1,1-trifluoropropan-2-yl]pyridine-3-sulfonamide, |
| 290 | 6-(5-chloro-3-cyano-1-cyclopentyl-1H-pyrrolo[2,3-b]pyridin-2-yl)-5-methyl-N-[(2S)-1,1,1-trifluoropropan-2-yl]pyridine-3-sulfonamide, |
| 291 | 6-(3-cyano-1-cyclobutyl-5-methyl-1H-pyrrolo[2,3-b]pyridin-2-yl)-5-methyl-N-[(2S)-1,1,1-trifluoropropan-2-yl]pyridine-3-sulfonamide, |
| 292 | 6-(3-cyano-1-cyclobutyl-5-methoxy-1H-pyrrolo[2,3-b]pyridin-2-yl)-5-methyl-N-[(2S)-1,1,1-trifluoropropan-2-yl]pyridine-3-sulfonamide, |
| 293 | N-tert-butyl-6-(3-cyano-1-cyclobutyl-5-methyl-1H-pyrrolo[2,3-b]pyridin-2-yl)pyridine-3-sulfonamide, |
| 294 | 6-(3-cyano-1-cyclopentyl-5-hydroxy-1H-pyrrolo[2,3-b]pyridin-2-yl)-N-[(2S)-1,1,1-trifluoropropan-2-yl]pyridine-3-sulfonamide, |
| 295 | 6-[3-cyano-1-(cyclopropylmethyl)-5-(trifluoromethyl)-1H-pyrrolo[2,3-b]pyridin-2-yl]-N-[(2S)-1,1,1-trifluoropropan-2-yl]pyridine-3-sulfonamide, |
| 296 | N-tert-butyl-6-[3-cyano-1-(cyclopropylmethyl)-5-(trifluoromethyl)-1H-pyrrolo[2,3-b]pyridin-2-yl]pyridine-3-sulfonamide, |
| 297 | N-tert-butyl-6-[3-cyano-1-cyclobutyl-5-(trifluoromethyl)-1H-pyrrolo[2,3-b]pyridin-2-yl]pyridine-3-sulfonamide, |
| 298 | 6-[3-cyano-1-cyclobutyl-5-(trifluoromethyl)-1H-pyrrolo[2,3-b]pyridin-2-yl]-4-methyl-N-[(2S)-1,1,1-trifluoropropan-2-yl]pyridine-3-sulfonamide, |
| 299 | N-[3-(3-cyano-1-cyclobutyl-5-methyl-1H-pyrrolo[2,3-b]pyridin-2-yl)phenyl]propane-2-sulfonamide, |
| 300 | 4-[3-cyano-1-cyclobutyl-5-(trifluoromethyl)-1H-pyrrolo[2,3-b]pyridin-2-yl]-N-[(2S)-1,1,1-trifluoropropan-2-yl]benzenesulfonamide, |
| 301 | 6-[3-cyano-1-cyclobutyl-5-(trifluoromethyl)-1H-pyrrolo[2,3-b]pyridin-2-yl]-5-methyl-N-[(2S)-1,1,1-trifluoropropan-2-yl]pyridine-3-sulfonamide, |
| 302 | 6-[3-cyano-1-cyclobutyl-5-(trifluoromethyl)-1H-pyrrolo[2,3-b]pyridin-2-yl]-N-cyclobutylpyridine-3-sulfonamide, |
| 303 | 6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 304 | 1-cyclobutyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide, |
| 305 | 6-[3-cyano-1-cyclopentyl-5-(methylsulfonyl)-1H-pyrrolo[2,3-b]pyridin-2-yl]-N-[(2S)-1,1,1-trifluoropropan-2-yl]pyridine-3-sulfonamide, |
| 306 | 6-[5-chloro-3-cyano-1-(pyridin-2-yl)-1H-pyrrolo[2,3-b]pyridin-2-yl]-N-[(2S)-1,1,1-trifluoropropan-2-yl]pyridine-3-sulfonamide, |
| 307 | 6-[5-chloro-3-cyano-1-(pyrazin-2-yl)-1H-pyrrolo[2,3-b]pyridin-2-yl]-N-[(2S)-1,1,1-trifluoropropan-2-yl]pyridine-3-sulfonamide, |
| 308 | 6-(5-chloro-3-cyano-1-phenyl-1H-pyrrolo[2,3-b]pyridin-2-yl)-N-[(2S)-1,1,1-trifluoropropan-2-yl]pyridine-3-sulfonamide, |
| 309 | 6-(3-cyano-1-cyclobutyl-5-methoxy-1H-pyrrolo[2,3-b]pyridin-2-yl)-N-cyclobutylpyridine-3-sulfonamide, |
| 310 | 6-(3-cyano-1-cyclobutyl-5-methoxy-1H-pyrrolo[2,3-b]pyridin-2-yl)-N-cyclopropylpyridine-3-sulfonamide, |
| 311 | 6-(3-cyano-1-cyclobutyl-5-methoxy-1H-pyrrolo[2,3-b]pyridin-2-yl)-N-(1-methylcyclopropyl)pyridine-3-sulfonamide, |
| 312 | 6-(3-cyano-1-cyclobutyl-5-methoxy-1H-pyrrolo[2,3-b]pyridin-2-yl)-N-[1-(trifluoromethyl)cyclopropyl]pyridine-3-sulfonamide, |
| 313 | 2-(3-cyano-1-cyclobutyl-5-methoxy-1H-pyrrolo[2,3-b]pyridin-2-yl)-N-(1-methylcyclopropyl)pyrimidine-5-sulfonamide, |
| 314 | 6-[1-phenyl-5-(trifluoromethyl)-1H-pyrrolo[2,3-b]pyridin-2-yl]-N-[(2S)-1,1,1-trifluoropropan-2-yl]pyridine-3-sulfonamide, |
| 315 | 6-[1-(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 316 | 6-[3-cyano-1-(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 317 | 6-[3-cyano-1-(pyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 318 | 6-[3-cyano-1-phenyl-5-(trifluoromethyl)-1H-pyrrolo[2,3-b]pyridin-2-yl]-N-[(2S)-1,1,1-trifluoropropan-2-yl]pyridine-3-sulfonamide, |
| 319 | 6-(3-cyano-5-fluoro-1-phenyl-1H-pyrrolo[2,3-b]pyridin-2-yl)-N-[(2S)-1,1,1-trifluoropropan-2-yl]pyridine-3-sulfonamide, |
| 320 | 6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide, |
| 321 | 6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide, |
| 322 | 6-[3-cyano-5-fluoro-1-(pyridin-2-yl)-1H-pyrrolo[2,3-b]pyridin-2-yl]-N-[(2S)-1,1,1-trifluoropropan-2-yl]pyridine-3-sulfonamide, |
| 323 | 6-[3-cyano-1-cyclobutyl-5-(methylsulfanyl)-1H-pyrrolo[2,3-b]pyridin-2-yl]-N-[(2S)-1,1,1-trifluoropropan-2-yl]pyridine-3-sulfonamide, |
| 324 | 5-chloro-1-cyclopentyl-2-(5-{[(2S)-1,1,1-trifluoropropan-2-yl]sulfamoyl}pyridin-2-yl)-1H-pyrrolo[2,3-b]pyridine-3-carboxamide, |
| 325 | 5-chloro-1-cyclobutyl-2-(5-{[1-(trifluoromethyl)cyclopropyl]sulfamoyl}pyridin-2-yl)-1H-pyrrolo[2,3-b]pyridine-3-carboxamide, |
| 326 | 5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxamide, |
| 327 | 2-[5-(tert-butylsulfamoyl)pyridin-2-yl]-5-chloro-1-cyclobutyl-1H-pyrrolo[2,3-b]pyridine-3-carboxamide, |
| 328 | 5-chloro-1-cyclobutyl-2-(4-{[1-(trifluoromethyl)cyclopropyl]sulfamoyl}phenyl)-1H-pyrrolo[2,3-b]pyridine-3-carboxamide, |
| 329 | 5-chloro-1-cyclobutyl-2-{4-[(1,1,1-trifluoro-2-methylpropan-2-yl)sulfamoyl]phenyl}-1H-pyrrolo[2,3-b]pyridine-3-carboxamide, |
| 330 | 1-cyclopentyl-5-(methylsulfanyl)-2-(5-{[1-(trifluoromethyl)cyclopropyl]sulfamoyl}pyridin-2-yl)-1H-pyrrolo[2,3-b]pyridine-3-carboxylic acid, |
| 331 | 5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxylic acid, |
| 332 | 6-[3-cyano-1-(5-methoxypyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 333 | 6-[3-cyano-1-(4-methoxypyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 334 | N-tert-butyl-4-[3-cyano-1-(pyrimidin-2-yl)-5-(trifluoromethyl)-1H-pyrrolo[2,3-b]pyridin-2-yl]benzenesulfonamide, |
| 335 | N-tert-butyl-4-[3-cyano-1-(pyrazin-2-yl)-5-(trifluoromethyl)-1H-pyrrolo[2,3-b]pyridin-2-yl]benzenesulfonamide, |
| 336 | N-tert-butyl-4-[3-cyano-1-(pyridin-2-yl)-5-(trifluoromethyl)-1H-pyrrolo[2,3-b]pyridin-2-yl]benzenesulfonamide, |
| 337 | N-tert-butyl-4-[3-cyano-1-phenyl-5-(trifluoromethyl)-1H-pyrrolo[2,3-b]pyridin-2-yl]benzenesulfonamide, |
| 338 | 6-[3-cyano-1-cyclobutyl-5-(trifluoromethyl)-1H-pyrrolo[2,3-b]pyridin-2-yl]-2-methyl-N-[(2S)-1,1,1-trifluoropropan-2-yl]pyridine-3-sulfonamide, |
| 339 | 6-[5-bromo-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide, |
| 340 | 6-[5-bromo-3-cyano-1-(pyrazin-2-yl)-1H-pyrrolo[2,3-b]pyridin-2-yl]-N-[(2S)-1,1,1-trifluoropropan-2-yl]pyridine-3-sulfonamide, |
| 341 | 1-cyclobutyl-5-methyl-2-{4-[(1,1,1-trifluoro-2-methylpropan-2-yl)sulfamoyl]phenyl}-1H-pyrrolo[2,3-b]pyridine-3-carboxamide, |
| 342 | 1-cyclobutyl-5-methyl-2-(4-{[1-(trifluoromethyl)cyclopropyl]sulfamoyl}phenyl)-1H-pyrrolo[2,3-b]pyridine-3-carboxamide, |

| Cpd | Name |
|---|---|
| 343 | 1-cyclobutyl-5-methyl-2-(4-{[(2S)-1,1,1-trifluoropropan-2-yl]sulfamoyl}phenyl)-1H-pyrrolo[2,3-b]pyridine-3-carboxamide, |
| 344 | 6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide, |
| 345 | 6-[3-cyano-5-methyl-1-(pyrimidin-2-yl)-1H-pyrrolo[2,3-b]pyridin-2-yl]-N-[(2S)-1,1,1-trifluoropropan-2-yl]pyridine-3-sulfonamide, |
| 346 | 6-[3-cyano-5-methyl-1-(pyridin-2-yl)-1H-pyrrolo[2,3-b]pyridin-2-yl]-N-[(2S)-1,1,1-trifluoropropan-2-yl]pyridine-3-sulfonamide, |
| 347 | 6-[3-cyano-5-methyl-1-(pyridin-3-yl)-1H-pyrrolo[2,3-b]pyridin-2-yl]-N-[(2S)-1,1,1-trifluoropropan-2-yl]pyridine-3-sulfonamide, |
| 348 | 6-(3-cyano-5-methyl-1-phenyl-1H-pyrrolo[2,3-b]pyridin-2-yl)-N-[(2S)-1,1,1-trifluoropropan-2-yl]pyridine-3-sulfonamide, |
| 349 | 6-[3-cyano-5-methyl-1-(pyrazin-2-yl)-1H-pyrrolo[2,3-b]pyridin-2-yl]-N-[(2S)-1,1,1-trifluoropropan-2-yl]pyridine-3-sulfonamide, |
| 350 | 6-{5-[benzyl(methyl)amino]-3-cyano-1-cyclobutyl-1H-pyrrolo[2,3-b]pyridin-2-yl}-N-[(2S)-1,1,1-trifluoropropan-2-yl]pyridine-3-sulfonamide, |
| 351 | 4-{5-[benzyl(methyl)amino]-3-cyano-1-cyclobutyl-1H-pyrrolo[2,3-b]pyridin-2-yl}-N-tert-butylbenzenesulfonamide, |
| 352 | N-(4-{5-[benzyl(methyl)amino]-3-cyano-1-cyclobutyl-1H-pyrrolo[2,3-b]pyridin-2-yl}phenyl)-2-methylpropane-2-sulfonamide, |
| 353 | 4-{5-[benzyl(methyl)amino]-3-cyano-1-cyclobutyl-1H-pyrrolo[2,3-b]pyridin-2-yl}-N-(1,1,1-trifluoro-2-methylpropan-2-yl)benzenesulfonamide, |
| 354 | 6-[3-cyano-1-(5-methylpyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 355 | 6-[3-cyano-1-(4-methylpyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 356 | 1-cyclobutyl-5-fluoro-2-(5-{[(2S)-1,1,1-trifluoropropan-2-yl]sulfamoyl}pyridin-2-yl)-1H-pyrrolo[2,3-b]pyridine-3-carboxamide, |
| 357 | 1-cyclopentyl-5-methoxy-2-(5-{[(2S)-1,1,1-trifluoropropan-2-yl]sulfamoyl}pyridin-2-yl)-1H-pyrrolo[2,3-b]pyridine-3-carboxamide, |
| 358 | 1-cyclopentyl-5-(methylsulfanyl)-2-{4-[(propan-2-ylsulfonyl)amino]phenyl}-1H-pyrrolo[2,3-b]pyridine-3-carboxamide, |
| 359 | 2-{4-[(tert-butylsulfonyl)amino]phenyl}-1-cyclopentyl-5-methoxy-1H-pyrrolo[2,3-b]pyridine-3-carboxamide, |
| 360 | 6-[3-cyano-1-cyclopropyl-5-(trifluoromethyl)-1H-pyrrolo[2,3-b]pyridin-2-yl]-N-[(2S)-1,1,1-trifluoropropan-2-yl]pyridine-3-sulfonamide, |
| 361 | 4-[3-cyano-1-cyclopropyl-5-(trifluoromethyl)-1H-pyrrolo[2,3-b]pyridin-2-yl]-N-(1,1,1-trifluoro-2-methylpropan-2-yl)benzenesulfonamide, |
| 362 | N-{4-[3-cyano-1-cyclopropyl-5-(trifluoromethyl)-1H-pyrrolo[2,3-b]pyridin-2-yl]phenyl}-2-methylpropane-2-sulfonamide, |
| 363 | [3-cyano-1-cyclobutyl-2-(5-{[(2S)-1,1,1-trifluoropropan-2-yl]sulfamoyl}pyridin-2-yl)-1H-pyrrolo[2,3-b]pyridin-5-yl](methyl)sulfoniumolate, |
| 364 | 4-[3-cyano-1-cyclobutyl-5-(methylsulfanyl)-1H-pyrrolo[2,3-b]pyridin-2-yl]-N-[1-(trifluoromethyl)cyclopropyl]benzenesulfonamide, |
| 365 | 6-[3-cyano-5-methoxy-1-(pyrazin-2-yl)-1H-pyrrolo[2,3-b]pyridin-2-yl]-N-[(2S)-1,1,1-trifluoropropan-2-yl]pyridine-3-sulfonamide, |
| 366 | 5-chloro-1-cyclobutyl-2-{5-[(1-methylcyclopropyl)sulfamoyl]pyridin-2-yl}-1H-pyrrolo[2,3-b]pyridine-3-carboxamide, |
| 367 | 1-cyclobutyl-2-(5-{[(2S)-1,1,1-trifluoropropan-2-yl]sulfamoyl}pyrimidin-2-yl)-1H-pyrrolo[2,3-b]pyridine-3-carboxamide, |
| 368 | 6-[3-cyano-5-methyl-1-(pyridin-4-yl)-1H-pyrrolo[2,3-b]pyridin-2-yl]-N-[(2S)-1,1,1-trifluoropropan-2-yl]pyridine-3-sulfonamide, |
| 369 | N-tert-butyl-4-(3-cyano-1-cyclobutyl-5-fluoro-1H-pyrrolo[2,3-b]pyridin-2-yl)benzenesulfonamide, |
| 370 | 6-[3-cyano-1-cyclobutyl-5-(methylsulfonyl)-1H-pyrrolo[2,3-b]pyridin-2-yl]-N-[(2S)-1,1,1-trifluoropropan-2-yl]pyridine-3-sulfonamide, |
| 371 | N-tert-butyl-4-(5-chloro-3-cyano-1-cyclobutyl-1H-pyrrolo[2,3-b]pyridin-2-yl)benzenesulfonamide, |
| 372 | 1-cyclobutyl-5-cyclopropyl-2-{4-[(1,1,1-trifluoro-2-methylpropan-2-yl)sulfamoyl]phenyl}-1H-pyrrolo[2,3-b]pyridine-3-carboxamide, |
| 373 | 1-cyclobutyl-5-cyclopropyl-2-(4-{[1-(trifluoromethyl)cyclopropyl]sulfamoyl}phenyl)-1H-pyrrolo[2,3-b]pyridine-3-carboxamide, |
| 374 | 1-cyclobutyl-5-cyclopropyl-2-(5-{[1-(trifluoromethyl)cyclopropyl]sulfamoyl}pyridin-2-yl)-1H-pyrrolo[2,3-b]pyridine-3-carboxamide, |
| 375 | 2-[4-(tert-butylsulfamoyl)phenyl]-1-cyclobutyl-5-cyclopropyl-1H-pyrrolo[2,3-b]pyridine-3-carboxamide |
| 376 | 2-[5-(tert-butylsulfamoyl)pyridin-2-yl]-1-cyclobutyl-5-cyclopropyl-1H-pyrrolo[2,3-b]pyridine-3-carboxamide, |
| 377 | 1-cyclobutyl-5-ethyl-2-(5-{[(2S)-1,1,1-trifluoropropan-2-yl]sulfamoyl}pyridin-2-yl)-1H-pyrrolo[2,3-b]pyridine-3-carboxamide, |
| 378 | 1-cyclobutyl-5-ethyl-2-{4-[(1,1,1-trifluoro-2-methylpropan-2-yl)sulfamoyl]phenyl}-1H-pyrrolo[2,3-b]pyridine-3-carboxamide, |
| 379 | 1-cyclobutyl-5-ethyl-2-(4-{[1-(trifluoromethyl)cyclopropyl]sulfamoyl}phenyl)-1H-pyrrolo[2,3-b]pyridine-3-carboxamide, |
| 380 | 1-cyclobutyl-5-ethyl-2-(5-{[1-(trifluoromethyl)cyclopropyl]sulfamoyl}pyridin-2-yl)-1H-pyrrolo[2,3-b]pyridine-3-carboxamide, |
| 381 | 2-[4-(tert-butylsulfamoyl)phenyl]-1-cyclobutyl-5-ethyl-1H-pyrrolo[2,3-b]pyridine-3-carboxamide, |
| 382 | 2-[5-(tert-butylsulfamoyl)pyridin-2-yl]-1-cyclobutyl-5-ethyl-1H-pyrrolo[2,3-b]pyridine-3-carboxamide, |
| 383 | 6-[3-cyano-5-methyl-1-(pyridazin-3-yl)-1H-pyrrolo[2,3-b]pyridin-2-yl]-N-[(2S)-1,1,1-trifluoropropan-2-yl]pyridine-3-sulfonamide, |
| 384 | 6-[3-cyano-5-methyl-1-(pyrimidin-5-yl)-1H-pyrrolo[2,3-b]pyridin-2-yl]-N-[(2S)-1,1,1-trifluoropropan-2-yl]pyridine-3-sulfonamide, |
| 385 | N-[4-(5-chloro-3-cyano-1-cyclobutyl-1H-pyrrolo[2,3-b]pyridin-2-yl)phenyl]-2-methylpropane-2-sulfonamide, |
| 386 | 1-cyclobutyl-5-(methylsulfanyl)-2-(5-{[(2S)-1,1,1-trifluoropropan-2-yl]sulfamoyl}pyridin-2-yl)-1H-pyrrolo[2,3-b]pyridine-3-carboxylic acid, |
| 387 | 2-{4-[(tert-butylsulfonyl)amino]phenyl}-1-cyclobutyl-5-(methylsulfanyl)-1H-pyrrolo[2,3-b]pyridine-3-carboxamide, |
| 388 | 1-cyclobutyl-2-{4-[(1,1,1-trifluoro-2-methylpropan-2-yl)sulfamoyl]phenyl}-1H-pyrrolo[2,3-b]pyridine-3-carboxamide, |
| 389 | 1-cyclobutyl-5-(methylsulfanyl)-2-(4-{[1-(trifluoromethyl)cyclopropyl]sulfamoyl}phenyl)-1H-pyrrolo[2,3-b]pyridine-3-carboxamide, |
| 390 | 1-cyclobutyl-5-(methylsulfanyl)-2-(4-{[1-(trifluoromethyl)cyclopropyl]sulfamoyl}phenyl)-1H-pyrrolo[2,3-b]pyridine-3-carboxylic acid, |
| 391 | 1-cyclobutyl-5-(methylsulfanyl)-2-{4-[(1,1,1-trifluoro-2-methylpropan-2-yl)sulfamoyl]phenyl}-1H-pyrrolo[2,3-b]pyridine-3-carboxamide, |
| 392 | 2-[4-(tert-butylsulfamoyl)phenyl]-1-cyclobutyl-5-(methylsulfanyl)-1H-pyrrolo[2,3-b]pyridine-3-carboxamide, |
| 393 | 2-[4-(tert-butylsulfamoyl)phenyl]-5-chloro-1-cyclobutyl-1H-pyrrolo[2,3-b]pyridine-3-carboxamide, |
| 394 | 6-[3-cyano-1-cyclobutyl-5-(methylamino)-1H-pyrrolo[2,3-b]pyridin-2-yl]-N-[(2S)-1,1,1-trifluoropropan-2-yl]pyridine-3-sulfonamide, |
| 395 | 6-[3-cyano-1-cyclobutyl-5-(trifluoromethyl)-1H-pyrrolo[2,3-b]pyridin-2-yl]-N-(1,1,1-trifluoro-2-methylpropan-2-yl)pyridine-3-sulfonamide, |
| 396 | 6-[3-cyano-1-cyclobutyl-5-(trifluoromethyl)-1H-pyrrolo[2,3-b]pyridin-2-yl]-N-[1-(trifluoromethyl)cyclopropyl]pyridine-3-sulfonamide, |
| 397 | 4-[3-cyano-1-cyclobutyl-5-(trifluoromethyl)-1H-pyrrolo[2,3-b]pyridin-2-yl]-N-[1-(trifluoromethyl)cyclopropyl]benzenesulfonamide, |
| 398 | 6-[3-cyano-1-cyclobutyl-5-(trifluoromethyl)-1H-pyrrolo[2,3-b]pyridin-2-yl]-N-(1-methylcyclopropyl)pyridine-3-sulfonamide, |
| 399 | 1-cyclobutyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide, |
| 400 | 1-cyclobutyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide, |
| 401 | 1-cyclobutyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide, |

| Cpd | Name |
|---|---|
| 402 | 1-cyclobutyl-5-(trifluoromethyl)-2-(4-{[1-(trifluoromethyl)cyclopropyl]sulfamoyl}phenyl)-1H-pyrrolo[2,3-b]pyridine-3-carboxamide, |
| 403 | 2-[4-(tert-butylsulfamoyl)phenyl]-1-cyclobutyl-5-(trifluoromethyl)-1H-pyrrolo[2,3-b]pyridine-3-carboxamide, |
| 404 | 2-{4-[(tert-butylsulfonyl)amino]phenyl}-1-cyclobutyl-5-(trifluoromethyl)-1H-pyrrolo[2,3-b]pyridine-3-carboxamide, |
| 405 | 6-[3-cyano-1-cyclobutyl-6-methyl-5-(trifluoromethyl)-1H-pyrrolo[2,3-b]pyridin-2-yl]-N-[(2S)-1,1,1-trifluoropropan-2-yl]pyridine-3-sulfonamide, |
| 406 | 1-cyclopentyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide, |
| 407 | 1-cyclopentyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide, |
| 408 | 1-cyclopentyl-5-(trifluoromethyl)-2-(4-{[1-(trifluoromethyl)cyclopropyl]sulfamoyl}phenyl)-1H-pyrrolo[2,3-b]pyridine-3-carboxamide, |
| 409 | 1-cyclopentyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide, |
| 410 | 1-cyclopentyl-5-methoxy-2-{5-[(1-methylcyclopropyl)sulfamoyl]pyridin-2-yl}-1H-pyrrolo[2,3-b]pyridine-3-carboxamide, |
| 411 | 6-[3-cyano-5-ethyl-1-(pyrazin-2-yl)-1H-pyrrolo[2,3-b]pyridin-2-yl]-N-[(2S)-1,1,1-trifluoropropan-2-yl]pyridine-3-sulfonamide, |
| 412 | 6-[3-cyano-5-ethyl-1-(4-fluoropyridin-2-yl)-1H-pyrrolo[2,3-b]pyridin-2-yl]-N-[(2S)-1,1,1-trifluoropropan-2-yl]pyridine-3-sulfonamide, |
| 413 | 6-(3-cyano-5-ethyl-1-phenyl-1H-pyrrolo[2,3-b]pyridin-2-yl)-N-[(2S)-1,1,1-trifluoropropan-2-yl]pyridine-3-sulfonamide, |
| 414 | 6-[3-cyano-5-ethyl-1-(pyridin-2-yl)-1H-pyrrolo[2,3-b]pyridin-2-yl]-N-[(2S)-1,1,1-trifluoropropan-2-yl]pyridine-3-sulfonamide, |
| 415 | 6-[3-cyano-1-cyclohexyl-5-(trifluoromethyl)-1H-pyrrolo[2,3-b]pyridin-2-yl]-N-[(2S)-1,1,1-trifluoropropan-2-yl]pyridine-3-sulfonamide, |
| 416 | 4-[3-cyano-1-cyclohexyl-5-(trifluoromethyl)-1H-pyrrolo[2,3-b]pyridin-2-yl]-N-[(2S)-1,1,1-trifluoropropan-2-yl]benzenesulfonamide, |
| 417 | 6-[3-cyano-1-cyclohexyl-5-(trifluoromethyl)-1H-pyrrolo[2,3-b]pyridin-2-yl]-N-(1,1,1-trifluoro-2-methylpropan-2-yl)pyridine-3-sulfonamide, |
| 418 | 4-[3-cyano-1-cyclohexyl-5-(trifluoromethyl)-1H-pyrrolo[2,3-b]pyridin-2-yl]-N-(1,1,1-trifluoro-2-methylpropan-2-yl)benzenesulfonamide, |
| 419 | 6-[3-cyano-1-cyclohexyl-5-(trifluoromethyl)-1H-pyrrolo[2,3-b]pyridin-2-yl]-N-[1-(trifluoromethyl)cyclopropyl]pyridine-3-sulfonamide, |
| 420 | 4-[3-cyano-1-cyclohexyl-5-(trifluoromethyl)-1H-pyrrolo[2,3-b]pyridin-2-yl]-N-[1-(trifluoromethyl)cyclopropyl]benzenesulfonamide, |
| 421 | 4-[3-cyano-1-cyclohexyl-5-(trifluoromethyl)-1H-pyrrolo[2,3-b]pyridin-2-yl]-N-(1-methylcyclopropyl)benzenesulfonamide, |
| 422 | N-tert-butyl-4-[3-cyano-1-cyclohexyl-5-(trifluoromethyl)-1H-pyrrolo[2,3-b]pyridin-2-yl]benzenesulfonamide, |
| 423 | 4-[3-cyano-1-cyclohexyl-5-(trifluoromethyl)-1H-pyrrolo[2,3-b]pyridin-2-yl]-N-[(2R)-1,1,1-trifluoropropan-2-yl]benzenesulfonamide, |
| 424 | N-{4-[3-cyano-1-cyclohexyl-5-(trifluoromethyl)-1H-pyrrolo[2,3-b]pyridin-2-yl]phenyl}-2-methylpropane-2-sulfonamide, |
| 425 | N-{4-[3-cyano-1-cyclohexyl-5-(trifluoromethyl)-1H-pyrrolo[2,3-b]pyridin-2-yl]phenyl}propane-2-sulfonamide, |
| 426 | N-{4-[3-cyano-1-cyclohexyl-5-(trifluoromethyl)-1H-pyrrolo[2,3-b]pyridin-2-yl]phenyl}-1-methylcyclopropanesulfonamide, |
| 427 | N-{4-[3-cyano-1-cyclohexyl-5-(trifluoromethyl)-1H-pyrrolo[2,3-b]pyridin-2-yl]phenyl}cyclopropanesulfonamide, |
| 428 | N-{4-[3-cyano-1-cyclohexyl-5-(trifluoromethyl)-1H-pyrrolo[2,3-b]pyridin-2-yl]phenyl}cyclobutanesulfonamide, |
| 429 | 6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 430 | 6-[3-cyano-5-methyl-1-(1,3-thiazol-5-yl)-1H-pyrrolo[2,3-b]pyridin-2-yl]-N-[(2S)-1,1,1-trifluoropropan-2-yl]pyridine-3-sulfonamide, |
| 431 | 6-[3-cyano-5-methyl-1-(pyrimidin-4-yl)-1H-pyrrolo[2,3-b]pyridin-2-yl]-N-[(2S)-1,1,1-trifluoropropan-2-yl]pyridine-3-sulfonamide, |
| 432 | 6-[3-cyano-1-(5-fluoropyridin-2-yl)-5-methyl-1H-pyrrolo[2,3-b]pyridin-2-yl]-N-[(2S)-1,1,1-trifluoropropan-2-yl]pyridine-3-sulfonamide, |
| 433 | 6-{3-cyano-5-methyl-1-[4-(trifluoromethyl)pyridin-2-yl]-1H-pyrrolo[2,3-b]pyridin-2-yl}-N-[(2S)-1,1,1-trifluoropropan-2-yl]pyridine-3-sulfonamide, |
| 434 | 6-[1-(4-aminopyridin-2-yl)-3-cyano-5-methyl-1H-pyrrolo[2,3-b]pyridin-2-yl]-N-[(2S)-1,1,1-trifluoropropan-2-yl]pyridine-3-sulfonamide, |
| 435 | 6-[1-(5-bromopyrimidin-2-yl)-3-cyano-5-methyl-1H-pyrrolo[2,3-b]pyridin-2-yl]-N-[(2S)-1,1,1-trifluoropropan-2-yl]pyridine-3-sulfonamide, |
| 436 | 6-[3-cyano-5-methyl-1-(pyridazin-4-yl)-1H-pyrrolo[2,3-b]pyridin-2-yl]-N-[(2S)-1,1,1-trifluoropropan-2-yl]pyridine-3-sulfonamide, |
| 437 | 1-cyclohexyl-5-(trifluoromethyl)-2-(4-{[(2S)-1,1,1-trifluoropropan-2-yl]sulfamoyl}phenyl)-1H-pyrrolo[2,3-b]pyridine-3-carboxamide, |
| 438 | 1-cyclohexyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide, |
| 439 | 1-cyclohexyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide, |
| 440 | 1-cyclohexyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide, |
| 441 | 1-cyclohexyl-5-(trifluoromethyl)-2-(4-{[1-(trifluoromethyl)cyclopropyl]sulfamoyl}phenyl)-1H-pyrrolo[2,3-b]pyridine-3-carboxamide, |
| 442 | 1-cyclohexyl-2-{4-[(1-methylcyclopropyl)sulfonyl]phenyl}-5-(trifluoromethyl)-1H-pyrrolo[2,3-b]pyridine-3-carboxamide, |
| 443 | 2-[4-(tert-butylsulfamoyl)phenyl]-1-cyclohexyl-5-(trifluoromethyl)-1H-pyrrolo[2,3-b]pyridine-3-carboxamide, |
| 444 | 1-cyclohexyl-5-(trifluoromethyl)-2-(4-{[(2R)-1,1,1-trifluoropropan-2-yl]sulfamoyl}phenyl)-1H-pyrrolo[2,3-b]pyridine-3-carboxamide, |
| 445 | 2-{4-[(tert-butylsulfonyl)amino]phenyl}-1-cyclohexyl-5-(trifluoromethyl)-1H-pyrrolo[2,3-b]pyridine-3-carboxamide, |
| 446 | 1-cyclohexyl-2-{4-[(propan-2-ylsulfonyl)amino]phenyl}-5-(trifluoromethyl)-1H-pyrrolo[2,3-b]pyridine-3-carboxamide, |
| 447 | 1-cyclohexyl-2-(4-{[(1-methylcyclopropyl)sulfonyl]amino}phenyl)-5-(trifluoromethyl)-1H-pyrrolo[2,3-b]pyridine-3-carboxamide, |
| 448 | 1-cyclohexyl-2-{4-[(cyclopropylsulfonyl)amino]phenyl}-5-(trifluoromethyl)-1H-pyrrolo[2,3-b]pyridine-3-carboxamide, |
| 449 | 2-{4-[(cyclobutylsulfonyl)amino]phenyl}-1-cyclohexyl-5-(trifluoromethyl)-1H-pyrrolo[2,3-b]pyridine-3-carboxamide, |
| 450 | 6-[3-cyano-5-methyl-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 451 | 6-[3-cyano-1-(5-isocyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide, |
| 452 | 6-[3-cyano-1-cyclobutyl-5-(difluoromethyl)-1H-pyrrolo[2,3-b]pyridin-2-yl]-N-[(2S)-1,1,1-trifluoropropan-2-yl]pyridine-3-sulfonamide, |
| 453 | 4-[3-cyano-1-cyclobutyl-5-(difluoromethyl)-1H-pyrrolo[2,3-b]pyridin-2-yl]-N-[(2S)-1,1,1-trifluoropropan-2-yl]benzenesulfonamide, |
| 454 | 2-[3-cyano-1-cyclobutyl-5-(difluoromethyl)-1H-pyrrolo[2,3-b]pyridin-2-yl]-N-[(2S)-1,1,1-trifluoropropan-2-yl]pyrimidine-5-sulfonamide, |
| 455 | 6-[3-cyano-1-cyclobutyl-5-(difluoromethyl)-1H-pyrrolo[2,3-b]pyridin-2-yl]-N-(propan-2-yl)pyridine-3-sulfonamide, |
| 456 | 6-[3-cyano-1-cyclobutyl-5-(difluoromethyl)-1H-pyrrolo[2,3-b]pyridin-2-yl]-N-(1,1,1-trifluoro-2-methylpropan-2-yl)pyridine-3-sulfonamide, |
| 457 | 6-[3-cyano-1-cyclobutyl-5-(difluoromethyl)-1H-pyrrolo[2,3-b]pyridin-2-yl]-N-[1-(trifluoromethyl)cyclopropyl]pyridine-3-sulfonamide, |
| 458 | 6-[3-cyano-1-cyclobutyl-5-(difluoromethyl)-1H-pyrrolo[2,3-b]pyridin-2-yl]-N-[(1S)-1-cyclopropylethyl]pyridine-3-sulfonamide, |
| 459 | N-{4-[3-cyano-1-cyclobutyl-5-(difluoromethyl)-1H-pyrrolo[2,3-b]pyridin-2-yl]phenyl}propane-2-sulfonamide, |
| 460 | N-{4-[3-cyano-1-cyclobutyl-5-(difluoromethyl)-1H-pyrrolo[2,3-b]pyridin-2-yl]phenyl}cyclopropanesulfonamide, |

| Cpd | Name |
|---|---|
| 461 | 6-[3-cyano-5-fluoro-1-(4-fluoropyridin-2-yl)-1H-pyrrolo[2,3-b]pyridin-2-yl]-N-[(2S)-1,1,1-trifluoropropan-2-yl]pyridine-3-sulfonamide, |
| 462 | 6-[3-cyano-5-fluoro-1-(5-fluoropyrimidin-2-yl)-1H-pyrrolo[2,3-b]pyridin-2-yl]-N-[(2S)-1,1,1-trifluoropropan-2-yl]pyridine-3-sulfonamide, |
| 463 | 6-[3-cyano-6-methyl-1-(pyrazin-2-yl)-1H-pyrrolo[3,2-b]pyridin-2-yl]-N-[(2S)-1,1,1-trifluoropropan-2-yl]pyridine-3-sulfonamide, |
| 464 | 6-[3-cyano-6-methyl-1-(pyrimidin-5-yl)-1H-pyrrolo[3,2-b]pyridin-2-yl]-N-[(2S)-1,1,1-trifluoropropan-2-yl]pyridine-3-sulfonamide, |
| 465 | 6-[3-cyano-6-methyl-1-(pyridin-2-yl)-1H-pyrrolo[3,2-b]pyridin-2-yl]-N-[(2S)-1,1,1-trifluoropropan-2-yl]pyridine-3-sulfonamide, |
| 466 | 6-[3-cyano-6-methyl-1-(pyridin-3-yl)-1H-pyrrolo[3,2-b]pyridin-2-yl]-N-[(2S)-1,1,1-trifluoropropan-2-yl]pyridine-3-sulfonamide, |
| 467 | 6-[3-cyano-1-(5-fluoropyridin-2-yl)-6-methyl-1H-pyrrolo[3,2-b]pyridin-2-yl]-N-[(2S)-1,1,1-trifluoropropan-2-yl]pyridine-3-sulfonamide, |
| 468 | 6-[3-cyano-6-methyl-1-(1,3-thiazol-4-yl)-1H-pyrrolo[3,2-b]pyridin-2-yl]-N-[(2S)-1,1,1-trifluoropropan-2-yl]pyridine-3-sulfonamide, |
| 469 | 1-cyclobutyl-5-(difluoromethyl)-2-(5-{[(2S)-1,1,1-trifluoropropan-2-yl]sulfamoyl}pyridin-2-yl)-1H-pyrrolo[2,3-b]pyridine-3-carboxamide, |
| 470 | 1-cyclobutyl-5-(difluoromethyl)-2-(5-{[(2S)-1,1,1-trifluoropropan-2-yl]sulfamoyl}pyrimidin-2-yl)-1H-pyrrolo[2,3-b]pyridine-3-carboxamide, |
| 471 | 1-cyclobutyl-5-(difluoromethyl)-2-{5-[(1,1,1-trifluoro-2-methylpropan-2-yl)sulfamoyl]pyridin-2-yl}-1H-pyrrolo[2,3-b]pyridine-3-carboxamide, |
| 472 | 1-cyclobutyl-5-(difluoromethyl)-2-(5-{[1-(trifluoromethyl)cyclopropyl]sulfamoyl}pyridin-2-yl)-1H-pyrrolo[2,3-b]pyridine-3-carboxamide, |
| 473 | 6-[3-cyano-5-ethyl-1-(5-fluoropyrimidin-2-yl)-1H-pyrrolo[2,3-b]pyridin-2-yl]-N-[(2S)-1,1,1-trifluoropropan-2-yl]pyridine-3-sulfonamide, |
| 474 | 6-[3-cyano-5-ethyl-1-(5-fluoropyridin-2-yl)-1H-pyrrolo[2,3-b]pyridin-2-yl]-N-[(2S)-1,1,1-trifluoropropan-2-yl]pyridine-3-sulfonamide, |
| 475 | 6-[3-cyano-6-methyl-1-(pyrimidin-2-yl)-1H-pyrrolo[3,2-b]pyridin-2-yl]-N-[(2S)-1,1,1-trifluoropropan-2-yl]pyridine-3-sulfonamide, |
| 476 | 6-(3-cyano-6-methyl-1-phenyl-1H-pyrrolo[3,2-b]pyridin-2-yl)-N-[(2S)-1,1,1-trifluoropropan-2-yl]pyridine-3-sulfonamide, |
| 477 | 6-[3-cyano-6-methyl-1-(1,3-thiazol-2-yl)-1H-pyrrolo[3,2-b]pyridin-2-yl]-N-[(2S)-1,1,1-trifluoropropan-2-yl]pyridine-3-sulfonamide, |
| 478 | 6-[3-cyano-6-methyl-1-(1,3-thiazol-5-yl)-1H-pyrrolo[3,2-b]pyridin-2-yl]-N-[(2S)-1,1,1-trifluoropropan-2-yl]pyridine-3-sulfonamide, |
| 479 | 6-{3-cyano-6-methyl-1-[4-(trifluoromethyl)pyridin-2-yl]-1H-pyrrolo[3,2-b]pyridin-2-yl}-N-[(2S)-1,1,1-trifluoropropan-2-yl]pyridine-3-sulfonamide, |
| 480 | 6-[3-cyano-6-methyl-1-(pyridazin-4-yl)-1H-pyrrolo[3,2-b]pyridin-2-yl]-N-[(2S)-1,1,1-trifluoropropan-2-yl]pyridine-3-sulfonamide, |
| 481 | 6-[3-cyano-6-methyl-1-(pyrimidin-4-yl)-1H-pyrrolo[3,2-b]pyridin-2-yl]-N-[(2S)-1,1,1-trifluoropropan-2-yl]pyridine-3-sulfonamide, |
| 482 | 6-[3-cyano-6-methyl-1-(pyridin-4-yl)-1H-pyrrolo[3,2-b]pyridin-2-yl]-N-[(2S)-1,1,1-trifluoropropan-2-yl]pyridine-3-sulfonamide, |
| 483 | 4-(3-cyano-1,5-dimethyl-1H-pyrrolo[2,3-b]pyridin-2-yl)-N-[(2S)-1,1,1-trifluoropropan-2-yl]benzenesulfonamide, |
| 484 | 4-(3-cyano-1-ethyl-5-methyl-1H-pyrrolo[2,3-b]pyridin-2-yl)-N-[(2S)-1,1,1-trifluoropropan-2-yl]benzenesulfonamide, |
| 485 | 4-(3-cyano-5-methyl-1-propyl-1H-pyrrolo[2,3-b]pyridin-2-yl)-N-[(2S)-1,1,1-trifluoropropan-2-yl]benzenesulfonamide, |
| 486 | 4-[3-cyano-5-methyl-1-(propan-2-yl)-1H-pyrrolo[2,3-b]pyridin-2-yl]-N-[(2S)-1,1,1-trifluoropropan-2-yl]benzenesulfonamide, |
| 487 | 4-[3-cyano-1-(cyclopropylmethyl)-5-methyl-1H-pyrrolo[2,3-b]pyridin-2-yl]-N-[(2S)-1,1,1-trifluoropropan-2-yl]benzenesulfonamide, |
| 488 | 4-[3-cyano-5-methyl-1-(2-methylpropyl)-1H-pyrrolo[2,3-b]pyridin-2-yl]-N-[(2S)-1,1,1-trifluoropropan-2-yl]benzenesulfonamide, |
| 489 | 4-[3-cyano-1-(cyclobutylmethyl)-5-methyl-1H-pyrrolo[2,3-b]pyridin-2-yl]-N-[(2S)-1,1,1-trifluoropropan-2-yl]benzenesulfonamide, |
| 490 | 6-(3-cyano-1,5-dimethyl-1H-pyrrolo[2,3-b]pyridin-2-yl)-N-[(2S)-1,1,1-trifluoropropan-2-yl]pyridine-3-sulfonamide, |
| 491 | 6-(3-cyano-1-ethyl-5-methyl-1H-pyrrolo[2,3-b]pyridin-2-yl)-N-[(2S)-1,1,1-trifluoropropan-2-yl]pyridine-3-sulfonamide, |
| 492 | 6-(3-cyano-5-methyl-1-propyl-1H-pyrrolo[2,3-b]pyridin-2-yl)-N-[(2S)-1,1,1-trifluoropropan-2-yl]pyridine-3-sulfonamide, |
| 493 | 6-[3-cyano-5-methyl-1-(propan-2-yl)-1H-pyrrolo[2,3-b]pyridin-2-yl]-N-[(2S)-1,1,1-trifluoropropan-2-yl]pyridine-3-sulfonamide, |
| 494 | 6-[3-cyano-1-(cyclopropylmethyl)-5-methyl-1H-pyrrolo[2,3-b]pyridin-2-yl]-N-[(2S)-1,1,1-trifluoropropan-2-yl]pyridine-3-sulfonamide, |
| 495 | 6-[3-cyano-5-methyl-1-(2-methylpropyl)-1H-pyrrolo[2,3-b]pyridin-2-yl]-N-[(2S)-1,1,1-trifluoropropan-2-yl]pyridine-3-sulfonamide |
| 496 | 6-[3-cyano-1-(cyclobutylmethyl)-5-methyl-1H-pyrrolo[2,3-b]pyridin-2-yl]-N-[(2S)-1,1,1-trifluoropropan-2-yl]pyridine-3-sulfonamide, |
| 497 | 6-[3-cyano-1-cyclobutyl-5-(dimethylamino)-1H-pyrrolo[2,3-b]pyridin-2-yl]-N-[(2S)-1,1,1-trifluoropropan-2-yl]pyridine-3-sulfonamide, |
| 498 | N-{4-[3-cyano-1-cyclobutyl-5-(dimethylamino)-1H-pyrrolo[2,3-b]pyridin-2-yl]phenyl}-2-methylpropane-2-sulfonamide, |
| 499 | N-{4-[3-cyano-1-cyclobutyl-5-(dimethylamino)-1H-pyrrolo[2,3-b]pyridin-2-yl]phenyl}-1-methylcyclopropanesulfonamide, |
| 500 | 4-[3-cyano-1-cyclobutyl-5-(dimethylamino)-1H-pyrrolo[2,3-b]pyridin-2-yl]-N-[(2S)-1,1,1-trifluoropropan-2-yl]benzenesulfonamide, |
| 501 | 6-[3-cyano-1-(2-fluorophenyl)-5-methyl-1H-pyrrolo[2,3-b]pyridin-2-yl]-N-[(2S)-1,1,1-trifluoropropan-2-yl]pyridine-3-sulfonamide, |
| 502 | 6-[3-cyano-1-(3-fluorophenyl)-5-methyl-1H-pyrrolo[2,3-b]pyridin-2-yl]-N-[(2S)-1,1,1-trifluoropropan-2-yl]pyridine-3-sulfonamide, |
| 503 | 6-[3-cyano-1-(4-fluorophenyl)-5-methyl-1H-pyrrolo[2,3-b]pyridin-2-yl]-N-[(2S)-1,1,1-trifluoropropan-2-yl]pyridine-3-sulfonamide |
| 504 | 6-[3-cyano-1-(2,5-difluorophenyl)-5-methyl-1H-pyrrolo[2,3-b]pyridin-2-yl]-N-[(2S)-1,1,1-trifluoropropan-2-yl]pyridine-3-sulfonamide, |
| 505 | 6-[3-cyano-1-(3,4-difluorophenyl)-5-methyl-1H-pyrrolo[2,3-b]pyridin-2-yl]-N-[(2S)-1,1,1-trifluoropropan-2-yl]pyridine-3-sulfonamide, |
| 506 | 6-[3-cyano-1-(3,5-difluorophenyl)-5-methyl-1H-pyrrolo[2,3-b]pyridin-2-yl]-N-[(2S)-1,1,1-trifluoropropan-2-yl]pyridine-3-sulfonamide, |
| 507 | 6-[3-cyano-5-methyl-1-(1,3-thiazol-4-yl)-1H-pyrrolo[2,3-b]pyridin-2-yl]-N-[(2S)-1,1,1-trifluoropropan-2-yl]pyridine-3-sulfonamide, |
| 508 | 6-[3-cyano-1-(6-cyanopyrimidin-4-yl)-5-methyl-1H-pyrrolo[2,3-b]pyridin-2-yl]-N-[(2S)-1,1,1-trifluoropropan-2-yl]pyridine-3-sulfonamide, |
| 509 | 6-[3-cyano-5-ethyl-1-(thiophen-2-yl)-1H-pyrrolo[2,3-b]pyridin-2-yl]-N-[(2S)-1,1,1-trifluoropropan-2-yl]pyridine-3-sulfonamide, |
| 510 | 6-[3-cyano-5-ethyl-1-(4-fluorophenyl)-1H-pyrrolo[2,3-b]pyridin-2-yl]-N-[(2S)-1,1,1-trifluoropropan-2-yl]pyridine-3-sulfonamide, |
| 511 | 6-[3-cyano-5-ethyl-1-(3-fluorophenyl)-1H-pyrrolo[2,3-b]pyridin-2-yl]-N-[(2S)-1,1,1-trifluoropropan-2-yl]pyridine-3-sulfonamide, |
| 512 | 6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 513 | 6-[3-cyano-1-cyclobutyl-5-(trifluoromethyl)-1H-pyrrolo[2,3-b]pyridin-2-yl]-N-[(2-deuterium)propan-2-yl]pyridine-3-sulfonamide, |
| 514 | 6-[3-cyano-1-(4-cyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide, |
| 515 | N-tert-butyl-6-[5-chloro-3-cyano-1-(1,3-thiazol-2-yl)-1H-pyrrolo[2,3-b]pyridin-2-yl]pyridine-3-sulfonamide, |
| 516 | N-tert-butyl-6-[3-cyano-1-phenyl-5-(trifluoromethyl)-1H-pyrrolo[2,3-b]pyridin-2-yl]pyridine-3-sulfonamide, |
| 517 | N-tert-butyl-6-[3-cyano-1-(4-fluorophenyl)-5-(trifluoromethyl)-1H-pyrrolo[2,3-b]pyridin-2-yl]pyridine-3-sulfonamide, |
| 518 | N-tert-butyl-6-[3-cyano-1-(pyridin-2-yl)-5-(trifluoromethyl)-1H-pyrrolo[2,3-b]pyridin-2-yl]pyridine-3-sulfonamide, |
| 519 | N-tert-butyl-6-(3-cyano-5-fluoro-1-phenyl-1H-pyrrolo[2,3-b]pyridin-2-yl)pyridine-3-sulfonamide, |
| 520 | N-tert-butyl-6-[3-cyano-5-fluoro-1-(4-fluorophenyl)-1H-pyrrolo[2,3-b]pyridin-2-yl]pyridine-3-sulfonamide, |
| 521 | N-tert-butyl-6-[3-cyano-5-fluoro-1-(pyrazin-2-yl)-1H-pyrrolo[2,3-b]pyridin-2-yl]pyridine-3-sulfonamide, |
| 522 | N-tert-butyl-6-[3-cyano-5-fluoro-1-(pyridin-2-yl)-1H-pyrrolo[2,3-b]pyridin-2-yl]pyridine-3-sulfonamide, |
| 523 | 2-[5-(tert-butylsulfamoyl)pyridin-2-yl]-1-phenyl-5-(trifluoromethyl)-1H-pyrrolo[2,3-b]pyridine-3-carboxamide, |

| Cpd | Name |
|---|---|
| 524 | N-tert-butyl-6-(3-cyano-5-methyl-1-phenyl-1H-pyrrolo[2,3-b]pyridin-2-yl)pyridine-3-sulfonamide, |
| 525 | N-tert-butyl-6-[3-cyano-5-methyl-1-(pyridin-2-yl)-1H-pyrrolo[2,3-b]pyridin-2-yl]pyridine-3-sulfonamide, |
| 526 | N-tert-butyl-6-[3-cyano-1-(pyrazin-2-yl)-5-(trifluoromethyl)-1H-pyrrolo[2,3-b]pyridin-2-yl]pyridine-3-sulfonamide or |
| 527 | 2-[5-(tert-butylsulfamoyl)pyridin-2-yl]-5-fluoro-1-phenyl-1H-pyrrolo[2,3-b]pyridine-3-carboxamide. |

In another embodiment of the present invention, a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a free acid, free base, salt, hydrate, solvate, clathrate, isotopologue, racemate, enantiomer, diastereomer, stereoisomer or polymorph form thereof is selected from:

| Cpd | Name |
|---|---|
| 10 | 6-(5-chloro-3-cyano-1-cyclopentyl-1H-pyrrolo[2,3-b]pyridin-2-yl)-N-(1,3-difluoropropan-2-yl)pyridine-3-sulfonamide, |
| 14 | 6-(5-chloro-3-cyano-1-cyclobutyl-1H-pyrrolo[2,3-b]pyridin-2-yl)-N-(1,3-difluoropropan-2-yl)pyridine-3-sulfonamide, |
| 22 | 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide, |
| 24 | 6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide, |
| 32 | 2-(3-cyano-1-cyclobutyl-6-methyl-1H-pyrrolo[3,2-c]pyridin-2-yl)-N-(propan-2-yl)pyrimidine-5-sulfonamide, |
| 37 | 2-(3-cyano-1-cyclobutyl-5-fluoro-1H-pyrrolo[2,3-b]pyridin-2-yl)-N-(propan-2-yl)pyrimidine-5-sulfonamide, |
| 42 | 2-(3-cyano-1-cyclobutyl-6-methoxy-1H-pyrrolo[2,3-b]pyridin-2-yl)-N-(1,3-difluoropropan-2-yl)pyrimidine-5-sulfonamide, |
| 45 | 6-(5-cyano-7-cyclobutyl-2-methyl-7H-pyrrolo[2,3-d]pyrimidin-6-yl)-N-[(1S)-1-cyclopropylethyl]pyridine-3-sulfonamide, |
| 51 | 6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide, |
| 52 | N-tert-butyl-6-(5-chloro-3-cyano-1-cyclobutyl-1H-pyrrolo[2,3-b]pyridin-2-yl)pyridine-3-sulfonamide, |
| 58 | 2-(5-chloro-3-cyano-1-cyclobutyl-1H-pyrrolo[2,3-b]pyridin-2-yl)-N-(propan-2-yl)pyrimidine-5-sulfonamide, |
| 69 | 6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide, |
| 90 | 4-(3-cyano-1-cyclobutyl-6-methyl-1H-pyrrolo[2,3-b]pyridin-2-yl)-N-[(2S)-1,1,1-trifluoropropan-2-yl]benzenesulfonamide, |
| 104 | 6-(5-chloro-3-cyano-1-cyclobutyl-1H-pyrrolo[2,3-c]pyridin-2-yl)-N-[(2R)-1,1,1-trifluoropropan-2-yl]pyridine-3-sulfonamide, |
| 128 | 6-(3-cyano-1-cyclobutyl-5-cyclopropyl-1H-pyrrolo[2,3-b]pyridin-2-yl)-N-(1-methylcyclopropyl)pyridine-3-sulfonamide, |
| 131 | 6-(3-cyano-1-cyclobutyl-5-cyclopropyl-1H-pyrrolo[2,3-b]pyridin-2-yl)-N-(1,3-difluoropropan-2-yl)pyridine-3-sulfonamide, |
| 148 | 6-(3-cyano-1-cyclobutyl-6-methyl-1H-pyrrolo[2,3-b]pyridin-2-yl)-N-cyclobutylpyridine-3-sulfonamide, |
| 157 | 6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide, |
| 158 | 6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide, |
| 170 | 6-(3-cyano-1-cyclopentyl-6-methyl-1H-pyrrolo[3,2-b]pyridin-2-yl)-N-[(2S)-1,1,1-trifluoropropan-2-yl]pyridine-3-sulfonamide, |
| 171 | 6-(3-cyano-1-cyclopentyl-6-methyl-1H-pyrrolo[3,2-b]pyridin-2-yl)-N-[(2R)-1,1,1-trifluoropropan-2-yl]pyridine-3-sulfonamide, |
| 172 | 6-(3-cyano-1-cyclopentyl-6-methyl-1H-pyrrolo[3,2-b]pyridin-2-yl)-N-[1-(trifluoromethyl)cyclopropyl]pyridine-3-sulfonamide, |
| 191 | 6-(3-cyano-1-cyclobutyl-5-ethyl-1H-pyrrolo[2,3-b]pyridin-2-yl)-N-(1,3-difluoropropan-2-yl)pyridine-3-sulfonamide, |
| 197 | 6-[3-cyano-1-cyclobutyl-5-(difluoromethoxy)-1H-pyrrolo[2,3-b]pyridin-2-yl]-N-[(2R)-1,1,1-trifluoropropan-2-yl]pyridine-3-sulfonamide, |
| 206 | 6-(3-cyano-1-cyclobutyl-6-methyl-1H-pyrrolo[3,2-b]pyridin-2-yl)-N-[(2S)-1,1,1-trifluoropropan-2-yl]pyridine-3-sulfonamide, |
| 232 | 6-(3-cyano-1-cyclobutyl-5-methoxy-1H-pyrrolo[2,3-b]pyridin-2-yl)-N-[(2S)-1,1,1-trifluorobutan-2-yl]pyridine-3-sulfonamide, |
| 270 | 6-[5-chloro-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide, |
| 285 | 2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide, |
| 303 | 6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 320 | 6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide, |
| 321 | 6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide, |
| 325 | 5-chloro-1-cyclobutyl-2-(5-{[1-(trifluoromethyl)cyclopropyl]sulfamoyl}pyridin-2-yl)-1H-pyrrolo[2,3-b]pyridine-3-carboxamide, |
| 326 | 5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxamide, |
| 335 | N-tert-butyl-4-[3-cyano-1-(pyrazin-2-yl)-5-(trifluoromethyl)-1H-pyrrolo[2,3-b]pyridin-2-yl]benzenesulfonamide, |
| 344 | 6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide, |
| 383 | 6-[3-cyano-5-methyl-1-(pyridazin-3-yl)-1H-pyrrolo[2,3-b]pyridin-2-yl]-N-[(2S)-1,1,1-trifluoropropan-2-yl]pyridine-3-sulfonamide, |
| 401 | 1-cyclobutyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide, |
| 429 | 6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 475 | 6-[3-cyano-6-methyl-1-(pyrimidin-2-yl)-1H-pyrrolo[3,2-b]pyridin-2-yl]-N-[(2S)-1,1,1-trifluoropropan-2-yl]pyridine-3-sulfonamide, |
| 512 | 6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 518 | N-tert-butyl-6-[3-cyano-1-(pyridin-2-yl)-5-(trifluoromethyl)-1H-pyrrolo[2,3-b]pyridin-2-yl]pyridine-3-sulfonamide or |
| 526 | N-tert-butyl-6-[3-cyano-1-(pyrazin-2-yl)-5-(trifluoromethyl)-1H-pyrrolo[2,3-b]pyridin-2-yl]pyridine-3-sulfonamide. |

In another embodiment of the present invention, a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a free acid, free base, salt, hydrate, solvate, clathrate, isotopologue, racemate, enantiomer, diastereomer, stereoisomer or polymorph form thereof is selected from:

| Cpd | Name |
|---|---|
| 22 | 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide, |
| 24 | 6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide, |
| 37 | 2-(3-cyano-1-cyclobutyl-5-fluoro-1H-pyrrolo[2,3-b]pyridin-2-yl)-N-(propan-2-yl)pyrimidine-5-sulfonamide, |
| 51 | 6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide, |
| 69 | 6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide, |
| 104 | 6-(5-chloro-3-cyano-1-cyclobutyl-1H-pyrrolo[2,3-c]pyridin-2-yl)-N-[(2R)-1,1,1-trifluoropropan-2-yl]pyridine-3-sulfonamide, |
| 157 | 6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide, |
| 158 | 6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide, |
| 170 | 6-(3-cyano-1-cyclopentyl-6-methyl-1H-pyrrolo[3,2-b]pyridin-2-yl)-N-[(2S)-1,1,1-trifluoropropan-2-yl]pyridine-3-sulfonamide, |

| Cpd | Name |
|---|---|
| 172 | 6-[3-cyano-1-cyclopentyl-6-methyl-1H-pyrrolo[3,2-b]pyridin-2-yl)-N-[1-(trifluoromethyl)cyclopropyl]pyridine-3-sulfonamide, |
| 285 | 2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide, |
| 303 | 6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, |
| 320 | 6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide, |
| 321 | 6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide, |
| 335 | N-tert-butyl-4-[3-cyano-1-(pyrazin-2-yl)-5-(trifluoromethyl)-1H-pyrrolo[2,3-b]pyridin-2-yl]benzenesulfonamide, |
| 344 | 6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide, |
| 429 | 6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 512 | 6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide, |
| 518 | N-tert-butyl-6-[3-cyano-1-(pyridin-2-yl)-5-(trifluoromethyl)-1H-pyrrolo[2,3-b]pyridin-2-yl]pyridine-3-sulfonamide or |
| 526 | N-tert-butyl-6-[3-cyano-1-(pyrazin-2-yl)-5-(trifluoromethyl)-1H-pyrrolo[2,3-b]pyridin-2-yl]pyridine-3-sulfonamide. |

Chemical Definitions

The chemical terms used above and throughout the description of the invention, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-4}$alkyl and the like. A $C_{1-8}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indole, indazolyl, isoindolyl, benzofuranyl, benzothienyl, benzimidazolyl, benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical may be optionally substituted on a carbon or nitrogen atom ring member where allowed by available valences.

As used herein, the term "$C_{2-8}$alkenyl-$C_{1-8}$alkyl" refers to a radical of the formula: —$C_{1-8}$alkyl-$C_{2-8}$alkenyl.

As used herein, the term "$C_{1-8}$alkoxy-$C_{1-8}$alkyl" refers to a radical of the formula: —$C_{1-8}$alkyl-O—$C_{1-8}$alkyl As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl or —O—$C_{1-8}$alkyl-N($C_{1-8}$alkyl-O—$C_{1-8}$alkyl)$_2$.

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl or —N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl or —$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl or —$C_{1-8}$alkyl-N($C_{1-8}$alkyl)$_2$.

As used herein, the term "$C_{1-8}$alkyl-amino-$C_{1-8}$alkyl-amino-$C_{1-8}$alkoxy" refers to a radical of the formula: —O—$C_{1-8}$alkyl-NH—$C_{1-8}$alkyl-NH—$C_{1-8}$alkyl or —O—$C_{1-8}$alkyl-N($C_{1-8}$alkyl-NH—$C_{1-8}$alkyl)$_2$.

As used herein, the term "$C_{1-8}$alkyl-amino-carbonyl" refers to a radical of the formula: —C(O)—NH—$C_{1-8}$alkyl or —C(O)—N($C_{1-8}$alkyl)$_2$.

As used herein, the term "$C_{1-8}$alkyl-amino-carbonyl-amino" refers to a radical of the formula: —NH—C(O)—NH—$C_{1-8}$alkyl or —NH—C(O)—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "(aryl-$C_{1-8}$alkyl)($C_{1-8}$alkyl)amino" refers to a radical of the formula: —N(aryl-$C_{1-8}$alkyl)($C_{1-8}$alkyl).

As used herein, the term "$C_{1-8}$alkyl-carbonyloxy" refers to a radical of the formula: —O—C(O)—$C_{1-8}$alkyl.

As used herein, the term "$C_{1-8}$alkyl-carbonyloxy-$C_{1-8}$alkoxy" refers to a radical of the formula: —O—$C_{1-8}$alkyl-O—C(O)—$C_{1-8}$alkyl.

As used herein, the term "$C_{1-8}$alkyl-carbonyloxy-$C_{1-8}$alkyl" refers to a radical of the formula: —$C_{1-8}$alkyl-O—C(O)—$C_{1-8}$alkyl.

As used herein, the term "$C_{1-8}$alkyl-sulfinyl" refers to a radical of the formula: —SO—$C_{1-8}$alkyl.

As used herein, the term "$C_{1-8}$alkyl-sulfonyl" refers to a radical of the formula: —SO$_2$—$C_{1-8}$alkyl.

As used herein, the term "amino-sulfonyl" refers to a radical of the formula: —SO$_2$—NH$_2$.

As used herein, the term "$C_{1-8}$alkyl-sulfonyl-amino" refers to a radical of the formula: —NH—SO$_2$—$C_{1-8}$alkyl.

As used herein, the term "$C_{1-8}$alkylthio" refers to a radical of the formula: —S—$C_{1-8}$alkyl.

As used herein, the term "$C_{2-8}$alkynyl-$C_{1-8}$alkyl" refers to a radical of the formula: —$C_{1-8}$alkyl-$C_{2-8}$alkynyl.

As used herein, the term "amino" refers to a radical of the formula: —NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino-$C_{1-8}$alkoxy" refers to a radical of the formula: —O—$C_{1-8}$alkyl-NH—$C_{1-8}$alkyl-NH$_2$ or —O—$C_{1-8}$alkyl-N($C_{1-8}$alkyl-NH$_2$)$_2$.

As used herein, the term "amino-carbonyl" refers to a radical of the formula: —C(O)—NH$_2$.

As used herein, the term "amino-carbonyl-amino" refers to a radical of the formula: —NH—C(O)—NH$_2$.

As used herein, the term "aryl-$C_{1-8}$alkoxy" refers to a radical of the formula: —O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-carbonyl-amino" refers to a radical of the formula: —NH—C(O)-aryl.

As used herein, the term "aryloxy" refers to a radical of the formula: —O-aryl.

As used herein, the term "carboxyl" refers to a radical of the formula: —COOH, —C(O)OH or —CO$_2$H.

As used herein, the term "carboxyl-amino" refers to a radical of the formula: —NH—COOH, —NH—C(O)OH or —NH—CO$_2$H.

As used herein, the term "cyano-$C_{1-8}$alkyl" refers to a radical of the formula: —$C_{1-8}$alkyl-CN.

As used herein, the term "$C_{3-14}$cycloalkyl-$C_{1-8}$alkoxy" refers to a radical of the formula: —O—$C_{1-8}$alkyl-$C_{3-14}$cycloalkyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyloxy" refers to a radical of the formula: —O—$C_{3-14}$cycloalkyl.

As used herein, the term "1-cyclopropyl-ethyl" refers to a radical of the formula: —CH(cyclopropyl)-CH$_3$.

As used herein, the term "formyl" refers to a radical of the formula: —C(O)—H

As used herein, the term "halo" or "halogen" generally refers to a halogen atom radical, including fluoro, chloro, bromo and iodo.

As used herein, the term "halo-$C_{2-8}$alkenyl" refers to a radical of the formula: —$C_{2-8}$alkenyl-halo, wherein $C_{2-8}$alkenyl may be partially or completely substituted where allowed by available valences with one or more halogen atoms, including fluoroethenyl, difluoroethenyl or difluoroallyl and the like. In some embodiments, difluoroethenyl includes 2,2-difluorovinyl or 1,2-difluorovinyl and the like; difluoroallyl includes 1,1-difluoroallyl and the like. In some embodiments, halo-$C_{2-8}$alkenyl includes halo-$C_{2-6}$alkenyl, halo-$C_{2-4}$alkenyl and the like.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms, including fluoromethoxy, difluoromethoxy, trifluoromethoxy, fluoroethoxy, difluoroethoxy or trifluoroethoxy and the like. In some embodiments, difluoroethoxy includes 2,2-difluoroethoxy, 1,2-difluoroethoxy or 1,1-difluoroethoxy and the like. In some embodiments, halo-$C_{1-8}$alkoxy includes halo-$C_{1-6}$alkoxy, halo-$C_{1-4}$alkoxy and the like.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms, including fluoromethyl, difluoromethyl, trifluoromethyl, fluoroethyl, difluoroethyl, trifluoroethyl, fluoroisopropyl, difluoroisopropyl, trifluoroisopropyl, fluoro-tert-butyl, difluoro-tert-butyl, trifluoro-tert-butyl and the like. In some embodiments, difluoroethyl includes 2,2-difluoroethyl, 1,2-difluoroethyl or 1,1-difluoroethyl and the like; difluoroisopropyl includes 1,3-difluoropropan-2-yl and the like; trifluoroisopropyl includes 1,1,1-trifluoropropan-2-yl and the like; trifluoro-tert-butyl includes 1,1,1-trifluoro-2-methylpropan-2-yl and the like. In some embodiments, halo-$C_{1-8}$alkyl includes halo-$C_{1-6}$alkyl, halo-$C_{1-4}$alkyl and the like.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryloxy" refers to a radical of the formula: —O-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-carbonyloxy" refers to a radical of the formula: —O—C(O)-heterocyclyl.

As used herein, the term "heterocyclyloxy" refers to a radical of the formula: —O-heterocyclyl.

As used herein, the term "hydroxy-$C_{1-8}$alkyl" refers to a radical of the formula: —$C_{1-8}$alkyl-OH, wherein $C_{1-8}$alkyl may be partially or completely substituted where allowed by available valences with one or more hydroxy radicals.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. It should also be noted that any carbon as well as heteroatom with valences that appear to be unsatisfied as described or shown herein is assumed to have a sufficient number of hydrogen atom(s) to satisfy the valences described or shown.

For the purposes of this invention, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In), the pattern of substitution at each occurrence is independent of the pattern at any other occurrence. Further, the use of a generic substituent variable on any formula or structure for a compound of the present invention is understood to include the replacement of the generic substituent with species substituents that are included within the particular genus, e.g., aryl may be replaced with phenyl or naphthalenyl and the like, and that the resulting compound is to be included within the scope of the compounds representative of the present invention.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means optional substitution with specified substituent variables, groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using ACD Labs Index Name software Version 10.0, provided by ACD Labs; and/or, were provided using the Autonom function of ChemDraw Ultra 10.0.4, provided by CambridgeSoft. When the compound name disclosed herein conflicts with the structure depicted, the structure shown will supercede the use of the name to define the compound intended.

Compound Forms

As used herein, the term "form" means a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) isolated for use selected from a free acid, free base, salt, hydrate, solvate, clathrate, isotopologue, racemate, enantiomer, diastereomer, stereoisomer, polymorph or tautomer form thereof.

As used herein, the term "isolated" means the physical state of a compound of Formula (I), Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Prodrugs and solvates of the compounds of the invention are also contemplated herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, through hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

One or more compounds of the invention may exist in unsolvated as well as solvated forms with pharmaceutically acceptable solvents such as water, ethanol, and the like, and it is intended that the invention embrace both solvated and unsolvated forms.

As used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of the invention may optionally be converted to a solvate. Preparation of solvates is generally known. The preparation of solvates of the antifungal fluconazole in ethyl acetate as well as from water has been described (see, M. Caira et al, *J. Pharmaceutical Sci.*, 93(3), 601-611 (2004)). Similar preparations of solvates, hemisolvate, hydrates and the like have also been described (see, E. C. van Tonder et al, *AAPS PharmSciTech.*, 5(1), article 12 (2004); and A. L. Bingham et al, *Chem. Commun.*, 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: carboxylic acid esters, sulfonate esters, amino acid esters phosphonate esters and mono-, di- or triphosphate esters.

Compounds of Formula I, and salts, solvates, esters and prodrugs thereof, may further exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention.

The compounds of the invention may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of the invention are (S) isomers and may exist as enantiomerically pure compositions substantially comprising only the (S) isomer. In another embodiment, the compounds of the invention are (R) isomers and may exist as enantiomerically pure compositions substantially comprising only the (R) isomer. As one of skill in the art will recognize, when more than one chiral center is present, the compounds of the invention may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the invention, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the invention, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present invention embraces all geometric and positional isomers. For example, if a compound of Formula (I) incorporates a double bond or a fused ring, both the cis- and trans-forms, as well as mixtures, are embraced within the scope of the invention. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures thereof, are embraced within the scope of the invention. Also, for example, all keto-enol and imine-enamine forms of the compounds are included in the invention. Individual stereoisomers of the compounds of the invention may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this invention.

Certain isotopically-enriched compounds of the present invention (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared by following procedures analogous to those disclosed in the Schemes and/or in the Examples hereinbelow, by substituting an appropriate isotopically-enriched reagent for a non-isotopically-enriched reagent.

When the compounds are enriched with deuterium, the deuterium-to-hydrogen ratio in the deuterated areas of the molecules substantially exceeds the naturally occurring deuterium-to-hydrogen ratio. Wikipedia (http://en.wikipedia.org/wiki/Deuterium) suggests that deuterium has a natural abundance in the oceans of Earth of approximately one atom in 6500 of hydrogen (~154 PPM). Deuterium thus accounts for approximately 0.015% (on a weight basis, 0.030%) of all naturally occurring hydrogen in the oceans on Earth. However, other sources suggest a much higher abundance of e.g. $6.10^{-4}$ (6 atoms in 10,000 or 0.06% atom basis).

Polymorphic crystalline and amorphous forms of the compounds of Formula (I), and of the salts, solvates, esters and prodrugs of the compounds of Formula (I), are further intended to be included in the present invention.

Use of the Invention

The present invention invention is directed to compounds useful for treating a viral infection by modulating viral replication. In accordance with the present invention, compounds that modulate HCV viral replication have been identified and methods of using these compounds for treating or ameliorating HCV infection or disorders or symptoms associated therewith are provided.

One embodiment of the present invention is directed to a method for treating a viral infection in a subject in need thereof comprising administering an effective amount of a compound of Formula (I) or a form thereof to the subject.

An embodiment of the present invention includes the use of a compound of Formula (I) or a form thereof in the manufacture of a medicament for treating a viral infection in a subject in need thereof comprising administering an effective amount of the medicament to the subject.

An embodiment of the present invention includes the use of a compound of Formula (I) or a form thereof in the preparation of a pharmaceutical kit comprising the compound of Formula (I) or a form thereof and instructions for administering the compound for treating a viral infection in a subject in need thereof.

For each of such embodiments for treating a viral infection in a subject in need thereof, the use of a compound of Formula (I) or a form thereof further includes a use of the compound of Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a form thereof.

Another embodiment of the present invention is directed to the use of a compound of Formula (I) or Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a form thereof for treating a viral infection by inhibiting viral replication.

An embodiment of the present invention includes the use of a compound of Formula (I) or Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a form thereof for treating or ameliorating HCV infection or disorders or symptoms associated therewith by inhibiting Hepatitis C viral replication.

An embodiment of the present invention includes a method for treating or ameliorating HCV infection or disorders or symptoms associated therewith in a subject in need thereof comprising administering an effective amount of a compound of Formula (I) or a form thereof to the subject.

An embodiment of the present invention includes the use of a compound of Formula (I) or a form thereof in the manufacture of a medicament for treating or ameliorating HCV infection or disorders or symptoms associated therewith in a subject in need thereof comprising administering an effective amount of the medicament to the subject.

An embodiment of the present invention includes the use of a compound of Formula (I) or a form thereof in the preparation of a pharmaceutical kit comprising the compound of Formula (I) or a form thereof and instructions for administering the compound for treating or ameliorating HCV infection or disorders or symptoms associated therewith in a subject in need thereof.

For each of such embodiments for treating or ameliorating HCV infection or disorders or symptoms associated therewith in a subject in need thereof, the use of a compound of Formula (I) or a form thereof further includes a use of the compound of Formula (Ia), Formula (Ib), Formula (Ic), Formula (Id), Formula (Ie), Formula (If), Formula (Ig), Formula (Ih), Formula (Ii), Formula (Ij), Formula (Ik), Formula (Il), Formula (Im) or Formula (In) or a form thereof.

In one respect, for each of such embodiments, the subject is treatment naive. In another respect, for each of such embodiments, the subject is not treatment naive.

As used herein, the term "treating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "subject" and "human".

Another aspect of the invention relates to a method for treating a viral infection by a wild type virus or a virus that is resistant to a currently available antiviral agent, in a subject in need thereof, comprising administering to the subject an effective amount of a compound of Formula (I) or a form thereof.

Nonlimiting examples of viral infections intended to be included within the scope of the invention include viral infections resulting from viruses of the picornavirus genus (such as poliovirus, hepatitis A virus, coxsackievirus and rhinovirus), viruses of the coronaviridae genus (such as severe acute respiratory syndrome (SARS)), viruses of the arbovirus genus, viruses of the flavivirus genus (such as hepatitis C virus, yellow fever, dengue and West Nile virus), herpesviruses (such as herpes simplex virus and Kaposi's sarcoma-associated herpesvirus and other viruses with a similar mode of replication), a human immunodeficiency virus (HIV), or a human leukemia virus (HTLV).

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

In general, the effective amount will be in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 70 to about 100 Kg.

The dose administered to achieve an effective target plasma concentration may also be administered based upon the weight of the subject or patient. Doses administered on a weight basis may be in the range of about 0.01 mg/kg/day to about 50 mg/kg/day, or about 0.015 mg/kg/day to about 20 mg/kg/day, or about 0.02 mg/kg/day to about 10 mg/kg/day, or about 0.025 mg/kg/day to about 10 mg/kg/day, or about 0.03 mg/kg/day to about 10 mg/kg/day, wherein said amount is orally administered once (once in approximately a 24 hour period), twice (once in approximately a 12 hour period) or thrice (once in approximately an 8 hour period) daily according to subject weight.

In another embodiment, where daily doses are adjusted based upon the weight of the subject or patient, compounds of the invention may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/kg/day. Daily doses adjusted based upon the weight of the subject or patient may be administered as a single, divided, or continuous dose. In embodiments where a dose of compound is given more than once per day, it may be administered twice, thrice, or more per day.

Within the scope of the present invention, the "effective amount" of a compound of Formula (I) or a form thereof for use in the manufacture of a medicament, the preparation of a pharmaceutical kit or in a method for treating or ameliorating HCV infection or disorders or symptoms associated therewith in a subject in need thereof, is intended to include an amount in a range of from about 1.0 mg to about 3500 mg administered once daily; 10.0 mg to about 600 mg administered once daily; 0.5 mg to about 2000 mg administered twice daily; or, an amount in a range of from about 5.0 mg to about 300 mg administered twice daily.

For example, the effective amount may be the amount required to treat a HCV infection, or the amount required to inhibit viral replication or infectivity, in a subject or, more specifically, in a human. In some instances, the desired effect can be determined by analyzing (1) the presence of HCV RNA; (2) the presence of anti-HCV antibodies; (3) the level of serum alanine amino transferase (ALT) and aspartate aminotransferase (AST) (ALT and AST are elevated in patients chronically infected with HCV); (4) hepatocellular damage resulting from HCV infection, including steatosis, fibrosis and cirrhosis; (5) hepatocellular carcinoma as a result of chronic HCV infection; and (6) extrahepatic sequelae (non-limiting examples include pruritis, encephalopathies, mental disorders such as anxiety or depression) of infection with HCV or other viruses. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to a compound of Formula (I) or a form thereof indicate an trough target plasma concentration ranging from approximately 0.001 μg/mL to approximately 50 μg/mL, from approximately 0.01 μg/mL to approximately 20 μg/mL, from approximately 0.05 μg/mL to approximately 10 μg/mL, or from approximately 0.1 μg/mL to approximately 5 μg/mL. To achieve such plasma concentrations, the compounds of the invention may be administered at doses that vary from 0.1 μg to 100,000 mg, depending upon the route of administration in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethinicity, age, weight, and gender of the subject, diet, time and frequency of administration, drug combination(s), reaction sensitivities, experience with other HCV therapies, and tolerance/response to therapy. Long-acting pharmaceutical compositions may be administered every 2, 3 or 4 days, once every week, or once every two weeks depending on half-life and clearance rate of the particular formulation.

The compounds and compositions of the present invention may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

Metabolites of the Compounds of the Invention

Also falling within the scope of the present invention are the in vivo metabolic products of the compounds described herein. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof.

Such products typically are identified by preparing a radio-labeled isotopologue (e.g. $C^{14}$ or $H^3$) of a compound of the invention, administering the radio-labeled compound in a detectable dose (e.g., greater than about 0.5 mg/kg) to a mammal such as rat, mouse, guinea pig, dog, monkey or human, allowing sufficient time for metabolism to occur (typically about 30 seconds to 30 hours), and identifying the metabolic conversion products from urine, bile, blood or other biological samples. These products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

Pharmaceutical Compositions

Embodiments of the present invention include the use of a compound of Formula (I) or a form thereof in a pharmaceutical composition for the prevention or treatment of a viral infection comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In some embodiments, the pharmaceutical composition is formulated to achieve a pH of from about pH 3 to about pH 7. In other embodiments, the pharmaceutical composition is formulated to achieve a pH of from about pH 5 to about pH 8.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions of the invention may be formulated as suspensions comprising a compound of Formula (I) or a form thereof in admixture with at least one pharmaceutically acceptable excipient suitable for the manufacture of a suspension. In yet other embodiments, pharmaceutical compositions of the invention may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of the invention may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound of the invention is formulated for oral administration in a lipid-based composition suitable for low solubility compounds. Lipid-based formulations can generally enhance the oral bioavailability of such compounds. As such, pharmaceutical compositions of the invention may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In other embodiments, the bioavailability of low solubility compounds may be enhanced using particle size optimization techniques including the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound of the present invention in the composition.

PREPARATION OF COMPOUNDS OF THE INVENTION

General Synthetic Examples

Methods for preparing certain compounds useful for treating or ameliorating HCV infection or disorders or symptoms associated therewith are available via standard, well-known synthetic methodology and, furthermore, have been disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which are incorporated herein by reference in their entirety and for all purposes.

Similarly, as disclosed herein, methods for preparing the compounds of the invention are available via standard, well-known synthetic methodology. Many of the azaindole starting materials used herein are commercially available or can be prepared via the routes described below using techniques known to those skilled in the art.

Scheme A

Compounds of Formula (I) can be prepared as described in Scheme A below.

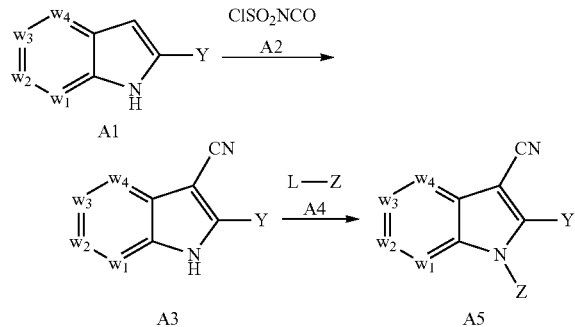

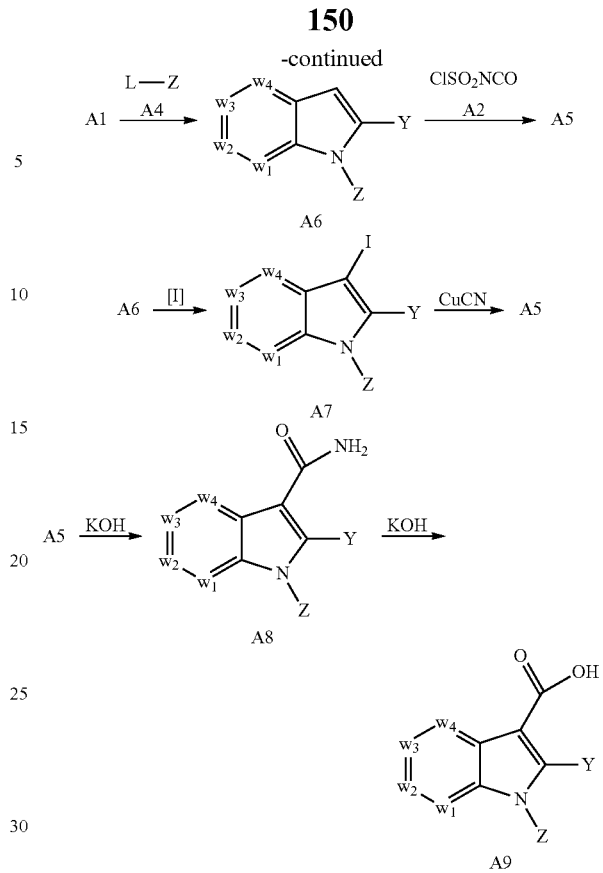

Substituted azaindole Compound A1 can be substituted on the 3-position with cyano using an appropriate cyanating agent Compound A2 (such as chlorosulfonyl isocyanate or a dialkyl phosphoryl isocyanate and the like) in a suitable solvent or solvent mixture (such as DMF, CH$_3$CN or dioxane and the like) to afford a Compound A3. Compound A3 can then be reacted with a reactive functional group Compound A4 (wherein L represents a leaving group and wherein Z is as previously defined) to afford a Compound A5, representative of a compound of Formula (I).

With respect to Compound A4, when the reactive functional group Z includes, but is not limited to, $C_{1-8}$alkyl and aryl-$C_{1-8}$alkyl and the L leaving group includes, but is not limited to, a halide (such as chloro, bromo or iodo) or an alkylsulfonate leaving group, the reaction can be carried out in a suitable solvent in the presence of an inorganic base (such as potassium carbonate or sodium hydride and the like) or an organic base (such as a trialkylamine and the like).

With respect to Compound A4, when the reactive functional group Z includes, but is not limited to, aryl or heteroaryl and the leaving group L includes, but is not limited to, a halide leaving group (such as chloro, bromo or iodo), the reaction can be carried out in a polar or nonpolar solvent at a temperature of from about ambient to about 200° C. in the presence of a copper catalyst (such as CuI and the like), and a base (such as Cs$_2$CO$_3$ or K$_3$PO$_4$ and the like), and optionally with an amine ligand (such as 1,2-bis(methylamino)ethane or 1,2-cyclohexanediamine and the like).

Alternatively, Compound A1 can be reacted with Compound A4 to give a Compound A6, representative of a compound of Formula (I) that can then be reacted with Compound A2 as described above to obtain Compound A5.

Additionally, iodination of Compound A6 provides Compound A7. Subsequent reaction of Compound A7 with copper cyanide (CuCN) under appropriate conditions provides Compound A5.

Reaction of the cyano group of Compound A5 under base conditions (such as potassium hydroxide) affords the primary amide Compound A8, representative of a compound of Formula (I). Further reaction with potassium hydroxide affords the carboxylic acid Compound A9, also representative of a compound of Formula (I).

Scheme B

Compounds of Formula (I), wherein X is an aldehyde, can be prepared as described in Scheme B below.

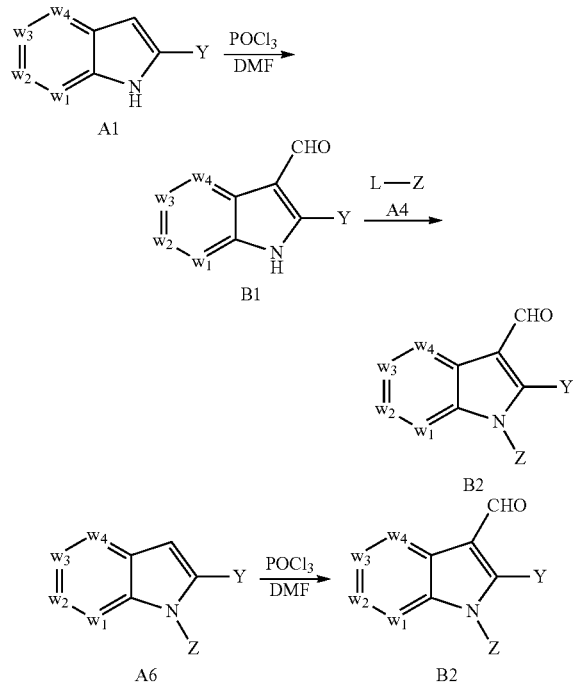

Aldehyde substituted azaindole Compound B1 can be prepared by reacting Compound A1 with a formylating reagent (such as phosphorous oxychloride in the presence of DMF). Conversion of Compound B1 to Compound B2, representative of a compound of Formula (I), can be accomplished by treatment with Compound A4 as previously described in Scheme A.

Alternatively, Compound A6 may be reacted with a formylating reagent to directly provide Compound B2.

Scheme C

Compounds of Formula (I), wherein X is an oxime, can be prepared as described in Scheme C below.

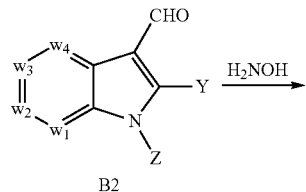

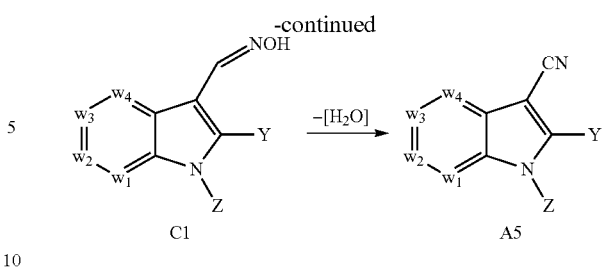

Aldehyde substituted azaindole Compound B2 can be converted to the oxime substituted azaindole Compound C1 via an aminating reagent (such as hydroxylamine). Conversion of Compound C1 via dehydration, by treatment with acetic anhydride and a base, or reaction with thionyl chloride affords Compound A5, representative of a compound of Formula (I).

Scheme D

Compounds of Formula (I), wherein X is carboxyl, amino-carbonyl or $C_{1-8}$alkyl-amino-carbonyl, can be prepared as described in Scheme D below.

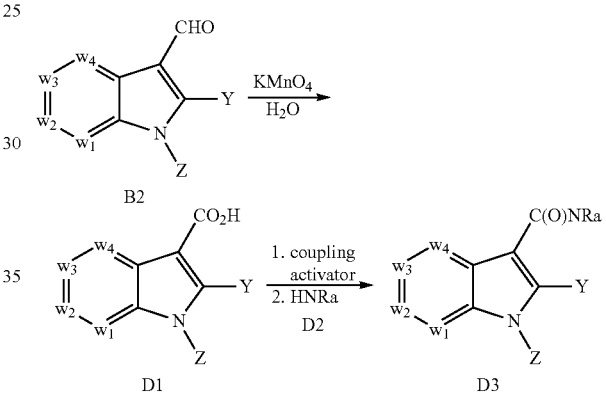

Compound B2 may be reacted with a reagent (such as potassium permanganate and the like) under aqueous conditions to provide Compound D1, representative of a compound of Formula (I).

Further, Compound D1 can be activated by a coupling activator (such as oxalyl chloride, Py-BOP, and the like) and then reacted with amine reagent D2 (wherein the nitrogen atom may be unsubstituted or mono- or di-substituted with Ra, wherein Ra is $C_{1-8}$alkyl) in a suitable solvent (such as DCM and the like) to provide amido substituted analog Compound D3, representative of a compound of Formula (I).

Scheme E

Compounds of Formula (I) can be prepared as described in Scheme E below.

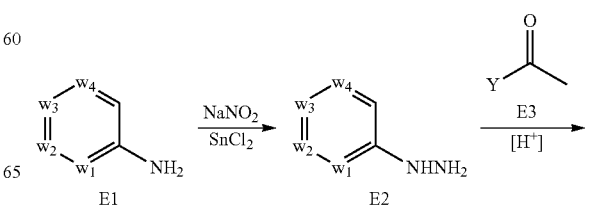

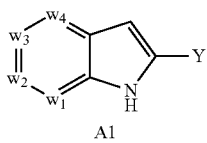

A1

Amino substituted Compound E1 can be diazotized and the resulting diazonium salt reduced to give the hydrazine Compound E2. Compound E2 is then reacted with ketone Compound E3 under acidic conditions to provide Compound A1, which may be carried forward as described in Scheme A to provide Compound A5, representative of a compound of Formula (I).

The conditions for the cyclization reaction between Compound E2 and Compound E3 can be carried out under typical conditions utilized by one skilled in the art. For example, acidic conditions may be provided using a Bronstead acid (such as acetic acid, hydrochloric acid or polyphosphoric acid and the like) or a Lewis acid (such as zinc chloride and the like). The reaction may be carried out in the presence of a co-solvent (such as CH$_2$Cl$_2$ or THF and the like), typically within a temperature range of from about 0° C. to about 120° C.

Scheme F

Compounds of Formula (I) can be prepared as described in Scheme F below.

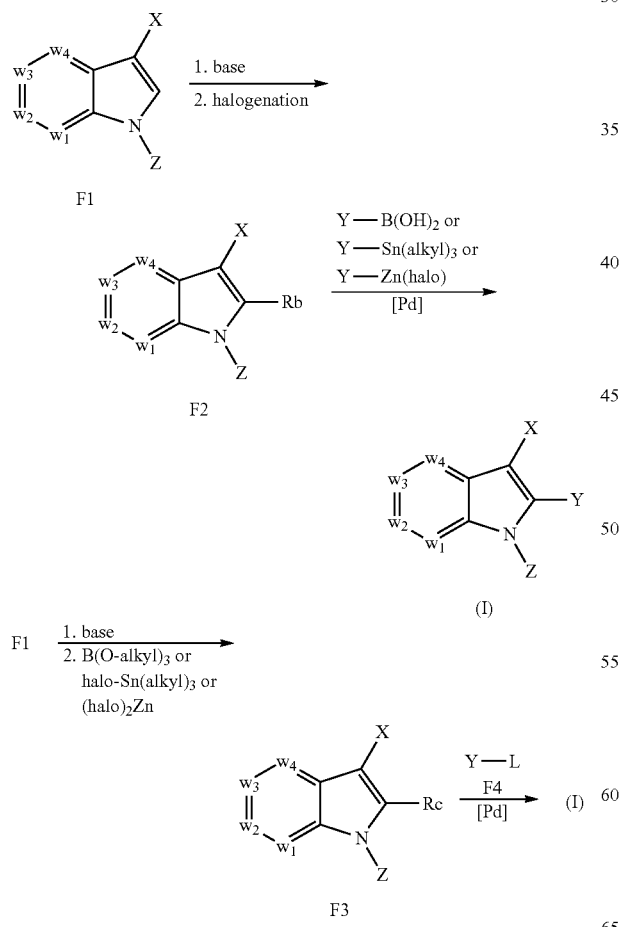

A Compound F1 can be converted to halogenated Compound F2 (wherein Rb represents a halogen atom such as iodo or bromo) by reaction with a strong base (such as n-butyl lithium, sec-butyl lithium, lithium diisopropylamide, lithium or potassium hexamethyldisilazide and the like) in the presence of a suitable unreactive solvent (such as ether or THF and the like) or in solvent mixtures containing such an unreactive solvent to provide an anion at the 2-position. The reaction is typically carried out in the range of from about −78° C. to about ambient temperature. Generation of the intermediate can be quenched with an electrophilic source of halogen (such as iodine, bromine or N-bromosuccinimide and the like) to afford Compound F2.

Compound F2 may then be reacted with a boronic acid in a Suzuki reaction or with trialkyl stannane in a Stille reaction or a zinc halide in a Negishi reaction in the presence of a palladium catalyst (such as tetrakis (triphenylphosphine) palladium (0), bis(triphenylphosphine) palladium (II) dichloride or palladium acetate) and an added phosphine ligand, to afford a compound of Formula (I).

The reaction is carried out in a suitable solvent (such as DMF, toluene, dimethoxy ethane, dioxane and the like) at a temperature from about ambient to about 150° C. For Suzuki conditions, the reaction may be run with a base under aqueous conditions (such as aqueous sodium carbonate or sodium bicarbonate and the like) or under anhydrous conditions (such as with cesium or potassium fluoride and the like). For Stille conditions, the reaction may be run with a copper co-catalyst (such as copper iodide and the like). For Negishi conditions, the reaction may be run with a nickel catalyst (such tetrakis (triphenylphosphine) nickel and the like).

Alternatively, Compound F1 can be converted to a Compound F3 derivative (wherein Rc represents boronic acid or trialkylstannane or zinc halide) by reacting the anion intermediate described above with a trialkylborate or halotrialkyl stannane derivative (wherein halo may be chloro, bromo or iodo) or a dihalozinc (wherein halo may be chloro or bromo), respectively. Compound F3 can then be reacted with a Compound F4 (wherein L represents a halide leaving group such as chloro, bromo or iodo), under either Suzuki, Stille or Negishi conditions to provide a compound of Formula (I).

Scheme G

Compounds of Formula (I), can be prepared as described in Scheme G below.

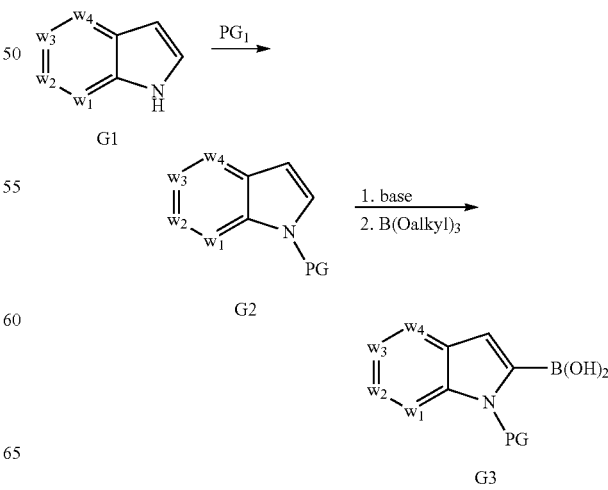

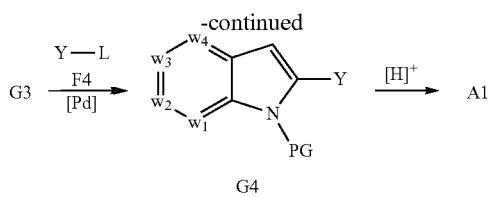

A Compound G1 may be protected by reaction with a protecting group (wherein PG$_1$ represents a reactive protecting group such as Boc anhydride and the like) to provide a Compound G2 (wherein PG represents a protecting group such as Boc, benzyl, alkyl, aryl-sulfonyl or trialkyl-silyl and the like). Treatment of Compound G2 with a strong base (such as lithium diisopropyl amide and the like) in an aprotic solvent (such as THF and the like), followed by quenching with a trialkylborate derivative obtains a Compound G3.

Reaction of Compound G3 with Compound F4 under reaction conditions described in Scheme F provides Compound G4. Removal of the protecting group affords Compound A1, which may be carried forward as described in Scheme A to provide Compound A5, representative of a compound of Formula (I).

Scheme H

Compounds of Formula (I), wherein X is cyano, can be prepared as described in Scheme H below.

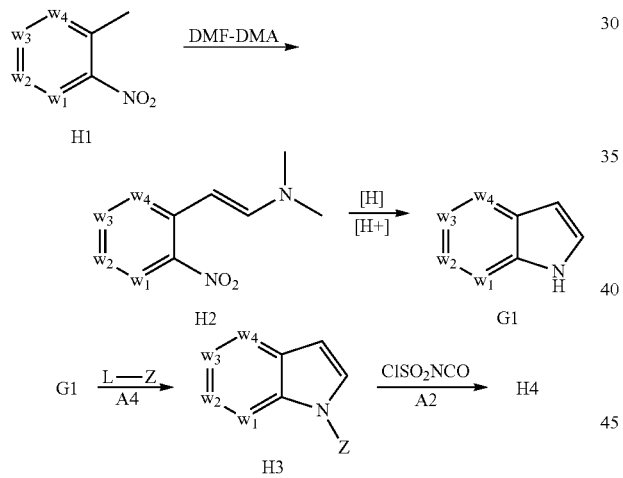

Compound H1 is reacted with dimethylformamide-dimethylacetal or the like to provide enamine Compound H2. Compound H2 can then be hydrogenated by employing suitable conditions (such as hydrogen gas and a suitable palladium catalyst or iron and acetic acid) in the presence of a proton source (such as methanol or acetic acid or the like) to afford Compound G1.

Compound G1 can then be reacted with a reactive functional group Compound A4 (wherein L represents a leaving group and wherein Z is as previously defined) to afford a Compound H3. Compound H3 can be substituted on the 3-position with cyano using an appropriate cyanating agent Compound A2 (such as chlorosulfonyl isocyanate or a dialkyl phosphoryl isocyanate and the like) in a suitable solvent or solvent mixture (such as DMF, CH$_3$CN or dioxane and the like) to afford a Compound H4, which can be carried forward in place of Compound F1 and converted to a compound representative of a compound of Formula (I) as shown in Scheme F.

Scheme I

Compounds of Formula (I) can be prepared as described in Scheme I below.

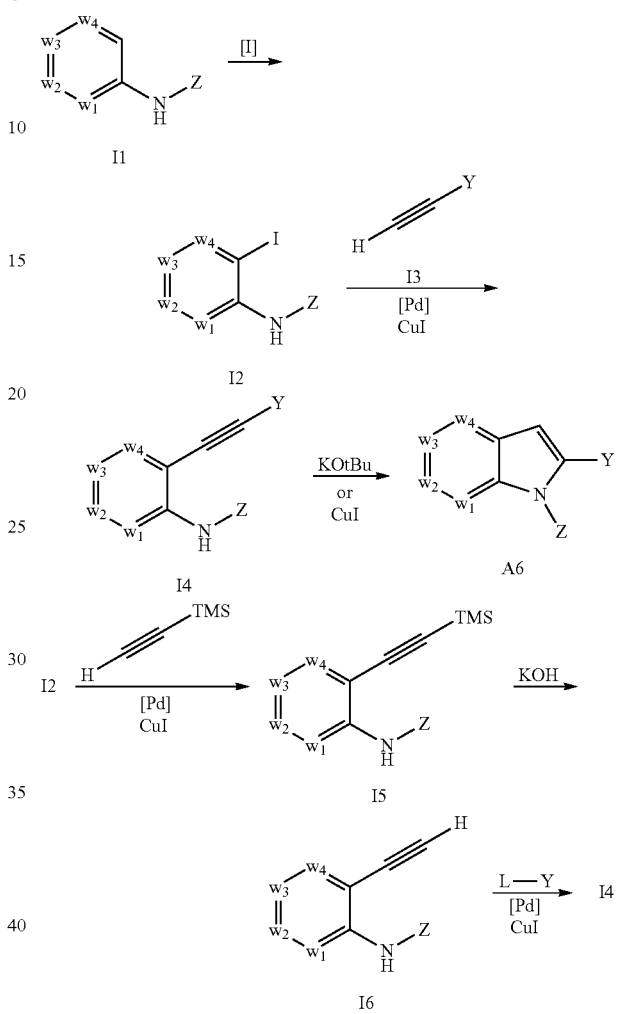

Compound I1 is iodinated under suitable conditions (such as potassium iodide and potassium iodate or iodine monochloride) to provide Compound I2. Compound I2 can then be reacted with a Compound I3 in a Sonogashira reaction in the presence of a suitable palladium catalyst (such as bis(triphenylphosphine)palladium dichloride and the like) and copper co-catalyst (such as copper iodide and the like) to afford Compound I4. Compound I4 is reacted with either potassium tert-butoxide or a suitable copper catalyst (such as copper iodide and the like) to provide Compound A6, representative of a compound of Formula (I).

Alternatively, Compound I2 can be reacted with trimethylsilylacetylene under Sonogashira conditions to give a Compound I5. Removal of the trimethylsilyl group is accomplished employing potassium hydroxide to afford Compound I6. Reaction of Compound I6 with a compound L-Y (where L and Y has previously been defined) under Sonogashira conditions provides Compound I4 which can then be further reacted as described above to obtain Compound A6.

Scheme J

Compounds of Formula (I) can be prepared as described in Scheme J below.

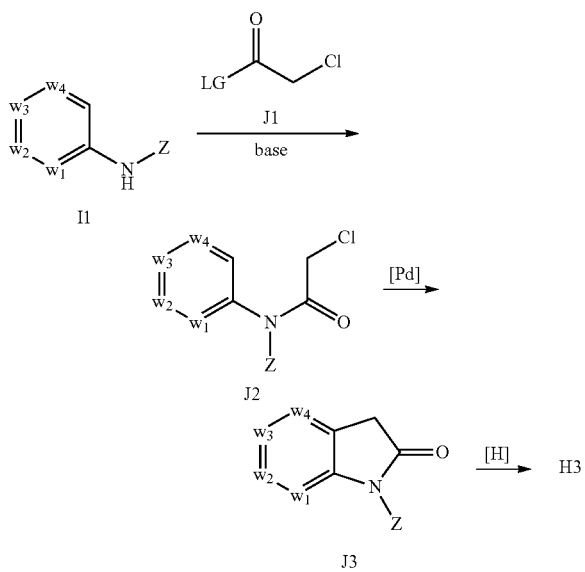

Compound I1 is reacted with Compound J1, a 2-chloroacyl reagent with a suitable leaving group (LG) (such as chloro acetyl chloride and the like) employing a base (such as a pyridine or potassium hydroxide and the like) to provide Compound J2. Compound J2 can then be reacted in the presence of a suitable palladium catalyst to afford Compound J3. Compound J3 is reacted with a suitable hydride source (such as DIBAL-H and the like) to provide Compound H3. Compound H3 can be carried be forward as shown in Scheme H to provide compounds representative of a compound of Formula (I).

Specific Synthetic Examples

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

Synthetic Examples

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

As used above, and throughout the description of the invention, the following abbreviations, unless otherwise indicated, shall be understood to have the following meanings:

| Abbreviation | Meaning |
| --- | --- |
| AcOH or HOAc | acetic acid |
| $^t$Bu or tBu | tert-butyl |
| CSI | chlorosulfonyl isocyanate |
| DCM | dichloromethane ($CH_2Cl_2$) |
| DIBAL-H | diisobutylaluminum hydride |
| DIPEA | diisopropylethylamine |
| DMF | dimethyl formamide |
| DMA | dimethyl acetamide |
| DME | dimethyl ether |
| DMSO | dimethylsulfoxide |
| EtOAc | ethyl acetate |
| EtOH | ethanol |
| HPLC | high performance liquid chromatography |
| LDA | lithium diisopropylamide |
| MeOH | methanol |
| m-CPBA | 3-chloroperoxybenzoic acid |
| MS | mass spectroscopy |
| MTBE | methyl tert-butyl ether |
| NMR | nuclear magnetic resonance |
| NMP | N-methyl-pyrrolidinone |
| Pd° | palladium |
| $^i$Pr | isopropyl |
| Py-BOP | benzotriazol-1-yl-oxytripyrrolidinophosphonium hexafluorophosphate |
| RT | room temperature |
| THF | tetrahydrofuran |
| TLC | thin layer chromatography |
| TMS | trimethylsilyl |

Example 1

6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide (Cpd 22)

Part A. Preparation of (S)-6-chloro-N-(1,1,1-trifluoropropan-2-yl)pyridine-3-sulfonamide

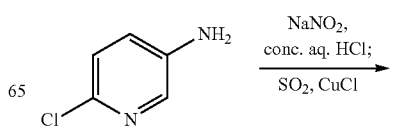

-continued

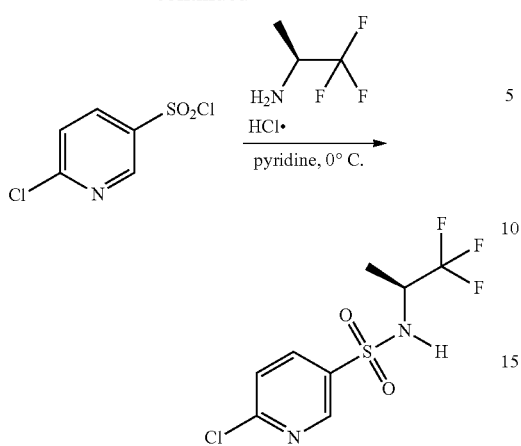

Step A: A solution of SO$_2$ was prepared by adding thionyl chloride (24.2 mL) into stirring water (144 mL) containing CuCl (87.0 mg). The solution was then stirred at room temperature overnight. 5-Amino-2-chloropyridine (10.0 g, 77.8 mmol) was added into stirring conc. HCl (80 mL) portionwise. The mixture was stirred until all solids were dissolved and was then cooled to −5° C. Into the mixture was added dropwise a solution of sodium nitrite (5.9 g, 85.6 mmol) dissolved in 24 mL of water while the temperature was kept between −5° C. and 0° C. The resulting mixture was stirred for 30 min after the completion of the addition and then added dropwise into the aqueous solution of SO$_2$. The temperature was kept below 0° C. during the addition. After the addition the mixture was stirred for 1 h below 0° C. and then filtered. The cake was washed with ice-cold water, dissolved in CH$_2$Cl$_2$, dried over Na$_2$SO$_4$ and concentrated to give 2-chloropyridine-5-sulfonyl chloride as a gray solid (13.6 g, 82%). $^1$H NMR (500 MHz, CDCl$_3$): δ 9.04 (1H, d, J=2.4 Hz), 8.27 (1H, dd, J=8.5 Hz, J=2.6 Hz), 7.62 (1H, dd, J=8.5 Hz, J=0.4 Hz).

Step B: 2-Chloropyridine-5-sulfonyl chloride (12 g, 56.6 mmol) was added to a solution of (S)-1,1,1-trifluoropropan-2-amine hydrochloride (7.8 g, 51.2 mmol) in pyridine (15 mL) at 0° C. The mixture was stirred at room temperature for 10 min and diluted with ethyl acetate (200 ml) and washed with 3N HCl (2×100 mL). The organic layer was dried over Na$_2$SO$_4$, filtered, and concentrated. The solid was triturated with hexane (2×40 mL) and filtered to provide (S)-6-chloro-N-(1,1,1-trifluoropropan-2-yl)pyridine-3-sulfonamide as an off-white solid (11.84 g, 75%). $^1$H NMR (500 MHz, CDCl$_3$): δ 8.81 (1H, d, J=2.4 Hz), 8.18 (1H, dd, J=2.5 Hz, 2.6 Hz), 7.51 (1H, d, J=8.8 Hz), 4.92 (1H, br s), 4.08 (1H, m), 1.45 (3H, d, J=7.0 Hz).

Part B: Preparation of (S)-6-(3-cyano-1-cyclobutyl-5-methoxy-1H-pyrrolo[2,3-b]pyridin-2-yl)-N-(1,1,1-trifluoropropan-2-yl)pyridine-3-sulfonamide

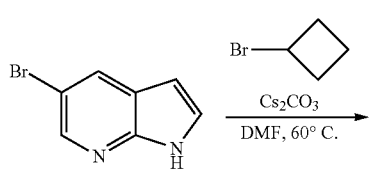

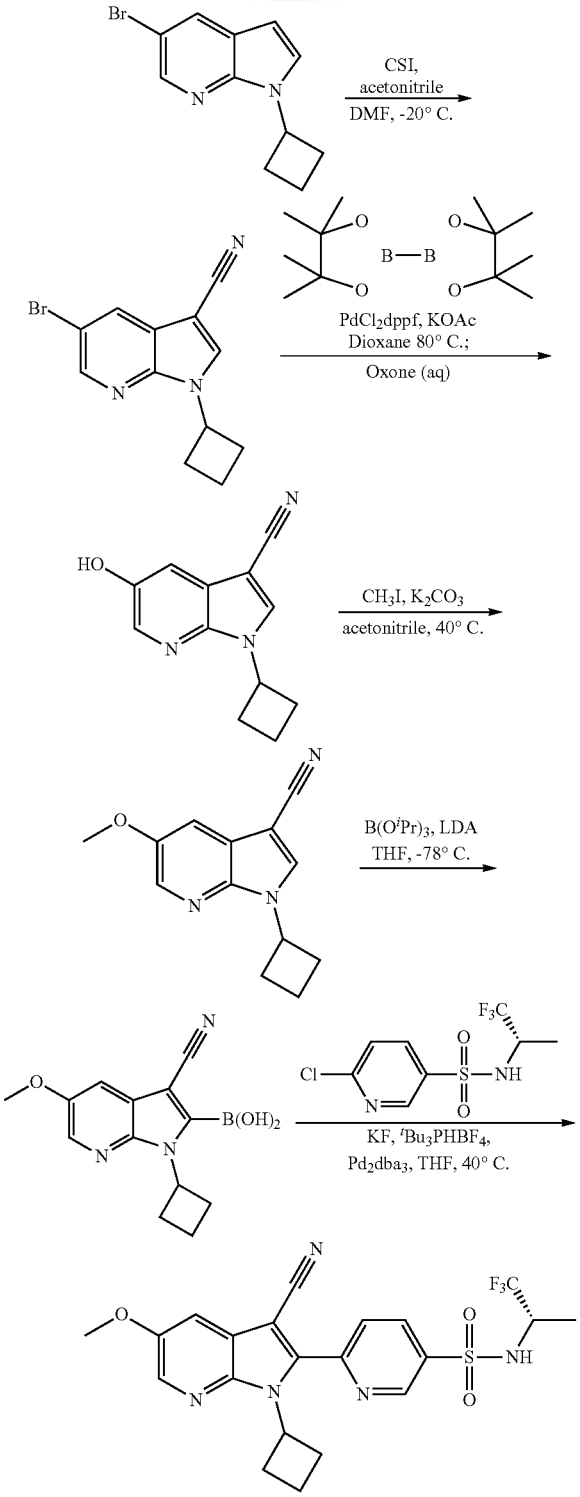

Step A: To a 1 L flask charged with 5-bromo-7-azaindole (50.0 g, 254 mmol) was added DMF (500 mL), cesium carbonate (207 g, 634 mmol) and cyclobutyl bromide (35.8 mL, 381 mmol). The reaction was stirred and heated at 60° C. and after 16 h another portion of cyclobutyl bromide (2.0 mL, 21.3 mmol) was added to the reaction. After 1 day, the reaction was cooled to room temperature and poured into ice water (2.5 L) with stirring. The oily suspension was washed with $CH_2Cl_2$ (3×500 mL). The combined organics were dried over $Na_2SO_4$ and then concentrated to give N-cyclobutyl-5-bromo-7-azaindole as a yellow solution in DMF (ca. 500 mL).

Step B: To the above solution of N-cyclobutyl-5-bromo-7-azaindole in DMF was added acetonitrile (500 mL) and the solution was cooled to −20° C. Chlorosulfonyl isocyanate (44.1 mL, 508 mmol) was dissolved in acetonitrile (100 mL) and added dropwise to the cooled reaction mixture. After 3 h at −20° C., the mixture was filtered, washed with water (3×100 mL), and dried in a stream of nitrogen to give N-cyclobutyl-3-cyano-5-bromo-7-azaindole as a white solid (47.6 g). The mother liquor was poured into ice water (2500 mL). The resulting solid was filtered, washed with water (3×100 mL), and dried in a stream of nitrogen. The resulting solid was suspended in 200 mL of 3:1 hexanes:acetonitrile, filtered, and washed with ether (50 mL) to give a second crop of N-cyclobutyl-3-cyano-5-bromo-7-azaindole as a white solid (13.8 g), (combined crops of product: 61% over 2 steps).

Step C: A 1 L round-bottom flask was charged with 5-bromo-1-cyclobutyl-1H-pyrrolo[2,3-b]pyridine-3-carbonitrile (50.4 g, 182 mmol), pinocolatoboron (60.2 g, 237 mmol), potassium acetate (53.7 g, 547 mmol), and $PdCl_2dppf$ (6.7 g, 9.1 mmol). The flask was purged using three cycles of vacuum and argon backfill. Dioxane (200 mL) was added via cannula and the resulting mixture was stirred at 80° C. for 14 h. After cooling, the mixture was diluted with $CH_2Cl_2$ (800 mL), and passed through a silica gel/celite pad. The mixture was concentrated under reduced pressure at 27° C. The residue was then dissolved in acetone (350 mL) and a slurry of OXONE® (225 g, 365 mmol) in water (350 mL) was added at 0° C. The mixture was stirred vigorously at room temperature for 15 min. Acetone was evaporated and water (800 ml) added. The resulting precipitate was filtered and washed with water. The solid was partitioned between ethyl acetate (1000 ml) and sat. aq. $NaHSO_3$ (500 mL). The organic phase was washed with brine, dried over $MgSO_4$, and concentrated. The residue was triturated with ethyl ether to afford 1-cyclobutyl-5-hydroxy-1H-pyrrolo[2,3-b]pyridine-3-carbonitrile as an off-white solid (22.5 g, 58% over two steps).

Step D: A mixture of 1-cyclobutyl-5-hydroxy-1H-pyrrolo[2,3-b]pyridine-3-carbonitrile (29.5 g, 138 mmol), potassium carbonate (38.2 g, 277 mmol), methyl iodide (29.5 g, 208 mmol) and acetonitrile (150 mL) was stirred at 40° C. overnight. After cooling, the reaction mixture was diluted with $CH_2Cl_2$ (1 L) and passed through a plug of silica gel/celite. The mixture was concentrated, suspended in ethyl ether/hexane (1:1) and collected on a filter to afford 28.4 g (90%) of 1-cyclobutyl-5-methoxy-1H-pyrrolo[2,3-b]pyridine-3-carbonitrile as an off-white solid.

Step E: To a solution of 1-cyclobutyl-5-methoxy-1H-pyrrolo[2,3-b]pyridine-3-carbonitrile (28.4 g, 125 mmol), and triisopropylborate (30.6 g, 162 mmol) in THF (200 mL) was added LDA (100 mL, 1.5 M in THF-cyclohexane) at −78° C. The mixture was stirred for 1 h and poured into hexane (1 L). The precipitate was collected by filtration and washed with hexanes. The solid was dissolved in water and acidified with 1N HCl. The mixture was extracted with ethyl acetate (1 L). The organic phase was washed with brine, dried over $MgSO_4$, and concentrated under reduced pressure at 27° C. The pale yellow solid was washed with hexanes and dried under vacuum at room temperature to afford 30.5 g (90%) of 3-cyano-1-cyclobutyl-5-methoxy-/H-pyrrolo[2,3-b]pyridin-2-ylboronic acid.

Step F: A 1 L round-bottom flask was charged with 3-cyano-1-cyclobutyl-5-methoxy-/H-pyrrolo[2,3-b]pyridin-2-ylboronic acid (30.5 g, 112 mmol), (S)-6-chloro-N-(1,1,1-trifluoropropan-2-yl)pyridine-3-sulfonamide (24.1 g, 83.4 mmol) [from Example 1, Part A, Step B above], potassium fluoride (65.4 g, 1.1 mol), $^tBu_3PHBF_4$ (3.9 g, 13.5 mmol) and $Pd_2dba_3$ (5.15, 5.62 mmol). The flask was purged using three cycles of vacuum and argon backfill. THF (200 mL) was added via cannula and the resulting mixture stirred at 40° C. for 2 h. The reaction mixture was diluted with $CH_2Cl_2$ (500 mL), and filtered through a plug of silica gel/celite, washing with $CH_2Cl_2$/hexane (1:1, 1 L).

Solid obtained was absorbed on silica gel (50 g) and purified on silica gel eluting with a series of solvent mixtures: 10% ethyl acetate in hexanes, 5% ethyl acetate in $CH_2Cl_2$:hexanes (1:1), and then 5% methanol in $CH_2Cl_2$. The concentrates were combined and triturated with ethyl ether to afford 36.0 g (90%) of the title compound as a white solid. Melting point: 171-172° C.; MS m/z 480.2 (M+H$^+$); $^1$H NMR (500 MHz, acetone-$d_6$): δ 9.30 (1H, m), 8.55 (1H, dd, J=8.0, 2.5 Hz), 8.30 (1H, d, J=3.0 Hz), 8.15 (1H, m), 7.73 (1H, d, J=3.0 Hz), 5.38 (1H, m), 4.40 (1H, m), 4.02 (3H, s), 3.28 (2H, m), 2.38 (2H, m), 1.91 (2H, m), 1.80 (3H, d, J=2.0 Hz).

Additional compounds representative of the present invention may be prepared according to the procedure of Example 1 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 1 | 4-[5-chloro-3-cyano-1-(cyclopropylmethyl)-1H-pyrrolo[2,3-b]pyridin-2-yl]-N-(propan-2-yl)benzenesulfonamide Prepared using commercially available 5-chloro-7-azaindole in place of 5-bromo-7-azaindole | 113-116 | 429.1 |
| 2 | 4-[3-cyano-1-(cyclopropylmethyl)-5-methoxy-1H-pyrrolo[2,3-b]pyridin-2-yl]-N-(propan-2-yl)benzenesulfonamide Prepared using commercially available 5-methoxy-7-azaindole in place of 5-bromo-7-azaindole | 151-153 | 425.2 |
| 4 | 4-[3-cyano-1-(cyclopropylmethyl)-5-fluoro-1H-pyrrolo[2,3-b]pyridin-2-yl]-N-(propan-2-yl)benzenesulfonamide Prepared using commercially available 5-fluoro-7-azaindole in place of 5-bromo-7-azaindole | 162-165 | 413.2 |
| 5 | 4-[3-cyano-1-(cyclopropylmethyl)-6-methyl-1H-pyrrolo[2,3-b]pyridin-2-yl]-N-(propan-2-yl)benzenesulfonamide Prepared using commercially available 6-methyl-7-azaindole in place of 5-bromo-7-azaindole | 175-177 | 409.5 |
| 6 | 4-(5-chloro-3-cyano-1-cyclobutyl-1H-pyrrolo[2,3-b]pyridin-2-yl)-N-(propan-2-yl)benzenesulfonamide Prepared using commercially available 5-chloro-7-azaindole in place of 5-bromo-7-azaindole | 172-175 | 428.9 |
| 7 | 4-(3-cyano-1-cyclobutyl-1H-pyrrolo[2,3-b]pyridin-2-yl)-N-(propan-2-yl)benzenesulfonamide Prepared using commercially available 7-azaindole in place of 5-bromo-7-azaindole | 198-200 | 394.8 |
| 8 | 4-(5-chloro-3-cyano-1-cyclobutyl-1H-pyrrolo[2,3-b]pyridin-2-yl)-N-(1,3-difluoropropan-2-yl)benzenesulfonamide Prepared using commercially available 5-chloro-7-azaindole in place of 5-bromo-7-azaindole | 234-238 | 465.1 |
| 221 | 6-(3-cyano-1-cyclopentyl-1H-pyrrolo[2,3-b]pyridin-2-yl)-N-[(2S)-1,1,1-trifluoropropan-2-yl]pyridine-3-sulfonamide Prepared using commercially available 7-azaindole in place of 5-bromo-7-azaindole | 157-159 | 464.2 |
| 232 | 6-(3-cyano-1-cyclobutyl-5-methoxy-1H-pyrrolo[2,3-b]pyridin-2-yl)-N-[(2S)-1,1,1-trifluorobutan-2-yl]pyridine-3-sulfonamide | 186-191 | 494.2 |

-continued

| Cpd | Name | m.p. | MS |
|---|---|---|---|
| 236 | 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide 1-oxide | 155-157 | 495.8 |
| 248 | 6-(3-cyano-1-cyclopentyl-5-methoxy-1H-pyrrolo[2,3-b]pyridin-2-yl)-N-[(2S)-1,1,1-trifluoropropan-2-yl]pyridine-3-sulfonamide | 178-180 | 493.7 |
| 257 | N-{[6-(3-cyano-1-cyclopentyl-5-methoxy-1H-pyrrolo[2,3-b]pyridin-2-yl)pyridin-3-yl]sulfonyl}-N-[(2S)-1,1,1-trifluoropropan-2-yl]acetamide | 169-173 | 535.7 |
| 261 | 6-(3-cyano-1-cyclobutyl-5-methoxy-1H-pyrrolo[2,3-b]pyridin-2-yl)-N-(1,1,1-trifluorobutan-2-yl)pyridine-3-sulfonamide | 185-190 | 494.2 |
| 268 | 6-(3-cyano-1-cyclopentyl-5-methoxy-1H-pyrrolo[2,3-b]pyridin-2-yl)-N-[(2R)-1,1,1-trifluoropropan-2-yl]pyridine-3-sulfonamide | 181-184 | 494.2 |
| 269 | 6-(3-cyano-1-cyclopentyl-5-methoxy-1H-pyrrolo[2,3-b]pyridin-2-yl)-N-(1-methylcyclopropyl)pyridine-3-sulfonamide | N/A | 451.6 |
| 271 | N-tert-butyl-6-(3-cyano-1-cyclobutyl-5-methoxy-1H-pyrrolo[2,3-b]pyridin-2-yl)pyridine-3-sulfonamide | 174-176 | 440.2 |
| 275 | 6-(3-cyano-1-cyclobutyl-5-hydroxy-1H-pyrrolo[2,3-b]pyridin-2-yl)-N-[(2S)-1,1,1-trifluoropropan-2-yl]pyridine-3-sulfonamide | 240-242 | 466.3 |
| 277 | 6-(3-cyano-1-cyclobutyl-5-methoxy-1H-pyrrolo[2,3-b]pyridin-2-yl)-4-methyl-N-[(2S)-1,1,1-trifluoropropan-2-yl]pyridine-3-sulfonamide | 175-179 | 494.1 |
| 292 | 6-(3-cyano-1-cyclobutyl-5-methoxy-1H-pyrrolo[2,3-b]pyridin-2-yl)-5-methyl-N-[(2S)-1,1,1-trifluoropropan-2-yl]pyridine-3-sulfonamide | 180-183 | 494.1 |
| 294 | 6-(3-cyano-1-cyclopentyl-5-hydroxy-1H-pyrrolo[2,3-b]pyridin-2-yl)-N-[(2S)-1,1,1-trifluoropropan-2-yl]pyridine-3-sulfonamide | 221-223 | 480.5 |
| 309 | 6-(3-cyano-1-cyclobutyl-5-methoxy-1H-pyrrolo[2,3-b]pyridin-2-yl)-N-cyclobutylpyridine-3-sulfonamide | 203-207 | 438.1 |
| 310 | 6-(3-cyano-1-cyclobutyl-5-methoxy-1H-pyrrolo[2,3-b]pyridin-2-yl)-N-cyclopropylpyridine-3-sulfonamide | 161-162 | 424.1 |
| 311 | 6-(3-cyano-1-cyclobutyl-5-methoxy-1H-pyrrolo[2,3-b]pyridin-2-yl)-N-(1-methylcyclopropyl)pyridine-3-sulfonamide | 179-181 | 438.1 |
| 312 | 6-(3-cyano-1-cyclobutyl-5-methoxy-1H-pyrrolo[2,3-b]pyridin-2-yl)-N-[1-(trifluoromethyl)cyclopropyl]pyridine-3-sulfonamide | N/A | 492.1 |
| 313 | 2-(3-cyano-1-cyclobutyl-5-methoxy-1H-pyrrolo[2,3-b]pyridin-2-yl)-N-(1-methylcyclopropyl)pyrimidine-5-sulfonamide | 209-212 | 439.1 |

Example 2

6-(5-chloro-3-cyano-1-cyclobutyl-1H-pyrrolo[2,3-c]pyridin-2-yl)-N-[(2R)-1,1,1-trifluoropropan-2-yl]pyridine-3-sulfonamide (Cpd 104)

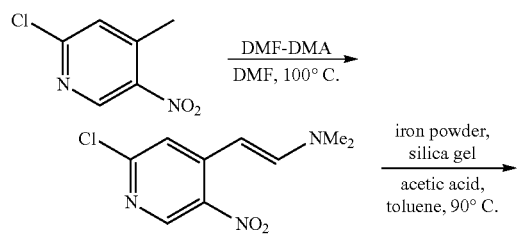

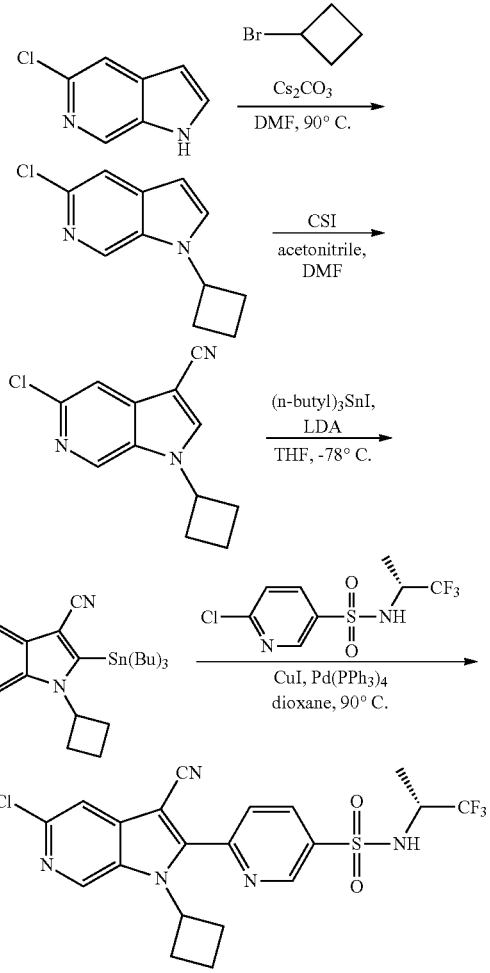

Step A: A 50 mL round-bottom flask was charged with 2-chloro-4-methyl-5-nitropyridine (6.06 g, 35.3 mmol), DMF (27 mL) and dimethylformamide dimethylacetal (9.4 mL, 70 mmol). The mixture was heated to 90° C. for 1 hr. After cooling, the mixture was poured into ice-water (300 mL) and the resulting precipitate collected on a filter to afford 7.05 g (96%) of (E)-2-(2-chloro-5-nitropyridin-4-yl)-N,N-dimethylethenamine.

Step B: A mixture of (E)-2-(2-chloro-5-nitropyridin-4-yl)-N,N-dimethylethenamine (2.77 g, 13.4 mmol), iron powder 7.50 mg (134 mmol), silica gel (13 g) toluene (50 mL) and acetic acid (30 mL) was heated at 90° C. for 1 hr. After cooling, the mixture was diluted with ethyl acetate (500 mL) and purified on silica gel eluting with 50% ethyl acetate in hexane to provide 1.1 g (54%) of 5-chloro-1H-pyrrolo[2,3-c]pyridine.

Step C: A sealed vessel containing 5-chloro-1H-pyrrolo[2,3-c]pyridine (500 mg, 3.27 mmol), cesium carbonate (2.35 g, 7.21 mmol), cyclobutyl bromide (885 mg, 6.55 mmol) and DMF (5 mL) was heated to 90° C. overnight. After cooling to room temperature water was added and the mixture extracted with ethyl acetate (3×20 mL). The organic phase was dried over MgSO₄ and concentrated to give 0.63 g (95%) of 5-chloro-1-cyclobutyl-1H-pyrrolo[2,3-c]pyridine-3-carbonitrile as a brown oil.

Step D: To a solution of 5-chloro-1-cyclobutyl-1H-pyrrolo[2,3-c]pyridine-3-carbonitrile (1.80 g, 8.73 mmol) in acetonitrile (10 mL) and DMF (10 mL) at 0° C. was added chlorosulfonyl isocyanate dropwise. The mixture was allowed to warm to 50° C. and stir for 1 hr. Water (10 mL) was slowly added and then the pH was adjusted to pH 9 using 1N HCl. The resulting precipitate was collected on a filter and dried under vacuum to provide 1.22 g (60%) of 5-chloro-1-cyclobutyl-1H-pyrrolo[2,3-c]pyridine-3-carbonitrile.

Step E: A mixture of 5-chloro-1-cyclobutyl-1H-pyrrolo[2,3-c]pyridine-3-carbonitrile (1.22 g, 5.28 mmol) in THF (8 mL) was cooled to −78° C. and LDA (4.2 mL, 1.5 M in cyclohexane-THF, 6.33 mmol) added. After 30 min tributyltin iodide (2.5 mL, 8.8 mmol) was added dropwise. After warming to room temperature the solvent was evaporated and the mixture was purified on silica gel eluting with 40% ethyl acetate in hexane to provide 1.59 g (58%) of 5-chloro-1-cyclobutyl-2-(tributylstannyl)-1H-pyrrolo[2,3-c]pyridine-3-carbonitrile.

Step F: A 5 mL round-bottom flask was charged with 5-chloro-1-cyclobutyl-2-(tributylstannyl)-1H-pyrrolo[2,3-c]pyridine-3-carbonitrile (100 mg, 0.192 mmol), (S)-4-chloro-N-(1,1,1-trifluoropropan-2-yl)benzenesulfonamide (50.2 mg, 0.17 mmol) [from Example 1, Part A, Step B above], Pd[(PPh$_3$)]$_4$ (22 mg, 0.019 mmol) and CuI (8 mg, 0.04 mmol). Dioxane (1 mL) was added and the mixture heated to 90° C. for 2 h. The mixture was concentrated and purified on silica gel eluting with 0-50% ethyl acetate in hexane to provide 56 mg (60%) of the title compound. Melting point: 181-185° C.; MS m/z 484.1 (M+H$^+$); $^1$H NMR (500 MHz, CDCl$_3$): δ 9.22 (s, 1H), 8.91 (s, 1H), 8.36 (q, 1H), 8.04 (d, 1H), 7.72 (s, 1H), 5.28 (m, 1H), 4.05 (m, 1H), 2.54 (m, 2H), 2.43 (m, 2H), 1.92 (m, 2H).

Additional compounds representative of the present invention may be prepared according to the procedure of Example 2 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 67 | 6-(5-chloro-3-cyano-1-cyclobutyl-1H-pyrrolo[2,3-c]pyridin-2-yl)-N-[(2S)-1,1,1-trifluoropropan-2-yl]pyridine-3-sulfonamide | 180-183 | 483.1 |
| 103 | 6-(3-cyano-1-cyclobutyl-1H-pyrrolo[2,3-c]pyridin-2-yl)-N-[(2S)-1,1,1-trifluoropropan-2-yl]pyridine-3-sulfonamide | 199-201 | 450.0 |
| 105 | 4-(5-chloro-3-cyano-1-cyclobutyl-1H-pyrrolo[2,3-c]pyridin-2-yl)-N-[(2R)-1,1,1-trifluoropropan-2-yl]benzenesulfonamide | 248-250 | 483.2 |
| 106 | 6-(5-chloro-3-cyano-1-cyclobutyl-1H-pyrrolo[2,3-c]pyridin-2-yl)-N-cyclopropylpyridine-3-sulfonamide | 170-172 | 428.2 |
| 165 | 6-(3-cyano-1-cyclobutyl-5-methyl-1H-pyrrolo[2,3-c]pyridin-2-yl)-N-[(2S)-1,1,1-trifluoropropan-2-yl]pyridine-3-sulfonamide | 185-188 | 464.2 |
| 166 | 6-(3-cyano-1-cyclobutyl-5-methyl-1H-pyrrolo[2,3-c]pyridin-2-yl)-N-[(2R)-1,1,1-trifluoropropan-2-yl]pyridine-3-sulfonamide | 195-198 | 464.2 |
| 167 | 4-(3-cyano-1-cyclobutyl-5-methyl-1H-pyrrolo[2,3-c]pyridin-2-yl)-N-[(2S)-1,1,1-trifluoropropan-2-yl]benzenesulfonamide | 188-191 | 463.3 |
| 168 | 6-(3-cyano-1-cyclobutyl-1H-pyrrolo[2,3-c]pyridine-2-yl)-N-(1-methylcyclopropyl)pyridine-3-sulfonamide | 185-190 | 422.2 |
| 219 | 4-(3-cyano-1-cyclobutyl-5-ethyl-1H-pyrrolo[2,3-c]pyridin-2-yl)-N-[(2S)-1,1,1-trifluoropropan-2-yl]benzenesulfonamide | 200-203 | 477.3 |
| 220 | N-[4-(3-cyano-1-cyclobutyl-5-ethyl-1H-pyrrolo[2,3-c]pyridin-2-yl)phenyl]propane-2-sulfonamide | 160-165 | 423.3 |
| 223 | 6-(3-cyano-1-cyclobutyl-5-cyclopropyl-1H-pyrrolo[2,3-c]pyridin-2-yl)-N-[(2S)-1,1,1-trifluoropropan-2-yl]pyridine-3-sulfonamide | 200-205 | 490.4 |
| 224 | 4-(3-cyano-1-cyclobutyl-5-cyclopropyl-1H-pyrrolo[2,3-c]pyridin-2-yl)-N-[(2S)-1,1,1-trifluoropropan-2-yl]benzenesulfonamide | 190-195 | 489.5 |

Example 3

6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide (Cpd 69)

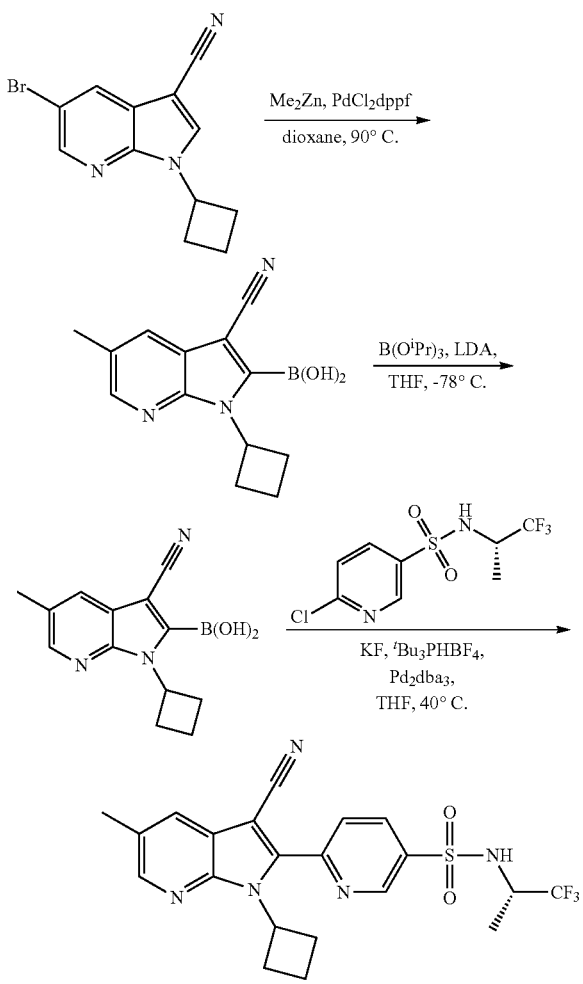

Step A: To a mixture of 5-bromo-1-cyclobutyl-1H-pyrrolo[2,3-b]pyridine-3-carbonitrile (7.50 g, 27.3 mmol) [from Example 1, Step B], PdCl$_2$dppf (4.47 g, 0.55 mmol) and dioxane (50 mL) was added dimethyl zinc (1.2 M in toluene, 45.6 mL, 54.7 mmol). The resulting mixture was stirred at 90° C. for 2 h. After cooling, the mixture was treated with methanol (15 mL) at 0° C. then partitioned between ethyl acetate and 1N HCl. The organic phase was washed with water and brine, dried over MgSO$_4$, and concentrated. The residue was purified on silica gel eluting with 5% ethyl acetate in hexanes to afford 4.7 g (81%) of 1-cyclobutyl-5-methyl-1H-pyrrolo[2,3-b]pyridine-3-carbonitrile as a off-white solid.

Step B: In a similar manner as Example 1, Step D, 3-cyano-1-cyclobutyl-5-methyl-1H-pyrrolo[2,3-b]pyridin-2-ylboronic acid was prepared (4.32 g, 85%).

Step C: The title compound was prepared in a similar manner as Example 1, Step E (4.6 g, 82%). Melting point: 177-179° C.; MS m/z 464.1 (M+H$^+$); $^1$H NMR (500 MHz, acetone-d$_6$): δ 9.30 (1H, m), 8.56 (1H, dd, J=8.5, 2.5 Hz), 8.43 (1H, d, J=2.0 Hz), 8.15 (1H, dd, J=8.5, 1.0 Hz), 7.98 (1H, dd, J=2.0, 0.5 Hz), 7.77 (1H, br, s), 5.38 (1H, m), 4.39 (1H, m), 3.26 (2H, m), 2.54 (3H, s), 2.38 (2H, m), 1.92 (2H, m), 1.82 (3H, d, J=2.5 Hz).

Additional compounds representative of the present invention may be prepared according to the procedure of Example 3 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 68 | 6-(3-cyano-1-cyclobutyl-5-methyl-1H-pyrrolo[2,3-b]pyridin-2-yl)-N-[(2R)-1,1,1-trifluoropropan-2-yl]pyridine-3-sulfonamide | 176-178 | 464.1 |
| 70 | 2-(3-cyano-1-cyclobutyl-5-methyl-1H-pyrrolo[2,3-b]pyridin-2-yl)-N-[(2R)-1,1,1-trifluoropropan-2-yl]pyrimidine-5-sulfonamide | 186-188 | 465.1 |
| 71 | 2-(3-cyano-1-cyclobutyl-5-methyl-1H-pyrrolo[2,3-b]pyridin-2-yl)-N-[(2S)-1,1,1-trifluoropropan-2-yl]pyrimidine-5-sulfonamide | 186-188 | 465.1 |
| 72 | 4-(3-cyano-1-cyclobutyl-5-methyl-1H-pyrrolo[2,3-b]pyridin-2-yl)-N-[(2R)-1,1,1-trifluoropropan-2-yl]benzenesulfonamide | 197-198 | 463.1 |
| 73 | 4-(3-cyano-1-cyclobutyl-5-methyl-1H-pyrrolo[2,3-b]pyridin-2-yl)-N-[(2S)-1,1,1-trifluoropropan-2-yl]benzenesulfonamide | 197-198 | 463.1 |
| 74 | 6-(3-cyano-1-cyclobutyl-5-methyl-1H-pyrrolo[2,3-b]pyridin-2-yl)-N-[1-(trifluoromethyl)cyclopropyl]pyridine-3-sulfonamide | 245-247 | 476.1 |
| 75 | 4-(3-cyano-1-cyclobutyl-5-methyl-1H-pyrrolo[2,3-b]pyridin-2-yl)-N-[1-(trifluoromethyl)cyclopropyl]benzenesulfonamide | 187-188 | 475.2 |
| 76 | 6-(3-cyano-1-cyclobutyl-5-methyl-1H-pyrrolo[2,3-b]pyridin-2-yl)-N-(1-methylcyclopropyl)pyridine-3-sulfonamide | 188-189 | 422.2 |
| 77 | 4-(3-cyano-1-cyclobutyl-5-methyl-1H-pyrrolo[2,3-b]pyridin-2-yl)-N-(1-methylcyclopropyl)benzenesulfonamide | 188-190 | 421.2 |
| 78 | 2-(3-cyano-1-cyclobutyl-5-methyl-1H-pyrrolo[2,3-b]pyridin-2-yl)-N-(propan-2-yl)pyrimidine-5-sulfonamide | 187-190 | 411.2 |
| 79 | 4-(3-cyano-1-cyclobutyl-5-methyl-1H-pyrrolo[2,3-b]pyridin-2-yl)-N-(1,1,1-trifluoro-2-methylpropan-2-yl)benzenesulfonamide | 180-181 | 477.2 |
| 115 | 4-(3-cyano-1-cyclobutyl-5-cyclopropyl-1H-pyrrolo[2,3-b]pyridin-2-yl)-N-[(2S)-1,1,1-trifluoropropan-2-yl]benzenesulfonamide | 196-203 | 489.3 |
| 116 | 4-(3-cyano-1-cyclobutyl-5-cyclopropyl-1H-pyrrolo[2,3-b]pyridin-2-yl)-N-[(2R)-1,1,1-trifluoropropan-2-yl]benzenesulfonamide | 190-195 | 489.3 |
| 117 | 6-(3-cyano-1-cyclobutyl-5-cyclopropyl-1H-pyrrolo[2,3-b]pyridin-2-yl)-N-[(2S)-1,1,1-trifluoropropan-2-yl]pyridine-3-sulfonamide | 136-144 | 489.9 |
| 118 | 6-(3-cyano-1-cyclobutyl-5-cyclopropyl-1H-pyrrolo[2,3-b]pyridin-2-yl)-N-[(2R)-1,1,1-trifluoropropan-2-yl]pyridine-3-sulfonamide | 138-147 | 490.3 |
| 119 | 2-(3-cyano-1-cyclobutyl-5-cyclopropyl-1H-pyrrolo[2,3-b]pyridin-2-yl)-N-[(2S)-1,1,1-trifluoropropan-2-yl]pyrimidine-5-sulfonamide | 176-183 | 491.2 |
| 120 | 2-(3-cyano-1-cyclobutyl-5-cyclopropyl-1H-pyrrolo[2,3-b]pyridin-2-yl)-N-[(2R)-1,1,1-trifluoropropan-2-yl]pyrimidine-5-sulfonamide | N/A | 491.2 |
| 121 | 4-(3-cyano-1-cyclobutyl-5-cyclopropyl-1H-pyrrolo[2,3-b]pyridin-2-yl)-N-(1,1,1-trifluoro-2-methylpropan-2-yl)benzenesulfonamide | 207-212 | 503.3 |
| 122 | 6-[3-cyano-1-cyclobutyl-5-(difluoromethoxy)-1H-pyrrolo[2,3-b]pyridin-2-yl]-N-[(2S)-1,1,1-trifluoropropan-2-yl]pyridine-3-sulfonamide | 155-156 | 516.2 |
| 123 | 4-(3-cyano-1-cyclobutyl-5-cyclopropyl-1H-pyrrolo[2,3-b]pyridin-2-yl)-N-[1-(trifluoromethyl)cyclopropyl]benzenesulfonamide | N/A | 501.3 |
| 124 | 6-(3-cyano-1-cyclobutyl-5-cyclopropyl-1H-pyrrolo[2,3-b]pyridin-2-yl)-N-[1-(trifluoromethyl)cyclopropyl]pyridine-3-sulfonamide | 163-171 | 502.2 |
| 125 | N-tert-butyl-4-(3-cyano-1-cyclobutyl-5-cyclopropyl-1H-pyrrolo[2,3-b]pyridin-2-yl)benzenesulfonamide | 210-215 | 449.3 |
| 126 | N-tert-butyl-6-(3-cyano-1-cyclobutyl-5-cyclopropyl-1H-pyrrolo[2,3-b]pyridin-2-yl)pyridine-3-sulfonamide | N/A | 450.3 |
| 127 | 4-(3-cyano-1-cyclobutyl-5-cyclopropyl-1H-pyrrolo[2,3-b]pyridin-2-yl)-N-(1-methylcyclopropyl)benzenesulfonamide | 152-161 | 447.3 |
| 128 | 6-(3-cyano-1-cyclobutyl-5-cyclopropyl-1H-pyrrolo[2,3-b]pyridin-2-yl)-N-(1-methylcyclopropyl)pyridine-3-sulfonamide | 178-185 | 448.3 |
| 129 | 2-(3-cyano-1-cyclobutyl-5-cyclopropyl-1H-pyrrolo[2,3-b]pyridin-2-yl)-N-(1-methylcyclopropyl)pyrimidine-5-sulfonamide | 161-169 | 449.3 |
| 130 | 4-(3-cyano-1-cyclobutyl-5-cyclopropyl-1H-pyrrolo[2,3-b]pyridin-2-yl)-N-(1,3-difluoropropan-2-yl)benzenesulfonamide | 225-230 | 471.3 |
| 131 | 6-(3-cyano-1-cyclobutyl-5-cyclopropyl-1H-pyrrolo[2,3-b]pyridin-2-yl)-N-(1,3-difluoropropan-2-yl)pyridine-3-sulfonamide | N/A | 472.2 |
| 132 | 2-(3-cyano-1-cyclobutyl-5-cyclopropyl-1H-pyrrolo[2,3-b]pyridin-2-yl)-N-(1,3-difluoropropan-2-yl)pyrimidine-5-sulfonamide | 189-197 | 473.2 |
| 133 | 6-(3-cyano-1-cyclobutyl-5-cyclopropyl-1H-pyrrolo[2,3-b]pyridin-2-yl)-N-cyclopropylpyridine-3-sulfonamide | 169-174 | 434.3 |
| 134 | 6-(3-cyano-1-cyclobutyl-5-cyclopropyl-1H-pyrrolo[2,3-b]pyridin-2-yl)-N-cyclobutylpyridine-3-sulfonamide | 189-197 | 448.3 |
| 135 | 5-(3-cyano-1-cyclobutyl-5-cyclopropyl-1H-pyrrolo[2,3-b]pyridin-2-yl)-N-(propan-2-yl)pyridine-2-sulfonamide | N/A | 436.2 |
| 136 | 2-(3-cyano-1-cyclobutyl-5-cyclopropyl-1H-pyrrolo[2,3-b]pyridin-2-yl)-N-(propan-2-yl)pyrimidine-5-sulfonamide | 187-195 | 437.3 |
| 155 | 4-(3-cyano-1-cyclobutyl-5-ethyl-1H-pyrrolo[2,3-b]pyridin-2-yl)-N-[(2S)-1,1,1-trifluoropropan-2-yl]benzenesulfonamide | 194-201 | 476.8 |
| 156 | 4-(3-cyano-1-cyclobutyl-5-ethyl-1H-pyrrolo[2,3-b]pyridin-2-yl)-N-[(2R)-1,1,1-trifluoropropan-2-yl]benzenesulfonamide | 194-201 | 476.9 |
| 157 | 6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide | N/A | 477.8 |
| 158 | 6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide | N/A | 477.9 |
| 159 | 2-(3-cyano-1-cyclobutyl-5-ethyl-1H-pyrrolo[2,3-b]pyridin-2-yl)-N-[(2S)-1,1,1-trifluoropropan-2-yl]pyrimidine-5-sulfonamide | N/A | 479.3 |
| 160 | 2-(3-cyano-1-cyclobutyl-5-ethyl-1H-pyrrolo[2,3-b]pyridin-2-yl)-N-[(2R)-1,1,1-trifluoropropan-2-yl]pyrimidine-5-sulfonamide | N/A | 479.3 |
| 182 | 4-(3-cyano-1-cyclobutyl-5-ethyl-1H-pyrrolo[2,3-b]pyridin-2-yl)-N-(1,1,1-trifluoro-2-methylpropan-2-yl)benzenesulfonamide | 190-195 | 491.3 |
| 183 | 4-(3-cyano-1-cyclobutyl-5-ethyl-1H-pyrrolo[2,3-b]pyridin-2-yl)-N-[1-(trifluoromethyl)cyclopropyl]benzenesulfonamide | 161-168 | 489.3 |

| Cpd | Name | m.p. | MS |
|---|---|---|---|
| 184 | 6-(3-cyano-1-cyclobutyl-5-ethyl-1H-pyrrolo[2,3-b]pyridin-2-yl)-N-[1-(trifluoro-methyl)cyclopropyl]pyridine-3-sulfonamide | 216-221 | 490.3 |
| 185 | N-tert-butyl-4-(3-cyano-1-cyclobutyl-5-ethyl-1H-pyrrolo[2,3-b]pyridin-2-yl)benzenesulfonamide | 190-196 | 437.3 |
| 186 | N-tert-butyl-6-(3-cyano-1-cyclobutyl-5-ethyl-1H-pyrrolo[2,3-b]pyridin-2-yl)pyridine-3-sulfonamide | N/A | 438.3 |
| 187 | 4-(3-cyano-1-cyclobutyl-5-ethyl-1H-pyrrolo[2,3-b]pyridin-2-yl)-N-(1-methylcyclopropyl)benzenesulfonamide | 157-163 | 435.3 |
| 188 | 6-(3-cyano-1-cyclobutyl-5-ethyl-1H-pyrrolo[2,3-b]pyridin-2-yl)-N-(1-methylcyclopropyl)pyridine-3-sulfonamide | N/A | 436.3 |
| 189 | 2-(3-cyano-1-cyclobutyl-5-ethyl-1H-pyrrolo[2,3-b]pyridin-2-yl)-N-(1-methylcyclopropyl)pyrimidine-5-sulfonamide | N/A | 437.3 |
| 190 | 4-(3-cyano-1-cyclobutyl-5-ethyl-1H-pyrrolo[2,3-b]pyridin-2-yl)-N-(1,3-difluoropropan-2-yl)benzenesulfonamide | 165-171 | 459.3 |
| 191 | 6-(3-cyano-1-cyclobutyl-5-ethyl-1H-pyrrolo[2,3-b]pyridin-2-yl)-N-(1,3-difluoropropan-2-yl)pyridine-3-sulfonamide | 157-165 | 460.3 |
| 192 | 2-(3-cyano-1-cyclobutyl-5-ethyl-1H-pyrrolo[2,3-b]pyridin-2-yl)-N-(1,3-difluoropropan-2-yl)pyrimidine-5-sulfonamide | N/A | 461.2 |
| 193 | 6-(3-cyano-1-cyclobutyl-5-ethyl-1H-pyrrolo[2,3-b]pyridin-2-yl)-N-cyclopropylpyridine-3-sulfonamide | N/A | 422.2 |
| 194 | 6-(3-cyano-1-cyclobutyl-5-ethyl-1H-pyrrolo[2,3-b]pyridin-2-yl)-N-cyclobutylpyridine-3-sulfonamide | 168-177 | 436.3 |
| 195 | 5-(3-cyano-1-cyclobutyl-5-ethyl-1H-pyrrolo[2,3-b]pyridin-2-yl)-N-(propan-2-yl)pyridine-2-sulfonamide | 195-202 | 424.3 |
| 196 | 2-(3-cyano-1-cyclobutyl-5-ethyl-1H-pyrrolo[2,3-b]pyridin-2-yl)-N-(propan-2-yl)pyrimidine-5-sulfonamide | 170-178 | 425.3 |
| 197 | 6-[3-cyano-1-cyclobutyl-5-(difluoromethoxy)-1H-pyrrolo[2,3-b]pyridin-2-yl]-N-[(2R)-1,1,1-trifluoropropan-2-yl]pyridine-3-sulfonamide | 149-151 | 515.9 |
| 198 | 4-[3-cyano-1-cyclobutyl-5-(difluoromethoxy)-1H-pyrrolo[2,3-b]pyridin-2-yl]-N-[(2S)-1,1,1-trifluoropropan-2-yl]benzenesulfonamide | 155-156 | 516.2 |
| 199 | 4-[3-cyano-1-cyclobutyl-5-(difluoromethoxy)-1H-pyrrolo[2,3-b]pyridin-2-yl]-N-[(2R)-1,1,1-trifluoropropan-2-yl]benzenesulfonamide | 199-200 | 514.8 |
| 200 | 6-[3-cyano-1-cyclobutyl-5-(difluoromethoxy)-1H-pyrrolo[2,3-b]pyridin-2-yl]-N-[(1S)-1-cyclopropylethyl]pyridine-3-sulfonamide | 199-200 | 514.9 |
| 201 | 6-[3-cyano-1-cyclobutyl-5-(difluoromethoxy)-1H-pyrrolo[2,3-b]pyridin-2-yl]-N-(1,1,1-trifluoro-2-methylpropan-2-yl)pyridine-3-sulfonamide | 168-169 | 529.8 |
| 202 | 6-(3-cyano-1-cyclobutyl-5-ethoxy-1H-pyrrolo[2,3-b]pyridin-2-yl)-N-[(2S)-1,1,1-trifluoropropan-2-yl]pyridine-3-sulfonamide | 181-182 | 493.9 |
| 203 | 6-(3-cyano-1-cyclobutyl-5-ethoxy-1H-pyrrolo[2,3-b]pyridin-2-yl)-N-[(2R)-1,1,1-trifluoropropan-2-yl]pyridine-3-sulfonamide | 180-181 | 493.8 |
| 204 | 6-(3-cyano-1-cyclobutyl-5-propoxy-1H-pyrrolo[2,3-b]pyridin-2-yl)-N-[(2S)-1,1,1-trifluoropropan-2-yl]pyridine-3-sulfonamide | 170-171 | 508.3 |
| 205 | 6-(3-cyano-1-cyclobutyl-5-propoxy-1H-pyrrolo[2,3-b]pyridin-2-yl)-N-[(2R)-1,1,1-trifluoropropan-2-yl]pyridine-3-sulfonamide | 169-170 | 508.3 |
| 218 | 6-[3-cyano-1-cyclobutyl-5-(propan-2-yloxy)-1H-pyrrolo[2,3-b]pyridin-2-yl]-N-[(2S)-1,1,1-trifluoropropan-2-yl]pyridine-3-sulfonamide | 168-169 | 507.8 |
| 227 | 6-[3-cyano-1-cyclobutyl-5-(trifluoromethyl)-1H-pyrrolo[2,3-b]pyridin-2-yl]-N-[(2S)-1,1,1-trifluoropropan-2-yl]pyridine-3-sulfonamide | 183-185 | 517.8 |
| 228 | 6-[3-cyano-1-cyclobutyl-5-(trifluoromethyl)-1H-pyrrolo[2,3-b]pyridin-2-yl]-N-[(2R)-1,1,1-trifluoropropan-2-yl]pyridine-3-sulfonamide | 190-192 | 517.8 |
| 229 | 6-[3-cyano-1-cyclopentyl-5-(trifluoromethyl)-1H-pyrrolo[2,3-b]pyridin-2-yl]-N-[(2S)-1,1,1-trifluoropropan-2-yl]pyridine-3-sulfonamide | 205-207 | 531.8 |
| 230 | 6-[3-cyano-1-cyclopentyl-5-(trifluoromethyl)-1H-pyrrolo[2,3-b]pyridin-2-yl]-N-[(2R)-1,1,1-trifluoropropan-2-yl]pyridine-3-sulfonamide | 208-210 | 531.8 |
| 233 | 6-(5-chloro-3-cyano-1-cyclopentyl-1H-pyrrolo[2,3-b]pyridin-2-yl)-N-[(2S)-1,1,1-trifluorobutan-2-yl]pyridine-3-sulfonamide | 180-185 | 512.2 |
| 237 | 6-[3-cyano-1-cyclobutyl-5-(thiophen-2-yl)-1H-pyrrolo[2,3-b]pyridin-2-yl]-N-[(2S)-1,1,1-trifluoropropan-2-yl]pyridine-3-sulfonamide | 206-208 | 532.1 |
| 238 | 6-[3-cyano-1-cyclobutyl-5-(thiophen-2-yl)-1H-pyrrolo[2,3-b]pyridin-2-yl]-N-[(2R)-1,1,1-trifluoropropan-2-yl]pyridine-3-sulfonamide | 198-199 | 532.2 |
| 239 | 6-[3-cyano-1-cyclobutyl-5-(pyrrolidin-1-yl)-1H-pyrrolo[2,3-b]pyridin-2-yl]-N-[(2S)-1,1,1-trifluoropropan-2-yl]pyridine-3-sulfonamide | 207-209 | 519.3 |
| 240 | 6-[3-cyano-1-cyclobutyl-5-(pyrrolidin-1-yl)-1H-pyrrolo[2,3-b]pyridin-2-yl]-N-[(2R)-1,1,1-trifluoropropan-2-yl]pyridine-3-sulfonamide | 207-209 | 519.3 |
| 244 | 6-[3-cyano-1-cyclobutyl-5-(trifluoromethyl)-1H-pyrrolo[2,3-b]pyridin-2-yl]-N-(propan-2-yl)pyridine-3-sulfonamide | 186-187 | 463.7 |
| 245 | 6-[3-cyano-1-cyclobutyl-5-(trifluoromethyl)-1H-pyrrolo[2,3-b]pyridin-2-yl]-N-cyclopropylpyridine-3-sulfonamide | N/A | 461.8 |
| 246 | N-{4-[3-cyano-1-cyclobutyl-5-(trifluoromethyl)-1H-pyrrolo[2,3-b]pyridin-2-yl]phenyl}cyclopropanesulfonamide | N/A | 460.8 |
| 247 | N-{4-[3-cyano-1-cyclobutyl-5-(trifluoromethyl)-1H-pyrrolo[2,3-b]pyridin-2-yl]phenyl}propane-1-sulfonamide | 180-181 | 462.7 |
| 249 | 6-(3-cyano-1-cyclopentyl-5-cyclopropyl-1H-pyrrolo[2,3-b]pyridin-2-yl)-N-[(2R)-1,1,1-trifluoropropan-2-yl]pyridine-3-sulfonamide | 155-164 | 503.4 |
| 250 | 6-(3-cyano-1-cyclopentyl-5-cyclopropyl-1H-pyrrolo[2,3-b]pyridin-2-yl)-N-[(2S)-1,1,1-trifluoropropan-2-yl]pyridine-3-sulfonamide | 157-167 | 503.5 |
| 251 | 6-(3-cyano-1-cyclopentyl-5-ethyl-1H-pyrrolo[2,3-b]pyridin-2-yl)-N-[(2R)-1,1,1-trifluoropropan-2-yl]pyridine-3-sulfonamide | N/A | 461.4 |
| 252 | 6-(3-cyano-1-cyclopentyl-5-ethyl-1H-pyrrolo[2,3-b]pyridin-2-yl)-N-[(2S)-1,1,1-trifluoropropan-2-yl]pyridine-3-sulfonamide | N/A | 491.4 |
| 253 | 6-(3-cyano-1-cyclopentyl-5-cyclopropyl-1H-pyrrolo[2,3-b]pyridin-2-yl)-N-(1-methylcyclopropyl)pyridine-3-sulfonamide | N/A | 461.5 |
| 254 | 6-(3-cyano-1-cyclopentyl-5-methyl-1H-pyrrolo[2,3-b]pyridin-2-yl)-N-[(2R)-1,1,1-trifluoropropan-2-yl]pyridine-3-sulfonamide | 155-162 | 477.4 |
| 255 | 6-(3-cyano-1-cyclopentyl-5-methyl-1H-pyrrolo[2,3-b]pyridin-2-yl)-N-[(2S)-1,1,1-trifluoropropan-2-yl]pyridine-3-sulfonamide | N/A | 478.3 |
| 256 | 6-(3-cyano-1-cyclopentyl-5-methyl-1H-pyrrolo[2,3-b]pyridin-2-yl)-N-(1-methylcyclopropyl)pyridine-3-sulfonamide | 143-153 | 436.2 |
| 260 | 6-(5-chloro-3-cyano-1-cyclopentyl-1H-pyrrolo[2,3-b]pyridin-2-yl)-N-(1,1,1-trifluorobutan-2-yl)pyridine-3-sulfonamide | 170-174 | 512.2 |
| 262 | 4-(3-cyano-1-cyclopentyl-5-methyl-1H-pyrrolo[2,3-b]pyridin-2-yl)-N-[(2R)-1,1,1-trifluoropropan-2-yl]benzenesulfonamide | 189-195 | 477.4 |
| 263 | 4-(3-cyano-1-cyclopentyl-5-methyl-1H-pyrrolo[2,3-b]pyridin-2-yl)-N-[(2S)-1,1,1-trifluoropropan-2-yl]benzenesulfonamide | 191-196 | 477.4 |
| 264 | 1-cyclobutyl-5-methyl-2-[4-(propan-2-ylamino)phenyl]-1H-pyrrolo[2,3-b]pyridine-3-carbonitrile | 193-199 | 345.5 |
| 265 | N-[4-(3-cyano-1-cyclobutyl-5-methyl-1H-pyrrolo[2,3-b]pyridin-2-yl)phenyl]-2-methylpropanamide | 134-140 | 373.5 |
| 266 | 1-[4-(3-cyano-1-cyclobutyl-5-methyl-1H-pyrrolo[2,3-b]pyridin-2-yl)phenyl]-3-propan-2-ylurea | 224-231 | 388.5 |
| 267 | N-[4-(3-cyano-1-cyclobutyl-5-methyl-1H-pyrrolo[2,3-b]pyridin-2-yl)phenyl]propane-2-sulfonamide | 155-164 | 409.4 |

| Cpd | Name | m.p. | MS |
|---|---|---|---|
| 272 | 6-[3-cyano-1-cyclopentyl-5-(methylsulfanyl)-1H-pyrrolo[2,3-b]pyridin-2-yl]-N-[(2S)-1,1,1-trifluoropropan-2-yl]pyridine-3-sulfonamide | 168-172 | 510.2 |
| 273 | 6-[3-cyano-1-cyclopentyl-5-(methylsulfanyl)-1H-pyrrolo[2,3-b]pyridin-2-yl]-N-[(2R)-1,1,1-trifluoropropan-2-yl]pyridine-3-sulfonamide | 124-127 | 509.3 |
| 274 | 6-[3-cyano-1-cyclopentyl-5-(methylsulfanyl)-1H-pyrrolo[2,3-b]pyridin-2-yl]-N-[1-(trifluoromethyl)cyclopropyl]pyridine-3-sulfonamide | 200-203 | 521.4 |
| 276 | 6-(5-chloro-3-cyano-1-cyclobutyl-1H-pyrrolo[2,3-b]pyridin-2-yl)-N-[(2S)-1,1,1-trifluorobutan-2-yl]pyridine-3-sulfonamide | 186-191 | 498.3 |
| 278 | 6-(5-chloro-3-cyano-1-cyclopentyl-1H-pyrrolo[2,3-b]pyridin-2-yl)-4-methyl-N-[(2S)-1,1,1-trifluoropropan-2-yl]pyridine-3-sulfonamide | 190-195 | 512.1 |
| 279 | 6-(3-cyano-1-cyclobutyl-5-methyl-1H-pyrrolo[2,3-b]pyridin-2-yl)-N-[(2S)-1,1,1-trifluorobutan-2-yl]pyridine-3-sulfonamide | 138-144 | 478.1 |
| 280 | 6-(5-chloro-3-cyano-1-cyclobutyl-1H-pyrrolo[2,3-b]pyridin-2-yl)-N-(1-methylcyclopropyl)pyridine-3-sulfonamide | N/A | 442.1 |
| 281 | 4-(5-chloro-3-cyano-1-cyclobutyl-1H-pyrrolo[2,3-b]pyridin-2-yl)-N-[1-(trifluoromethyl)cyclopropyl]benzenesulfonamide | N/A | 495.1 |
| 282 | 4-(5-chloro-3-cyano-1-cyclobutyl-1H-pyrrolo[2,3-b]pyridin-2-yl)-N-(1,1,1-trifluoro-2-methylpropan-2-yl)benzenesulfonamide | N/A | 497.2 |
| 283 | 6-(5-chloro-3-cyano-1-cyclobutyl-1H-pyrrolo[2,3-b]pyridin-2-yl)-N-cyclobutylpyridine-3-sulfonamide | 178-180 | 442.1 |
| 284 | 4-(5-chloro-3-cyano-1-cyclobutyl-1H-pyrrolo[2,3-b]pyridin-2-yl)-N-(1-methylcyclopropyl)benzenesulfonamide | N/A | 441.1 |
| 285 | 2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide | 205-207 | 485.1 |
| 286 | 2-(5-chloro-3-cyano-1-cyclobutyl-1H-pyrrolo[2,3-b]pyridin-2-yl)-N-(1-methylcyclopropyl)pyrimidine-5-sulfonamide | 237-240 | 443.1 |
| 289 | 6-(3-cyano-1-cyclobutyl-5-methyl-1H-pyrrolo[2,3-b]pyridin-2-yl)-4-methyl-N-[(2S)-1,1,1-trifluoropropan-2-yl]pyridine-3-sulfonamide | 218-223 | 478.2 |
| 290 | 6-(5-chloro-3-cyano-1-cyclopentyl-1H-pyrrolo[2,3-b]pyridin-2-yl)-5-methyl-N-[(2S)-1,1,1-trifluoropropan-2-yl]pyridine-3-sulfonamide | 240-245 | 512.5 |
| 291 | 6-(3-cyano-1-cyclobutyl-5-methyl-1H-pyrrolo[2,3-b]pyridin-2-yl)-5-methyl-N-[(2S)-1,1,1-trifluoropropan-2-yl]pyridine-3-sulfonamide | 181-185 | 478.1 |
| 293 | N-tert-butyl-6-(3-cyano-1-cyclobutyl-5-methyl-1H-pyrrolo[2,3-b]pyridin-2-yl)pyridine-3-sulfonamide | 173-175 | 424.6 |
| 295 | 6-[3-cyano-1-(cyclopropylmethyl)-5-(trifluoromethyl)-1H-pyrrolo[2,3-b]pyridin-2-yl]-N-[(2S)-1,1,1-trifluoropropan-2-yl]pyridine-3-sulfonamide | 193-195 | 518.7 |
| 296 | N-tert-butyl-6-[3-cyano-1-(cyclopropylmethyl)-5-(trifluoromethyl)-1H-pyrrolo[2,3-b]pyridin-2-yl]pyridine-3-sulfonamide | 179-180 | 478.6 |
| 297 | N-tert-butyl-6-[3-cyano-1-cyclobutyl-5-(trifluoromethyl)-1H-pyrrolo[2,3-b]pyridin-2-yl]pyridine-3-sulfonamide | 176-178 | 478.7 |
| 298 | 6-[3-cyano-1-cyclobutyl-5-(trifluoromethyl)-1H-pyrrolo[2,3-b]pyridin-2-yl]-4-methyl-N-[(2S)-1,1,1-trifluoropropan-2-yl]pyridine-3-sulfonamide | 166-171 | 532.8 |
| 299 | N-[3-(3-cyano-1-cyclobutyl-5-methyl-1H-pyrrolo[2,3-b]pyridin-2-yl)phenyl]propane-2-sulfonamide | 166-173 | 409.4 |
| 300 | 4-[3-cyano-1-cyclobutyl-5-(trifluoromethyl)-1H-pyrrolo[2,3-b]pyridin-2-yl]-N-[(2S)-1,1,1-trifluoropropan-2-yl]benzenesulfonamide | 218-220 | 517.1 |
| 301 | 6-[3-cyano-1-cyclobutyl-5-(trifluoromethyl)-1H-pyrrolo[2,3-b]pyridin-2-yl]-5-methyl-N-[(2S)-1,1,1-trifluoropropan-2-yl]pyridine-3-sulfonamide | 190-194 | 532.2 |
| 302 | 6-[3-cyano-1-cyclobutyl-5-(trifluoromethyl)-1H-pyrrolo[2,3-b]pyridin-2-yl]-N-cyclobutylpyridine-3-sulfonamide | 197-199 | 476.5 |
| 305 | 6-[3-cyano-1-cyclopentyl-5-(methylsulfonyl)-1H-pyrrolo[2,3-b]pyridin-2-yl]-N-[(2S)-1,1,1-trifluoropropan-2-yl]pyridine-3-sulfonamide | 260-261 | 542.2 |
| 323 | 6-[3-cyano-1-cyclobutyl-5-(methylsulfanyl)-1H-pyrrolo[2,3-b]pyridin-2-yl]-N-[(2S)-1,1,1-trifluoropropan-2-yl]pyridine-3-sulfonamide | 154-158 | 496.0 |
| 338 | 6-[3-cyano-1-cyclobutyl-5-(trifluoromethyl)-1H-pyrrolo[2,3-b]pyridin-2-yl]-2-methyl-N-[(2S)-1,1,1-trifluoropropan-2-yl]pyridine-3-sulfonamide | 162-165 | 532.2 |
| 350 | 6-{5-[benzyl(methyl)amino]-3-cyano-1-cyclobutyl-1H-pyrrolo[2,3-b]pyridin-2-yl}-N-[(2S)-1,1,1-trifluoropropan-2-yl]pyridine-3-sulfonamide | N/A | 568.0 |
| 351 | 4-{5-[benzyl(methyl)amino]-3-cyano-1-cyclobutyl-1H-pyrrolo[2,3-b]pyridin-2-yl}-N-tert-butylbenzenesulfonamide | 168-171 | 527.0 |
| 352 | N-(4-{5-[benzyl(methyl)amino]-3-cyano-1-cyclobutyl-1H-pyrrolo[2,3-b]pyridin-2-yl}phenyl)-2-methylpropane-2-sulfonamide | N/A | 527.0 |
| 353 | 4-{5-[benzyl(methyl)amino]-3-cyano-1-cyclobutyl-1H-pyrrolo[2,3-b]pyridin-2-yl}-N-(1,1,1-trifluoro-2-methylpropan-2-yl)benzenesulfonamide | N/A | 581.9 |
| 360 | 6-[3-cyano-1-cyclopropyl-5-(trifluoromethyl)-1H-pyrrolo[2,3-b]pyridin-2-yl]-N-[(2S)-1,1,1-trifluoropropan-2-yl]pyridine-3-sulfonamide | 194-196 | 504.0 |
| 361 | 4-[3-cyano-1-cyclopropyl-5-(trifluoromethyl)-1H-pyrrolo[2,3-b]pyridin-2-yl]-N-(1,1,1-trifluoro-2-methylpropan-2-yl)benzenesulfonamide | N/A | 517.1 |
| 362 | N-{4-[3-cyano-1-cyclopropyl-5-(trifluoromethyl)-1H-pyrrolo[2,3-b]pyridin-2-yl]phenyl}-2-methylpropane-2-sulfonamide | N/A | 463.1 |
| 363 | [3-cyano-1-cyclobutyl-2-(5-{[(2S)-1,1,1-trifluoropropan-2-yl]sulfamoyl}pyridin-2-yl)-1H-pyrrolo[2,3-b]pyridin-5-yl](methyl)sulfoniumolate | 257-258 | 512.0 |
| 364 | 4-[3-cyano-1-cyclobutyl-5-(methylsulfanyl)-1H-pyrrolo[2,3-b]pyridin-2-yl]-N-[1-(trifluoromethyl)cyclopropyl]benzenesulfonamide | 197-199 | 507.0 |
| 368 | 6-[3-cyano-5-methyl-1-(pyridin-4-yl)-1H-pyrrolo[2,3-b]pyridin-2-yl]-N-[(2S)-1,1,1-trifluoropropan-2-yl]pyridine-3-sulfonamide | 243-245 | 488.2 |
| 369 | N-tert-butyl-4-(3-cyano-1-cyclobutyl-5-fluoro-1H-pyrrolo[2,3-b]pyridin-2-yl)benzenesulfonamide | N/A | 427.0 |
| 370 | 6-[3-cyano-1-cyclobutyl-5-(methylsulfonyl)-1H-pyrrolo[2,3-b]pyridin-2-yl]-N-[(2S)-1,1,1-trifluoropropan-2-yl]pyridine-3-sulfonamide | N/A | 528.0 |
| 371 | N-tert-butyl-4-(5-chloro-3-cyano-1-cyclobutyl-1H-pyrrolo[2,3-b]pyridin-2-yl)benzenesulfonamide | 244-246 | 443.0 |
| 385 | N-[4-(5-chloro-3-cyano-1-cyclobutyl-1H-pyrrolo[2,3-b]pyridin-2-yl)phenyl]-2-methylpropane-2-sulfonamide | 240-241 | 443.1 |
| 394 | 6-[3-cyano-1-cyclobutyl-5-(methylamino)-1H-pyrrolo[2,3-b]pyridin-2-yl]-N-[(2S)-1,1,1-trifluoropropan-2-yl]pyridine-3-sulfonamide | N/A | 479.1 |
| 395 | 6-[3-cyano-1-cyclobutyl-5-(trifluoromethyl)-1H-pyrrolo[2,3-b]pyridin-2-yl]-N-(1,1,1-trifluoro-2-methylpropan-2-yl)pyridine-3-sulfonamide | 174-176 | 532.1 |
| 396 | 6-[3-cyano-1-cyclobutyl-5-(trifluoromethyl)-1H-pyrrolo[2,3-b]pyridin-2-yl]-N-[1-(trifluoromethyl)cyclopropyl]pyridine-3-sulfonamide | 156-158 | 530.0 |
| 397 | 4-[3-cyano-1-cyclobutyl-5-(trifluoromethyl)-1H-pyrrolo[2,3-b]pyridin-2-yl]-N-[1-(trifluoromethyl)cyclopropyl]benzenesulfonamide | N/A | 529.0 |
| 398 | 6-[3-cyano-1-cyclobutyl-5-(trifluoromethyl)-1H-pyrrolo[2,3-b]pyridin-2-yl]-N-(1-methylcyclopropyl)pyridine-3-sulfonamide | 172-175 | 476.1 |
| 415 | 6-[3-cyano-1-cyclohexyl-5-(trifluoromethyl)-1H-pyrrolo[2,3-b]pyridin-2-yl]-N-[(2S)-1,1,1-trifluoropropan-2-yl]pyridine-3-sulfonamide | 204-206 | 546.5 |
| 416 | 4-[3-cyano-1-cyclohexyl-5-(trifluoromethyl)-1H-pyrrolo[2,3-b]pyridin-2-yl]-N-[(2S)-1,1,1-trifluoropropan-2-yl]benzenesulfonamide | 190-192 | 545.5 |
| 417 | 6-[3-cyano-1-cyclohexyl-5-(trifluoromethyl)-1H-pyrrolo[2,3-b]pyridin-2-yl]-N-(1,1,1-trifluoro-2-methylpropan-2-yl)pyridine-3-sulfonamide | 177-179 | 560.6 |

-continued

| Cpd | Name | m.p. | MS |
|---|---|---|---|
| 418 | 4-[3-cyano-1-cyclohexyl-5-(trifluoromethyl)-1H-pyrrolo[2,3-b]pyridin-2-yl]-N-(1,1,1-trifluoro-2-methylpropan-2-yl)benzenesulfonamide | 203-205 | 559.7 |
| 419 | 6-[3-cyano-1-cyclohexyl-5-(trifluoromethyl)-1H-pyrrolo[2,3-b]pyridin-2-yl]-N-[1-(trifluoromethyl)cyclopropyl]pyridine-3-sulfonamide | 192-193 | 558.2 |
| 420 | 4-[3-cyano-1-cyclohexyl-5-(trifluoromethyl)-1H-pyrrolo[2,3-b]pyridin-2-yl]-N-[1-(trifluoromethyl)cyclopropyl]benzenesulfonamide | 195-197 | 557.2 |
| 421 | 4-[3-cyano-1-cyclohexyl-5-(trifluoromethyl)-1H-pyrrolo[2,3-b]pyridin-2-yl]-N-(1-methylcyclopropyl)benzenesulfonamide | 173-175 | 503.5 |
| 422 | N-tert-butyl-4-[3-cyano-1-cyclohexyl-5-(trifluoromethyl)-1H-pyrrolo[2,3-b]pyridin-2-yl]benzenesulfonamide | 176-178 | 505.5 |
| 423 | 4-[3-cyano-1-cyclohexyl-5-(trifluoromethyl)-1H-pyrrolo[2,3-b]pyridin-2-yl]-N-[(2R)-1,1,1-trifluoropropan-2-yl]benzenesulfonamide | 185-187 | 545.6 |
| 424 | N-{4-[3-cyano-1-cyclohexyl-5-(trifluoromethyl)-1H-pyrrolo[2,3-b]pyridin-2-yl]phenyl}-2-methylpropane-2-sulfonamide | 245-247 | 505.7 |
| 425 | N-{4-[3-cyano-1-cyclohexyl-5-(trifluoromethyl)-1H-pyrrolo[2,3-b]pyridin-2-yl]phenyl}propane-2-sulfonamide | 228-230 | 491.5 |
| 426 | N-{4-[3-cyano-1-cyclohexyl-5-(trifluoromethyl)-1H-pyrrolo[2,3-b]pyridin-2-yl]phenyl}-1-methylcyclopropanesulfonamide | 255-256 | 503.5 |
| 427 | N-{4-[3-cyano-1-cyclohexyl-5-(trifluoromethyl)-1H-pyrrolo[2,3-b]pyridin-2-yl]phenyl}cyclopropanesulfonamide | 225-227 | 489.4 |
| 428 | N-{4-[3-cyano-1-cyclohexyl-5-(trifluoromethyl)-1H-pyrrolo[2,3-b]pyridin-2-yl]phenyl}cyclobutanesulfonamide | 234-236 | 503.5 |
| 452 | 6-[3-cyano-1-cyclobutyl-5-(difluoromethyl)-1H-pyrrolo[2,3-b]pyridin-2-yl]-N-[(2S)-1,1,1-trifluoropropan-2-yl]pyridine-3-sulfonamide | 158-159 | 500.2 |
| 453 | 4-[3-cyano-1-cyclobutyl-5-(difluoromethyl)-1H-pyrrolo[2,3-b]pyridin-2-yl]-N-[(2S)-1,1,1-trifluoropropan-2-yl]benzenesulfonamide | 203-205 | 499.5 |
| 454 | 2-[3-cyano-1-cyclobutyl-5-(difluoromethyl)-1H-pyrrolo[2,3-b]pyridin-2-yl]-N-[(2S)-1,1,1-trifluoropropan-2-yl]pyrimidine-5-sulfonamide | 155-156 | 501.3 |
| 455 | 6-[3-cyano-1-cyclobutyl-5-(difluoromethyl)-1H-pyrrolo[2,3-b]pyridin-2-yl]-N-(propan-2-yl)pyridine-3-sulfonamide | 189-190 | 446.4 |
| 456 | 6-[3-cyano-1-cyclobutyl-5-(difluoromethyl)-1H-pyrrolo[2,3-b]pyridin-2-yl]-N-(1,1,1-trifluoro-2-methylpropan-2-yl)pyridine-3-sulfonamide | N/A | 514.4 |
| 457 | 6-[3-cyano-1-cyclobutyl-5-(difluoromethyl)-1H-pyrrolo[2,3-b]pyridin-2-yl]-N-[1-(trifluoromethyl)cyclopropyl]pyridine-3-sulfonamide | N/A | 512.4 |
| 458 | 6-[3-cyano-1-cyclobutyl-5-(difluoromethyl)-1H-pyrrolo[2,3-b]pyridin-2-yl]-N-[(1S)-1-cyclopropylethyl]pyridine-3-sulfonamide | 164-165 | 472.4 |
| 459 | N-{4-[3-cyano-1-cyclobutyl-5-(difluoromethyl)-1H-pyrrolo[2,3-b]pyridin-2-yl]phenyl}propane-2-sulfonamide | 179-180 | 445.5 |
| 460 | N-{4-[3-cyano-1-cyclobutyl-5-(difluoromethyl)-1H-pyrrolo[2,3-b]pyridin-2-yl]phenyl}cyclopropanesulfonamide | 193-195 | 443.3 |
| 483 | 4-(3-cyano-1,5-dimethyl-1H-pyrrolo[2,3-b]pyridin-2-yl)-N-[(2S)-1,1,1-trifluoropropan-2-yl]benzenesulfonamide | 165-170 | 423.5 |
| 484 | 4-(3-cyano-1-ethyl-5-methyl-1H-pyrrolo[2,3-b]pyridin-2-yl)-N-[(2S)-1,1,1-trifluoropropan-2-yl]benzenesulfonamide | 147-152 | 437.7 |
| 485 | 4-(3-cyano-5-methyl-1-propyl-1H-pyrrolo[2,3-b]pyridin-2-yl)-N-[(2S)-1,1,1-trifluoropropan-2-yl]benzenesulfonamide | 235-240 | 451.3 |
| 486 | 4-[3-cyano-5-methyl-1-(propan-2-yl)-1H-pyrrolo[2,3-b]pyridin-2-yl]-N-[(2S)-1,1,1-trifluoropropan-2-yl]benzenesulfonamide | 197-202 | 451.7 |
| 487 | 4-[3-cyano-1-(cyclopropylmethyl)-5-methyl-1H-pyrrolo[2,3-b]pyridin-2-yl]-N-[(2S)-1,1,1-trifluoropropan-2-yl]benzenesulfonamide | 175-181 | 463.6 |
| 488 | 4-[3-cyano-5-methyl-1-(2-methylpropyl)-1H-pyrrolo[2,3-b]pyridin-2-yl]-N-[(2S)-1,1,1-trifluoropropan-2-yl]benzenesulfonamide | 168-176 | 465.6 |
| 489 | 4-[3-cyano-1-(cyclobutylmethyl)-5-methyl-1H-pyrrolo[2,3-b]pyridin-2-yl]-N-[(2S)-1,1,1-trifluoropropan-2-yl]benzenesulfonamide | 154-158 | 477.6 |
| 490 | 6-(3-cyano-1,5-dimethyl-1H-pyrrolo[2,3-b]pyridin-2-yl)-N-[(2S)-1,1,1-trifluoropropan-2-yl]pyridine-3-sulfonamide | 182-186 | 424.3 |
| 491 | 6-(3-cyano-1-ethyl-5-methyl-1H-pyrrolo[2,3-b]pyridin-2-yl)-N-[(2S)-1,1,1-trifluoropropan-2-yl]pyridine-3-sulfonamide | 168-171 | 438.4 |
| 492 | 6-(3-cyano-5-methyl-1-propyl-1H-pyrrolo[2,3-b]pyridin-2-yl)-N-[(2S)-1,1,1-trifluoropropan-2-yl]pyridine-3-sulfonamide | 145-149 | 452.5 |
| 493 | 6-[3-cyano-5-methyl-1-(propan-2-yl)-1H-pyrrolo[2,3-b]pyridin-2-yl]-N-[(2S)-1,1,1-trifluoropropan-2-yl]pyridine-3-sulfonamide | 157-162 | 452.5 |
| 494 | 6-[3-cyano-1-(cyclopropylmethyl)-5-methyl-1H-pyrrolo[2,3-b]pyridin-2-yl]-N-[(2S)-1,1,1-trifluoropropan-2-yl]pyridine-3-sulfonamide | 198-204 | 464.5 |
| 495 | 6-[3-cyano-5-methyl-1-(2-methylpropyl)-1H-pyrrolo[2,3-b]pyridin-2-yl]-N-[(2S)-1,1,1-trifluoropropan-2-yl]pyridine-3-sulfonamide | 125-130 | 466.5 |
| 496 | 6-[3-cyano-1-(cyclobutylmethyl)-5-methyl-1H-pyrrolo[2,3-b]pyridin-2-yl]-N-[(2S)-1,1,1-trifluoropropan-2-yl]pyridine-3-sulfonamide | 135-139 | 478.3 |
| 497 | 6-[3-cyano-1-cyclobutyl-5-(dimethylamino)-1H-pyrrolo[2,3-b]pyridin-2-yl]-N-[(2S)-1,1,1-trifluoropropan-2-yl]pyridine-3-sulfonamide | 183-185 | 493.4 |
| 498 | N-{4-[3-cyano-1-cyclobutyl-5-(dimethylamino)-1H-pyrrolo[2,3-b]pyridin-2-yl]phenyl}-2-methylpropane-2-sulfonamide | 200-202 | 452.4 |
| 499 | N-{4-[3-cyano-1-cyclobutyl-5-(dimethylamino)-1H-pyrrolo[2,3-b]pyridin-2-yl]phenyl}-1-methylcyclopropanesulfonamide | 209-213 | 450.3 |
| 500 | 4-[3-cyano-1-cyclobutyl-5-(dimethylamino)-1H-pyrrolo[2,3-b]pyridin-2-yl]-N-[(2S)-1,1,1-trifluoropropan-2-yl]benzenesulfonamide | 198-200 | 492.3 |

Example 4

6-(3-cyano-1-cyclobutyl-6-methyl-1H-pyrrolo[2,3-b]pyridin-2-yl)-N-cyclobutylpyridine-3-sulfonamide (Cpd 148)

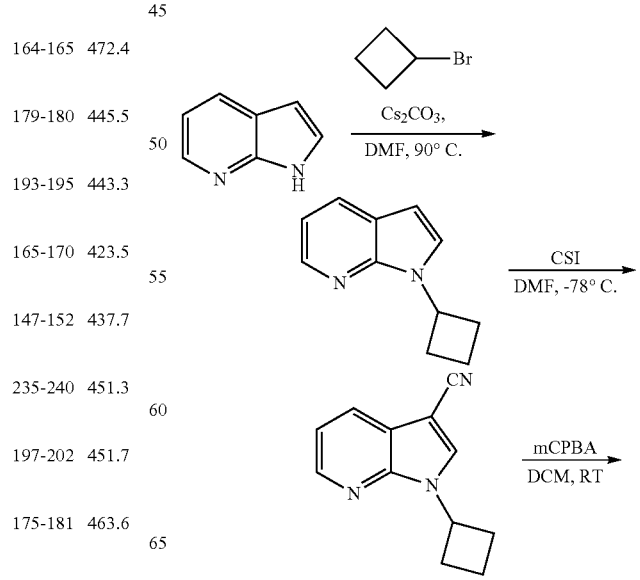

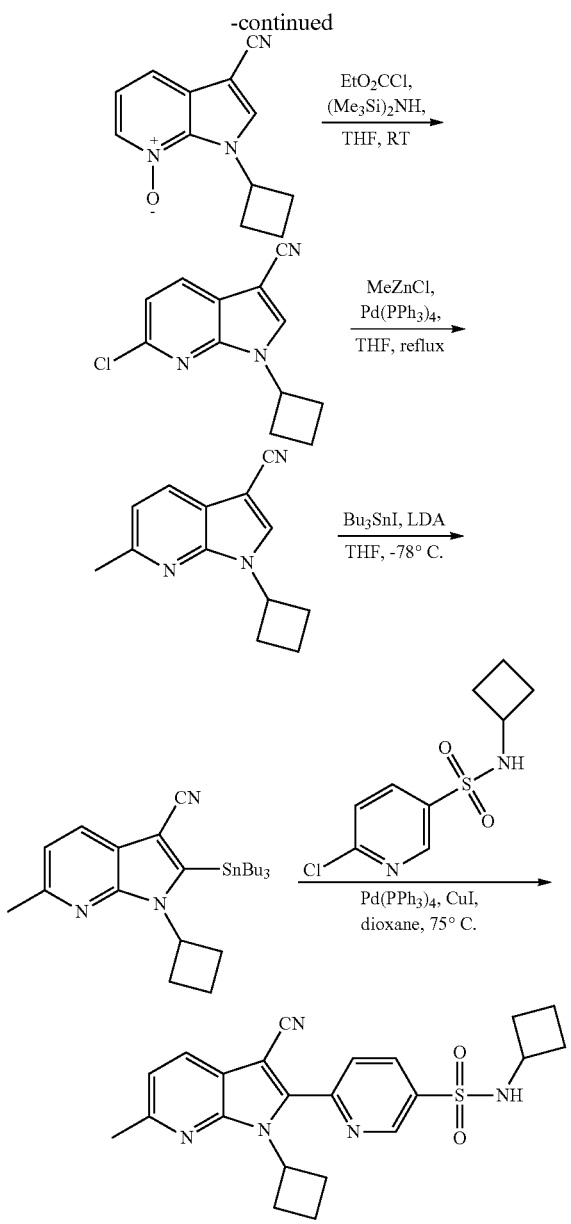

Step A: In a similar manner as Example 2, Step C, 1-cyclobutyl-1H-pyrrolo[2,3-b]pyridine was prepared. The compound was isolated in DMF and taken on to the next step without further purification.

Step B: In a similar manner as Example 2, Step D, 1-cyclobutyl-1H-pyrrolo[2,3-b]pyridine-3-carbonitrile was prepared (27.6 g, 66% for two steps).

Step C: A 500 mL round bottom flask was charged with 1-cyclobutyl-1H-pyrrolo[2,3-b]pyridine-3-carbonitrile (25.0 g, 126 mmol), 3-chloroperoxybenzoic acid (52.1 g, 232 mmol, 77%), and $CH_2Cl_2$ (250 mL). The mixture was stirred at room temperature overnight and filtered. The solids were washed with diethyl ether (50 mL), hexanes (100 mL), and $CH_2Cl_2$ (2×50 mL). The filtrate and combined washings were concentrated and purified on silica gel eluting with a series of solvent mixtures (1:1 ether:chloroform, then acetone, then 20% methanol in acetone) to afford 16.2 g (60%) of 3-cyano-1-cyclobutyl-1H-pyrrolo[2,3-b]pyridine 7-oxide.

Step D: A 500 mL round-bottom flask was charged with 3-cyano-1-cyclobutyl-1H-pyrrolo[2,3-b]pyridine 7-oxide (12.0 g, 56.3 mmol), hexamethyldisilazane (11.7 mL, 56.3 mmol), and THF (200 mL). Ethyl chloroformate (10.8 mL, 113 mmol) was dissolved in THF (20 mL) and added dropwise at room temperature. After stirring overnight starting material still remained so an additional portion of ethyl chloroformate (5 mL) was added dropwise and the reaction was stirred for an additional 2 h. The reaction was poured into sat. aq. $NaHCO_3$ and extracted with $CH_2Cl_2$ (2×200 mL). The combined organics were washed with brine (200 mL), dried over $Na_2SO_4$, and concentrated. The resulting solid was suspended in methanol (10 mL) and filtered to produce 7.92 g (61%) of 6-chloro-1-cyclobutyl-1H-pyrrolo[2,3-b]pyridine-3-carbonitrile as a beige solid.

Step E: A round-bottom flask was charged with methyl magnesium bromide (36 mL, 3.0 M in diethyl ether, 110 mmol) and cooled to −78° C. Zinc chloride (108 mL, 1.0 M in diethyl ether, 108 mmol) was added dropwise to the cooled mixture. The reaction was allowed to warm to room temperature and stir for 1 h. The mixture was transferred via cannula into a round-bottom flask charged with 6-chloro-1-cyclobutyl-1H-pyrrolo[2,3-b]pyridine-3-carbonitrile (5.0 g, 21.6 mmol) and THF (50 mL) and then $Pd[(PPh_3)]_4$ (1.0 g, 0.863 mmol) was added. The mixture was heated to 70° C. for 5 days. The mixture was cooled to room temperature, poured into ice water (500 mL) and extracted with $CH_2Cl_2$ (3×100 mL). The combined organics were dried over $Na_2SO_4$, and concentrated. The residue was purified on silica gel eluting with 0-20% ethyl acetate in a mixture of 1:1 hexanes:chloroform to give 4.19 g (91%) of 1-cyclobutyl-6-methyl-1H-pyrrolo[2,3-b]pyridine-3-carbonitrile.

Step F: In a similar manner as Example 2, Step E, 1-cyclobutyl-6-methyl-2-(tributylstannyl)-1H-pyrrolo[2,3-b]pyridine-3-carbonitrile was prepared (5.20 g, 55%).

Step G: In a similar manner as Example 2, Step F the title compound was prepared from 1-cyclobutyl-6-methyl-2-(tributylstannyl)-1H-pyrrolo[2,3-b]pyridine-3-carbonitrile and 6-chloro-N-cyclobutylpyridine-3-sulfonamide [prepared in a similar manner as Example 1, Step B] and after purification by preparative HPLC provided the product as a yellow powder (84.9 mg, 40%). Melting point: 151-160° C.; MS m/z 421.9 (M+H$^+$); $^1$H NMR (500 MHz, DMSO-d$_6$): 1.45-1.61 (m, 2 H) 1.67-1.90 (m, 4 H) 1.93-2.05 (m, 2 H) 2.26-2.35 (m, 2 H) 2.66 (s, 3 H) 2.91-3.08 (m, 2 H) 3.72-3.88 (m, 1 H) 5.12-5.27 (m, 1 H) 7.32 (d, J=8.20 Hz, 1 H) 8.06-8.15 (m, 2 H) 8.39-8.48 (m, 2 H) 9.17 (dd, J=2.36, 0.79 Hz, 1 H)

Additional compounds representative of the present invention may be prepared according to the procedure of Example 4 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
| --- | --- | --- | --- |
| 9 | 6-(3-cyano-1-cyclobutyl-5-methoxy-1H-pyrrolo[2,3-b]pyridin-2-yl)-N-(1,3-difluoropropan-2-yl)pyridine-3-sulfonamide Prepared using commercially available 5-methoxy-7-azaindole in place of 7-azaindole | 161-163 | 462.1 |
| 10 | 6-(5-chloro-3-cyano-1-cyclopentyl-1H-pyrrolo[2,3-b]pyridin-2-yl)-N-(1,3-difluoropropan-2-yl)pyridine-3-sulfonamide Prepared using commercially available 5-chloro-7-azaindole in place of 7-azaindole | 208-209 | 479.9 |

| Cpd | Name | m.p. | MS |
|---|---|---|---|
| 11 | 2-(3-cyano-1-cyclobutyl-5-methoxy-1H-pyrrolo[2,3-b]pyridin-2-yl)-N-(1,3-difluoropropan-2-yl)pyrimidine-5-sulfonamide<br>Prepared using commercially available 5-methoxy-7-azaindole in place of 7-azaindole | 194-196 | 463.2 |
| 12 | 6-(3-cyano-1-cyclobutyl-5-fluoro-1H-pyrrolo[2,3-b]pyridin-2-yl)-N-(1,3-difluoropropan-2-yl)pyridine-3-sulfonamide<br>Prepared using commercially available 5-fluoro-7-azaindole in place of 7-azaindole | 155-157 | 450.2 |
| 13 | 2-(5-chloro-3-cyano-1-cyclobutyl-1H-pyrrolo[2,3-b]pyridin-2-yl)-N-(1,3-difluoropropan-2-yl)pyrimidine-5-sulfonamide<br>Prepared using commercially available 5-chloro-7-azaindole in place of 7-azaindole | 199-200 | 467.2 |
| 14 | 6-(5-chloro-3-cyano-1-cyclobutyl-1H-pyrrolo[2,3-b]pyridin-2-yl)-N-(1,3-difluoropropan-2-yl)pyridine-3-sulfonamide<br>Prepared using commercially available 5-chloro-7-azaindole in place of 7-azaindole | 176-178 | 465.8 |
| 16 | 2-(3-cyano-1-cyclobutyl-5-fluoro-1H-pyrrolo[2,3-b]pyridin-2-yl)-N-(1,3-difluoropropan-2-yl)pyrimidine-5-sulfonamide<br>Prepared using commercially available 5-fluoro-7-azaindole in place of 7-azaindole | 204-206 | 450.9 |
| 17 | 2-(5-chloro-3-cyano-1-cyclopentyl-1H-pyrrolo[2,3-b]pyridin-2-yl)-N-(1,3-difluoropropan-2-yl)pyrimidine-5-sulfonamide<br>Prepared using commercially available 5-chloro-7-azaindole in place of 7-azaindole | 247-248 | 481.3 |
| 18 | 6-(3-cyano-1-cyclobutyl-1H-pyrrolo[2,3-b]pyridin-2-yl)-N-[(2S)-1,1,1-trifluoropropan-2-yl]pyridine-3-sulfonamide<br>Prepared using commercially available 7-azaindole in place of 7-azaindole | 183-185 | 450.3 |
| 21 | 2-(3-cyano-1-cyclobutyl-5-fluoro-1H-pyrrolo[2,3-b]pyridin-2-yl)-N-[(2S)-1,1,1-trifluoropropan-2-yl]pyrimidine-5-sulfonamide<br>Prepared using commercially available 5-fluoro-7-azaindole in place of 7-azaindole | 186-187 | 469.2 |
| 23 | 2-(3-cyano-1-cyclobutyl-5-methoxy-1H-pyrrolo[2,3-b]pyridin-2-yl)-N-[(2S)-1,1,1-trifluoropropan-2-yl]pyrimidine-5-sulfonamide<br>Prepared using commercially available 5-methoxy-7-azaindole in place of 7-azaindole | 193-196 | 481.3 |
| 24 | 6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide<br>Prepared using commercially available 5-chloro-7-azaindole in place of 7-azaindole | 197-199 | 498.2 |
| 25 | 2-(5-chloro-3-cyano-1-cyclopentyl-1H-pyrrolo[2,3-b]pyridin-2-yl)-N-[(2S)-1,1,1-trifluoropropan-2-yl]pyrimidine-5-sulfonamide<br>Prepared using commercially available 5-chloro-7-azaindole in place of 7-azaindole | 206-208 | 499.2 |
| 34 | 4-(3-cyano-1-cyclobutyl-1H-pyrrolo[2,3-b]pyridin-2-yl)-N-(1,3-difluoropropan-2-yl)benzenesulfonamide<br>Prepared using commercially available 7-azaindole in place of 7-azaindole | 180-182 | 431.1 |
| 35 | 6-(3-cyano-1-cyclobutyl-1H-pyrrolo[2,3-b]pyridin-2-yl)-N-[(2R)-1,1,1-trifluoropropan-2-yl]pyridine-3-sulfonamide<br>Prepared using commercially available 7-azaindole in place of 7-azaindole | 184-186 | 450.2 |
| 36 | 2-(3-cyano-1-cyclobutyl-1H-pyrrolo[2,3-b]pyridin-2-yl)-N-(propan-2-yl)pyrimidine-5-sulfonamide<br>Prepared using commercially available 7-azaindole in place of 7-azaindole | 197-199 | 397.1 |
| 37 | 2-(3-cyano-1-cyclobutyl-5-fluoro-1H-pyrrolo[2,3-b]pyridin-2-yl)-N-(propan-2-yl)pyrimidine-5-sulfonamide<br>Prepared using commercially available 5-fluoro-7-azaindole in place of 7-azaindole | 207-209 | 415.2 |
| 47 | 6-(3-cyano-1-cyclobutyl-5-fluoro-1H-pyrrolo[2,3-b]pyridin-2-yl)-N-[(2R)-1,1,1-trifluoropropan-2-yl]pyridine-3-sulfonamide<br>Prepared using commercially available 5-fluoro-7-azaindole in place of 7-azaindole | 167-169 | 468.8 |
| 48 | 6-(3-cyano-1-cyclobutyl-5-methoxy-1H-pyrrolo[2,3-b]pyridin-2-yl)-N-[(2R)-1,1,1-trifluoropropan-2-yl]pyridine-3-sulfonamide<br>Prepared using commercially available 5-methoxy-7-azaindole in place of 7-azaindole | N/A | 480.8 |
| 49 | 2-(3-cyano-1-cyclobutyl-5-methoxy-1H-pyrrolo[2,3-b]pyridin-2-yl)-N-(propan-2-yl)pyrimidine-5-sulfonamide<br>Prepared using commercially available 5-methoxy-7-azaindole in place of 7-azaindole | 215-217 | 427.2 |
| 50 | 6-(5-chloro-3-cyano-1-cyclobutyl-1H-pyrrolo[2,3-b]pyridin-2-yl)-N-[(2R)-1,1,1-trifluoropropan-2-yl]pyridine-3-sulfonamide<br>Prepared using commercially available 5-chloro-7-azaindole in place of 7-azaindole | 202-203 | 484.2 |
| 51 | 6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide<br>Prepared using commercially available 5-chloro-7-azaindole in place of 7-azaindole | 203-204 | 484.3 |
| 52 | N-tert-butyl-6-(5-chloro-3-cyano-1-cyclobutyl-1H-pyrrolo[2,3-b]pyridin-2-yl)pyridine-3-sulfonamide<br>Prepared using commercially available 5-chloro-7-azaindole in place of 7-azaindole | 207-208 | 444.4 |
| 56 | 6-(5-chloro-3-cyano-1-cyclobutyl-1H-pyrrolo[2,3-b]pyridin-2-yl)-N-(1,1,1-trifluoro-2-methylpropan-2-yl)pyridine-3-sulfonamide<br>Prepared using commercially available 5-chloro-7-azaindole in place of 7-azaindole | 221-222 | 498.4 |
| 57 | 6-(5-chloro-3-cyano-1-cyclobutyl-1H-pyrrolo[2,3-b]pyridin-2-yl)-N-[1-(trifluoromethyl)cyclopropyl]pyridine-3-sulfonamide<br>Prepared using commercially available 5-chloro-7-azaindole in place of 7-azaindole | 254-255 | 496.3 |
| 58 | 2-(5-chloro-3-cyano-1-cyclobutyl-1H-pyrrolo[2,3-b]pyridin-2-yl)-N-(propan-2-yl)pyrimidine-5-sulfonamide<br>Prepared using commercially available 5-chloro-7-azaindole in place of 7-azaindole | 224-225 | 431.1 |
| 59 | 6-[5-chloro-3-cyano-1-(cyclopropylmethyl)-1H-pyrrolo[2,3-b]pyridin-2-yl]-N-[(2R)-1,1,1-trifluoropropan-2-yl]pyridine-3-sulfonamide<br>Prepared using commercially available 5-chloro-7-azaindole in place of 7-azaindole | 224-226 | 484.3 |
| 60 | 6-[3-cyano-1-(cyclopropylmethyl)-5-fluoro-1H-pyrrolo[2,3-b]pyridin-2-yl]-N-[(2R)-1,1,1-trifluoropropan-2-yl]pyridine-3-sulfonamide<br>Prepared using commercially available 5-fluoro-7-azaindole in place of 7-azaindole | 185-187 | 468.1 |
| 61 | 4-(5-chloro-3-cyano-1-cyclobutyl-1H-pyrrolo[2,3-b]pyridin-2-yl)-N-[(2S)-1,1,1-trifluoropropan-2-yl]benzenesulfonamide<br>Prepared using commercially available 5-chloro-7-azaindole in place of 7-azaindole | 220-222 | 483.0 |
| 63 | 6-[5-chloro-3-cyano-1-(cyclopropylmethyl)-1H-pyrrolo[2,3-b]pyridin-2-yl]-N-[(2S)-1,1,1-trifluoropropan-2-yl]pyridine-3-sulfonamide<br>Prepared using commercially available 5-chloro-7-azaindole in place of 7-azaindole | 226-227 | 484.1 |
| 64 | 6-[3-cyano-1-(cyclopropylmethyl)-5-fluoro-1H-pyrrolo[2,3-b]pyridin-2-yl]-N-[(2S)-1,1,1-trifluoropropan-2-yl]pyridine-3-sulfonamide<br>Prepared using commercially available 5-fluoro-7-azaindole in place of 7-azaindole | 186-188 | 468.2 |
| 65 | 4-(3-cyano-1-cyclobutyl-5-methoxy-1H-pyrrolo[2,3-b]pyridin-2-yl)-N-(1,3-difluoropropan-2-yl)benzenesulfonamide<br>Prepared using commercially available 5-methoxy-7-azaindole in place of 7-azaindole | 215-218 | 461.1 |

| Cpd | Name | m.p. | MS |
|---|---|---|---|
| 66 | 6-[3-cyano-1-(cyclopropylmethyl)-5-methoxy-1H-pyrrolo[2,3-b]pyridin-2-yl]-N-[(2S)-1,1,1-trifluoropropan-2-yl]pyridine-3-sulfonamide Prepared using commercially available 5-methoxy-7-azaindole in place of 7-azaindole | 136-140 | 480.1 |
| 90 | 4-(3-cyano-1-cyclobutyl-6-methyl-1H-pyrrolo[2,3-b]pyridin-2-yl)-N-[(2S)-1,1,1-trifluoropropan-2-yl]benzenesulfonamide | 169-177 | 463.1 |
| 91 | 4-(3-cyano-1-cyclobutyl-6-methyl-1H-pyrrolo[2,3-b]pyridin-2-yl)-N-[(2R)-1,1,1-trifluoropropan-2-yl]benzenesulfonamide | N/A | 463.1 |
| 92 | 6-(3-cyano-1-cyclobutyl-6-methyl-1H-pyrrolo[2,3-b]pyridin-2-yl)-N-[(2S)-1,1,1-trifluoropropan-2-yl]pyridine-3-sulfonamide | N/A | 464.2 |
| 93 | 6-(3-cyano-1-cyclobutyl-6-methyl-1H-pyrrolo[2,3-b]pyridin-2-yl)-N-[(2R)-1,1,1-trifluoropropan-2-yl]pyridine-3-sulfonamide | N/A | 464.2 |
| 94 | 6-(3-cyano-1-cyclobutyl-6-methyl-1H-pyrrolo[2,3-b]pyridin-2-yl)-N-[1-(trifluoromethyl)cyclopropyl]pyridine-3-sulfonamide | 230-236 | 476.2 |
| 95 | 2-(3-cyano-1-cyclobutyl-6-methyl-1H-pyrrolo[2,3-b]pyridin-2-yl)-N-(propan-2-yl)pyrimidine-5-sulfonamide | N/A | 411.2 |
| 96 | 5-(3-cyano-1-cyclobutyl-6-methyl-1H-pyrrolo[2,3-b]pyridin-2-yl)-N-(propan-2-yl)pyridine-2-sulfonamide | 211-216 | 410.2 |
| 107 | 6-(3,5-dicyano-1-cyclobutyl-1H-pyrrolo[2,3-b]pyridin-2-yl)-N-[(2R)-1,1,1-trifluoropropan-2-yl]pyridine-3-sulfonamide Prepared using commercially available 5-cyano-7-azaindole in place of 7-azaindole | 202-203 | 475.2 |
| 108 | 6-(3,5-dicyano-1-cyclobutyl-1H-pyrrolo[2,3-b]pyridin-2-yl)-N-[(2S)-1,1,1-trifluoropropan-2-yl]pyridine-3-sulfonamide Prepared using commercially available 5-cyano-7-azaindole in place of 7-azaindole | 203-204 | 475.2 |
| 109 | 2-(3,5-dicyano-1-cyclobutyl-1H-pyrrolo[2,3-b]pyridin-2-yl)-N-[(2S)-1,1,1-trifluoropropan-2-yl]pyrimidine-5-sulfonamide Prepared using commercially available 5-cyano-7-azaindole in place of 7-azaindole | 216-219 | 476.2 |
| 110 | 4-(3,5-dicyano-1-cyclobutyl-1H-pyrrolo[2,3-b]pyridin-2-yl)-N-[(2S)-1,1,1-trifluoropropan-2-yl]benzenesulfonamide Prepared using commercially available 5-cyano-7-azaindole in place of 7-azaindole | 241-243 | 471.9 (M − 1) |
| 111 | 6-(3,5-dicyano-1-cyclobutyl-1H-pyrrolo[2,3-b]pyridin-2-yl)-N-[1-(trifluoromethyl)cyclopropyl]pyridine-3-sulfonamide Prepared using commercially available 5-cyano-7-azaindole in place of 7-azaindole | 207-208 | 486.9 |
| 112 | 4-(3,5-dicyano-1-cyclobutyl-1H-pyrrolo[2,3-b]pyridin-2-yl)-N-[1-(trifluoromethyl)cyclopropyl]benzenesulfonamide Prepared using commercially available 5-cyano-7-azaindole in place of 7-azaindole | 231-233 | 483.6 (M − 1) |
| 113 | 6-(3,5-dicyano-1-cyclobutyl-1H-pyrrolo[2,3-b]pyridin-2-yl)-N-(1-methylcyclopropyl)pyridine-3-sulfonamide Prepared using commercially available 5-cyano-7-azaindole in place of 7-azaindole | 198-200 | 433.0 |
| 114 | 2-(3,5-dicyano-1-cyclobutyl-1H-pyrrolo[2,3-b]pyridin-2-yl)-N-(1-methylcyclopropyl)pyrimidine-5-sulfonamide Prepared using commercially available 5-cyano-7-azaindole in place of 7-azaindole | 229-231 | 433.9 |
| 137 | 2-(3-cyano-1-cyclobutyl-6-methyl-1H-pyrrolo[2,3-b]pyridin-2-yl)-N-[(2S)-1,1,1-trifluoropropan-2-yl]pyrimidine-5-sulfonamide | 207-212 | 465.2 |
| 138 | 2-(3-cyano-1-cyclobutyl-6-methyl-1H-pyrrolo[2,3-b]pyridin-2-yl)-N-[(2R)-1,1,1-trifluoropropan-2-yl]pyrimidine-5-sulfonamide | 205-209 | 465.2 |
| 139 | 4-(3-cyano-1-cyclobutyl-6-methyl-1H-pyrrolo[2,3-b]pyridin-2-yl)-N-(1,1,1-trifluoro-2-methylpropan-2-yl)benzenesulfonamide | N/A | 468.1 |
| 140 | 4-(3-cyano-1-cyclobutyl-6-methyl-1H-pyrrolo[2,3-b]pyridin-2-yl)-N-[1-(trifluoromethyl)cyclopropyl]benzenesulfonamide | 205-212 | 475.3 |
| 141 | N-tert-butyl-4-(3-cyano-1-cyclobutyl-6-methyl-1H-pyrrolo[2,3-b]pyridin-2-yl)benzenesulfonamide | 194-200 | 423.3 |
| 142 | N-tert-butyl-6-(3-cyano-1-cyclobutyl-6-methyl-1H-pyrrolo[2,3-b]pyridin-2-yl)pyridine-3-sulfonamide | 181-187 | 424.3 |
| 143 | 4-(3-cyano-1-cyclobutyl-6-methyl-1H-pyrrolo[2,3-b]pyridin-2-yl)-N-(1-methylcyclopropyl)benzenesulfonamide | 200-207 | 421.3 |
| 144 | 2-(3-cyano-1-cyclobutyl-6-methyl-1H-pyrrolo[2,3-b]pyridin-2-yl)-N-(1-methylcyclopropyl)pyrimidine-5-sulfonamide | 224-232 | 423.3 |
| 145 | 4-(3-cyano-1-cyclobutyl-6-methyl-1H-pyrrolo[2,3-b]pyridin-2-yl)-N-(1,3-difluoropropan-2-yl)benzenesulfonamide | 182-193 | 444.9 |
| 146 | 6-(3-cyano-1-cyclobutyl-6-methyl-1H-pyrrolo[2,3-b]pyridin-2-yl)-N-(1,3-difluoropropan-2-yl)pyridine-3-sulfonamide | 180-188 | 445.9 |
| 147 | 2-(3-cyano-1-cyclobutyl-6-methyl-1H-pyrrolo[2,3-b]pyridin-2-yl)-N-(1,3-difluoropropan-2-yl)pyrimidine-5-sulfonamide | 211-217 | 447.0 |
| 149 | 4-(3-cyano-1-cyclobutyl-6-cyclopropyl-1H-pyrrolo[2,3-b]pyridin-2-yl)-N-[(2S)-1,1,1-trifluoropropan-2-yl]benzenesulfonamide | N/A | 488.9 |
| 150 | 4-(3-cyano-1-cyclobutyl-6-cyclopropyl-1H-pyrrolo[2,3-b]pyridin-2-yl)-N-[(2R)-1,1,1-trifluoropropan-2-yl]benzenesulfonamide | N/A | 488.9 |
| 151 | 6-(3-cyano-1-cyclobutyl-6-cyclopropyl-1H-pyrrolo[2,3-b]pyridin-2-yl)-N-[(2S)-1,1,1-trifluoropropan-2-yl]pyridine-3-sulfonamide | 170-176 | 489.9 |
| 152 | 6-(3-cyano-1-cyclobutyl-6-cyclopropyl-1H-pyrrolo[2,3-b]pyridin-2-yl)-N-[(2R)-1,1,1-trifluoropropan-2-yl]pyridine-3-sulfonamide | 170-176 | 489.9 |
| 153 | 2-(3-cyano-1-cyclobutyl-6-cyclopropyl-1H-pyrrolo[2,3-b]pyridin-2-yl)-N-[(2S)-1,1,1-trifluoropropan-2-yl]pyrimidine-5-sulfonamide | N/A | 490.9 |
| 154 | 2-(3-cyano-1-cyclobutyl-6-cyclopropyl-1H-pyrrolo[2,3-b]pyridin-2-yl)-N-[(2R)-1,1,1-trifluoropropan-2-yl]pyrimidine-5-sulfonamide | 244-249 | 490.9 |
| 161 | 6-(6-chloro-3-cyano-1-cyclobutyl-1H-pyrrolo[2,3-b]pyridin-2-yl)-N-[(2S)-1,1,1-trifluoropropan-2-yl]pyridine-3-sulfonamide | 172-178 | 484.2 |
| 162 | 6-(6-chloro-3-cyano-1-cyclobutyl-1H-pyrrolo[2,3-b]pyridin-2-yl)-N-[(2R)-1,1,1-trifluoropropan-2-yl]pyridine-3-sulfonamide | 172-178 | 484.2 |
| 169 | 6-(3-cyano-1-cyclobutyl-5-fluoro-1H-pyrrolo[2,3-b]pyridin-2-yl)-N-[(2S)-1,1,1-trifluoropropan-2-yl]pyridine-3-sulfonamide | 172-174 | 468.1 |
| 242 | 6-(3-cyano-1-cyclobutyl-5-methoxy-6-methyl-1H-pyrrolo[2,3-b]pyridin-2-yl)-N-[(2S)-1,1,1-trifluoropropan-2-yl]pyridine-3-sulfonamide | 175-177 | 493.8 |
| 243 | 6-(3-cyano-1-cyclobutyl-5-methoxy-6-methyl-1H-pyrrolo[2,3-b]pyridin-2-yl)-N-[(2R)-1,1,1-trifluoropropan-2-yl]pyridine-3-sulfonamide | 175-177 | 493.8 |
| 258 | 6-(3-cyano-1-cyclobutyl-6-ethyl-5-methoxy-1H-pyrrolo[2,3-b]pyridin-2-yl)-N-[(2S)-1,1,1-trifluoropropan-2-yl]pyridine-3-sulfonamide | 186-189 | 507.8 |
| 259 | 6-(3-cyano-1-cyclobutyl-6-ethyl-5-methoxy-1H-pyrrolo[2,3-b]pyridin-2-yl)-N-[(2R)-1,1,1-trifluoropropan-2-yl]pyridine-3-sulfonamide | 189-199 | 508.3 |
| 405 | 6-[3-cyano-1-cyclobutyl-6-methyl-5-(trifluoromethyl)-1H-pyrrolo[2,3-b]pyridin-2-yl]-N-[(2S)-1,1,1-trifluoropropan-2-yl]pyridine-3-sulfonamide | 201-203 | 532.2 |

Example 5

2-(3-cyano-1-cyclobutyl-6-methoxy-1H-pyrrolo[2,3-b]pyridin-2-yl)-N-(1,3-difluoropropan-2-yl)pyrimidine-5-sulfonamide (Cpd 42)

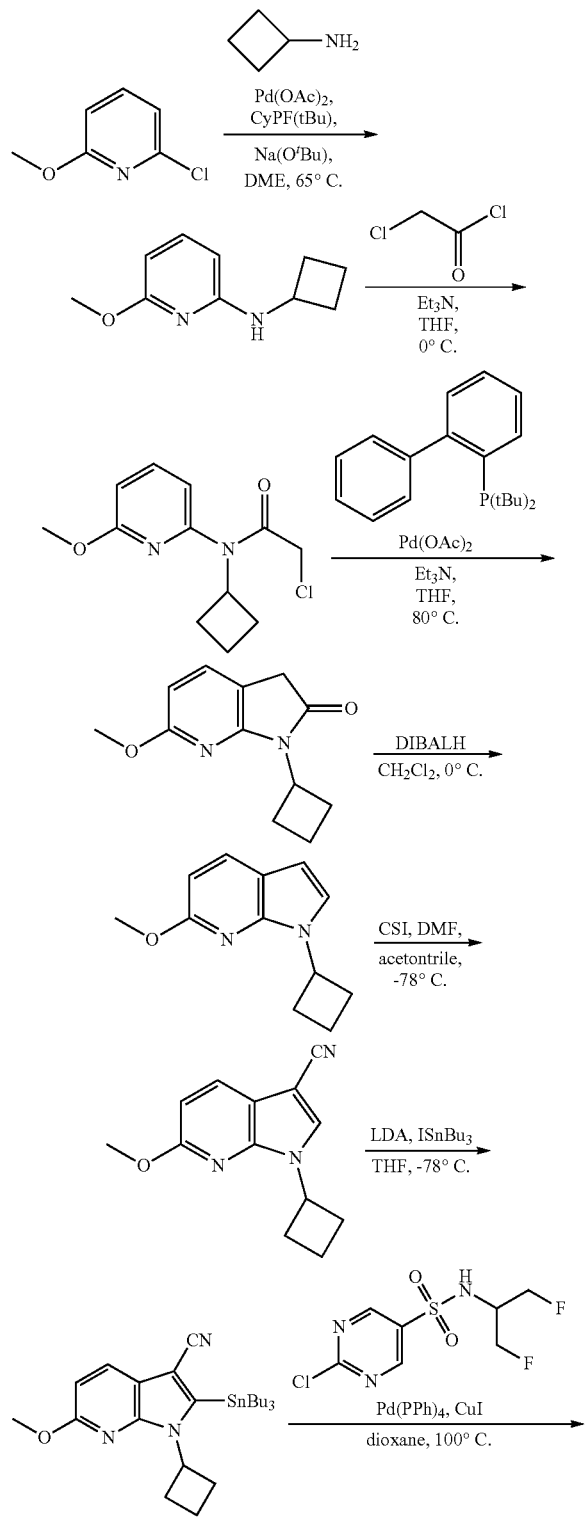

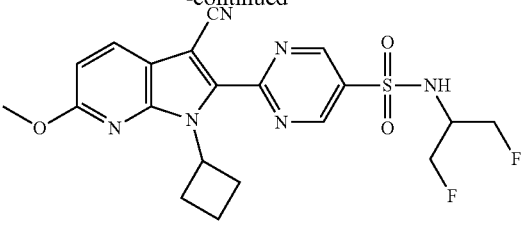

Step A: To a solution of NaO'Bu in DME (60 mL) was added 6-methoxy-2-chloropyridine (15.0 g, 104 mmol) in DME (30 mL) at 0° C. followed by addition of Pd(OAc)$_2$ (47 mg, 0.21 mmol) and (R)-(−)-1-[(S)-2-(dicyclohexylphosphino)ferrocenyl]ethyl di-tert-butylphosphine (116 mg, 0.21 mmol) in DME (30 ml). The reaction mixture was purged using three cycles of vacuum and argon backfill and stirred at 65° C. overnight. The reaction mixture was filtered through a plug of celite, concentrated and the residue purified on silica gel eluting with 30% ethyl acetate in hexanes to afford 18.6 g (100%) of N-cyclobutyl-6-methoxypyridin-2-amine as a solid.

Step B: To a solution of N-cyclobutyl-6-methoxypyridin-2-amine (11.3 g, 61.9 mmol), Et$_3$N (13.8 mL, 99.0 mmol) in THF (110 mL) was added chloroacetyl chloride (7.4 mL, 92.9 mmol) dropwise at 0° C. After addition, the reaction mixture was stirred at 0° C. for 5 h until complete consumption of the starting material monitored by TLC. The mixture was partitioned between ethyl acetate and water, the organic phase washed with brine, dried over MgSO$_4$, and concentrated. The residue was triturated with ethyl ether to afford 12.5 g (77%) of 2-chloro-N-cyclobutyl-N-(6-methoxypyridin-2-yl)acetamide as an off-white solid.

Step C: To a 250 mL round-bottom flask fitted with a septum was charged with 2-chloro-N-cyclobutyl-N-(6-methoxypyridin-2-yl)acetamide (7.5 g, 29.5 mmol), biphenyl-2-yl-di-tert-butylphosphine (1.76 g, 5.90 mmol), palladium acetate (662 mg, 2.9 mmol) and toluene (60 mL). The reaction vessel was purged using three cycles of vacuum and argon backfill, and Et$_3$N (5.44 mL, 39.2 mmol) was added. The resulting mixture was stirred at 80° C. for 3 h. After cooling, the mixture was partitioned between ethyl acetate and sat. aq. 1,3,5-triazine-2,4,6-trithio trisodium salt solution. The aqueous phase was extracted with ethyl acetate (5×30 mL). The combined organic phase was washed with water and brine, dried over MgSO$_4$, and concentrated. The residue was purified on silica gel eluting with 2.5% ethyl acetate in hexanes to afford 4.1 g (64%) of 1-cyclobutyl-6-methoxy-1H-pyrrolo[2,3-b]pyridin-2(3H)-one as a light-yellow solid.

Step D: To a solution of 1-cyclobutyl-6-methoxy-1H-pyrrolo[2,3-b]pyridin-2(3H)-one (3.4 g, 15.5 mmol) in CH$_2$Cl$_2$ (20 mL) was added DIBAL-H (23.3 ml, 1.0 M in CH$_2$Cl$_2$) at 0° C. The resulting mixture was stirred at room temperature for 2 h. To this mixture was added sat. aq. potassium sodium tartrate solution (10 mL) and the mixture was stirred at room temperature for 5 h. The organic layer was washed with water and brine, dried over MgSO$_4$, and concentrated. The residue was purified on silica gel eluting with 10% ethyl acetate in hexanes to give 1.5 g (48%) of 1-cyclobutyl-6-methoxy-1H-pyrrolo[2,3-b]pyridine as a clear oil.

Step E: In a similar manner as Example 2, Step D, 1-cyclobutyl-6-methoxy-1H-pyrrolo[2,3-b]pyridine-3-carbonitrile was prepared (1.72 g, 56%).

Step F: In a similar manner as Example 2, Step E, 1-cyclobutyl-6-methyl-2-(tributylstannyl)-1H-pyrrolo[2,3-b]pyridine-3-carbonitrile was prepared (5.30 g, 100%).

Step G: In a similar manner as Example 2, Step F the title compound was prepared from 1-cyclobutyl-6-methyl-2-(tributylstannyl)-1H-pyrrolo[2,3-b]pyridine-3-carbonitrile and 2-chloro-N-(1,3-difluoropropan-2-yl)pyrimidine-5-sulfonamide [prepared in a similar manner as Example 1, Step B] (0.13 g, 79%). Melting point: 229-230° C.; MS m/z 463.8 (M+H$^+$); $^1$H NMR (500 MHz, acetone-d$_6$): δ 9.37 (2H, s, overlap), 8.09 (1H, d, J=4.3 Hz), 7.72 (1H, br, s), 6.89 (1H, d, J=8.7 Hz), 6.03 (1H, m), 4.66 (2H, d, J=5.1 Hz), 4.56 (2H, d, J=5.1 Hz), 4.16 (1H, m), 4.10 (3H, s), 3.43 (2H, m), 2.80 (1H, m), 2.46 (2H, m), 1.89 (1H, m).

Additional compounds representative of the present invention may be prepared according to the procedure of Example 5 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 40 | 6-(3-cyano-1-cyclobutyl-6-methoxy-1H-pyrrolo[2,3-b]pyridin-2-yl)-N-[(2S)-1,1,1-trifluoropropan-2-yl]pyridine-3-sulfonamide | 193-194 | 480.8 |
| 41 | 6-(3-cyano-1-cyclobutyl-6-methoxy-1H-pyrrolo[2,3-b]pyridin-2-yl)-N-(1,3-difluoropropan-2-yl)pyridine-3-sulfonamide | 194-195 | 462.9 |
| 43 | 4-(3-cyano-1-cyclobutyl-6-methoxy-1H-pyrrolo[2,3-b]pyridin-2-yl)-N-(1,3-difluoropropan-2-yl)benzenesulfonamide | 213-215 | 440.0 |
| 44 | N-tert-butyl-4-(3-cyano-1-cyclobutyl-6-methoxy-1H-pyrrolo[2,3-b]pyridin-2-yl)benzenesulfonamide | 155-157 | 437.5 |
| 54 | 6-[3-cyano-1-cyclobutyl-6-(difluoromethoxy)-1H-pyrrolo[2,3-b]pyridin-2-yl]-N-[(2S)-1,1,1-trifluoropropan-2-yl]pyridine-3-sulfonamide | 176-177 | 516.8 |
| 55 | 2-[3-cyano-1-cyclobutyl-6-(difluoromethoxy)-1H-pyrrolo[2,3-b]pyridin-2-yl]-N-(1,3-difluoropropan-2-yl)pyrimidine-5-sulfonamide | 234-236 | 499.4 |
| 241 | 6-(3-cyano-1-cyclobutyl-5-methoxy-6-methyl-1H-pyrrolo[2,3-b]pyridin-2-yl)-N-[(2S)-1,1,1-trifluoropropan-2-yl]pyridine-3-sulfonamide | 175-177 | 493.8 |

Example 6

2-(3-cyano-1-cyclobutyl-6-methyl-1H-pyrrolo[3,2-c]pyridin-2-yl)-N-(propan-2-yl)pyrimidine-5-sulfonamide (Cpd 32)

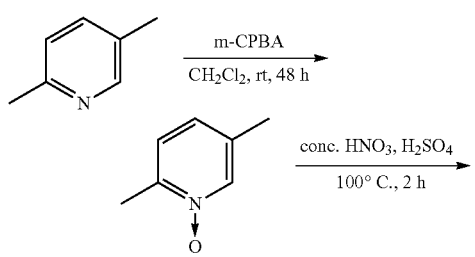

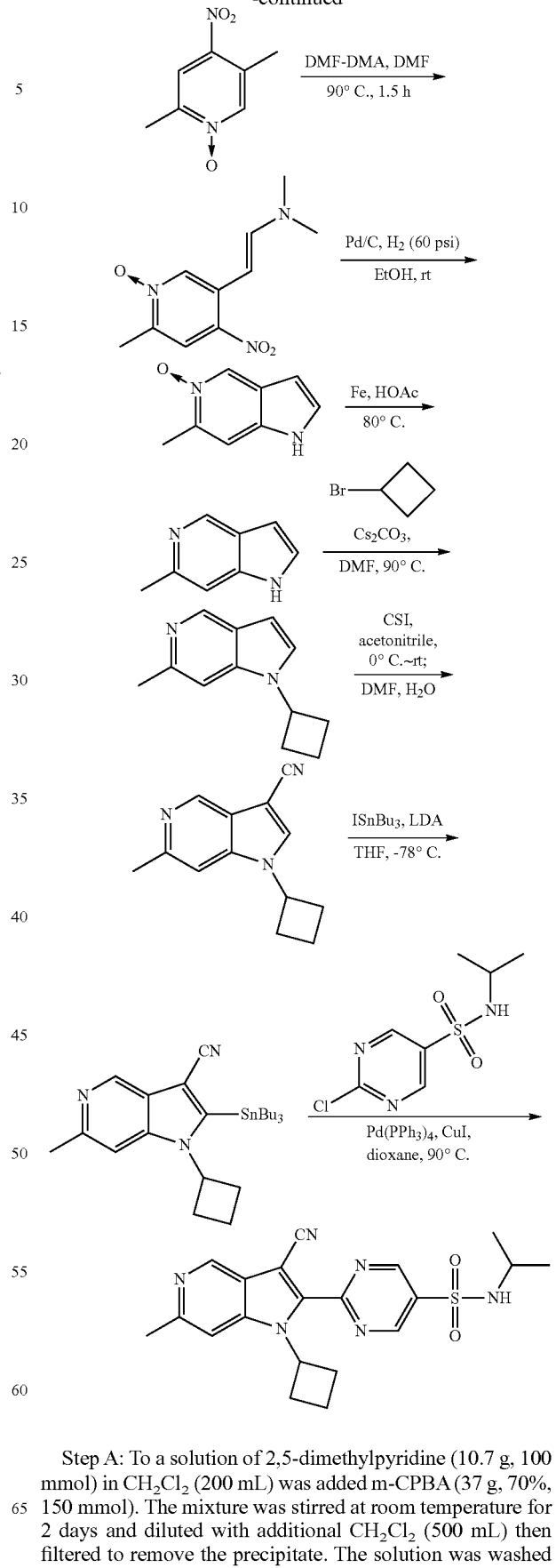

Step A: To a solution of 2,5-dimethylpyridine (10.7 g, 100 mmol) in CH$_2$Cl$_2$ (200 mL) was added m-CPBA (37 g, 70%, 150 mmol). The mixture was stirred at room temperature for 2 days and diluted with additional CH$_2$Cl$_2$ (500 mL) then filtered to remove the precipitate. The solution was washed with sat. aq. Na₂CO₃, dried over Na₂SO₄, and passed through a silica gel pad (100 g) to give 2,5-dimethylpyridine 1-oxide as colorless oil.

Step B: To conc. H₂SO₄ (12 mL) at 0° C. was added 2,5-dimethylpyridine 1-oxide (from above) portionwise, followed by the addition of fuming nitric acid (10 mL). This mixture was stirred at 100° C. for 2 h, cooled to room temperature, poured onto ice and neutralized with solid Na₂CO₃. The resulting precipitate was collected on a filter and purified on silica gel eluting with 50-100% ethyl acetate in hexanes to provide 5.87 g (91%, two steps) of 2,5-dimethyl-4-nitropyridine-1-oxide.

Step C: To a solution of 2,5-dimethyl-4-nitropyridine-1-oxide (5.04 g, 30.0 mmol) in DMF (25 mL) was added dimethylformamide dimethylacetal (8.0 mL, 60.0 mmol). The mixture was stirred at 90° C. for 1.5 h. The mixture was concentrated and the residue was hydrogenated with palladium on carbon (10%, 0.7 g, 0.65 mmol) in ethanol (100 mL) at 60 psi in a Parr shaker for 4 h. The mixture was filtered through a plug of celite and concentrated to provide crude 6-methyl-5-azaindole-5-oxide (4.82 g) which was used in the next step without further purification.

Step D: The above intermediate, 6-methyl-5-azaindole-5-oxide (4.82 g), was mixed with acetic acid (50 mL) and iron powder (3.4 g, 60 mmol) and stirred at 80° C. for 5 h. Acetic acid was removed on a rotoevaporator. The residue was treated with CH₂Cl₂ (100 mL) and water (20 mL) and neutralized with solid Na₂CO₃. The organic layer was separated, dried over Na₂SO₄, and concentrated to give 6-methyl-5-azaindole (2.04 g, 52% two steps).

Step E: To 6-methyl-5-azaindole (2.04 g, 15.5 mmol) was added DMF (10 mL), cyclobutyl bromide (1.75 mL, 18.5 mmol), and cesium carbonate (10.11 g, 31.0 mmol) and the mixture was stirred at 90° C. for 2 days. After cooling to room temperature, the mixture was diluted with water (100 mL) and extracted with CH₂Cl₂ (3×20 mL). The combined extracts were washed with brine, dried over anhydrous Na₂SO₄, and concentrated. The residue was purified on silica gel eluting with ethyl acetate to provide 1.69 g (59%) of 1-cyclobutyl-6-methyl-5-azaindole.

Step F: To 1-cyclobutyl-6-methyl-5-azaindole (1.69 g, 9.1 mmol) was added acetonitrile (10 mL) and chlorosulfonyl isocyanate (1.98 g, 1.22 mL, 14.0 mmol). The mixture was stirred at room temperature for 1 h followed by the addition of DMF (2.5 mL). After stirring for 30 min, ice-water (50 mL) was added and the mixture was neutralized with solid Na₂CO₃. The resulting precipitate was collected on a filter, washed with water and dried in air to give 1.24 g (64%) of 1-cyclobutyl-3-cyano-6-methyl-5-azaindole.

Step G: In a similar manner as Example 2, Step E, was prepared (2.37 g, 100%).

Step H: In a similar manner as Example 2, Step F the title compound was prepared from 1-cyclobutyl-6-methyl-2-(tributylstannyl)-1H-pyrrolo[3,2-c]pyridine-3-carbonitrile and 2-chloro-N-isopropylpyrimidine-5-sulfonamide [prepared in a similar manner as Example 1, Step B] (66 mg, 40%). Melting point: 242-243° C.; MS m/z 411.0 (M+H⁺); ¹H NMR (500 MHz, CDCl₃): δ 9.25 (1H, s), 9.01 (1H, d, J=0.83 Hz), 7.39 (1H, s), 5.70-5.61 (1H, m), 4.54 (1H, d, J=8.07 Hz), 3.67-3.58 (2H, m), 3.42 (6H, d, J=5.38 Hz), 2.71-2.60 (5H, m), 2.49-2.41 (2H, m), 2.01-1.81 (2H, m), 1.17 (6H, d, J=6.55 Hz m), 1.37-1.31 (2H, m).

Additional compounds representative of the present invention may be prepared according to the procedure of Example 6 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m.p. | MS |
|---|---|---|---|
| 26 | 6-(3-cyano-1-cyclobutyl-6-methyl-1H-pyrrolo[3,2-c]pyridin-2-yl)-N-(1,3-difluoropropan-2-yl)pyridine-3-sulfonamide | 216-218 | 446.1 |
| 27 | 2-(3-cyano-1-cyclobutyl-6-methyl-1H-pyrrolo[3,2-c]pyridin-2-yl)-N-(1,3-difluoropropan-2-yl)pyrimidine-5-sulfonamide | 234-236 | 447.1 |
| 28 | 6-(3-cyano-1-cyclobutyl-6-methyl-1H-pyrrolo[3,2-c]pyridin-2-yl)-N-[(2S)-1,1,1-trifluoropropan-2-yl]pyridine-3-sulfonamide | 189-191 | 464.1 |
| 29 | 6-(3-cyano-1-cyclobutyl-6-methyl-1H-pyrrolo[3,2-c]pyridin-2-yl)-N-[(2R)-1,1,1-trifluoropropan-2-yl]pyridine-3-sulfonamide | 176-178 | 464.2 |
| 30 | 4-(3-cyano-1-cyclobutyl-6-methyl-1H-pyrrolo[3,2-c]pyridin-2-yl)-N-[(2S)-1,1,1-trifluoropropan-2-yl]benzenesulfonamide | 248-249 | 463.2 |
| 31 | 4-(3-cyano-1-cyclobutyl-6-methyl-1H-pyrrolo[3,2-c]pyridin-2-yl)-N-[(2R)-1,1,1-trifluoropropan-2-yl]benzenesulfonamide | 247-249 | 463.2 |
| 33 | 4-(3-cyano-1-cyclobutyl-6-methyl-1H-pyrrolo[3,2-c]pyridin-2-yl)-N-(1,3-difluoropropan-2-yl)benzenesulfonamide | 234-236 | 445.3 |
| 80 | 6-(6-chloro-3-cyano-1-cyclopentyl-1H-pyrrolo[3,2-c]pyridin-2-yl)-N-[(2S)-1,1,1-trifluoropropan-2-yl]pyridine-3-sulfonamide | 235-237 | 497.9 |
| 81 | 6-(6-chloro-3-cyano-1-cyclopentyl-1H-pyrrolo[3,2-c]pyridin-2-yl)-N-[(2R)-1,1,1-trifluoropropan-2-yl]pyridine-3-sulfonamide | 239-240 | 497.9 |
| 82 | 6-(6-chloro-3-cyano-1-cyclopentyl-1H-pyrrolo[3,2-c]pyridin-2-yl)-N-(1,3-difluoropropan-2-yl)pyridine-3-sulfonamide | 231-233 | 480.0 |
| 83 | 6-(6-chloro-3-cyano-1-cyclopentyl-1H-pyrrolo[3,2-c]pyridin-2-yl)-N-[1-(trifluoromethyl)cyclopropyl]pyridine-3-sulfonamide | 225-227 | 509.9 |
| 84 | 6-(6-chloro-3-cyano-1-cyclopentyl-1H-pyrrolo[3,2-c]pyridin-2-yl)-N-(1-methylcyclopropyl)pyridine-3-sulfonamide | 209-211 | 456.0 |
| 85 | 2-(6-chloro-3-cyano-1-cyclopentyl-1H-pyrrolo[3,2-c]pyridin-2-yl)-N-(propan-2-yl)pyrimidine-5-sulfonamide | 249-250 | 445.2 |
| 86 | 2-(6-chloro-3-cyano-1-cyclopentyl-1H-pyrrolo[3,2-c]pyridin-2-yl)-N-(1,3-difluoropropan-2-yl)pyrimidine-5-sulfonamide | 224-226 | 481.1 |
| 87 | 4-(6-chloro-3-cyano-1-cyclopentyl-1H-pyrrolo[3,2-c]pyridin-2-yl)-N-[(2S)-1,1,1-trifluoropropan-2-yl]benzenesulfonamide | 238-240 | 497.2 |
| 88 | 4-(6-chloro-3-cyano-1-cyclopentyl-1H-pyrrolo[3,2-c]pyridin-2-yl)-N-[(2R)-1,1,1-trifluoropropan-2-yl]benzenesulfonamide | 239-241 | 497.2 |
| 89 | 4-(6-chloro-3-cyano-1-cyclopentyl-1H-pyrrolo[3,2-c]pyridin-2-yl)-N-[1-(trifluoromethyl)cyclopropyl]benzenesulfonamide | 288-289 | 509.1 |
| 97 | 6-(6-chloro-3-cyano-1-cyclobutyl-1H-pyrrolo[3,2-c]pyridin-2-yl)-N-(1,3-difluoropropan-2-yl)pyridine-3-sulfonamide | 215-216 | 466.2 |
| 98 | 6-(6-chloro-3-cyano-1-cyclobutyl-1H-pyrrolo[3,2-c]pyridin-2-yl)-N-[1-(trifluoromethyl)cyclopropyl]pyridine-3-sulfonamide | 227-228 | 496.2 |
| 99 | 6-(6-chloro-3-cyano-1-cyclobutyl-1H-pyrrolo[3,2-c]pyridin-2-yl)-N-(1-methylcyclopropyl)pyridine-3-sulfonamide | 167-168 | 442.2 |
| 100 | 2-(6-chloro-3-cyano-1-cyclobutyl-1H-pyrrolo[3,2-c]pyridin-2-yl)-N-(propan-2-yl)pyrimidine-5-sulfonamide | 238-239 | 431.0 |
| 101 | 2-(6-chloro-3-cyano-1-cyclobutyl-1H-pyrrolo[3,2-c]pyridin-2-yl)-N-(1,3-difluoropropan-2-yl)pyrimidine-5-sulfonamide | 237-238 | 467.0 |
| 102 | 4-(6-chloro-3-cyano-1-cyclobutyl-1H-pyrrolo[3,2-c]pyridin-2-yl)-N-[(2S)-1,1,1-trifluoropropan-2-yl]benzenesulfonamide | 202-203 | 482.9 |

Example 7

6-(3-cyano-1-cyclopentyl-6-methyl-1H-pyrrolo[3,2-b]pyridin-2-yl)-N-[1-(trifluoromethyl)cyclopropyl]pyridine-3-sulfonamide (Cpd 172)

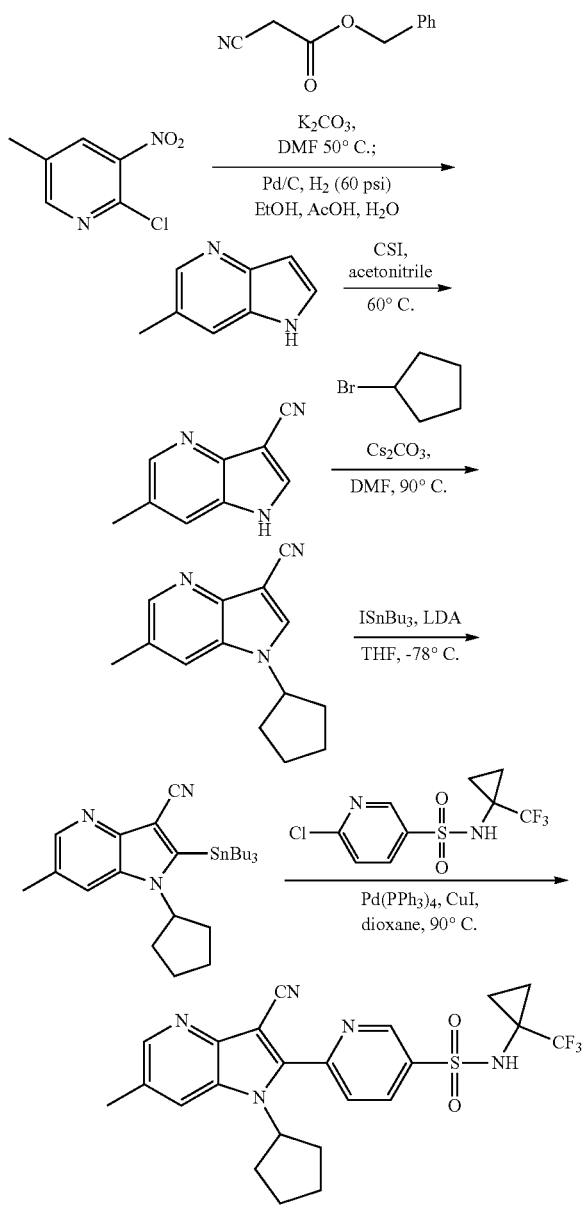

Step A: A 250 mL round-bottom flask was charged with 1-chloro-2-nitro-5-methylpyridine (8.6 g, 50 mmol), K₂CO₃ (17.3 g, 125 mmol), benzyl 2-cyanoacetate (10.5 g, 60 mmol) and DMF (50 mL). The mixture was stirred at 50° C. for 4 h and poured into ice-water and acidified with 6N HCl. The resulting precipitate was collected on a filter and washed thoroughly with water and dried in air overnight. The solid was place in a 500 mL hydrogenation bottle with ethanol (100 mL), acetic acid (10 mL), H₂O (10 mL) and palladium on carbon (20%, 1.5 g, 2.8 mmol). The mixture was hydrogenated on a Parr shaker at 60 psi at room temperature overnight, filtered through a plug of celite and concentrated. The residue was treated with aq. NH₄OH (10 mL) and CH₂Cl₂ (100 mL) and purified on silica gel eluting with 50-100% ethyl acetate in CH₂Cl₂ to provide 4.0 g (60% two steps) of 6-methyl-4-azaindole as white powder.

Step B: To a solution of 6-methyl-4-azaindole (3.3 g, 25 mmol) in acetonitrile (25 mL) was added chlorosulfonyl isocyanate (5.4 mL, 63 mmol). The mixture was stirred at 60° C. for 6 h. The mixture was then brought to room temperature and DMF (5.0 mL) added. After stirring for 1 h, ice-water (100 mL) was added to the mixture. The resulting precipitate was collected on a filter, washed with water and dried in air to give 2.2 g (56%) of 3-cyano-6-methyl-4-azaindole. This was used directly in the next step without further purification.

Step C: In a similar manner as Example 2, Step C, 3-cyano-1-cyclopentyl-6-methyl-4-azaindole was prepared (0.83 g, 62%).

Step D: In a similar manner as Example 2, Step E, 1-cyclopentyl-6-methyl-2-(tributylstannyl)-1H-pyrrolo[3,2-b]pyridine-3-carbonitrile was prepared (1.6 g, 84%).

Step E: In a similar manner as Example 2, Step F the title compound was prepared (46 mg, 38%) from 1-cyclopentyl-6-methyl-2-(tributylstannyl)-1H-pyrrolo[3,2-b]pyridine-3-carbonitrile and 6-chloro-N-(1-(trifluoromethyl)cyclopropyl)pyridine-3-sulfonamide [prepared in a similar manner as Example 1, Step B]. Melting point: 249-251° C.; MS m/z 489.9 (M+H⁺); ¹H NMR (500 MHz, CDCl₃): δ 9.24 (1H, d, J=2.3), 8.52 (1H, s), 8.36 (1H, dd, J=8.3, 2.3 Hz), 8.12 (1H, d, J=8.3 Hz), 7.68 (1H, s), 5.71 (1H, br, s), 5.21-5.31 (1H, m), 2.55 (3H, s), 2.27-2.17 (2H, m), 2.09-1.99 (2H, m), 1.82-1.73 (2H, m), 1.52-1.46 (2H, m), 1.37-1.31 (2H, m).

Additional compounds representative of the present invention may be prepared according to the procedure of Example 7 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m.p. | MS |
|---|---|---|---|
| 3 | N-{4-[3-cyano-1-(cyclopropylmethyl)-5-methoxy-1H-pyrrolo[3,2-b]pyridin-2-yl]phenyl}propane-2-sulfonamide<br>Prepared using commercially available 5-methoxy-4-azaindole in place of 6-methyl-4-azaindole | 230-232 | 425.2 |
| 15 | 6-(3-cyano-1-cyclobutyl-5-methoxy-1H-pyrrolo[3,2-b]pyridin-2-yl)-N-(1,3-difluoropropan-2-yl)pyridine-3-sulfonamide<br>Prepared using commercially available 5-methoxy-4-azaindole in place of 6-methyl-4-azaindole | 199-201 | 462.1 |
| 19 | 2-(3-cyano-1-cyclobutyl-5-methoxy-1H-pyrrolo[3,2-b]pyridin-2-yl)-N-(1,3-difluoropropan-2-yl)pyrimidine-5-sulfonamide<br>Prepared using commercially available 5-methoxy-4-azaindole in place of 6-methyl-4-azaindole | 241-243 | 463.1 |
| 20 | 6-(3-cyano-1-cyclobutyl-5-methoxy-1H-pyrrolo[3,2-b]pyridin-2-yl)-N-[(2S)-1,1,1-trifluoropropan-2-yl]pyridine-3-sulfonamide<br>Prepared using commercially available 5-methoxy-4-azaindole in place of 6-methyl-4-azaindole | N/A | 480.2 |
| 170 | 6-(3-cyano-1-cyclopentyl-6-methyl-1H-pyrrolo[3,2-b]pyridin-2-yl)-N-[(2S)-1,1,1-trifluoropropan-2-yl]pyridine-3-sulfonamide | 210-212 | 477.9 |
| 171 | 6-(3-cyano-1-cyclopentyl-6-methyl-1H-pyrrolo[3,2-b]pyridin-2-yl)-N-[(2R)-1,1,1-trifluoropropan-2-yl]pyridine-3-sulfonamide | 215-217 | 477.9 |
| 173 | 6-(3-cyano-1-cyclopentyl-6-methyl-1H-pyrrolo[3,2-b]pyridin-2-yl)-N-(1,1,1-trifluoro-2-methylpropan-2-yl)pyridine-3-sulfonamide | 265-267 | 491.9 |

-continued

| Cpd | Name | m.p. | MS |
|---|---|---|---|
| 174 | 6-(3-cyano-1-cyclopentyl-6-methyl-1H-pyrrolo[3,2-b]pyridin-2-yl)-N-(1-methylcyclopropyl)pyridine-3-sulfonamide | 215-217 | 436.0 |
| 175 | N-tert-butyl-6-(3-cyano-1-cyclopentyl-6-methyl-1H-pyrrolo[3,2-b]pyridin-2-yl)pyridine-3-sulfonamide | 267-269 | 438.0 |
| 176 | 6-(3-cyano-1-cyclopentyl-6-methyl-1H-pyrrolo[3,2-b]pyridin-2-yl)-N-(1,3-difluoropropan-2-yl)pyridine-3-sulfonamide | 248-249 | 460.0 |
| 177 | 2-(3-cyano-1-cyclopentyl-6-methyl-1H-pyrrolo[3,2-b]pyridin-2-yl)-N-(1,3-difluoropropan-2-yl)pyrimidine-5-sulfonamide | 256-258 | 460.9 |
| 178 | 2-(3-cyano-1-cyclopentyl-6-methyl-1H-pyrrolo[3,2-b]pyridin-2-yl)-N-(propan-2-yl)pyrimidine-5-sulfonamide | 263-265 | 425.0 |
| 179 | 2-(3-cyano-1-cyclopentyl-6-methyl-1H-pyrrolo[3,2-b]pyridin-2-yl)-N-[(2S)-1,1,1-trifluoropropan-2-yl]pyrimidine-5-sulfonamide | 262-264 | 478.9 |
| 180 | 4-(3-cyano-1-cyclopentyl-6-methyl-1H-pyrrolo[3,2-b]pyridin-2-yl)-N-[(2S)-1,1,1-trifluoropropan-2-yl]benzenesulfonamide | 278-279 | 476.9 |
| 181 | 4-(3-cyano-1-cyclopentyl-6-methyl-1H-pyrrolo[3,2-b]pyridin-2-yl)-N-[(2R)-1,1,1-trifluoropropan-2-yl]benzenesulfonamide | 281-283 | 476.9 |
| 206 | 6-(3-cyano-1-cyclobutyl-6-methyl-1H-pyrrolo[3,2-b]pyridin-2-yl)-N-[(2S)-1,1,1-trifluoropropan-2-yl]pyridine-3-sulfonamide | 217-218 | 464.2 |
| 207 | 6-(3-cyano-1-cyclobutyl-6-methyl-1H-pyrrolo[3,2-b]pyridin-2-yl)-N-[(2R)-1,1,1-trifluoropropan-2-yl]pyridine-3-sulfonamide | 207-209 | 464.2 |
| 208 | 6-(3-cyano-1-cyclobutyl-6-methyl-1H-pyrrolo[3,2-b]pyridin-2-yl)-N-[1-(trifluoromethyl)cyclopropyl]pyridine-3-sulfonamide | 248-249 | 476.2 |
| 209 | 6-(3-cyano-1-cyclobutyl-6-methyl-1H-pyrrolo[3,2-b]pyridin-2-yl)-N-(1,1,1-trifluoro-2-methylpropan-2-yl)pyridine-3-sulfonamide | 238-240 | 478.3 |
| 210 | 6-(3-cyano-1-cyclobutyl-6-methyl-1H-pyrrolo[3,2-b]pyridin-2-yl)-N-(1-methylcyclopropyl)pyridine-3-sulfonamide | 187-188 | 422.2 |
| 211 | N-tert-butyl-6-(3-cyano-1-cyclobutyl-6-methyl-1H-pyrrolo[3,2-b]pyridin-2-yl)pyridine-3-sulfonamide | 227-229 | 424.3 |
| 212 | 6-(3-cyano-1-cyclobutyl-6-methyl-1H-pyrrolo[3,2-b]pyridin-2-yl)-N-(1,3-difluoropropan-2-yl)pyridine-3-sulfonamide | 219-221 | 445.8 |
| 213 | 2-(3-cyano-1-cyclobutyl-6-methyl-1H-pyrrolo[3,2-b]pyridin-2-yl)-N-(1,3-difluoropropan-2-yl)pyrimidine-5-sulfonamide | 269-271 | 446.8 |
| 214 | 2-(3-cyano-1-cyclobutyl-6-methyl-1H-pyrrolo[3,2-b]pyridin-2-yl)-N-(propan-2-yl)pyrimidine-5-sulfonamide | 278-280 | 410.9 |
| 215 | 2-(3-cyano-1-cyclobutyl-6-methyl-1H-pyrrolo[3,2-b]pyridin-2-yl)-N-[(2S)-1,1,1-trifluoropropan-2-yl]pyrimidine-5-sulfonamide | 268-269 | 465.2 |
| 216 | 4-(3-cyano-1-cyclobutyl-6-methyl-1H-pyrrolo[3,2-b]pyridin-2-yl)-N-[(2S)-1,1,1-trifluoropropan-2-yl]benzenesulfonamide | 245-246 | 462.9 |
| 217 | 4-(3-cyano-1-cyclobutyl-6-methyl-1H-pyrrolo[3,2-b]pyridin-2-yl)-N-[(2R)-1,1,1-trifluoropropan-2-yl]benzenesulfonamide | 252-253 | 462.8 |
| 222 | 6-(3-cyano-1-cyclopentyl-5-methyl-1H-pyrrolo[3,2-b]pyridin-2-yl)-N-[(2S)-1,1,1-trifluoropropan-2-yl]pyridine-3-sulfonamide | N/A | 485.5 |
| 234 | 6-(6-chloro-3-cyano-1-cyclobutyl-1H-pyrrolo[3,2-b]pyridin-2-yl)-N-[(2S)-1,1,1-trifluoropropan-2-yl]pyridine-3-sulfonamide | 201-205 | 485.1 |
| 235 | 4-(6-chloro-3-cyano-1-cyclobutyl-1H-pyrrolo[3,2-b]pyridin-2-yl)-N-[(2S)-1,1,1-trifluoropropan-2-yl]benzenesulfonamide | 205-210 | 484.1 |
| 287 | 4-(6-chloro-3-cyano-1-cyclohexyl-1H-pyrrolo[3,2-b]pyridin-2-yl)-N-[(2S)-1,1,1-trifluoropropan-2-yl]benzenesulfonamide | 300-305 | 512.1 |
| 288 | N-[4-(6-chloro-3-cyano-1-cyclohexyl-1H-pyrrolo[3,2-b]pyridin-2-yl)phenyl]-2-methylpropane-2-sulfonamide | 279-283 | 472.2 |

Example 8

6-(5-cyano-7-cyclobutyl-2-methyl-7H-pyrrolo[2,3-d]pyrimidin-6-yl)-N-[(1S)-1-cyclopropylethyl]pyridine-3-sulfonamide (Cpd 45)

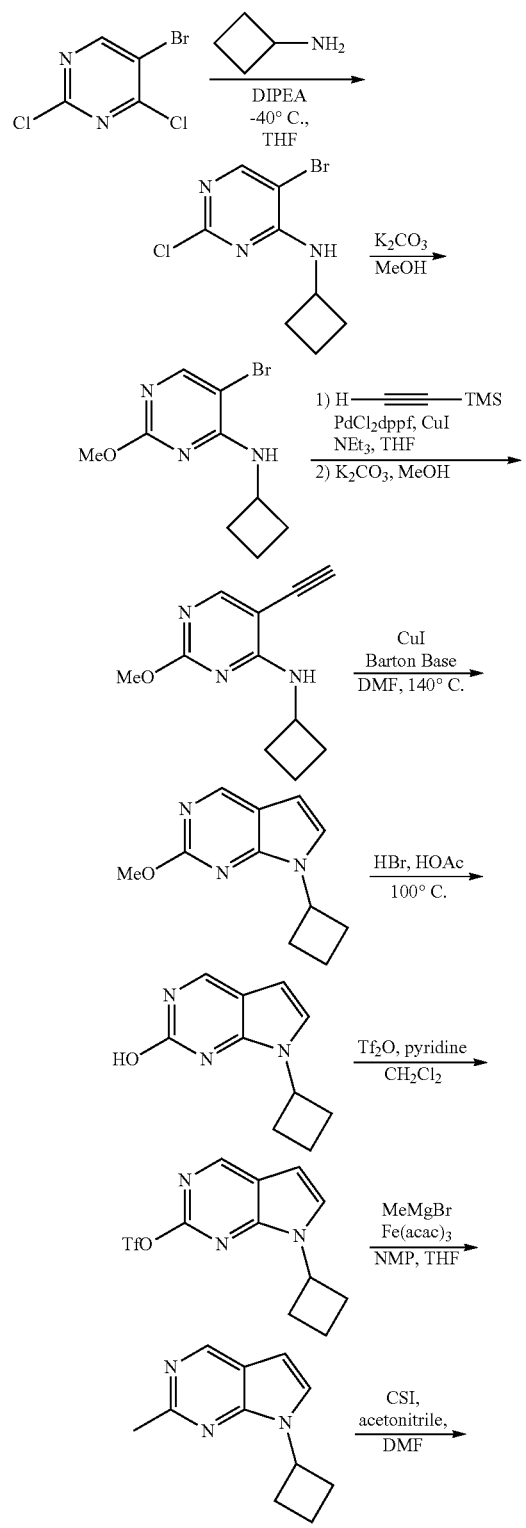

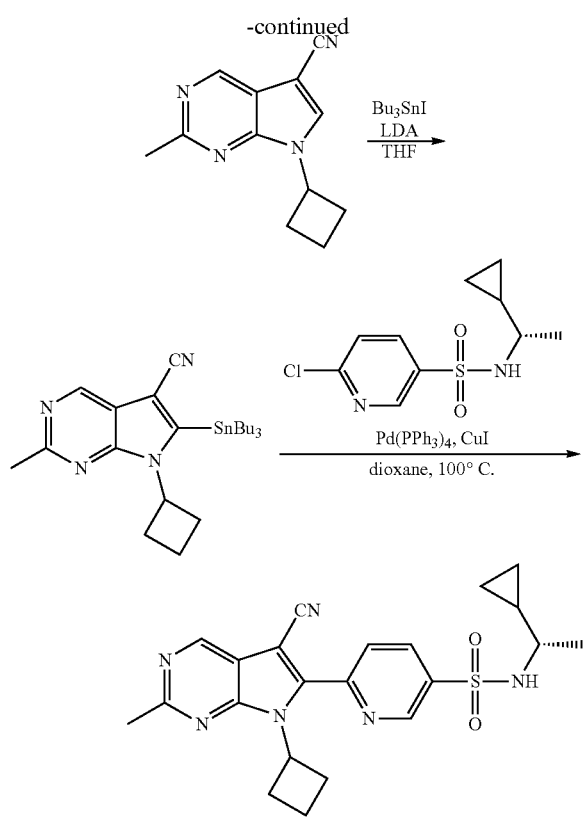

Step A: To a solution of 5-bromo-2,4-dichloropyrimidine (5.0 g, 21.9 mmol) and diisopropylethylamine (5.4 mL, 32.8 mmol) in THF (20 mL) at −40° C. was added dropwise a solution of cyclobutylamine (1.56 g, 21.9 mmol) in THF (20 mL). The mixture was warmed to room temperature and concentrated. The residue was taken up in ethyl acetate and filtered through a plug of silica. The filtrate was concentrated to provide 6.0 g of 5-bromo-2-chloro-N-cyclobutylpyrimidin-4-amine as an oil which was used in the next step without further purification.

Step B: The oil obtained above, 5-bromo-2-chloro-N-cyclobutylpyrimidin-4-amine, was stirred with solid $K_2CO_3$ (6.0 g, 43.5 mmol) in methanol (20 mL) at room temperature overnight and 60° C. for 8 h. The mixture was concentrated and the residue taken up in ethyl acetate and filtered through a plug of silica. The filtrate was collected and concentrated to provide 5.7 g (100% for 2 steps) of 5-bromo-N-cyclobutyl-2-methoxypyrimidin-4-amine.

Step C: A mixture of 5-bromo-N-cyclobutyl-2-methoxy-pyrimidin-4-amine (5.7 g, 21.9 mmol), trimethylsilylacetylene (4.63 mL, 32.85 mmol), $PdCl_2dppf$ (0.8 g, 1.1 mmol), CuI (0.21 g, 1.1 mmol) and $Et_3N$ (4.56 mL, 32.8 mmol) in THF (50 mL) was stirred at 70° C. overnight and then filtered through a plug of silica. The filtrate was concentrated, taken up in methanol (80 mL) and stirred with solid $K_2CO_3$ (6.0 g, 43.5 mmol) for 30 min. The mixture was concentrated and purified on silica gel eluting with 50-100% ethyl acetate in $CH_2Cl_2$ to give 3.5 g (79%) of N-cyclobutyl-5-ethynyl-2-methoxypyrimidin-4-amine.

Step D: A mixture of N-cyclobutyl-5-ethynyl-2-methoxy-pyrimidin-4-amine (3.5 g, 17.24 mmol), CuI (6.57 g, 34.48 mmol), 2-tert-butyl-1,1,3,3-tetramethylguanidine (3.9 g, 22.8 mmol) and DBU (3.34 g, 22 mmol) in DMF (50 mL) was stirred at 140° C. for 3 h and at room temperature overnight. Methanol (50 mL) was added followed by trimethylsilyl cyanide (12 mL) and DCM (300 mL). The mixture was sonicated for 20 min, stirred at room temperature for 1 h then filtered through a plug of silica. The filtrate was concentrated and purified on silica gel eluting with 5-45% ethyl acetate in hexanes to provide 2.83 g (82%) of 7-cyclobutyl-2-methoxy-7H-pyrrolo[2,3-d]pyrimidine as an oil.

Step E: A mixture of 7-cyclobutyl-2-methoxy-7H-pyrrolo[2,3-d]pyrimidine (0.9 g, 4.43 mmol) in 48% aq. HBr (3.0 mL) and acetic acid (3.0 mL) was stirred at 100° C. for 5 h. The mixture was cooled to room temperature, poured into ice-water (20 mL), and neutralized with aq. $NH_4OH$ to pH ~6. The resulting precipitate was collected on a filter and dried to give 0.64 g (74%) of 7-cyclobutyl-7H-pyrrolo[2,3-d]pyrimidin-2-ol.

Step F: Into a mixture of 7-cyclobutyl-7H-pyrrolo[2,3-d]pyrimidin-2-ol (0.64 g, 3.39 mmol) and pyridine (0.41 mL, 5.07 mmol) in $CH_2Cl_2$ (12 mL) at 0° C. was added a solution of triflic anhydride (0.6 mL, 3.56 mmol) in $CH_2Cl_2$ (6 mL) dropwise. The mixture was stirred at 0° C. for 1 h then washed with ice-water, 1N HCl and brine, dried over $Na_2SO_4$ and concentrated to provide 0.99 g (91%) of 7-cyclobutyl-7H-pyrrolo[2,3-d]pyrimidin-2-yl trifluoromethanesulfonate.

Step G: Into a solution of 7-cyclobutyl-7H-pyrrolo[2,3-d]pyrimidin-2-yl trifluoromethanesulfonate (0.99 g, 3.08 mmol), $Fe(acac)_3$ (54 mg, 0.15 mmol) in NMP (2.0 mL) and THF (18 mL) at 0° C. was added a solution of methylmagnesium bromide (3.0 M in diethyl ether, 1.23 mL, 3.69 mmol). The mixture was stirred for 30 min, diluted with diethyl ether and treated with sat. aq. $NH_4Cl$. The organic layer was separated, dried over $Na_2SO_4$, concentrated and purified on silica gel eluting with 10-30% ethyl acetate in $CH_2Cl_2$ to provide 0.39 g (67%) of 7-cyclobutyl-2-methyl-7H-pyrrolo[2,3-d]pyrimidine.

Step H: In a similar manner as Example 7 Step B, 7-cyclobutyl-2-methyl-7H-pyrrolo[2,3-d]pyrimidine-5-carbonitrile was prepared (0.28 g, 64%).

Step I: In a similar manner as Example 2, Step E, 7-cyclobutyl-2-methyl-6-(tributylstannyl)-7H-pyrrolo[2,3-d]pyrimidine-5-carbonitrile was prepared (0.40 g, 67%).

Step J: In a similar manner as Example 2, Step F the title compound was prepared (62 mg, 54%) from 7-cyclobutyl-2-methyl-6-(tributylstannyl)-7H-pyrrolo[2,3-d]pyrimidine-5-carbonitrile and (S)-6-chloro-N-(1-cyclopropylethyl)pyridine-3-sulfonamide [prepared in a similar manner as Example 1, Step B]. Melting point: 155-157° C.; MS m/z 437.5 (M+H$^+$); $^1$H NMR (500 MHz, CDCl$_3$): δ 9.28 (1H, d, J=1.6 Hz), 9.09 (1H, s), 8.39 (1H, dd, J=8.2 Hz, J=2.2 Hz), 8.00 (1H, d, J=8.2 Hz), 5.28-5.22 (1H, m), 4.84 (1H, d, J=6.9 Hz), 3.21-3.14 (2H, m), 2.90-2.86 (1H, m), 2.87 (3H, s), 2.40-2.36 (2H, m), 2.02-1.94 (1H, m), 1.84-1.73 (1H, m), 1.26 (3H, d, J=6.6 Hz), 0.88-0.80 (1H, m), 0.62-0.50 (1H, m), 0.45-0.37 (1H, m), 0.24-0.17 (1H, m), 0.15-0.10 (1H, m).

Additional compounds representative of the present invention may be prepared according to the procedure of Example 8 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
|---|---|---|---|
| 38 | 6-(5-cyano-7-cyclobutyl-2-methoxy-7H-pyrrolo[2,3-d]pyrimidin-6-yl)-N-[(2S)-1,1,1-trifluoropropan-2-yl]pyridine-3-sulfonamide | N/A | 481.8 |

-continued

| Cpd | Name | m.p. | MS |
|---|---|---|---|
| 39 | 6-(5-cyano-7-cyclobutyl-2-methoxy-7H-pyrrolo[2,3-d]pyrimidin-6-yl)-N-[(2R)-1,1,1-trifluoropropan-2-yl]pyridine-3-sulfonamide | N/A | 481.8 |
| 46 | 6-(5-cyano-7-cyclobutyl-2-methyl-7H-pyrrolo[2,3-d]pyrimidin-6-yl)-N-[(2R)-1,1,1-trifluoropropan-2-yl]pyridine-3-sulfonamide | 166-168 | 465.9 |
| 53 | 4-(5-cyano-7-cyclobutyl-2-methyl-7H-pyrrolo[2,3-d]pyrimidin-6-yl)-N-(1,1,1-trifluoro-2-methylpropan-2-yl)benzenesulfonamide | 211-214 | 478.4 |
| 62 | 6-[5-cyano-7-cyclobutyl-2-(difluoromethoxy)-7H-pyrrolo[2,3-d]pyrimidin-6-yl]-N-[(2S)-1,1,1-trifluoropropan-2-yl]pyridine-3-sulfonamide | 172-174 | 517.1 |
| 163 | 6-(5-cyano-7-cyclopentyl-2-methyl-7H-pyrrolo[2,3-d]pyrimidin-6-yl)-N-[(2S)-1,1,1-trifluoropropan-2-yl]pyridine-3-sulfonamide | 212-215 | 479.2 |
| 164 | 4-(5-cyano-7-cyclopentyl-2-methyl-7H-pyrrolo[2,3-d]pyrimidin-6-yl)-N-[(2S)-1,1,1-trifluoropropan-2-yl]benzenesulfonamide | 202-204 | 478.2 |

Example 9

1-cyclobutyl-5-(methylthio)-2-(4-(N-(1-(trifluoromethyl)cyclopropyl)sulfamoyl)phenyl)-1H-pyrrolo[2,3-b]pyridine-3-carboxamide (Cpd 389) and

1-cyclobutyl-5-(methylthio)-2-(4-(N-(1-(trifluoromethyl)cyclopropyl)sulfamoyl)phenyl)-1H-pyrrolo[2,3-b]pyridine-3-carboxylic acid (Cpd 390)

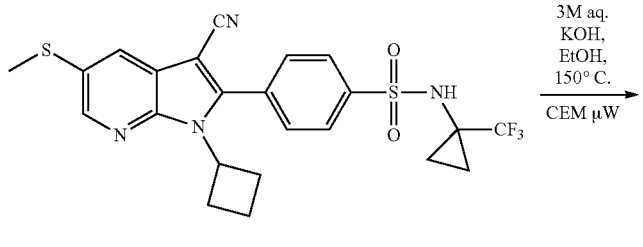
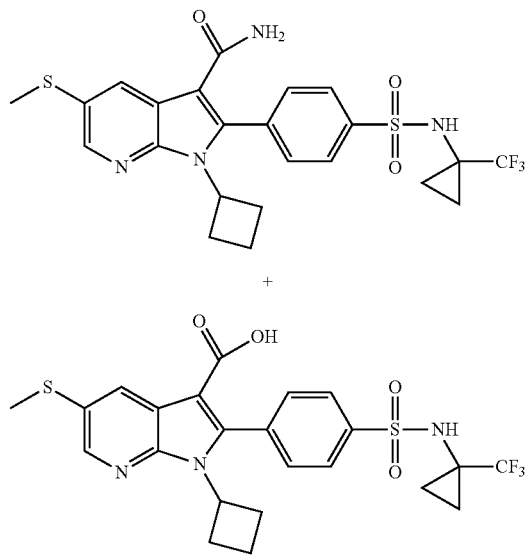

A solution of 4-(3-cyano-1-cyclobutyl-5-(methylthio)-1H-pyrrolo[2,3-b]pyridin-2-yl)-N-(1-(trifluoromethyl)cyclopropyl)benzenesulfonamide (0.1012 g, 0.1998 mmol) in 3M KOH (1 mL) and ethanol (1 mL) was irradiated in a CEM microwave with Powermax®, at 150° C. for two hours with stirring. After cooling to room temperature water (2 mL) was added to the mixture of Cpd 389 and Cpd 390 which was extracted with ethyl acetate (4×3 mL), dried over $Na_2SO_4$, concentrated and chromatographed over silica eluting with 0-10% methanol in $CH_2Cl_2$ to provide both Cpd 389 and Cpd 390. Concentration of fractions provided 1-cyclobutyl-5-(methylthio)-2-(4-(N-(1-(trifluoromethyl)cyclopropyl)sulfamoyl)phenyl)-1H-pyrrolo[2,3-b]pyridine-3-carboxylic acid (6.2 mg, 6%) as a white solid; MS m/z 526.1 (M+H$^+$); $^1$HNMR (500 MHz, acetone-d$_6$) δ 8.39 (d, J=2.20 Hz, 1H), 8.29 (d, J=2.49 Hz, 1H), 7.90-7.86 (m, 2H), 7.61-7.58 (m, 2H), 4.61-4.50 (m, 1H), 3.21-3.10 (m, 2H), 2.46 (s, 3H), 2.11-2.04 (m, 2H), 1.94-1.91 (m, 3H), 1.78-1.70 (m, 1H), 1.60-1.49 (m, 1H), 1.18-1.11 (m, 2H).

Additional compounds representative of the present invention may be prepared according to the procedure of Example 9, Cpd 390, by substituting the appropriate starting materials, reagents and reaction conditions and include compounds selected from (wherein MS represents mass spec as MH$^+$(unless otherwise indicated), m.p. represents melting point in ° C. and N/A indicates that the data was not obtained):

| Cpd | Name | m.p. | MS |
|---|---|---|---|
| 330 | 1-cyclopentyl-5-(methylsulfanyl)-2-(5-{[1-(trifluoromethyl)cyclopropyl]sulfamoyl}pyridin-2-yl)-1H-pyrrolo[2,3-b]pyridine-3-carboxylic acid | N/A | 541.1 |
| 331 | 5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxylic acid | N/A | 517.0 |
| 386 | 1-cyclobutyl-5-(methylsulfanyl)-2-(5-{[(2S)-1,1,1-trifluoropropan-2-yl]sulfamoyl}pyridin-2-yl)-1H-pyrrolo[2,3-b]pyridine-3-carboxylic acid | N/A | 515.1 |

Fractions containing the Cmpd 389 were taken up in 10% methanol and passed through a plug of basic alumina to provide 1-cyclobutyl-5-(methylthio)-2-(4-(N-(1-(trifluoromethyl)cyclopropyl)sulfamoyl)phenyl)-1H-pyrrolo[2,3-b]pyridine-3-carboxamide as a white crystalline solid (15.9 mg, 15%); Melting point: 121-122° C.; MS m/z 525.1 (M+H$^+$); $^1$HNMR (500 MHz, acetone-d$_6$) δ 8.40 (d, J=2.20 Hz, 1H), 8.27 (d, J=2.20 Hz, 1H), 7.97-7.94 (m, 2H), 7.69-7.66 (m, 2H), 6.40-5.79 (br. s, 1H), 5.79-5.26 (br. s, 1H), 4.57-4.46 (m, 1H), 3.21-3.10 (m, 2H), 2.44 (s, 3H), 2.12-2.02 (m, 2H), 1.93-1.90 (m, 3H), 1.77-1.69 (m, 1H), 1.59-1.48 (m, 1H), 1.22-1.12 (m, 2H).

Additional compounds representative of the present invention may be prepared according to the procedure of Example 9, Cpd 389, by substituting the appropriate starting materials, reagents and reaction conditions and include compounds selected from (wherein MS represents mass spec as MH⁺(unless otherwise indicated), m.p. represents melting point in ° C. and N/A indicates that the data was not obtained):

| Cpd | Name | m.p. | MS |
|---|---|---|---|
| 226 | 1-cyclobutyl-5-methoxy-2-(5-{[(2S)-1,1,1-trifluoropropan-2-yl]sulfamoyl}pyridin-2-yl)-1H-pyrrolo[2,3-b]pyridine-3-carboxamide | 233-235 | 498.3 |
| 304 | 1-cyclobutyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide | 219-221 | 536.2 |
| 324 | 5-chloro-1-cyclopentyl-2-(5-{[(2S)-1,1,1-trifluoropropan-2-yl]sulfamoyl}pyridin-2-yl)-1H-pyrrolo[2,3-b]pyridine-3-carboxamide | 289-295 | 516.3 |
| 325 | 5-chloro-1-cyclobutyl-2-(5-{[1-(trifluoromethyl)cyclopropyl]sulfamoyl}pyridin-2-yl)-1H-pyrrolo[2,3-b]pyridine-3-carboxamide | 238-240 | 514.1 |
| 326 | 5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxamide | 239-241 | 516.0 |
| 327 | 2-[5-(tert-butylsulfamoyl)pyridin-2-yl]-5-chloro-1-cyclobutyl-1H-pyrrolo[2,3-b]pyridine-3-carboxamide | 240-241 | 462.1 |
| 328 | 5-chloro-1-cyclobutyl-2-(4-{[1-(trifluoromethyl)cyclopropyl]sulfamoyl}phenyl)-1H-pyrrolo[2,3-b]pyridine-3-carboxamide | 271-272 | 513.0 |
| 329 | 5-chloro-1-cyclobutyl-2-{4-[(1,1,1-trifluoro-2-methylpropan-2-yl)sulfamoyl]phenyl}-1H-pyrrolo[2,3-b]pyridine-3-carboxamide | 263-265 | 515.0 |
| 341 | 1-cyclobutyl-5-methyl-2-{4-[(1,1,1-trifluoro-2-methylpropan-2-yl)sulfamoyl]phenyl}-1H-pyrrolo[2,3-b]pyridine-3-carboxamide | 235-237 | 495.2 |
| 342 | 1-cyclobutyl-5-methyl-2-(4-{[1-(trifluoromethyl)cyclopropyl]sulfamoyl}phenyl)-1H-pyrrolo[2,3-b]pyridine-3-carboxamide | N/A | 493.5 |
| 343 | 1-cyclobutyl-5-methyl-2-(4-{[(2S)-1,1,1-trifluoropropan-2-yl]sulfamoyl}phenyl)-1H-pyrrolo[2,3-b]pyridine-3-carboxamide | N/A | 482.1 |
| 356 | 1-cyclobutyl-5-fluoro-2-(5-{[(2S)-1,1,1-trifluoropropan-2-yl]sulfamoyl}pyridin-2-yl)-1H-pyrrolo[2,3-b]pyridine-3-carboxamide | 223-225 | 486.0 |
| 357 | 1-cyclopentyl-5-methoxy-2-(5-{[(2S)-1,1,1-trifluoropropan-2-yl]sulfamoyl}pyridin-2-yl)-1H-pyrrolo[2,3-b]pyridine-3-carboxamide | 263-264 | 512.1 |
| 358 | 1-cyclopentyl-5-(methylsulfanyl)-2-{4-[(propan-2-ylsulfonyl)amino]phenyl}-1H-pyrrolo[2,3-b]pyridine-3-carboxamide | 250-252 | 472.0 |
| 359 | 2-{4-[(tert-butylsulfonyl)amino]phenyl}-1-cyclopentyl-5-methoxy-1H-pyrrolo[2,3-b]pyridine-3-carboxamide | 269-272 | 470.0 |
| 366 | 5-chloro-1-cyclobutyl-2-{5-[(1-methylcyclopropyl)sulfamoyl]pyridin-2-yl}-1H-pyrrolo[2,3-b]pyridine-3-carboxamide | N/A | 460.0 |
| 367 | 1-cyclobutyl-2-(5-{[(2S)-1,1,1-trifluoropropan-2-yl]sulfamoyl}pyrimidin-2-yl)-1H-pyrrolo[2,3-b]pyridine-3-carboxamide | N/A | 469.1 |
| 372 | 1-cyclobutyl-5-cyclopropyl-2-{4-[(1,1,1-trifluoro-2-methylpropan-2-yl)sulfamoyl]phenyl}-1H-pyrrolo[2,3-b]pyridine-3-carboxamide | N/A | M − 1 = 519.2 |
| 373 | 1-cyclobutyl-5-cyclopropyl-2-(4-{[1-(trifluoromethyl)cyclopropyl]sulfamoyl}phenyl)-1H-pyrrolo[2,3-b]pyridine-3-carboxamide | 224-229 | M − 1 = 517.2 |
| 374 | 1-cyclobutyl-5-cyclopropyl-2-(5-{[1-(trifluoromethyl)cyclopropyl]sulfamoyl}pyridin-2-yl)-1H-pyrrolo[2,3-b]pyridine-3-carboxamide | N/A | M − 1 = 518.1 |
| 375 | 2-[4-(tert-butylsulfamoyl)phenyl]-1-cyclobutyl-5-cyclopropyl-1H-pyrrolo[2,3-b]pyridine-3-carboxamide | N/A | M − 1 = 465.1 |
| 376 | 2-[5-(tert-butylsulfamoyl)pyridin-2-yl]-1-cyclobutyl-5-cyclopropyl-1H-pyrrolo[2,3-b]pyridine-3-carboxamide | 245-252 | M − 1 = 466.1 |
| 377 | 1-cyclobutyl-5-ethyl-2-(5-{[(2S)-1,1,1-trifluoropropan-2-yl]sulfamoyl}pyridin-2-yl)-1H-pyrrolo[2,3-b]pyridine-3-carboxamide | 236-240 | M − 1 = 494.1 |
| 378 | 1-cyclobutyl-5-ethyl-2-{4-[(1,1,1-trifluoro-2-methylpropan-2-yl)sulfamoyl]phenyl}-1H-pyrrolo[2,3-b]pyridine-3-carboxamide | 185-193 | M − 1 = 507.2 |
| 379 | 1-cyclobutyl-5-ethyl-2-(4-{[1-(trifluoromethyl)cyclopropyl]sulfamoyl}phenyl)-1H-pyrrolo[2,3-b]pyridine-3-carboxamide | 173-179 | M − 1 = 505.1 |
| 380 | 1-cyclobutyl-5-ethyl-2-(5-{[1-(trifluoromethyl)cyclopropyl]sulfamoyl}pyridin-2-yl)-1H-pyrrolo[2,3-b]pyridine-3-carboxamide | N/A | M − 1 = 506.2 |
| 381 | 2-[4-(tert-butylsulfamoyl)phenyl]-1-cyclobutyl-5-ethyl-1H-pyrrolo[2,3-b]pyridine-3-carboxamide | 204-210 | M − 1 = 435.2 |
| 382 | 2-[5-(tert-butylsulfamoyl)pyridin-2-yl]-1-cyclobutyl-5-ethyl-1H-pyrrolo[2,3-b]pyridine-3-carboxamide | N/A | M − 1 = 454.2 |
| 387 | 2-{4-[(tert-butylsulfonyl)amino]phenyl}-1-cyclobutyl-5-(methylsulfanyl)-1H-pyrrolo[2,3-b]pyridine-3-carboxamide | 240-241 | 473.2 |
| 388 | 1-cyclobutyl-2-{4-[(1,1,1-trifluoro-2-methylpropan-2-yl)sulfamoyl]phenyl}-1H-pyrrolo[2,3-b]pyridine-3-carboxamide | 240-242 | 481.1 |
| 391 | 1-cyclobutyl-5-(methylsulfanyl)-2-{4-[(1,1,1-trifluoro-2-methylpropan-2-yl)sulfamoyl]phenyl}-1H-pyrrolo[2,3-b]pyridine-3-carboxamide | 204-205 | 527.1 |
| 392 | 2-[4-(tert-butylsulfamoyl)phenyl]-1-cyclobutyl-5-(methylsulfanyl)-1H-pyrrolo[2,3-b]pyridine-3-carboxamide | 224-226 | 473.1 |
| 393 | 2-[4-(tert-butylsulfamoyl)phenyl]-5-chloro-1-cyclobutyl-1H-pyrrolo[2,3-b]pyridine-3-carboxamide | 269-270 | 461.0 |
| 399 | 1-cyclobutyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide | 217-219 | 550.0 |
| 400 | 1-cyclobutyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide | 230-235 | 548.0 |
| 401 | 1-cyclobutyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide | 239-241 | 549.0 |
| 402 | 1-cyclobutyl-5-(trifluoromethyl)-2-(4-{[1-(trifluoromethyl)cyclopropyl]sulfamoyl}phenyl)-1H-pyrrolo[2,3-b]pyridine-3-carboxamide | 261-263 | 547.0 |
| 403 | 2-[4-(tert-butylsulfamoyl)phenyl]-1-cyclobutyl-5-(trifluoromethyl)-1H-pyrrolo[2,3-b]pyridine-3-carboxamide | 255-257 | 495.1 |
| 404 | 2-{4-[(tert-butylsulfonyl)amino]phenyl}-1-cyclobutyl-5-(trifluoromethyl)-1H-pyrrolo[2,3-b]pyridine-3-carboxamide | 257-259 | 495.1 |
| 406 | 1-cyclopentyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide | 244-246 | 564.2 |
| 407 | 1-cyclopentyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide | 262-264 | 562.2 |
| 408 | 1-cyclopentyl-5-(trifluoromethyl)-2-(4-{[1-(trifluoromethyl)cyclopropyl]sulfamoyl}phenyl)-1H-pyrrolo[2,3-b]pyridine-3-carboxamide | 277-279 | 561.2 |
| 409 | 1-cyclopentyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide | 261-263 | 550.2 |

-continued

| Cpd | Name | m.p. | MS |
|---|---|---|---|
| 410 | 1-cyclopentyl-5-methoxy-2-{5-[(1-methylcyclopropyl)sulfamoyl]pyridin-2-yl}-1H-pyrrolo[2,3-b]pyridine-3-carboxamide | N/A | 470.3 |
| 437 | 1-cyclohexyl-5-(trifluoromethyl)-2-(4-{[(2S)-1,1,1-trifluoropropan-2-yl]sulfamoyl}phenyl)-1H-pyrrolo[2,3-b]pyridine-3-carboxamide | 291-293 | 563.2 |
| 438 | 1-cyclohexyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide | 250-252 | 578.2 |
| 439 | 1-cyclohexyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide | 280-283 | 577.2 |
| 440 | 1-cyclohexyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide | 272-275 | 576.2 |
| 441 | 1-cyclohexyl-5-(trifluoromethyl)-2-(4-{[1-(trifluoromethyl)cyclopropyl]sulfamoyl}phenyl)-1H-pyrrolo[2,3-b]pyridine-3-carboxamide | 303-306 | 575.4 |
| 442 | 1-cyclohexyl-2-{4-[(1-methylcyclopropyl)sulfamoyl]phenyl}-5-(trifluoromethyl)-1H-pyrrolo[2,3-b]pyridine-3-carboxamide | 284-286 | 521.2 |
| 443 | 2-[4-(tert-butylsulfamoyl)phenyl]-1-cyclohexyl-5-(trifluoromethyl)-1H-pyrrolo[2,3-b]pyridine-3-carboxamide | 290-292 | 523.2 |
| 444 | 1-cyclohexyl-5-(trifluoromethyl)-2-(4-{[(2R)-1,1,1-trifluoropropan-2-yl]sulfamoyl}phenyl)-1H-pyrrolo[2,3-b]pyridine-3-carboxamide | 285-287 | 563.2 |
| 445 | 2-{4-[(tert-butylsulfonyl)amino]phenyl}-1-cyclohexyl-5-(trifluoromethyl)-1H-pyrrolo[2,3-b]pyridine-3-carboxamide | N/A | 523.3 |
| 446 | 1-cyclohexyl-2-{4-[(propan-2-ylsulfonyl)amino]phenyl}-5-(trifluoromethyl)-1H-pyrrolo[2,3-b]pyridine-3-carboxamide | 203-205 | 509.2 |
| 447 | 1-cyclohexyl-2-(4-{[(1-methylcyclopropyl)sulfonyl]amino}phenyl)-5-(trifluoromethyl)-1H-pyrrolo[2,3-b]pyridine-3-carboxamide | 268-270 | 521.4 |
| 448 | 1-cyclohexyl-2-{4-[(cyclopropylsulfonyl)amino]phenyl}-5-(trifluoromethyl)-1H-pyrrolo[2,3-b]pyridine-3-carboxamide | 220-222 | 507.5 |
| 449 | 2-{4-[(cyclobutylsulfonyl)amino]phenyl}-1-cyclohexyl-5-(trifluoromethyl)-1H-pyrrolo[2,3-b]pyridine-3-carboxamide | 256-258 | 521.5 |
| 469 | 1-cyclobutyl-5-(difluoromethyl)-2-(5-{[(2S)-1,1,1-trifluoropropan-2-yl]sulfamoyl}pyridin-2-yl)-1H-pyrrolo[2,3-b]pyridine-3-carboxamide | 206-208 | 518.7 |
| 470 | 1-cyclobutyl-5-(difluoromethyl)-2-(5-{[(2S)-1,1,1-trifluoropropan-2-yl]sulfamoyl}pyrimidin-2-yl)-1H-pyrrolo[2,3-b]pyridine-3-carboxamide | 199-201 | 519.6 |
| 471 | 1-cyclobutyl-5-(difluoromethyl)-2-{5-[(1,1,1-trifluoro-2-methylpropan-2-yl)sulfamoyl]pyridin-2-yl}-1H-pyrrolo[2,3-b]pyridine-3-carboxamide | 205-207 | 532.7 |
| 472 | 1-cyclobutyl-5-(difluoromethyl)-2-(5-{[1-(trifluoromethyl)cyclopropyl]sulfamoyl}pyridin-2-yl)-1H-pyrrolo[2,3-b]pyridine-3-carboxamide | 210-212 | 530.7 |
| 523 | 2-[5-(tert-butylsulfamoyl)pyridin-2-yl]-1-phenyl-5-(trifluoromethyl)-1H-pyrrolo[2,3-b]pyridine-3-carboxamide | 241.8-243 | 518.3 |
| 527 | 2-[5-(tert-butylsulfamoyl)pyridin-2-yl]-5-fluoro-1-phenyl-1H-pyrrolo[2,3-b]pyridine-3-carboxamide | 275.2-276.9 | 468.4 |

Example 10

(S)-6-(1-phenyl-5-(trifluoromethyl)-1H-pyrrolo[2,3-b]pyridine-2-yl)-N-(1,1,1-trifluoropropan-2-yl)pyridine-3-sulfonamide (Cmpd 314)

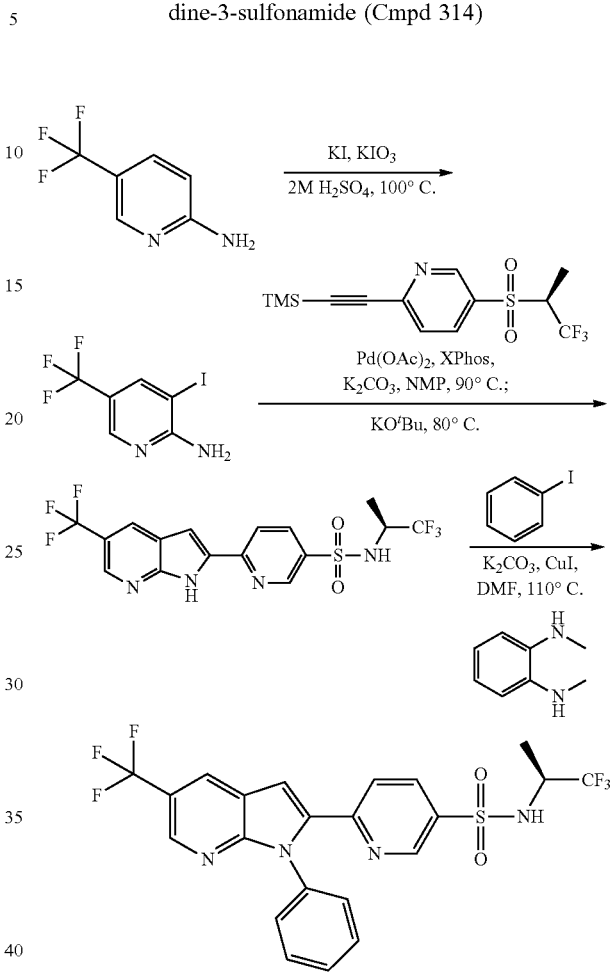

Step A: To a solution of 2-amino-5-trifluoropyridine (7.5 g, 45.1 mmol) and KIO$_3$ (4.0 g, 18.7 mmol) in H$_2$SO$_4$ (2 M, 50 mL) was added an aq. KI solution (7.5 g in 30 mL of water, 45.1 mmol) dropwise at 100° C. The resulting mixture was stirred at 100° C. overnight. After cooling, the mixture was quenched with sat. aq. NaHCO$_3$ and solid NaHSO$_3$ was added until the solution was colorless. The resulting precipitate was collected by filtration and washed with water. The solid was dissolved in CH$_2$Cl$_2$, dried over MgSO$_4$ and concentrated to afford 3-iodo-5-(trifluoromethyl)pyridine-2-amine (12.9 g, quant.) as a yellow solid.

Step B: A round-bottom flask charged with 3-iodo-5-(trifluoromethyl)pyridine-2-amine (2.5 g, 8.7 mmol), Pd(OAc)$_2$ (48.8 mg, 0.2 mmol), 2-dicyclohexylphosphino-2',4',6'-triisopropylbiphenyl (248.8 mg, 0.5 mmol) and K$_2$CO$_3$ (1.8 g, 13.1 mmol) was degassed and back-filled with N$_2$. To the mixture was added NMP (20 mL) which was then stirred at 90° C. overnight. After cooling, KO$^t$Bu was added and the resulting mixture stirred at 90° C. for 6 h, followed by adding ice-water to it. The precipitate was collected by filtration, washed with water and acetone. The solid was dissolved in ethyl acetate, dried over MgSO$_4$, and concentrated to afford (S)-6-(5-(trifluoromethyl)-1H-pyrrolo[2,3-b]pyridine-2-yl)-N-(1,1,1-trifluoropropan-2-yl)pyridine-3-sulfonamide (3.0 g, 79%).

Step C: To a mixture of (S)-6-(5-(trifluoromethyl)-1H-pyrrolo[2,3-b]pyridine-2-yl)-N-(1,1,1-trifluoropropan-2-yl)pyridine-3-sulfonamide (505.0 mg, 1.2 mmol), iodobenzene (470.1 mg, 2.4 mmol), CuI (43.7 mg, 0.24 mmol), $K_2CO_3$ (476.1 mg, 3.6 mmol) and DMF (1.2 mL) was added N,N-dimethylcyclohexane-1,2-diamine (65.4 mg, 0.48 mmol) under $N_2$. The mixture was stirred at 110° C. for 2 days. After cooling, the mixture was added water and acidified with acetic acid, followed by extraction with ethyl acetate. The organic phase was washed in the sequence of water (twice), sat. aq. $NaHCO_3$ and brine. The organic phase was dried over $MgSO_4$ and concentrated. The residue was purified by silica gel chromatography, eluting with 10-30% ethyl acetate in hexanes to afford (S)-6-(1-phenyl-5-(trifluoromethyl)-1H-pyrrolo[2,3-b]pyridine-2-yl)-N-(1,1,1-trifluoropropan-2-yl)pyridine-3-sulfonamide (321 mg, 53%) as an off-white solid. MS m/z 515.4 (M+H$^+$).

Additional compounds representative of the present invention may be prepared according to the procedure of Example 10 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
| --- | --- | --- | --- |
| 315 | 6-[1-(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide | N/A | 517.1 |

Example 11

(S)-6-(3-cyano-1-phenyl-5-(trifluoromethyl)-1H-pyrrolo[2,3-b]pyridine-2-yl)-N-(1,1,1-trifluoropropan-2-yl)pyridine-3-sulfonamide (Cmpd 318)

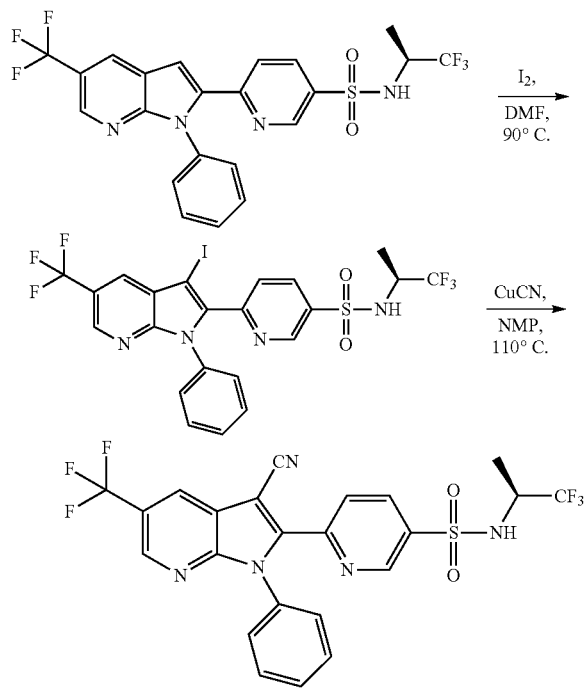

Step A: A mixture of (S)-6-(1-phenyl-5-(trifluoromethyl)-1H-pyrrolo[2,3-b]pyridine-2-yl)-N-(1,1,1-trifluoropropan-2-yl)pyridine-3-sulfonamide (102 mg, 0.2 mmol), iodine (402 mg, 1.6 mmol) and DMF (0.5 mL) was stirred at 90° C. for 4 h. After cooling, the mixture was partitioned between ethyl acetate and sat. aq. $NaHSO_3$. The organic phase was washed with water and brine, dried over $MgSO_4$, evaporated to provide (S)-6-(3-iodo-1-phenyl-5-(trifluoromethyl)-1H-pyrrolo[2,3-b]pyridin-2-yl)-N-(1,1,1-trifluoropropan-2-yl)pyridine-3-sulfonamide as a residue. The residue was used directly without further purification.

Step B: The residue from above, (S)-6-(3-iodo-1-phenyl-5-(trifluoromethyl)-1H-pyrrolo[2,3-b]pyridin-2-yl)-N-(1,1,1-trifluoropropan-2-yl)pyridine-3-sulfonamide, and CuCN (138.9 mg, 1.6 mmol) were suspended in NMP (0.4 ml) and heated at 110° C. overnight. The mixture was partitioned between ethyl acetate and $NH_3OH/NH_4Cl/H_2O$ (1:3:1). The organic phase was washed with sat. aq. $NH_4Cl$, dried over $MgSO_4$ and concentrated. The residue was purified by silica gel chromatography, eluting with 20-40% ethyl acetate in hexanes to produce of (S)-6-(3-cyano-1-phenyl-5-(trifluoromethyl)-1H-pyrrolo[2,3-b]pyridine-2-yl)-N-(1,1,1-trifluoropropan-2-yl)pyridine-3-sulfonamide (76.0 mg, 71%) as a white solid. Melting point: 186-188° C.; MS m/z 540.1 (M+H$^+$); $^1$H NMR δ (500 MHz, acetone-$d_6$): δ 9.09 (1H, dd, J=2.2 Hz, J=0.55 Hz), 8.83 (1H, m), 8.72 (1H, m), 8.37 (1H, m), 7.82 (1H, m), 7.55 (4H, m), 7.50 (1H, m), 4.31 (3H, m), 3.28 (3H, d, J=7.0 Hz).

Additional compounds representative of the present invention may be prepared according to the procedure of Example 11 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
| --- | --- | --- | --- |
| 270 | 6-[5-chloro-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide | 223-225 | 507.4 |
| 303 | 6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 213-215 | 542.2 |
| 306 | 6-[5-chloro-3-cyano-1-(pyridin-2-yl)-1H-pyrrolo[2,3-b]pyridin-2-yl]-N-[(2S)-1,1,1-trifluoropropan-2-yl]pyridine-3-sulfonamide | 179-181 | 507.0 |
| 307 | 6-[5-chloro-3-cyano-1-(pyrazin-2-yl)-1H-pyrrolo[2,3-b]pyridin-2-yl]-N-[(2S)-1,1,1-trifluoropropan-2-yl]pyridine-3-sulfonamide | 247-249 | 508.0 |
| 308 | 6-(5-chloro-3-cyano-1-phenyl-1H-pyrrolo[2,3-b]pyridin-2-yl)-N-[(2S)-1,1,1-trifluoropropan-2-yl]pyridine-3-sulfonamide | 211-213 | 506.0 |
| 316 | 6-[3-cyano-1-(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 226-228 | 542.1 |
| 317 | 6-[3-cyano-1-(pyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 110-112 | 541.1 |
| 318 | 6-[3-cyano-1-phenyl-5-(trifluoromethyl)-1H-pyrrolo[2,3-b]pyridin-2-yl]-N-[(2S)-1,1,1-trifluoropropan-2-yl]pyridine-3-sulfonamide | 186-188 | 540.1 |
| 320 | 6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide | 171-173 | 492.0 |
| 321 | 6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide | 212-214 | 492.0 |
| 322 | 6-[3-cyano-5-fluoro-1-(pyridin-2-yl)-1H-pyrrolo[2,3-b]pyridin-2-yl]-N-[(2S)-1,1,1-trifluoropropan-2-yl]pyridine-3-sulfonamide | 229-231 | 491.1 |
| 332 | 6-[3-cyano-1-(5-methoxypyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 203-206 | 571.0 |

-continued

| Cpd | Name | m.p. | MS |
|---|---|---|---|
| 333 | 6-[3-cyano-1-(4-methoxypyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 209-211 | 572.1 |
| 334 | N-tert-butyl-4-[3-cyano-1-(pyrimidin-2-yl)-5-(trifluoromethyl)-1H-pyrrolo[2,3-b]pyridin-2-yl]benzenesulfonamide | 228-230 | 501.1 |
| 335 | N-tert-butyl-4-[3-cyano-1-(pyrazin-2-yl)-5-(trifluoromethyl)-1H-pyrrolo[2,3-b]pyridin-2-yl]benzenesulfonamide | 190-192 | 501.1 |
| 336 | N-tert-butyl-4-[3-cyano-1-(pyridin-2-yl)-5-(trifluoromethyl)-1H-pyrrolo[2,3-b]pyridin-2-yl]benzenesulfonamide | 227-230 | 500.1 |
| 337 | N-tert-butyl-4-[3-cyano-1-phenyl-5-(trifluoromethyl)-1H-pyrrolo[2,3-b]pyridin-2-yl]benzenesulfonamide | 206-208 | 499.1 |
| 339 | 6-[5-bromo-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide | 223-225 | 554.2 |
| 340 | 6-[5-bromo-3-cyano-1-(pyrazin-2-yl)-1H-pyrrolo[2,3-b]pyridin-2-yl]-N-[(2S)-1,1,1-trifluoropropan-2-yl]pyridine-3-sulfonamide | 247-248 | 554.0 |
| 344 | 6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide | 219-221 | 514.9 |
| 345 | 6-[3-cyano-5-methyl-1-(pyrimidin-2-yl)-1H-pyrrolo[2,3-b]pyridin-2-yl]-N-[(2S)-1,1,1-trifluoropropan-2-yl]pyridine-3-sulfonamide | 221-223 | 486.9 |
| 346 | 6-[3-cyano-5-methyl-1-(pyridin-2-yl)-1H-pyrrolo[2,3-b]pyridin-2-yl]-N-[(2S)-1,1,1-trifluoropropan-2-yl]pyridine-3-sulfonamide | 165-167 | 485.9 |
| 347 | 6-[3-cyano-5-methyl-1-(pyridin-3-yl)-1H-pyrrolo[2,3-b]pyridin-2-yl]-N-[(2S)-1,1,1-trifluoropropan-2-yl]pyridine-3-sulfonamide | 205-207 | 485.9 |
| 348 | 6-(3-cyano-5-methyl-1-phenyl-1H-pyrrolo[2,3-b]pyridin-2-yl)-N-[(2S)-1,1,1-trifluoropropan-2-yl]pyridine-3-sulfonamide | 220-222 | 485.0 |
| 349 | 6-[3-cyano-5-methyl-1-(pyrazin-2-yl)-1H-pyrrolo[2,3-b]pyridin-2-yl]-N-[(2S)-1,1,1-trifluoropropan-2-yl]pyridine-3-sulfonamide | 220-222 | 486.9 |
| 354 | 6-[3-cyano-1-(5-methylpyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide | N/A | 556.0 |
| 355 | 6-[3-cyano-1-(4-methylpyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide | 176-180 | 556.0 |
| 365 | 6-[3-cyano-5-methoxy-1-(pyrazin-2-yl)-1H-pyrrolo[2,3-b]pyridin-2-yl]-N-[(2S)-1,1,1-trifluoropropan-2-yl]pyridine-3-sulfonamide | 220-225 | 504.0 |
| 383 | 6-[3-cyano-5-methyl-1-(pyridazin-3-yl)-1H-pyrrolo[2,3-b]pyridin-2-yl]-N-[(2S)-1,1,1-trifluoropropan-2-yl]pyridine-3-sulfonamide | 150-153 (decompose) | 488.0 |
| 384 | 6-[3-cyano-5-methyl-1-(pyrimidin-5-yl)-1H-pyrrolo[2,3-b]pyridin-2-yl]-N-[(2S)-1,1,1-trifluoropropan-2-yl]pyridine-3-sulfonamide | 231-233 | 488.0 |
| 411 | 6-[3-cyano-5-ethyl-1-(pyrazin-2-yl)-1H-pyrrolo[2,3-b]pyridin-2-yl]-N-[(2S)-1,1,1-trifluoropropan-2-yl]pyridine-3-sulfonamide | 195-200 | 502.5 |
| 412 | 6-[3-cyano-5-ethyl-1-(4-fluoropyridin-2-yl)-1H-pyrrolo[2,3-b]pyridin-2-yl]-N-[(2S)-1,1,1-trifluoropropan-2-yl]pyridine-3-sulfonamide | 201-205 | 519.5 |
| 413 | 6-(3-cyano-5-ethyl-1-phenyl-1H-pyrrolo[2,3-b]pyridin-2-yl)-N-[(2S)-1,1,1-trifluoropropan-2-yl]pyridine-3-sulfonamide | 135-140 | 500.4 |
| 414 | 6-[3-cyano-5-ethyl-1-(pyridin-2-yl)-1H-pyrrolo[2,3-b]pyridin-2-yl]-N-[(2S)-1,1,1-trifluoropropan-2-yl]pyridine-3-sulfonamide | 190-195 | 501.4 |
| 429 | 6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide | 181-183 | 513.3 |
| 430 | 6-[3-cyano-5-methyl-1-(1,3-thiazol-5-yl)-1H-pyrrolo[2,3-b]pyridin-2-yl]-N-[(2S)-1,1,1-trifluoropropan-2-yl]pyridine-3-sulfonamide | 176-178 | 493.5 |
| 431 | 6-[3-cyano-5-methyl-1-(pyrimidin-4-yl)-1H-pyrrolo[2,3-b]pyridin-2-yl]-N-[(2S)-1,1,1-trifluoropropan-2-yl]pyridine-3-sulfonamide | 233-235 | 488.4 |
| 432 | 6-[3-cyano-1-(5-fluoropyridin-2-yl)-5-methyl-1H-pyrrolo[2,3-b]pyridin-2-yl]-N-[(2S)-1,1,1-trifluoropropan-2-yl]pyridine-3-sulfonamide | 199-200 | 505.3 |
| 433 | 6-{3-cyano-5-methyl-1-[4-(trifluoromethyl)pyridin-2-yl]-1H-pyrrolo[2,3-b]pyridin-2-yl}-N-[(2S)-1,1,1-trifluoropropan-2-yl]pyridine-3-sulfonamide | 192-194 | 555.4 |
| 434 | 6-[1-(4-aminopyridin-2-yl)-3-cyano-5-methyl-1H-pyrrolo[2,3-b]pyridin-2-yl]-N-[(2S)-1,1,1-trifluoropropan-2-yl]pyridine-3-sulfonamide | 202-203 | 502.5 |
| 435 | 6-[1-(5-bromopyrimidin-2-yl)-3-cyano-5-methyl-1H-pyrrolo[2,3-b]pyridin-2-yl]-N-[(2S)-1,1,1-trifluoropropan-2-yl]pyridine-3-sulfonamide | 169-171 | 568.3 |
| 436 | 6-[3-cyano-5-methyl-1-(pyridazin-4-yl)-1H-pyrrolo[2,3-b]pyridin-2-yl]-N-[(2S)-1,1,1-trifluoropropan-2-yl]pyridine-3-sulfonamide | 196-198 | 488.4 |
| 450 | 6-[3-cyano-5-methyl-1-(1,3-thiazol-2-yl)-1H-pyrrolo[2,3-b]pyridin-2-yl]-N-[(2S)-1,1,1-trifluoropropan-2-yl]pyridine-3-sulfonamide | 208-210 | 493.4 |
| 451 | 6-[3-cyano-1-(5-isocyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide | N/A | 518.3 |
| 461 | 6-[3-cyano-5-fluoro-1-(4-fluoropyridin-2-yl)-1H-pyrrolo[2,3-b]pyridin-2-yl]-N-[(2S)-1,1,1-trifluoropropan-2-yl]pyridine-3-sulfonamide | 186-188 | 509.4 |
| 462 | 6-[3-cyano-5-fluoro-1-(5-fluoropyrimidin-2-yl)-1H-pyrrolo[2,3-b]pyridin-2-yl]-N-[(2S)-1,1,1-trifluoropropan-2-yl]pyridine-3-sulfonamide | 180-182 | 510.5 |
| 463 | 6-[3-cyano-6-methyl-1-(pyrazin-2-yl)-1H-pyrrolo[3,2-b]pyridin-2-yl]-N-[(2S)-1,1,1-trifluoropropan-2-yl]pyridine-3-sulfonamide | 288-289 | 488.6 |
| 464 | 6-[3-cyano-6-methyl-1-(pyrimidin-5-yl)-1H-pyrrolo[3,2-b]pyridin-2-yl]-N-[(2S)-1,1,1-trifluoropropan-2-yl]pyridine-3-sulfonamide | 229-230 | 488.6 |
| 465 | 6-[3-cyano-6-methyl-1-(pyridin-2-yl)-1H-pyrrolo[3,2-b]pyridin-2-yl]-N-[(2S)-1,1,1-trifluoropropan-2-yl]pyridine-3-sulfonamide | 242-244 | 487.6 |
| 466 | 6-[3-cyano-6-methyl-1-(pyridin-3-yl)-1H-pyrrolo[3,2-b]pyridin-2-yl]-N-[(2S)-1,1,1-trifluoropropan-2-yl]pyridine-3-sulfonamide | 278-279 | 487.2 |
| 467 | 6-[3-cyano-1-(5-fluoropyridin-2-yl)-6-methyl-1H-pyrrolo[3,2-b]pyridin-2-yl]-N-[(2S)-1,1,1-trifluoropropan-2-yl]pyridine-3-sulfonamide | 263-265 | 505.2 |
| 468 | 6-[3-cyano-6-methyl-1-(1,3-thiazol-4-yl)-1H-pyrrolo[3,2-b]pyridin-2-yl]-N-[(2S)-1,1,1-trifluoropropan-2-yl]pyridine-3-sulfonamide | 244-245 | 493.2 |
| 473 | 6-[3-cyano-5-ethyl-1-(5-fluoropyrimidin-2-yl)-1H-pyrrolo[2,3-b]pyridin-2-yl]-N-[(2S)-1,1,1-trifluoropropan-2-yl]pyridine-3-sulfonamide | 175-177 | 520.1 |
| 474 | 6-[3-cyano-5-ethyl-1-(5-fluoropyridin-2-yl)-1H-pyrrolo[2,3-b]pyridin-2-yl]-N-[(2S)-1,1,1-trifluoropropan-2-yl]pyridine-3-sulfonamide | 175-177 | 519.5 |
| 475 | 6-[3-cyano-6-methyl-1-(pyrimidin-2-yl)-1H-pyrrolo[3,2-b]pyridin-2-yl]-N-[(2S)-1,1,1-trifluoropropan-2-yl]pyridine-3-sulfonamide | 226-228 | 488.2 |
| 476 | 6-(3-cyano-6-methyl-1-phenyl-1H-pyrrolo[3,2-b]pyridin-2-yl)-N-[(2S)-1,1,1-trifluoropropan-2-yl]pyridine-3-sulfonamide | 245-247 | 486.2 |
| 477 | 6-[3-cyano-6-methyl-1-(1,3-thiazol-2-yl)-1H-pyrrolo[3,2-b]pyridin-2-yl]-N-[(2S)-1,1,1-trifluoropropan-2-yl]pyridine-3-sulfonamide | 230-232 | 493.2 |
| 478 | 6-[3-cyano-6-methyl-1-(1,3-thiazol-5-yl)-1H-pyrrolo[3,2-b]pyridin-2-yl]-N-[(2S)-1,1,1-trifluoropropan-2-yl]pyridine-3-sulfonamide | 273-275 | 493.2 |
| 479 | 6-{3-cyano-6-methyl-1-[4-(trifluoromethyl)pyridin-2-yl]-1H-pyrrolo[3,2-b]pyridin-2-yl}-N-[(2S)-1,1,1-trifluoropropan-2-yl]pyridine-3-sulfonamide | 245-246 | 555.2 |
| 480 | 6-[3-cyano-6-methyl-1-(pyridazin-4-yl)-1H-pyrrolo[3,2-b]pyridin-2-yl]-N-[(2S)-1,1,1-trifluoropropan-2-yl]pyridine-3-sulfonamide | 283-285 | 488.2 |

| Cpd | Name | m.p. | MS |
|---|---|---|---|
| 481 | 6-[3-cyano-6-methyl-1-(pyrimidin-4-yl)-1H-pyrrolo[3,2-b]pyridin-2-yl]-N-[(2S)-1,1,1-trifluoropropan-2-yl]pyridine-3-sulfonamide | 265-267 | 488.2 |
| 482 | 6-[3-cyano-6-methyl-1-(pyridin-4-yl)-1H-pyrrolo[3,2-b]pyridin-2-yl]-N-[(2S)-1,1,1-trifluoropropan-2-yl]pyridine-3-sulfonamide | 303-305 | 487.2 |
| 501 | 6-[3-cyano-1-(2-fluorophenyl)-5-methyl-1H-pyrrolo[2,3-b]pyridin-2-yl]-N-[(2S)-1,1,1-trifluoropropan-2-yl]pyridine-3-sulfonamide | 128 decomp. | 504.2 |
| 502 | 6-[3-cyano-1-(3-fluorophenyl)-5-methyl-1H-pyrrolo[2,3-b]pyridin-2-yl]-N-[(2S)-1,1,1-trifluoropropan-2-yl]pyridine-3-sulfonamide | 238-240 | 504.2 |
| 503 | 6-[3-cyano-1-(4-fluorophenyl)-5-methyl-1H-pyrrolo[2,3-b]pyridin-2-yl]-N-[(2S)-1,1,1-trifluoropropan-2-yl]pyridine-3-sulfonamide | 253-254 | 504.2 |
| 504 | 6-[3-cyano-1-(2,5-difluorophenyl)-5-methyl-1H-pyrrolo[2,3-b]pyridin-2-yl]-N-[(2S)-1,1,1-trifluoropropan-2-yl]pyridine-3-sulfonamide | 232-234 | 522.2 |
| 505 | 6-[3-cyano-1-(3,4-difluorophenyl)-5-methyl-1H-pyrrolo[2,3-b]pyridin-2-yl]-N-[(2S)-1,1,1-trifluoropropan-2-yl]pyridine-3-sulfonamide | 250-252 | 522.2 |
| 506 | 6-[3-cyano-1-(3,5-difluorophenyl)-5-methyl-1H-pyrrolo[2,3-b]pyridin-2-yl]-N-[(2S)-1,1,1-trifluoropropan-2-yl]pyridine-3-sulfonamide | 260-262 | 522.2 |
| 507 | 6-[3-cyano-5-methyl-1-(1,3-thiazol-4-yl)-1H-pyrrolo[2,3-b]pyridin-2-yl]-N-[(2S)-1,1,1-trifluoropropan-2-yl]pyridine-3-sulfonamide | 186-188 | 493.2 |
| 508 | 6-[3-cyano-1-(6-cyanopyrimidin-4-yl)-5-methyl-1H-pyrrolo[2,3-b]pyridin-2-yl]-N-[(2S)-1,1,1-trifluoropropan-2-yl]pyridine-3-sulfonamide | 120-122 | 513.2 |
| 509 | 6-[3-cyano-5-ethyl-1-(thiophen-2-yl)-1H-pyrrolo[2,3-b]pyridin-2-yl]-N-[(2S)-1,1,1-trifluoropropan-2-yl]pyridine-3-sulfonamide | 169-171 | 506.1 |
| 510 | 6-[3-cyano-5-ethyl-1-(4-fluorophenyl)-1H-pyrrolo[2,3-b]pyridin-2-yl]-N-[(2S)-1,1,1-trifluoropropan-2-yl]pyridine-3-sulfonamide | 212-214 | 518.2 |
| 511 | 6-[3-cyano-5-ethyl-1-(3-fluorophenyl)-1H-pyrrolo[2,3-b]pyridin-2-yl]-N-[(2S)-1,1,1-trifluoropropan-2-yl]pyridine-3-sulfonamide | 195-197 | 518.2 |
| 512 | 6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide | 229-231 | 507.2 |
| 514 | 6-[3-cyano-1-(4-cyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide | 259-261 | 518.3 |
| 515 | N-tert-butyl-6-[5-chloro-3-cyano-1-(1,3-thiazol-2-yl)-1H-pyrrolo[2,3-b]pyridin-2-yl]pyridine-3-sulfonamide | 216-218 | 473.7 |
| 516 | N-tert-butyl-6-[3-cyano-1-phenyl-5-(trifluoromethyl)-1H-pyrrolo[2,3-b]pyridin-2-yl]pyridine-3-sulfonamide | 201.2-202.4 | 500.3 |
| 517 | N-tert-butyl-6-[3-cyano-1-(4-fluorophenyl)-5-(trifluoromethyl)-1H-pyrrolo[2,3-b]pyridin-2-yl]pyridine-3-sulfonamide | 228.3-229.4 | 518.2 |
| 518 | N-tert-butyl-6-[3-cyano-1-(pyridin-2-yl)-5-(trifluoromethyl)-1H-pyrrolo[2,3-b]pyridin-2-yl]pyridine-3-sulfonamide | 210.4-211.8 | 501.2 |
| 519 | N-tert-butyl-6-(3-cyano-5-fluoro-1-phenyl-1H-pyrrolo[2,3-b]pyridin-2-yl)pyridine-3-sulfonamide | 239.4-241.5 | 450.4 |
| 520 | N-tert-butyl-6-[3-cyano-5-fluoro-1-(4-fluorophenyl)-1H-pyrrolo[2,3-b]pyridin-2-yl]pyridine-3-sulfonamide | 259.1-260.7 | 468.3 |
| 521 | N-tert-butyl-6-[3-cyano-5-fluoro-1-(pyrazin-2-yl)-1H-pyrrolo[2,3-b]pyridin-2-yl]pyridine-3-sulfonamide | 245-247 | 452.3 |
| 522 | N-tert-butyl-6-[3-cyano-5-fluoro-1-(pyridin-2-yl)-1H-pyrrolo[2,3-b]pyridin-2-yl]pyridine-3-sulfonamide | 202.2-204.3 | 451.3 |
| 524 | N-tert-butyl-6-(3-cyano-5-methyl-1-phenyl-1H-pyrrolo[2,3-b]pyridin-2-yl)pyridine-3-sulfonamide | 228.6-229.3 | 446.4 |
| 525 | N-tert-butyl-6-[3-cyano-5-methyl-1-(pyridin-2-yl)-1H-pyrrolo[2,3-b]pyridin-2-yl]pyridine-3-sulfonamide | 214.2-215.4 | 447.4 |
| 526 | N-tert-butyl-6-[3-cyano-1-(pyrazin-2-yl)-5-(trifluoromethyl)-1H-pyrrolo[2,3-b]pyridin-2-yl]pyridine-3-sulfonamide | 214.2-215.4 | 502.3 |

Example 12

6-[3-cyano-1-cyclobutyl-5-(trifluoromethyl)-1H-pyrrolo[2,3-b]pyridin-2-yl]-N-[(2-deuterium)propan-2-yl]pyridine-3-sulfonamide (Cmpd 513)

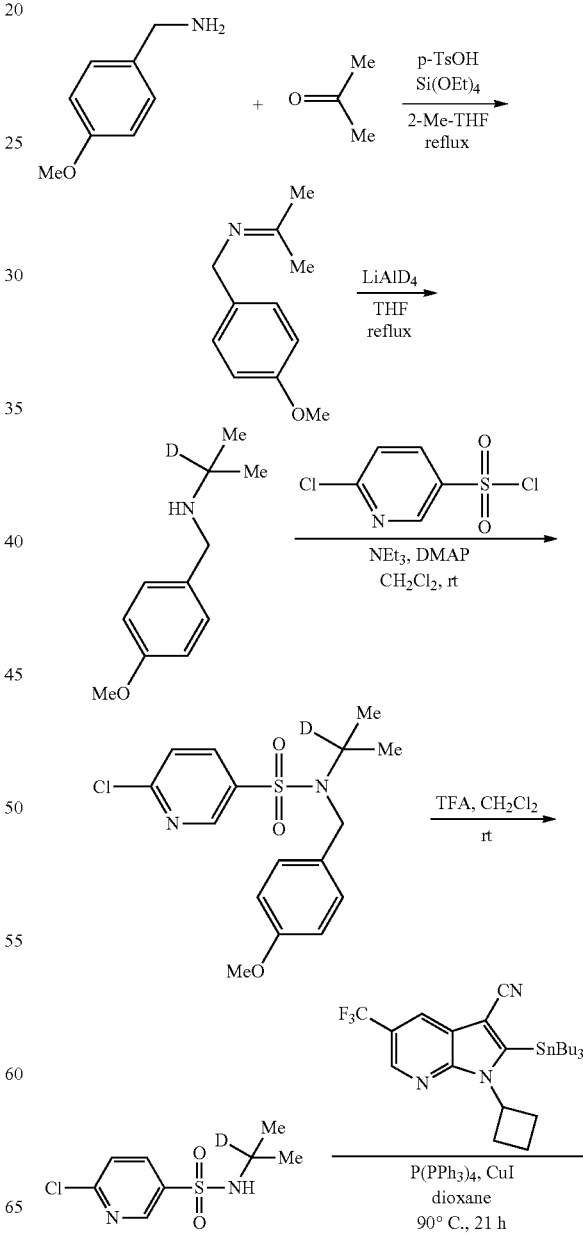

-continued

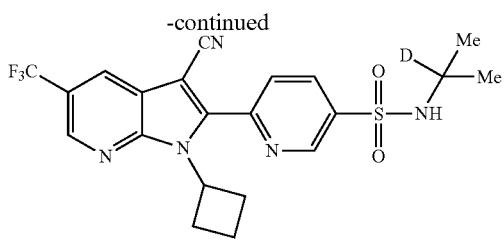

Step A: To a solution of p-toluenesulfonic acid monohydrate (364 mg, 1.9 mmol) and 2-methyltetrahydrofuran (80 mL) were added 4-methoxybenzylamine (5.0 mL, 38 mmol), tetraethylorthosilicate (4.3 mL, 19 mmol), and acetone (6.2 mL, 84 mmol). The mixture was stirred at reflux for 18 hours, cooled to room temperature, and filtered, rinsing the filter cake with EtOAc. The filtrate was concentrated using a rotary evaporator and used without further purification.

Step B: The residue from above was added as a solution in THF (30 mL), dropwise over 5 minutes, to a suspension of lithium aluminum deuteride (3.2 g, 76.2 mmol) in THF (160 mL) at room temperature. The mixture was stirred at reflux for 19 hours. The mixture was then cooled to 0° C., and MTBE (100 mL) was added, followed by the slow, sequential addition of $H_2O$ (3.2 mL), aq. NaOH (5 N, 3.2 mL), and $H_2O$ (10 mL). The mixture was stirred at room temperature for 30 minutes, $MgSO_4$ was added, and the mixture was stirred at room temperature for an additional 30 minutes. The mixture was filtered through Celite and the filter cake was rinsed with MTBE. The filtrate was concentrated using a rotary evaporator and used without further purification.

Step C: The residue from above was added $CH_2Cl_2$ (200 mL), triethylamine (16 mL, 115 mmol), and 4-(dimethylamino)pyridine (234 mg, 1.9 mmol). The mixture was cooled to 0° C., and 6-chloropyridine-3-sulfonyl chloride (8.9 g, 42 mmol) was added. The mixture was stirred at room temperature for 16 h and then concentrated using a rotary evaporator. The residue was added to EtOAc (400 mL) and $H_2O$ (150 mL). The organic layer was washed with aq. HCl (3 N, 3×150 mL) and brine (150 mL), dried with $Na_2SO_4$, and concentrated using a rotary evaporator. The residue was purified using silica gel chromatography (120 g $SiO_2$, 0% to 20% EtOAc in hexanes), providing 6-chloro-N-(2-deutero-propan-2-yl)-N-(4-methoxybenzyl)pyridine-3-sulfonamide (4.4 g, 33% from 4-methoxybenzylamine).

Step D: The above material was added to $CH_2Cl_2$ (30 mL). The mixture was cooled to 0° C. and trifluoroacetic acid (30 mL) was added. The mixture was stirred at room temperature for 16.5 hours, concentrated using a rotary evaporator, added to sat. aq. $NaHCO_3$ (100 mL), and extracted with $CH_2Cl_2$ (3×100 mL). The combined organic extracts were dried with $Na_2SO_4$ and concentrated. The residue was purified using silica gel chromatography (120 g $SiO_2$, 0% to 30% EtOAc in hexanes), followed by a wash with cold 2:1 hexanes:$CH_2Cl_2$ (12 mL), providing 6-chloro-N-(2-deutero-propan-2-yl)pyridine-3-sulfonamide (2.3 g, 78%).

Step E: 6-chloro-N-(2-deutero-propan-2-yl)pyridine-3-sulfonamide (379 mg, 1.6 mmol) and 1-cyclobutyl-2-(tributylstannyl)-5-(trifluoromethyl)-1H-pyrrolo[2,3-b]pyridine-3-carbonitrile (891 mg, 1.6 mmol, synthesized in a manner analogous to Example 4) were converted into compound 513 (385 mg, 52%) in a manner analogous to Example 4. Melting point: 191-193° C.; MS m/z 466.1 (M+H$^+$); $^1$H NMR (500 MHz, acetone-d$_6$) δ 9.26 (1H, dd, J=2.3, 0.8 Hz), 8.87 (1H, d, J=1.7 Hz), 8.57 (1H, dd, J=2.1, 0.6 Hz), 8.54 (1H, dd, J=8.2, 2.3 Hz), 8.18 (1H, dd, J=8.2, 0.6 Hz), 6.91 (1H, br), 5.41 (1H, m), 3.20 (2H, m), 2.38 (2H, m), 1.92 (1H, m), 1.80 (1H, m), 1.12 (6H, s).

BIOLOGICAL EXAMPLES

The following biological examples demonstrate the usefulness of the compounds of the present invention for treating viral infections.

Example 1

HCV Replicon Assay

The lack of reliable and readily accessible cell-culture and small animal models permissive for HCV replication has limited the development of new anti-HCV agents. Self-replicating subgenomic HCV systems, termed HCV replicons, have been described and have been widely used to assess the efficacy of anti-HCV inhibitors (see Blight K J, et al., 2000, Efficient initiation of HCV RNA replication in cell culture. Science 290:1972-1974; Blight K J, et al., 2002, Highly permissive cell lines for subgenomic and genomic hepatitis C virus RNA replication. J Virol 76:13001-13014; Ikeda M, et al., 2002. Selectable subgenomic and genome-length dicistronic RNAs derived from an infectious molecular clone of the HCV-N strain of hepatitis C virus replicate efficiently in cultured Huh7 cells. J Virol 76:2997-3006; Lohmann V, et al., 1999, Replication of subgenomic hepatitis C virus RNAs in a hepatoma cell line. Science 285:110-113; Pietschmann T, et al., 2002, Persistent and transient replication of full-length hepatitis C virus genomes in cell culture. J Virol 76:4008-4021; and, Pietschmann T, et al., 2001, Characterization of cell lines carrying self-replicating hepatitis C virus RNAs. J Virol 75:1252-1264).

As described in U.S. Pat. No. 6,630,343, HCV inhibitors are analyzed in the bicistronic replicon by quantitating replicon RNA (GenBank Accession No. AJ242654) reduction and/or the Fluc reporter signal. Replicon-containing cells may be cultured with a test compound of the present invention for up to 3 days. Interferon (IFN) is used as a positive control. In general, the replicon $IC_{50}$ values shown in Table 1 represent $IC_{50}$ values determined by replicon RNA reduction.

As shown in Table 1, test compounds of the present invention may demonstrate a replicon RNA reduction $IC_{50}$ value of from greater than about 2 μM to about 5 μM (*), an $IC_{50}$ value of between about 0.5 μM to about 2 μM (), or an $IC_{50}$ value of less than about 0.5 μM (*).

TABLE 1

| Replicon $IC_{50}$ (M) | |
|---|---|
| Cpd | $IC_{50}$ |
| 1 | *** |
| 2 | *** |
| 3 | *** |
| 4 | * |
| 5 | *** |
| 6 | *** |
| 7 | ** |
| 8 | ** |
| 9 | *** |
| 10 | *** |
| 11 | ** |
| 12 | ** |

TABLE 1-continued

Replicon IC$_{50}$ (M)

| Cpd | IC$_{50}$ |
|---|---|
| 13 | *** |
| 14 | *** |
| 15 | ** |
| 16 | ** |
| 17 | ** |
| 18 | ** |
| 19 | * |
| 20 | ** |
| 21 | *** |
| 22 | ** |
| 23 | ** |
| 24 | *** |
| 25 | ** |
| 26 | ** |
| 27 | *** |
| 28 | * |
| 29 | *** |
| 30 | *** |
| 31 | *** |
| 32 | *** |
| 33 | *** |
| 34 | *** |
| 35 | *** |
| 36 | *** |
| 37 | *** |
| 38 | *** |
| 39 | * |
| 40 | ** |
| 41 | *** |
| 42 | *** |
| 43 | *** |
| 44 | *** |
| 45 | *** |
| 46 | *** |
| 47 | *** |
| 48 | *** |
| 49 | *** |
| 50 | *** |
| 51 | *** |
| 52 | *** |
| 53 | *** |
| 54 | *** |
| 55 | *** |
| 56 | *** |
| 57 | *** |
| 58 | *** |
| 59 | ** |
| 60 | *** |
| 61 | *** |
| 62 | *** |
| 63 | *** |
| 64 | *** |
| 65 | *** |
| 66 | *** |
| 67 | *** |
| 68 | *** |
| 69 | *** |
| 70 | *** |
| 71 | *** |
| 72 | *** |
| 73 | *** |
| 74 | *** |
| 75 | *** |
| 76 | ** |
| 77 | *** |
| 78 | *** |
| 79 | *** |
| 80 | *** |
| 81 | *** |
| 82 | *** |
| 83 | *** |
| 84 | *** |
| 85 | *** |
| 86 | *** |
| 87 | *** |
| 88 | *** |

TABLE 1-continued

Replicon IC$_{50}$ (M)

| Cpd | IC$_{50}$ |
|---|---|
| 89 | * |
| 90 | *** |
| 91 | *** |
| 92 | *** |
| 93 | *** |
| 94 | *** |
| 95 | ** |
| 96 | *** |
| 97 | *** |
| 98 | *** |
| 99 | *** |
| 100 | *** |
| 101 | *** |
| 102 | *** |
| 103 | *** |
| 104 | *** |
| 105 | *** |
| 106 | *** |
| 107 | *** |
| 108 | *** |
| 109 | *** |
| 110 | *** |
| 111 | *** |
| 112 | *** |
| 113 | *** |
| 114 | *** |
| 115 | ** |
| 116 | *** |
| 117 | *** |
| 118 | *** |
| 119 | *** |
| 120 | *** |
| 121 | *** |
| 122 | *** |
| 123 | *** |
| 124 | *** |
| 125 | *** |
| 126 | *** |
| 127 | *** |
| 128 | *** |
| 129 | *** |
| 130 | *** |
| 131 | *** |
| 132 | *** |
| 133 | *** |
| 134 | *** |
| 135 | *** |
| 136 | *** |
| 137 | *** |
| 138 | ** |
| 139 | ** |
| 140 | ** |
| 141 | ** |
| 142 | *** |
| 143 | *** |
| 144 | *** |
| 145 | *** |
| 146 | *** |
| 147 | *** |
| 148 | *** |
| 149 | *** |
| 150 | *** |
| 151 | *** |
| 152 | *** |
| 153 | *** |
| 154 | *** |
| 155 | *** |
| 156 | ** |
| 157 | *** |
| 158 | *** |
| 159 | *** |
| 160 | *** |
| 161 | *** |
| 162 | *** |
| 163 | ** |
| 164 | ** |

TABLE 1-continued

Replicon IC$_{50}$ (M)

| Cpd | IC$_{50}$ |
|---|---|
| 165 | ** |
| 166 | *** |
| 167 | *** |
| 168 | *** |
| 169 | *** |
| 170 | *** |
| 171 | *** |
| 172 | *** |
| 173 | *** |
| 174 | *** |
| 175 | *** |
| 176 | *** |
| 177 | *** |
| 178 | *** |
| 179 | *** |
| 180 | ** |
| 181 | *** |
| 182 | *** |
| 183 | ** |
| 184 | *** |
| 185 | *** |
| 186 | *** |
| 187 | *** |
| 188 | *** |
| 189 | *** |
| 190 | *** |
| 191 | ** |
| 192 | *** |
| 193 | *** |
| 194 | *** |
| 195 | *** |
| 196 | *** |
| 197 | *** |
| 198 | ** |
| 199 | *** |
| 200 | ** |
| 201 | *** |
| 202 | *** |
| 203 | *** |
| 204 | *** |
| 205 | *** |
| 206 | ** |
| 207 | ** |
| 208 | *** |
| 209 | *** |
| 210 | *** |
| 211 | *** |
| 212 | *** |
| 213 | *** |
| 214 | *** |
| 215 | ** |
| 216 | ** |
| 217 | * |
| 218 | *** |
| 219 | *** |
| 220 | *** |
| 221 | *** |
| 222 | *** |
| 223 | ** |
| 224 | *** |
| 226 | *** |
| 227 | *** |
| 228 | *** |
| 229 | *** |
| 230 | *** |
| 232 | *** |
| 233 | *** |
| 234 | *** |
| 235 | ** |
| 236 | * |
| 237 | * |
| 238 | * |
| 239 | ** |
| 240 | ** |
| 241 | *** |
| 242 | *** |

TABLE 1-continued

Replicon IC$_{50}$ (M)

| Cpd | IC$_{50}$ |
|---|---|
| 243 | * |
| 244 | *** |
| 245 | *** |
| 246 | ** |
| 247 | ** |
| 248 | *** |
| 249 | ** |
| 250 | *** |
| 251 | *** |
| 252 | *** |
| 253 | ** |
| 254 | *** |
| 255 | *** |
| 256 | ** |
| 257 | *** |
| 258 | *** |
| 259 | * |
| 260 | *** |
| 261 | *** |
| 262 | *** |
| 263 | *** |
| 264 | *** |
| 265 | ** |
| 266 | *** |
| 267 | ** |
| 268 | ** |
| 269 | *** |
| 270 | *** |
| 271 | ** |
| 272 | *** |
| 273 | *** |
| 274 | *** |
| 275 | *** |
| 276 | *** |
| 277 | *** |
| 278 | *** |
| 279 | *** |
| 280 | *** |
| 281 | *** |
| 282 | *** |
| 283 | *** |
| 284 | *** |
| 285 | *** |
| 286 | *** |
| 287 | ** |
| 288 | ** |
| 289 | *** |
| 290 | *** |
| 291 | *** |
| 292 | *** |
| 293 | *** |
| 294 | *** |
| 295 | *** |
| 296 | *** |
| 297 | *** |
| 298 | *** |
| 299 | * |
| 300 | *** |
| 301 | *** |
| 302 | *** |
| 303 | *** |
| 304 | *** |
| 305 | *** |
| 306 | *** |
| 307 | *** |
| 308 | *** |
| 309 | *** |
| 310 | *** |
| 311 | *** |
| 312 | *** |
| 313 | *** |
| 314 | ** |
| 315 | *** |
| 316 | *** |
| 317 | *** |
| 318 | *** |

TABLE 1-continued

Replicon IC$_{50}$ (M)

| Cpd | IC$_{50}$ |
|---|---|
| 319 | *** |
| 320 | *** |
| 321 | *** |
| 322 | *** |
| 323 | *** |
| 324 | *** |
| 325 | *** |
| 326 | *** |
| 327 | *** |
| 328 | *** |
| 329 | *** |
| 330 | * |
| 331 | ** |
| 332 | ** |
| 333 | * |
| 334 | * |
| 335 | *** |
| 336 | ** |
| 337 | ** |
| 338 | *** |
| 339 | *** |
| 340 | *** |
| 341 | *** |
| 342 | *** |
| 343 | *** |
| 344 | *** |
| 345 | *** |
| 346 | *** |
| 347 | *** |
| 348 | *** |
| 349 | *** |
| 350 | *** |
| 351 | * |
| 352 | ** |
| 353 | * |
| 354 | *** |
| 355 | *** |
| 356 | *** |
| 357 | *** |
| 358 | *** |
| 359 | *** |
| 360 | *** |
| 361 | * |
| 362 | ** |
| 363 | *** |
| 364 | *** |
| 365 | *** |
| 366 | *** |
| 367 | * |
| 368 | *** |
| 369 | ** |
| 370 | *** |
| 371 | *** |
| 372 | *** |
| 373 | *** |
| 374 | *** |
| 375 | *** |
| 376 | *** |
| 377 | *** |
| 378 | *** |
| 379 | *** |
| 380 | *** |
| 381 | *** |
| 382 | ** |
| 383 | *** |
| 384 | *** |
| 385 | *** |
| 386 | ** |
| 387 | *** |
| 388 | ** |
| 389 | *** |
| 390 | ** |
| 391 | *** |
| 392 | *** |
| 393 | *** |
| 394 | *** |

TABLE 1-continued

Replicon IC$_{50}$ (M)

| Cpd | IC$_{50}$ |
|---|---|
| 395 | *** |
| 396 | *** |
| 397 | *** |
| 398 | *** |
| 399 | *** |
| 400 | *** |
| 401 | *** |
| 402 | *** |
| 403 | *** |
| 404 | *** |
| 405 | *** |
| 406 | *** |
| 407 | *** |
| 408 | *** |
| 409 | *** |
| 410 | ** |
| 411 | *** |
| 412 | *** |
| 413 | *** |
| 414 | *** |
| 415 | *** |
| 416 | *** |
| 417 | *** |
| 418 | *** |
| 419 | *** |
| 420 | *** |
| 421 | *** |
| 422 | *** |
| 423 | *** |
| 424 | *** |
| 425 | *** |
| 426 | *** |
| 427 | *** |
| 428 | *** |
| 429 | *** |
| 430 | *** |
| 431 | *** |
| 432 | *** |
| 433 | *** |
| 434 | * |
| 435 | ** |
| 436 | *** |
| 437 | *** |
| 438 | *** |
| 439 | *** |
| 440 | *** |
| 441 | *** |
| 442 | *** |
| 443 | *** |
| 444 | *** |
| 445 | *** |
| 446 | *** |
| 447 | *** |
| 448 | ** |
| 449 | ** |
| 450 | *** |
| 451 | *** |
| 452 | *** |
| 453 | *** |
| 454 | *** |
| 455 | *** |
| 456 | *** |
| 457 | *** |
| 458 | *** |
| 459 | *** |
| 460 | *** |
| 461 | *** |
| 462 | *** |
| 463 | *** |
| 464 | * |
| 465 | *** |
| 466 | *** |
| 467 | *** |
| 468 | *** |
| 469 | *** |
| 470 | *** |

TABLE 1-continued

| Replicon IC$_{50}$ (M) | |
|---|---|
| Cpd | IC$_{50}$ |
| 471 | *** |
| 472 | *** |
| 473 | *** |
| 474 | *** |
| 475 | *** |
| 476 | *** |
| 477 | *** |
| 478 | ** |
| 479 | ** |
| 480 | * |
| 481 | *** |
| 482 | *** |
| 483 | ** |
| 484 | ** |
| 485 | *** |
| 486 | *** |
| 487 | *** |
| 488 | *** |
| 489 | *** |
| 490 | ** |
| 491 | *** |
| 492 | *** |
| 493 | *** |
| 494 | *** |
| 495 | *** |
| 496 | *** |
| 497 | *** |
| 498 | *** |
| 499 | *** |
| 500 | *** |
| 501 | *** |
| 502 | *** |
| 503 | *** |
| 504 | *** |
| 505 | *** |
| 506 | *** |
| 507 | *** |
| 508 | *** |
| 509 | *** |
| 510 | *** |
| 511 | *** |
| 512 | *** |
| 513 | *** |
| 514 | ** |
| 515 | *** |
| 516 | *** |
| 517 | ** |
| 518 | *** |
| 519 | *** |
| 520 | * |
| 521 | *** |
| 522 | *** |
| 523 | *** |
| 524 | ** |
| 525 | ** |
| 526 | *** |
| 527 | ** |

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed is:

1. A compound of Formula (Ia):

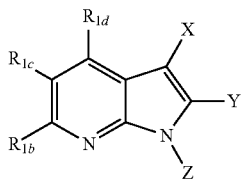

(Ia)

or a salt, hydrate, solvate, racemate, enantiomer, diastereomer, or stereoisomer thereof, wherein X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl-;

Y is phenyl, pyridinyl or pyrimidinyl each substituted with —SO$_2$N(R$_4$)—R$_5$, wherein phenyl, pyridinyl and pyrimidinyl are each optionally substituted with one or two additional substituents independently selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

$R_{1b}$, $R_{1c}$, and $R_{1d}$ are each selected from hydrogen, halogen, hydroxy, cyano, nitro, $C_{1-8}$alkyl, methyl, ethyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, (aryl-$C_{1-8}$alkyl)($C_{1-8}$alkyl)amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkyl-sulfonyl-amino, $C_{1-8}$alkylthio, $C_{1-8}$alkyl-sulfonyl, $C_{1-8}$alkyl-sulfinyl, $C_{3-14}$cycloalkyl, cyclopropyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

R$_4$ is hydrogen or C$_{1-8}$alkyl, optionally substituted on C$_{1-8}$alkyl with one or more substituents each selected from halogen, hydroxy, cyano or C$_{1-8}$alkoxy; and R$_5$ is hydrogen, C$_{1-8}$alkyl, hydroxy-C$_{1-8}$alkyl, halo-C$_{1-8}$alkyl, cyano-C$_{1-8}$alkyl, C$_{1-8}$alkoxy-C$_{1-8}$alkyl, amino-C$_{1-8}$alkyl, C$_{1-8}$alkyl-amino-C$_{1-8}$alkyl, C$_{1-8}$alkyl-carbonyl, C$_{1-8}$alkoxy-carbonyl, C$_{3-14}$cycloalkyl, C$_{3-14}$cycloalkyl-C$_{1-8}$alkyl, aryl, aryl-C$_{1-8}$alkyl, heteroaryl, heteroaryl-C$_{1-8}$alkyl, heterocyclyl or heterocyclyl-C$_{1-8}$alkyl, wherein each instance of aryl, heteroaryl, heterocyclyl and C$_{3-14}$cycloalkyl is optionally substituted with one or two substituents each selected from halogen, C$_{1-8}$alkyl, halo-C$_{1-8}$alkyl, C$_{1-8}$alkoxy, halo-C$_{1-8}$alkoxy, amino or C$_{1-8}$alkyl-amino.

2. The compound of claim 1, wherein

X is hydrogen, cyano, amino-carbonyl or C$_{1-8}$alkyl-amino-carbonyl;

Z is C$_{1-8}$alkyl, C$_{3-14}$cycloalkyl, C$_{3-14}$cycloalkenyl, C$_{3-14}$cycloalkyl-C$_{1-8}$alkyl, aryl, aryl-C$_{1-8}$alkyl, heteroaryl, heteroaryl-C$_{1-8}$alkyl, heterocyclyl or heterocyclyl-C$_{1-8}$alkyl, wherein each instance of aryl and heteroaryl is optionally substituted with a substituent selected from cyano, halogen, C$_{1-8}$alkyl, C$_{1-8}$alkoxy, amino or C$_{1-8}$alkyl-amino R$_{1b}$, R$_{1c}$, and R$_{1d}$ are each selected from hydrogen, halogen, hydroxy, cyano, C$_{1-8}$alkyl, hydroxy-C$_{1-8}$alkyl, halo-C$_{1-8}$alkyl, halo-C$_{2-8}$alkenyl, C$_{1-8}$alkoxy, halo-C$_{1-8}$alkoxy, C$_{1-8}$alkyl-carbonyl, C$_{1-8}$alkoxy-carbonyl, C$_{1-8}$alkyl-carbonyloxy, amino, amino-C$_{1-8}$alkyl, C$_{1-8}$alkyl-amino-C$_{1-8}$alkyl, C$_{1-8}$alkylthio, C$_{1-8}$alkyl-sulfinyl, C$_{1-8}$alkyl-sulfonyl, C$_{3-14}$cycloalkyl, C$_{3-14}$cycloalkyl-C$_{1-8}$alkyl, C$_{3-14}$cycloalkyl-C$_{1-8}$alkoxy, C$_{3-14}$cycloalkyloxy, aryl, aryl-C$_{1-8}$alkyl, aryl-C$_{1-8}$alkoxy, aryloxy, heteroaryl, heteroaryl-C$_{1-8}$alkyl, heteroaryl-C$_{1-8}$alkoxy, heteroaryloxy, heterocyclyl, heterocyclyl-C$_{1-8}$alkyl, heterocyclyl-C$_{1-8}$alkoxy or heterocyclyloxy;

R$_4$ is hydrogen or C$_{1-8}$alkyl; and

R$_5$ is hydrogen, C$_{1-8}$alkyl, hydroxy-C$_{1-8}$alkyl, halo-C$_{1-8}$alkyl, cyano-C$_{1-8}$alkyl, C$_{3-14}$cycloalkyl or C$_{3-14}$cycloalkyl-C$_{1-8}$alkyl, wherein each instance of C$_{3-14}$cycloalkyl is optionally substituted with one or two substituents each selected from halogen, C$_{1-8}$alkyl or halo-C$_{1-8}$alkyl.

3. The compound of claim 1, wherein

X is cyano;

Z is C$_{1-8}$alkyl, C$_{3-14}$cycloalkyl, C$_{3-14}$cycloalkyl-C$_{1-8}$alkyl, aryl, aryl-C$_{1-8}$alkyl, heteroaryl, heteroaryl-C$_{1-8}$alkyl, heterocyclyl or heterocyclyl-C$_{1-8}$alkyl, wherein each instance of aryl and heteroaryl is optionally substituted with a substituent selected from cyano, halogen, C$_{1-8}$alkyl, C$_{1-8}$alkoxy, amino or C$_{1-8}$alkyl-amino;

R$_{1b}$, R$_{1c}$, and R$_{1d}$ are each selected from hydrogen, halogen, cyano, C$_{1-8}$alkyl, halo-C$_{1-8}$alkyl, C$_{1-8}$alkoxy, halo-C$_{1-8}$alkoxy, C$_{1-8}$alkylthio, C$_{1-8}$alkyl-sulfinyl, C$_{1-8}$alkyl-sulfonyl, C$_{3-14}$cycloalkyl, C$_{3-14}$cycloalkyl-C$_{1-8}$alkyl, C$_{3-14}$cycloalkyl-C$_{1-8}$alkoxy, C$_{3-14}$cycloalkyloxy, aryl, aryl-C$_{1-8}$alkyl, aryl-C$_{1-8}$alkoxy, aryloxy, heteroaryl, heteroaryl-C$_{1-8}$alkyl, heteroaryl-C$_{1-8}$alkoxy, heteroaryloxy, heterocyclyl, heterocyclyl-C$_{1-8}$alkyl or heterocyclyl-C$_{1-8}$alkoxy;

R$_4$ is hydrogen; and

R$_5$ is C$_{1-8}$alkyl, halo-C$_{1-8}$alkyl, C$_{3-14}$cycloalkyl or C$_{3-14}$cycloalkyl-C$_{1-8}$alkyl, wherein each instance of C$_{3-14}$cycloalkyl is optionally substituted with one or two substituents each selected from C$_{1-8}$alkyl or halo-C$_{1-8}$alkyl.

4. The compound of claim 1, wherein

Z is cyclobutyl, cyclopentyl or cyclopropyl-C$_{1-8}$alkyl;

R$_{1b}$, R$_{1c}$, and R$_{1d}$ are each selected from hydrogen, chloro, fluoro, cyano, methyl, ethyl, methoxy, ethoxy, propoxy, isopropoxy, difluoromethoxy or cyclopropyl; and R$_5$ is isopropyl, tert-butyl, difluoroisopropyl, trifluoroisopropyl, trifluoro-tert-butyl, cyclopropyl, cyclobutyl or 1-cyclopropyl-ethyl, wherein each instance of cyclopropyl is optionally substituted with one or two substituents each selected from methyl or trifluoromethyl.

5. The compound of claim 1, wherein R$_{1b}$, R$_{1b}$, and R$_{1d}$ are each independently selected from hydrogen, halogen, hydroxy, cyano, C$_{1-8}$alkyl, hydroxy-C$_{1-8}$alkyl, halo-C$_{1-8}$alkyl, halo-C$_{2-8}$alkenyl, C$_{1-8}$alkoxy, halo-C$_{1-8}$alkoxy, C$_{1-8}$alkyl-carbonyl, C$_{1-8}$alkoxy-carbonyl, C$_{1-8}$alkyl-carbonyloxy, amino, amino-C$_{1-8}$alkyl, C$_{1-8}$alkyl-amino-C$_{1-8}$alkyl, C$_{1-8}$alkylthio, C$_{1-8}$alkyl-sulfinyl, C$_{1-8}$alkyl-sulfonyl, C$_{3-14}$cycloalkyl, C$_{3-14}$cycloalkyl-C$_{1-8}$alkyl, C$_{3-14}$cycloalkyl-C$_{1-8}$alkoxy, C$_{3-14}$cycloalkyloxy, aryl, aryl-C$_{1-8}$alkyl, aryl-C$_{1-8}$alkoxy, aryloxy, heteroaryl, heteroaryl-C$_{1-8}$alkyl, heteroaryl-C$_{1-8}$alkoxy, heteroaryloxy, heterocyclyl, heterocyclyl-C$_{1-8}$alkyl, heterocyclyl-C$_{1-8}$alkoxy or heterocyclyloxy.

6. The compound of claim 5, wherein R$_{1b}$, R$_{1c}$, and R$_{1d}$ are each independently selected from hydrogen, halogen, cyano, C$_{1-8}$alkyl, halo-C$_{1-8}$alkyl, C$_{1-8}$alkoxy, halo-C$_{1-8}$alkoxy, C$_{1-8}$alkylthio, C$_{1-8}$alkyl-sulfinyl, C$_{1-8}$alkyl-sulfonyl, C$_{3-14}$cycloalkyl, C$_{3-14}$cycloalkyl-C$_{1-8}$alkyl, C$_{3-14}$cycloalkyl-C$_{1-8}$alkoxy, C$_{3-14}$cycloalkyloxy, aryl, aryl-C$_{1-8}$alkyl, aryl-C$_{1-8}$alkoxy, aryloxy, heteroaryl, heteroaryl-C$_{1-8}$alkyl, heteroaryl-C$_{1-8}$alkoxy, heteroaryloxy, heterocyclyl, heterocyclyl-C$_{1-8}$alkyl or heterocyclyl-C$_{1-8}$alkoxy.

7. The compound of claim 6, wherein R$_{1b}$, R$_{1c}$, and R$_{1d}$ are each independently selected from hydrogen, halogen, cyano, C$_{1-8}$alkyl, C$_{1-8}$alkoxy, halo-C$_{1-8}$alkoxy or C$_{3-14}$cycloalkyl.

8. The compound of claim 1, wherein the compound or a salt, hydrate, solvate, racemate, enantiomer, diastereomer, or stereoisomer thereof is selected from:

4-[5-chloro-3-cyano-1-(cyclopropylmethyl)-1H-pyrrolo[2,3-b]pyridin-2-yl]-N-(propan-2-yl)benzenesulfonamide, 4-[3-cyano-1-(cyclopropylmethyl)-5-methoxy-1H-pyrrolo[2,3-b]pyridin-2-yl]-N-(propan-2-yl)benzenesulfonamide, 4-[3-cyano-1-(cyclopropylmethyl)-5-fluoro-1H-pyrrolo[2,3-b]pyridin-2-yl]-N-(propan-2-yl)benzenesulfonamide, 4-[3-cyano-1-(cyclopropylmethyl)-6-methyl-1H-pyrrolo[2,3-b]pyridin-2-yl]-N-(propan-2-yl)benzenesulfonamide, 4-(5-chloro-3-cyano-1-cyclobutyl-1H-pyrrolo[2,3-b]pyridin-2-yl)-N-(propan-2-yl)benzenesulfonamide, 4-(3-cyano-1-cyclobutyl-1H-pyrrolo[2,3-b]pyridin-2-yl)-N-(propan-2-yl)benzenesulfonamide, 4-(5-chloro-3-cyano-1-cyclobutyl-1H-pyrrolo[2,3-b]pyridin-2-yl)-N-(1,3-difluoropropan-2-yl)benzenesulfonamide, 6-(3-cyano-1-cyclobutyl-5-methoxy-1H-pyrrolo[2,3-b]pyridin-2-yl)-N-(1,3-difluoropropan-2-yl)pyridine-3-sulfonamide, 6-(5-chloro-3-cyano-1-cyclopentyl-1H-pyrrolo[2,3-b]
pyridin-2-yl)-N-(1,3-difluoropropan-2-yl)pyridine-3-
sulfonamide,
2-(3-cyano-1-cyclobutyl-5-methoxy-1H-pyrrolo[2,3-b]
pyridin-2-yl)-N-(1,3-difluoropropan-2-yl)pyrimidine-
5-sulfonamide,
6-(3-cyano-1-cyclobutyl-5-fluoro-1H-pyrrolo[2,3-b]pyri-
din-2-yl)-N-(1,3-difluoropropan-2-yl)pyridine-3-sulfo-
namide,
2-(5-chloro-3-cyano-1-cyclobutyl-1H-pyrrolo[2,3-b]
pyridin-2-yl)-N-(1,3-difluoropropan-2-yl)pyrimidine-
5-sulfonamide,
6-(5-chloro-3-cyano-1-cyclobutyl-1H-pyrrolo[2,3-b]
pyridin-2-yl)-N-(1,3-difluoropropan-2-yl)pyridine-3-
sulfonamide,
2-(3-cyano-1-cyclobutyl-5-fluoro-1H-pyrrolo[2,3-b]pyri-
din-2-yl)-N-(1,3-difluoropropan-2-yl)pyrimidine-5-
sulfonamide,
2-(5-chloro-3-cyano-1-cyclopentyl-1H-pyrrolo[2,3-b]
pyridin-2-yl)-N-(1,3-difluoropropan-2-yl)pyrimidine-
5-sulfonamide,
6-(3-cyano-1-cyclobutyl-1H-pyrrolo[2,3-b]pyridin-2-yl)-
N-[(2S)-1,1,1-trifluoropropan-2-yl]pyridine-3-sulfona-
mide,
2-(3-cyano-1-cyclobutyl-5-fluoro-1H-pyrrolo[2,3-b]pyri-
din-2-yl)-N-[(2S)-1,1,1-trifluoropropan-2-yl]pyrimi-
dine-5-sulfonamide,
6-(3-cyano-1-cyclobutyl-5-methoxy-1H-pyrrolo[2,3-b]
pyridin-2-yl)-N-[(2S)-1,1,1-trifluoropropan-2-yl]pyri-
dine-3-sulfonamide,
2-(3-cyano-1-cyclobutyl-5-methoxy-1H-pyrrolo[2,3-b]
pyridin-2-yl)-N-[(2S)-1,1,1-trifluoropropan-2-yl]py-
rimidine-5-sulfonamide,
6-(5-chloro-3-cyano-1-cyclopentyl-1H-pyrrolo[2,3-b]
pyridin-2-yl)-N-[(2S)-1,1,1-trifluoropropan-2-yl]pyri-
dine-3-sulfonamide,
2-(5-chloro-3-cyano-1-cyclopentyl-1H-pyrrolo[2,3-b]
pyridin-2-yl)-N-[(2S)-1,1,1-trifluoropropan-2-yl]py-
rimidine-5-sulfonamide,
4-(3-cyano-1-cyclobutyl-1H-pyrrolo[2,3-b]pyridin-2-yl)-
N-(1,3-difluoropropan-2-yl)benzenesulfonamide,
6-(3-cyano-1-cyclobutyl-1H-pyrrolo[2,3-b]pyridin-2-yl)-
N-[(2R)-1,1,1-trifluoropropan-2-yl]pyridine-3-sulfo-
namide,
2-(3-cyano-1-cyclobutyl-1H-pyrrolo[2,3-b]pyridin-2-yl)-
N-(propan-2-yl)pyrimidine-5-sulfonamide,
2-(3-cyano-1-cyclobutyl-5-fluoro-1H-pyrrolo[2,3-b]pyri-
din-2-yl)-N-(propan-2-yl)pyrimidine-5-sulfonamide,
6-(3-cyano-1-cyclobutyl-6-methoxy-1H-pyrrolo[2,3-b]
pyridin-2-yl)-N-[(2S)-1,1,1-trifluoropropan-2-yl]pyri-
dine-3-sulfonamide,
6-(3-cyano-1-cyclobutyl-6-methoxy-1H-pyrrolo[2,3-b]
pyridin-2-yl)-N-(1,3-difluoropropan-2-yl)pyridine-3-
sulfonamide,
2-(3-cyano-1-cyclobutyl-6-methoxy-1H-pyrrolo[2,3-b]
pyridin-2-yl)-N-(1,3-difluoropropan-2-yl)pyrimidine-
5-sulfonamide,
4-(3-cyano-1-cyclobutyl-6-methoxy-1H-pyrrolo[2,3-b]
pyridin-2-yl)-N-(1,3-difluoropropan-2-yl)benzenesul-
fonamide,
N-tert-butyl-4-(3-cyano-1-cyclobutyl-6-methoxy-1H-
pyrrolo[2,3-b]pyridin-2-yl)benzenesulfonamide,
6-(3-cyano-1-cyclobutyl-5-fluoro-1H-pyrrolo[2,3-b]pyri-
din-2-yl)-N-[(2R)-1,1,1-trifluoropropan-2-yl]pyridine-
3-sulfonamide,
6-(3-cyano-1-cyclobutyl-5-methoxy-1H-pyrrolo[2,3-b]
pyridin-2-yl)-N-[(2R)-1,1,1-trifluoropropan-2-yl]pyri-
dine-3-sulfonamide,
2-(3-cyano-1-cyclobutyl-5-methoxy-1H-pyrrolo[2,3-b]
pyridin-2-yl)-N-(propan-2-yl)pyrimidine-5-sulfona-
mide,
6-(5-chloro-3-cyano-1-cyclobutyl-1H-pyrrolo[2,3-b]
pyridin-2-yl)-N-[(2R)-1,1,1-trifluoropropan-2-yl]pyri-
dine-3-sulfonamide,
6-(5-chloro-3-cyano-1-cyclobutyl-1H-pyrrolo[2,3-b]
pyridin-2-yl)-N-[(2S)-1,1,1-trifluoropropan-2-yl]pyri-
dine-3-sulfonamide,
N-tert-butyl-6-(5-chloro-3-cyano-1-cyclobutyl-1H-pyr-
rolo[2,3-b]pyridin-2-yl)pyridine-3-sulfonamide,
6-[3-cyano-1-cyclobutyl-6-(difluoromethoxy)-1H-pyr-
rolo[2,3-b]pyridin-2-yl]-N-[(2S)-1,1,1-trifluoropro-
pan-2-yl]pyridine-3-sulfonamide,
2-[3-cyano-1-cyclobutyl-6-(difluoromethoxy)-1H-pyr-
rolo[2,3-b]pyridin-2-yl]-N-(1,3-difluoropropan-2-yl)
pyrimidine-5-sulfonamide,
6-(5-chloro-3-cyano-1-cyclobutyl-1H-pyrrolo[2,3-b]
pyridin-2-yl)-N-(1,1,1-trifluoro-2-methylpropan-2-yl)
pyridine-3-sulfonamide,
6-(5-chloro-3-cyano-1-cyclobutyl-1H-pyrrolo[2,3-b]
pyridin-2-yl)-N-[1-(trifluoromethyl)cyclopropyl]pyri-
dine-3-sulfonamide,
2-(5-chloro-3-cyano-1-cyclobutyl-1H-pyrrolo[2,3-b]
pyridin-2-yl)-N-(propan-2-yl)pyrimidine-5-sulfona-
mide,
6-[5-chloro-3-cyano-1-(cyclopropylmethyl)-1H-pyrrolo
[2,3-b]pyridin-2-yl]-N-[(2R)-1,1,1-trifluoropropan-2-
yl]pyridine-3-sulfonamide,
6-[3-cyano-1-(cyclopropylmethyl)-5-fluoro-1H-pyrrolo
[2,3-b]pyridin-2-yl]-N-[(2R)-1,1,1-trifluoropropan-2-
yl]pyridine-3-sulfonamide,
4-(5-chloro-3-cyano-1-cyclobutyl-1H-pyrrolo[2,3-b]
pyridin-2-yl)-N-[(2S)-1,1,1-trifluoropropan-2-yl]ben-
zenesulfonamide,
6-[5-chloro-3-cyano-1-(cyclopropylmethyl)-1H-pyrrolo
[2,3-b]pyridin-2-yl]-N-[(2S)-1,1,1-trifluoropropan-2-
yl]pyridine-3-sulfonamide,
6-[3-cyano-1-(cyclopropylmethyl)-5-fluoro-1H-pyrrolo
[2,3-b]pyridin-2-yl]-N-[(2S)-1,1,1-trifluoropropan-2-
yl]pyridine-3-sulfonamide,
4-(3-cyano-1-cyclobutyl-5-methoxy-1H-pyrrolo[2,3-b]
pyridin-2-yl)-N-(1,3-difluoropropan-2-yl)benzenesul-
fonamide,
6-[3-cyano-1-(cyclopropylmethyl)-5-methoxy-1H-pyr-
rolo[2,3-b]pyridin-2-yl]-N-[(2S)-1,1,1-trifluoropro-
pan-2-yl]pyridine-3-sulfonamide,
6-(3-cyano-1-cyclobutyl-5-methyl-1H-pyrrolo[2,3-b]
pyridin-2-yl)-N-[(2R)-1,1,1-trifluoropropan-2-yl]pyri-
dine-3-sulfonamide,
6-(3-cyano-1-cyclobutyl-5-methyl-1H-pyrrolo[2,3-b]
pyridin-2-yl)-N-[(2S)-1,1,1-trifluoropropan-2-yl]pyri-
dine-3-sulfonamide,
2-(3-cyano-1-cyclobutyl-5-methyl-1H-pyrrolo[2,3-b]
pyridin-2-yl)-N-[(2R)-1,1,1-trifluoropropan-2-yl]py-
rimidine-5-sulfonamide,
2-(3-cyano-1-cyclobutyl-5-methyl-1H-pyrrolo[2,3-b]
pyridin-2-yl)-N-[(2S)-1,1,1-trifluoropropan-2-yl]py-
rimidine-5-sulfonamide,
4-(3-cyano-1-cyclobutyl-5-methyl-1H-pyrrolo[2,3-b]
pyridin-2-yl)-N-[(2R)-1,1,1-trifluoropropan-2-yl]ben-
zenesulfonamide, 4-(3-cyano-1-cyclobutyl-5-methyl-1H-pyrrolo[2,3-b]pyridin-2-yl)-N-[(2S)-1,1,1-trifluoropropan-2-yl]benzenesulfonamide,
6-(3-cyano-1-cyclobutyl-5-methyl-1H-pyrrolo[2,3-b]pyridin-2-yl)-N-[1-(trifluoromethyl)cyclopropyl]pyridine-3-sulfonamide,
4-(3-cyano-1-cyclobutyl-5-methyl-1H-pyrrolo[2,3-b]pyridin-2-yl)-N-[1-(trifluoromethyl)cyclopropyl]benzenesulfonamide,
6-(3-cyano-1-cyclobutyl-5-methyl-1H-pyrrolo[2,3-b]pyridin-2-yl)-N-(1-methylcyclopropyl)pyridine-3-sulfonamide,
4-(3-cyano-1-cyclobutyl-5-methyl-1H-pyrrolo[2,3-b]pyridin-2-yl)-N-(1-methylcyclopropyl)benzenesulfonamide,
2-(3-cyano-1-cyclobutyl-5-methyl-1H-pyrrolo[2,3-b]pyridin-2-yl)-N-(propan-2-yl)pyrimidine-5-sulfonamide,
4-(3-cyano-1-cyclobutyl-5-methyl-1H-pyrrolo[2,3-b]pyridin-2-yl)-N-(1,1,1-trifluoro-2-methylpropan-2-yl)benzenesulfonamide,
4-(3-cyano-1-cyclobutyl-6-methyl-1H-pyrrolo[2,3-b]pyridin-2-yl)-N-[(2S)-1,1,1-trifluoropropan-2-yl]benzenesulfonamide,
4-(3-cyano-1-cyclobutyl-6-methyl-1H-pyrrolo[2,3-b]pyridin-2-yl)-N-[(2R)-1,1,1-trifluoropropan-2-yl]benzenesulfonamide,
6-(3-cyano-1-cyclobutyl-6-methyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-6-methyl-1H-pyrrolo[2,3-b]pyridin-2-yl)-N-[(2R)-1,1,1-trifluoropropan-2-yl]pyridine-3-sulfonamide,
6-(3-cyano-1-cyclobutyl-6-methyl-1H-pyrrolo[2,3-b]pyridin-2-yl)-N-[1-(trifluoromethyl)cyclopropyl]pyridine-3-sulfonamide,
2-(3-cyano-1-cyclobutyl-6-methyl-1H-pyrrolo[2,3-b]pyridin-2-yl)-N-(propan-2-yl)pyrimidine-5-sulfonamide,
5-(3-cyano-1-cyclobutyl-6-methyl-1H-pyrrolo[2,3-b]pyridin-2-yl)-N-(propan-2-yl)pyridine-2-sulfonamide,
6-(3,5-dicyano-1-cyclobutyl-1H-pyrrolo[2,3-b]pyridin-2-yl)-N-[(2R)-1,1,1-trifluoropropan-2-yl]pyridine-3-sulfonamide,
6-(3,5-dicyano-1-cyclobutyl-1H-pyrrolo[2,3-b]pyridin-2-yl)-N-[(2S)-1,1,1-trifluoropropan-2-yl]pyridine-3-sulfonamide,
2-(3,5-dicyano-1-cyclobutyl-1H-pyrrolo[2,3-b]pyridin-2-yl)-N-[(2S)-1,1,1-trifluoropropan-2-yl]pyrimidine-5-sulfonamide,
4-(3,5-dicyano-1-cyclobutyl-1H-pyrrolo[2,3-b]pyridin-2-yl)-N-[(2S)-1,1,1-trifluoropropan-2-yl]benzenesulfonamide,
6-(3,5-dicyano-1-cyclobutyl-1H-pyrrolo[2,3-b]pyridin-2-yl)-N-[1-(trifluoromethyl)cyclopropyl]pyridine-3-sulfonamide,
4-(3,5-dicyano-1-cyclobutyl-1H-pyrrolo[2,3-b]pyridin-2-yl)-N-[1-(trifluoromethyl)cyclopropyl]benzenesulfonamide,
6-(3,5-dicyano-1-cyclobutyl-1H-pyrrolo[2,3-b]pyridin-2-yl)-N-(1-methylcyclopropyl)pyridine-3-sulfonamide,
2-(3,5-dicyano-1-cyclobutyl-1H-pyrrolo[2,3-b]pyridin-2-yl)-N-(1-methylcyclopropyl)pyrimidine-5-sulfonamide,
4-(3-cyano-1-cyclobutyl-5-cyclopropyl-1H-pyrrolo[2,3-b]pyridin-2-yl)-N-[(2S)-1,1,1-trifluoropropan-2-yl]benzenesulfonamide,
4-(3-cyano-1-cyclobutyl-5-cyclopropyl-1H-pyrrolo[2,3-b]pyridin-2-yl)-N-[(2R)-1,1,1-trifluoropropan-2-yl]benzenesulfonamide,
6-(3-cyano-1-cyclobutyl-5-cyclopropyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-cyclopropyl-1H-pyrrolo[2,3-b]pyridin-2-yl)-N-[(2R)-1,1,1-trifluoropropan-2-yl]pyridine-3-sulfonamide,
2-(3-cyano-1-cyclobutyl-5-cyclopropyl-1H-pyrrolo[2,3-b]pyridin-2-yl)-N-[(2S)-1,1,1-trifluoropropan-2-yl]pyrimidine-5-sulfonamide,
2-(3-cyano-1-cyclobutyl-5-cyclopropyl-1H-pyrrolo[2,3-b]pyridin-2-yl)-N-[(2R)-1,1,1-trifluoropropan-2-yl]pyrimidine-5-sulfonamide,
4-(3-cyano-1-cyclobutyl-5-cyclopropyl-1H-pyrrolo[2,3-b]pyridin-2-yl)-N-(1,1,1-trifluoro-2-methylpropan-2-yl)benzenesulfonamide,
6-[3-cyano-1-cyclobutyl-5-(difluoromethoxy)-1H-pyrrolo[2,3-b]pyridin-2-yl]-N-[(2S)-1,1,1-trifluoropropan-2-yl]pyridine-3-sulfonamide,
4-(3-cyano-1-cyclobutyl-5-cyclopropyl-1H-pyrrolo[2,3-b]pyridin-2-yl)-N-[1-(trifluoromethyl)cyclopropyl]benzenesulfonamide,
6-(3-cyano-1-cyclobutyl-5-cyclopropyl-1H-pyrrolo[2,3-b]pyridin-2-yl)-N-[1-(trifluoromethyl)cyclopropyl]pyridine-3-sulfonamide,
N-tert-butyl-4-(3-cyano-1-cyclobutyl-5-cyclopropyl-1H-pyrrolo[2,3-b]pyridin-2-yl)benzenesulfonamide,
N-tert-butyl-6-(3-cyano-1-cyclobutyl-5-cyclopropyl-1H-pyrrolo[2,3-b]pyridin-2-yl)pyridine-3-sulfonamide,
4-(3-cyano-1-cyclobutyl-5-cyclopropyl-1H-pyrrolo[2,3-b]pyridin-2-yl)-N-(1-methylcyclopropyl)benzenesulfonamide,
6-(3-cyano-1-cyclobutyl-5-cyclopropyl-1H-pyrrolo[2,3-b]pyridin-2-yl)-N-(1-methylcyclopropyl)pyridine-3-sulfonamide,
2-(3-cyano-1-cyclobutyl-5-cyclopropyl-1H-pyrrolo[2,3-b]pyridin-2-yl)-N-(1-methylcyclopropyl)pyrimidine-5-sulfonamide,
4-(3-cyano-1-cyclobutyl-5-cyclopropyl-1H-pyrrolo[2,3-b]pyridin-2-yl)-N-(1,3-difluoropropan-2-yl)benzenesulfonamide,
6-(3-cyano-1-cyclobutyl-5-cyclopropyl-1H-pyrrolo[2,3-b]pyridin-2-yl)-N-(1,3-difluoropropan-2-yl)pyridine-3-sulfonamide,
2-(3-cyano-1-cyclobutyl-5-cyclopropyl-1H-pyrrolo[2,3-b]pyridin-2-yl)-N-(1,3-difluoropropan-2-yl)pyrimidine-5-sulfonamide,
6-(3-cyano-1-cyclobutyl-5-cyclopropyl-1H-pyrrolo[2,3-b]pyridin-2-yl)-N-cyclopropylpyridine-3-sulfonamide,
6-(3-cyano-1-cyclobutyl-5-cyclopropyl-1H-pyrrolo[2,3-b]pyridin-2-yl)-N-cyclobutylpyridine-3-sulfonamide,
5-(3-cyano-1-cyclobutyl-5-cyclopropyl-1H-pyrrolo[2,3-b]pyridin-2-yl)-N-(propan-2-yl)pyridine-2-sulfonamide,
2-(3-cyano-1-cyclobutyl-5-cyclopropyl-1H-pyrrolo[2,3-b]pyridin-2-yl)-N-(propan-2-yl)pyrimidine-5-sulfonamide,
2-(3-cyano-1-cyclobutyl-6-methyl-1H-pyrrolo[2,3-b]pyridin-2-yl)-N-[(2S)-1,1,1-trifluoropropan-2-yl]pyrimidine-5-sulfonamide,
2-(3-cyano-1-cyclobutyl-6-methyl-1H-pyrrolo[2,3-b]pyridin-2-yl)-N-[(2R)-1,1,1-trifluoropropan-2-yl]pyrimidine-5-sulfonamide, 4-(3-cyano-1-cyclobutyl-6-methyl-1H-pyrrolo[2,3-b]pyridin-2-yl)-N-(1,1,1-trifluoro-2-methylpropan-2-yl)benzenesulfonamide,
4-(3-cyano-1-cyclobutyl-6-methyl-1H-pyrrolo[2,3-b]pyridin-2-yl)-N-[1-(trifluoromethyl)cyclopropyl]benzenesulfonamide,
N-tert-butyl-4-(3-cyano-1-cyclobutyl-6-methyl-1H-pyrrolo[2,3-b]pyridin-2-yl)benzenesulfonamide,
N-tert-butyl-6-(3-cyano-1-cyclobutyl-6-methyl-1H-pyrrolo[2,3-b]pyridin-2-yl)pyridine-3-sulfonamide,
4-(3-cyano-1-cyclobutyl-6-methyl-1H-pyrrolo[2,3-b]pyridin-2-yl)-N-(1-methylcyclopropyl)benzenesulfonamide,
2-(3-cyano-1-cyclobutyl-6-methyl-1H-pyrrolo[2,3-b]pyridin-2-yl)-N-(1-methylcyclopropyl)pyrimidine-5-sulfonamide,
4-(3-cyano-1-cyclobutyl-6-methyl-1H-pyrrolo[2,3-b]pyridin-2-yl)-N-(1,3-difluoropropan-2-yl)benzenesulfonamide,
6-(3-cyano-1-cyclobutyl-6-methyl-1H-pyrrolo[2,3-b]pyridin-2-yl)-N-(1,3-difluoropropan-2-yl)pyridine-3-sulfonamide,
2-(3-cyano-1-cyclobutyl-6-methyl-1H-pyrrolo[2,3-b]pyridin-2-yl)-N-(1,3-difluoropropan-2-yl)pyrimidine-5-sulfonamide,
6-(3-cyano-1-cyclobutyl-6-methyl-1H-pyrrolo[2,3-b]pyridin-2-yl)-N-cyclobutylpyridine-3-sulfonamide,
4-(3-cyano-1-cyclobutyl-6-cyclopropyl-1H-pyrrolo[2,3-b]pyridin-2-yl)-N-[(2S)-1,1,1-trifluoropropan-2-yl]benzenesulfonamide,
4-(3-cyano-1-cyclobutyl-6-cyclopropyl-1H-pyrrolo[2,3-b]pyridin-2-yl)-N-[(2R)-1,1,1-trifluoropropan-2-yl]benzenesulfonamide,
6-(3-cyano-1-cyclobutyl-6-cyclopropyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-6-cyclopropyl-1H-pyrrolo[2,3-b]pyridin-2-yl)-N-[(2R)-1,1,1-trifluoropropan-2-yl]pyridine-3-sulfonamide,
2-(3-cyano-1-cyclobutyl-6-cyclopropyl-1H-pyrrolo[2,3-b]pyridin-2-yl)-N-[(2S)-1,1,1-trifluoropropan-2-yl]pyrimidine-5-sulfonamide,
2-(3-cyano-1-cyclobutyl-6-cyclopropyl-1H-pyrrolo[2,3-b]pyridin-2-yl)-N-[(2R)-1,1,1-trifluoropropan-2-yl]pyrimidine-5-sulfonamide,
4-(3-cyano-1-cyclobutyl-5-ethyl-1H-pyrrolo[2,3-b]pyridin-2-yl)-N-[(2S)-1,1,1-trifluoropropan-2-yl]benzenesulfonamide,
4-(3-cyano-1-cyclobutyl-5-ethyl-1H-pyrrolo[2,3-b]pyridin-2-yl)-N-[(2R)-1,1,1-trifluoropropan-2-yl]benzenesulfonamide,
6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide,
2-(3-cyano-1-cyclobutyl-5-ethyl-1H-pyrrolo[2,3-b]pyridin-2-yl)-N-[(2S)-1,1,1-trifluoropropan-2-yl]pyrimidine-5-sulfonamide,
2-(3-cyano-1-cyclobutyl-5-ethyl-1H-pyrrolo[2,3-b]pyridin-2-yl)-N-[(2R)-1,1,1-trifluoropropan-2-yl]pyrimidine-5-sulfonamide,
6-(6-chloro-3-cyano-1-cyclobutyl-1H-pyrrolo[2,3-b]pyridin-2-yl)-N-[(2S)-1,1,1-trifluoropropan-2-yl]pyridine-3-sulfonamide,
6-(6-chloro-3-cyano-1-cyclobutyl-1H-pyrrolo[2,3-b]pyridin-2-yl)-N-[(2R)-1,1,1-trifluoropropan-2-yl]pyridine-3-sulfonamide,
6-(3-cyano-1-cyclobutyl-5-fluoro-1H-pyrrolo[2,3-b]pyridin-2-yl)-N-[(2S)-1,1,1-trifluoropropan-2-yl]pyridine-3-sulfonamide,
4-(3-cyano-1-cyclobutyl-5-ethyl-1H-pyrrolo[2,3-b]pyridin-2-yl)-N-(1,1,1-trifluoro-2-methylpropan-2-yl)benzenesulfonamide,
4-(3-cyano-1-cyclobutyl-5-ethyl-1H-pyrrolo[2,3-b]pyridin-2-yl)-N-[1-(trifluoromethyl)cyclopropyl]benzenesulfonamide,
6-(3-cyano-1-cyclobutyl-5-ethyl-1H-pyrrolo[2,3-b]pyridin-2-yl)-N-[1-(trifluoromethyl)cyclopropyl]pyridine-3-sulfonamide,
N-tert-butyl-4-(3-cyano-1-cyclobutyl-5-ethyl-1H-pyrrolo[2,3-b]pyridin-2-yl)benzenesulfonamide,
N-tert-butyl-6-(3-cyano-1-cyclobutyl-5-ethyl-1H-pyrrolo[2,3-b]pyridin-2-yl)pyridine-3-sulfonamide,
4-(3-cyano-1-cyclobutyl-5-ethyl-1H-pyrrolo[2,3-b]pyridin-2-yl)-N-(1-methylcyclopropyl)benzenesulfonamide,
6-(3-cyano-1-cyclobutyl-5-ethyl-1H-pyrrolo[2,3-b]pyridin-2-yl)-N-(1-methylcyclopropyl)pyridine-3-sulfonamide,
2-(3-cyano-1-cyclobutyl-5-ethyl-1H-pyrrolo[2,3-b]pyridin-2-yl)-N-(1-methylcyclopropyl)pyrimidine-5-sulfonamide,
4-(3-cyano-1-cyclobutyl-5-ethyl-1H-pyrrolo[2,3-b]pyridin-2-yl)-N-(1,3-difluoropropan-2-yl)benzenesulfonamide,
6-(3-cyano-1-cyclobutyl-5-ethyl-1H-pyrrolo[2,3-b]pyridin-2-yl)-N-(1,3-difluoropropan-2-yl)pyridine-3-sulfonamide,
2-(3-cyano-1-cyclobutyl-5-ethyl-1H-pyrrolo[2,3-b]pyridin-2-yl)-N-(1,3-difluoropropan-2-yl)pyrimidine-5-sulfonamide,
6-(3-cyano-1-cyclobutyl-5-ethyl-1H-pyrrolo[2,3-b]pyridin-2-yl)-N-cyclopropylpyridine-3-sulfonamide,
6-(3-cyano-1-cyclobutyl-5-ethyl-1H-pyrrolo[2,3-b]pyridin-2-yl)-N-cyclobutylpyridine-3-sulfonamide,
5-(3-cyano-1-cyclobutyl-5-ethyl-1H-pyrrolo[2,3-b]pyridin-2-yl)-N-(propan-2-yl)pyridine-2-sulfonamide,
2-(3-cyano-1-cyclobutyl-5-ethyl-1H-pyrrolo[2,3-b]pyridin-2-yl)-N-(propan-2-yl)pyrimidine-5-sulfonamide,
6-[3-cyano-1-cyclobutyl-5-(difluoromethoxy)-1H-pyrrolo[2,3-b]pyridin-2-yl]-N-[(2R)-1,1,1-trifluoropropan-2-yl]pyridine-3-sulfonamide,
4-[3-cyano-1-cyclobutyl-5-(difluoromethoxy)-1H-pyrrolo[2,3-b]pyridin-2-yl]-N-[(2S)-1,1,1-trifluoropropan-2-yl]benzenesulfonamide,
4-[3-cyano-1-cyclobutyl-5-(difluoromethoxy)-1H-pyrrolo[2,3-b]pyridin-2-yl]-N-[(2R)-1,1,1-trifluoropropan-2-yl]benzenesulfonamide,
6-[3-cyano-1-cyclobutyl-5-(difluoromethoxy)-1H-pyrrolo[2,3-b]pyridin-2-yl]-N-[(1 S)-1-cyclopropylethyl]pyridine-3-sulfonamide,
6-[3-cyano-1-cyclobutyl-5-(difluoromethoxy)-1H-pyrrolo[2,3-b]pyridin-2-yl]-N-(1,1,1-trifluoro-2-methylpropan-2-yl)pyridine-3-sulfonamide,
6-(3-cyano-1-cyclobutyl-5-ethoxy-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-ethoxy-1H-pyrrolo[2,3-b]pyridin-2-yl)-N-[(2R)-1,1,1-trifluoropropan-2-yl]pyridine-3-sulfonamide, 6-(3-cyano-1-cyclobutyl-5-propoxy-1H-pyrrolo[2,3-b]pyridin-2-yl)-N-[(2S)-1,1,1-trifluoropropan-2-yl]pyridine-3-sulfonamide, 6-(3-cyano-1-cyclobutyl-5-propoxy-1H-pyrrolo[2,3-b]pyridin-2-yl)-N-[(2R)-1,1,1-trifluoropropan-2-yl]pyridine-3-sulfonamide, 6-[3-cyano-1-cyclobutyl-5-(propan-2-yloxy)-1H-pyrrolo[2,3-b]pyridin-2-yl]-N-[(2S)-1,1,1-trifluoropropan-2-yl]pyridine-3-sulfonamide, 6-(3-cyano-1-cyclopentyl-1H-pyrrolo[2,3-b]pyridin-2-yl)-N-[(2S)-1,1,1-trifluoropropan-2-yl]pyridine-3-sulfonamide, 1-cyclobutyl-5-methoxy-2-(5-{[(2S)-1,1,1-trifluoropropan-2-yl]sulfamoyl}pyridin-2-yl)-1H-pyrrolo[2,3-b]pyridine-3-carboxamide, 6-[3-cyano-1-cyclobutyl-5-(trifluoromethyl)-1H-pyrrolo[2,3-b]pyridin-2-yl]-N-[(2S)-1,1,1-trifluoropropan-2-yl]pyridine-3-sulfonamide, 6-[3-cyano-1-cyclobutyl-5-(trifluoromethyl)-1H-pyrrolo[2,3-b]pyridin-2-yl]-N-[(2R)-1,1,1-trifluoropropan-2-yl]pyridine-3-sulfonamide, 6-[3-cyano-1-cyclopentyl-5-(trifluoromethyl)-1H-pyrrolo[2,3-b]pyridin-2-yl]-N-[(2S)-1,1,1-trifluoropropan-2-yl]pyridine-3-sulfonamide, 6-[3-cyano-1-cyclopentyl-5-(trifluoromethyl)-1H-pyrrolo[2,3-b]pyridin-2-yl]-N-[(2R)-1,1,1-trifluoropropan-2-yl]pyridine-3-sulfonamide, 6-(3-cyano-1-cyclobutyl-5-methoxy-1H-pyrrolo[2,3-b]pyridin-2-yl)-N-[(2S)-1,1,1-trifluorobutan-2-yl]pyridine-3-sulfonamide, 6-(5-chloro-3-cyano-1-cyclopentyl-1H-pyrrolo[2,3-b]pyridin-2-yl)-N-[(2S)-1,1,1-trifluorobutan-2-yl]pyridine-3-sulfonamide, 6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide 1-oxide, 6-[3-cyano-1-cyclobutyl-5-(thiophen-2-yl)-1H-pyrrolo[2,3-b]pyridin-2-yl]-N-[(2S)-1,1,1-trifluoropropan-2-yl]pyridine-3-sulfonamide, 6-[3-cyano-1-cyclobutyl-5-(thiophen-2-yl)-1H-pyrrolo[2,3-b]pyridin-2-yl]-N-[(2R)-1,1,1-trifluoropropan-2-yl]pyridine-3-sulfonamide, 6-[3-cyano-1-cyclobutyl-5-(pyrrolidin-1-yl)-1H-pyrrolo[2,3-b]pyridin-2-yl]-N-[(2S)-1,1,1-trifluoropropan-2-yl]pyridine-3-sulfonamide, 6-[3-cyano-1-cyclobutyl-5-(pyrrolidin-1-yl)-1H-pyrrolo[2,3-b]pyridin-2-yl]-N-[(2R)-1,1,1-trifluoropropan-2-yl]pyridine-3-sulfonamide, 6-(3,6-dicyano-1-cyclobutyl-1H-pyrrolo[2,3-b]pyridin-2-yl)-N-[(2S)-1,1,1-trifluoropropan-2-yl]pyridine-3-sulfonamide, 6-(3-cyano-1-cyclobutyl-5-methoxy-6-methyl-1H-pyrrolo[2,3-b]pyridin-2-yl)-N-[(2S)-1,1,1-trifluoropropan-2-yl]pyridine-3-sulfonamide, 6-(3-cyano-1-cyclobutyl-5-methoxy-6-methyl-1H-pyrrolo[2,3-b]pyridin-2-yl)-N-[(2R)-1,1,1-trifluoropropan-2-yl]pyridine-3-sulfonamide, 6-[3-cyano-1-cyclobutyl-5-(trifluoromethyl)-1H-pyrrolo[2,3-b]pyridin-2-yl]-N-(propan-2-yl)pyridine-3-sulfonamide, 6-[3-cyano-1-cyclobutyl-5-(trifluoromethyl)-1H-pyrrolo[2,3-b]pyridin-2-yl]-N-cyclopropylpyridine-3-sulfonamide, 6-(3-cyano-1-cyclopentyl-5-methoxy-1H-pyrrolo[2,3-b]pyridin-2-yl)-N-[(2S)-1,1,1-trifluoropropan-2-yl]pyridine-3-sulfonamide, 6-(3-cyano-1-cyclopentyl-5-cyclopropyl-1H-pyrrolo[2,3-b]pyridin-2-yl)-N-[(2R)-1,1,1-trifluoropropan-2-yl]pyridine-3-sulfonamide, 6-(3-cyano-1-cyclopentyl-5-cyclopropyl-1H-pyrrolo[2,3-b]pyridin-2-yl)-N-[(2S)-1,1,1-trifluoropropan-2-yl]pyridine-3-sulfonamide, 6-(3-cyano-1-cyclopentyl-5-ethyl-1H-pyrrolo[2,3-b]pyridin-2-yl)-N-[(2R)-1,1,1-trifluoropropan-2-yl]pyridine-3-sulfonamide, 6-(3-cyano-1-cyclopentyl-5-ethyl-1H-pyrrolo[2,3-b]pyridin-2-yl)-N-[(2S)-1,1,1-trifluoropropan-2-yl]pyridine-3-sulfonamide, 6-(3-cyano-1-cyclopentyl-5-cyclopropyl-1H-pyrrolo[2,3-b]pyridin-2-yl)-N-(1-methylcyclopropyl)pyridine-3-sulfonamide, 6-(3-cyano-1-cyclopentyl-5-methyl-1H-pyrrolo[2,3-b]pyridin-2-yl)-N-[(2R)-1,1,1-trifluoropropan-2-yl]pyridine-3-sulfonamide, 6-(3-cyano-1-cyclopentyl-5-methyl-1H-pyrrolo[2,3-b]pyridin-2-yl)-N-[(2S)-1,1,1-trifluoropropan-2-yl]pyridine-3-sulfonamide, 6-(3-cyano-1-cyclopentyl-5-methyl-1H-pyrrolo[2,3-b]pyridin-2-yl)-N-(1-methylcyclopropyl)pyridine-3-sulfonamide, N-{[6-(3-cyano-1-cyclopentyl-5-methoxy-1H-pyrrolo[2,3-b]pyridin-2-yl)pyridin-3-yl]sulfonyl}-N-[(2S)-1,1,1-trifluoropropan-2-yl]acetamide, 6-(3-cyano-1-cyclobutyl-6-ethyl-5-methoxy-1H-pyrrolo[2,3-b]pyridin-2-yl)-N-[(2S)-1,1,1-trifluoropropan-2-yl]pyridine-3-sulfonamide, 6-(3-cyano-1-cyclobutyl-6-ethyl-5-methoxy-1H-pyrrolo[2,3-b]pyridin-2-yl)-N-[(2R)-1,1,1-trifluoropropan-2-yl]pyridine-3-sulfonamide, 6-(5-chloro-3-cyano-1-cyclopentyl-1H-pyrrolo[2,3-b]pyridin-2-yl)-N-(1,1,1-trifluorobutan-2-yl)pyridine-3-sulfonamide, 6-(3-cyano-1-cyclobutyl-5-methoxy-1H-pyrrolo[2,3-b]pyridin-2-yl)-N-(1,1,1-trifluorobutan-2-yl)pyridine-3-sulfonamide, 4-(3-cyano-1-cyclopentyl-5-methyl-1H-pyrrolo[2,3-b]pyridin-2-yl)-N-[(2R)-1,1,1-trifluoropropan-2-yl]benzenesulfonamide, 4-(3-cyano-1-cyclopentyl-5-methyl-1H-pyrrolo[2,3-b]pyridin-2-yl)-N-[(2S)-1,1,1-trifluoropropan-2-yl]benzenesulfonamide, 6-(3-cyano-1-cyclopentyl-5-methoxy-1H-pyrrolo[2,3-b]pyridin-2-yl)-N-[(2R)-1,1,1-trifluoropropan-2-yl]pyridine-3-sulfonamide, 6-(3-cyano-1-cyclopentyl-5-methoxy-1H-pyrrolo[2,3-b]pyridin-2-yl)-N-(1-methylcyclopropyl)pyridine-3-sulfonamide, 6-[5-chloro-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide, N-tert-butyl-6-(3-cyano-1-cyclobutyl-5-methoxy-1H-pyrrolo[2,3-b]pyridin-2-yl)pyridine-3-sulfonamide, 6-[3-cyano-1-cyclopentyl-5-(methylsulfanyl)-1H-pyrrolo[2,3-b]pyridin-2-yl]-N-[(2S)-1,1,1-trifluoropropan-2-yl]pyridine-3-sulfonamide, 6-[3-cyano-1-cyclopentyl-5-(methylsulfanyl)-1H-pyrrolo[2,3-b]pyridin-2-yl]-N-[(2R)-1,1,1-trifluoropropan-2-yl]pyridine-3-sulfonamide, 6-[3-cyano-1-cyclopentyl-5-(methylsulfanyl)-1H-pyrrolo[2,3-b]pyridin-2-yl]-N-[1-(trifluoromethyl)cyclopropyl]pyridine-3-sulfonamide, 6-(3-cyano-1-cyclobutyl-5-hydroxy-1H-pyrrolo[2,3-b]pyridin-2-yl)-N-[(2S)-1,1,1-trifluoropropan-2-yl]pyridine-3-sulfonamide, 6-(5-chloro-3-cyano-1-cyclobutyl-1H-pyrrolo[2,3-b]pyridin-2-yl)-N-[(2S)-1,1,1-trifluorobutan-2-yl]pyridine-3-sulfonamide, 6-(3-cyano-1-cyclobutyl-5-methoxy-1H-pyrrolo[2,3-b]pyridin-2-yl)-4-methyl-N-[(2S)-1,1,1-trifluoropropan-2-yl]pyridine-3-sulfonamide, 6-(5-chloro-3-cyano-1-cyclopentyl-1H-pyrrolo[2,3-b]pyridin-2-yl)-4-methyl-N-[(2S)-1,1,1-trifluoropropan-2-yl]pyridine-3-sulfonamide, 6-(3-cyano-1-cyclobutyl-5-methyl-1H-pyrrolo[2,3-b]pyridin-2-yl)-N-[(2S)-1,1,1-trifluorobutan-2-yl]pyridine-3-sulfonamide, 6-(5-chloro-3-cyano-1-cyclobutyl-1H-pyrrolo[2,3-b]pyridin-2-yl)-N-(1-methylcyclopropyl)pyridine-3-sulfonamide, 4-(5-chloro-3-cyano-1-cyclobutyl-1H-pyrrolo[2,3-b]pyridin-2-yl)-N-[1-(trifluoromethyl)cyclopropyl]benzenesulfonamide, 4-(5-chloro-3-cyano-1-cyclobutyl-1H-pyrrolo[2,3-b]pyridin-2-yl)-N-(1,1,1-trifluoro-2-methylpropan-2-yl)benzenesulfonamide, 6-(5-chloro-3-cyano-1-cyclobutyl-1H-pyrrolo[2,3-b]pyridin-2-yl)-N-cyclobutylpyridine-3-sulfonamide, 4-(5-chloro-3-cyano-1-cyclobutyl-1H-pyrrolo[2,3-b]pyridin-2-yl)-N-(1-methylcyclopropyl)benzenesulfonamide, 2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide, 2-(5-chloro-3-cyano-1-cyclobutyl-1H-pyrrolo[2,3-b]pyridin-2-yl)-N-(1-methylcyclopropyl)pyrimidine-5-sulfonamide, 6-(3-cyano-1-cyclobutyl-5-methyl-1H-pyrrolo[2,3-b]pyridin-2-yl)-4-methyl-N-[(2S)-1,1,1-trifluoropropan-2-yl]pyridine-3-sulfonamide, 6-(5-chloro-3-cyano-1-cyclopentyl-1H-pyrrolo[2,3-b]pyridin-2-yl)-5-methyl-N-[(2S)-1,1,1-trifluoropropan-2-yl]pyridine-3-sulfonamide, 6-(3-cyano-1-cyclobutyl-5-methyl-1H-pyrrolo[2,3-b]pyridin-2-yl)-5-methyl-N-[(2S)-1,1,1-trifluoropropan-2-yl]pyridine-3-sulfonamide, 6-(3-cyano-1-cyclobutyl-5-methoxy-1H-pyrrolo[2,3-b]pyridin-2-yl)-5-methyl-N-[(2S)-1,1,1-trifluoropropan-2-yl]pyridine-3-sulfonamide, N-tert-butyl-6-(3-cyano-1-cyclobutyl-5-methyl-1H-pyrrolo[2,3-b]pyridin-2-yl)pyridine-3-sulfonamide, 6-(3-cyano-1-cyclopentyl-5-hydroxy-1H-pyrrolo[2,3-b]pyridin-2-yl)-N-[(2S)-1,1,1-trifluoropropan-2-yl]pyridine-3-sulfonamide, 6-[3-cyano-1-(cyclopropylmethyl)-5-(trifluoromethyl)-1H-pyrrolo[2,3-b]pyridin-2-yl]-N-[(2S)-1,1,1-trifluoropropan-2-yl]pyridine-3-sulfonamide, N-tert-butyl-6-[3-cyano-1-(cyclopropylmethyl)-5-(trifluoromethyl)-1H-pyrrolo[2,3-b]pyridin-2-yl]pyridine-3-sulfonamide, N-tert-butyl-6-[3-cyano-1-cyclobutyl-5-(trifluoromethyl)-1H-pyrrolo[2,3-b]pyridin-2-yl]pyridine-3-sulfonamide, 6-[3-cyano-1-cyclobutyl-5-(trifluoromethyl)-1H-pyrrolo[2,3-b]pyridin-2-yl]-4-methyl-N-[(2S)-1,1,1-trifluoropropan-2-yl]pyridine-3-sulfonamide, 4-[3-cyano-1-cyclobutyl-5-(trifluoromethyl)-1H-pyrrolo[2,3-b]pyridin-2-yl]-N-[(2S)-1,1,1-trifluoropropan-2-yl]benzenesulfonamide, 6-[3-cyano-1-cyclobutyl-5-(trifluoromethyl)-1H-pyrrolo[2,3-b]pyridin-2-yl]-5-methyl-N-[(2S)-1,1,1-trifluoropropan-2-yl]pyridine-3-sulfonamide, 6-[3-cyano-1-cyclobutyl-5-(trifluoromethyl)-1H-pyrrolo[2,3-b]pyridin-2-yl]-N-cyclobutylpyridine-3-sulfonamide, 6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide, 1-cyclobutyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide, 6-[3-cyano-1-cyclopentyl-5-(methylsulfonyl)-1H-pyrrolo[2,3-b]pyridin-2-yl]-N-[(2S)-1,1,1-trifluoropropan-2-yl]pyridine-3-sulfonamide, 6-[5-chloro-3-cyano-1-(pyridin-2-yl)-1H-pyrrolo[2,3-b]pyridin-2-yl]-N-[(2S)-1,1,1-trifluoropropan-2-yl]pyridine-3-sulfonamide, 6-[5-chloro-3-cyano-1-(pyrazin-2-yl)-1H-pyrrolo[2,3-b]pyridin-2-yl]-N-[(2S)-1,1,1-trifluoropropan-2-yl]pyridine-3-sulfonamide, 6-(5-chloro-3-cyano-1-phenyl-1H-pyrrolo[2,3-b]pyridin-2-yl)-N-[(2S)-1,1,1-trifluoropropan-2-yl]pyridine-3-sulfonamide, 6-(3-cyano-1-cyclobutyl-5-methoxy-1H-pyrrolo[2,3-b]pyridin-2-yl)-N-cyclobutylpyridine-3-sulfonamide, 6-(3-cyano-1-cyclobutyl-5-methoxy-1H-pyrrolo[2,3-b]pyridin-2-yl)-N-cyclopropylpyridine-3-sulfonamide, 6-(3-cyano-1-cyclobutyl-5-methoxy-1H-pyrrolo[2,3-b]pyridin-2-yl)-N-(1-methylcyclopropyl)pyridine-3-sulfonamide, 6-(3-cyano-1-cyclobutyl-5-methoxy-1H-pyrrolo[2,3-b]pyridin-2-yl)-N-[1-(trifluoromethyl)cyclopropyl]pyridine-3-sulfonamide, 2-(3-cyano-1-cyclobutyl-5-methoxy-1H-pyrrolo[2,3-b]pyridin-2-yl)-N-(1-methylcyclopropyl)pyrimidine-5-sulfonamide, 6-[1-phenyl-5-(trifluoromethyl)-1H-pyrrolo[2,3-b]pyridin-2-yl]-N-[(2S)-1,1,1-trifluoropropan-2-yl]pyridine-3-sulfonamide, 6-[1(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide, 6-[3-cyano-1-(pyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide, 6-[3-cyano-1-(pyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide, 6-[3-cyano-1-phenyl-5-(trifluoromethyl)-1H-pyrrolo[2,3-b]pyridin-2-yl]-N-[(2S)-1,1,1-trifluoropropan-2-yl]pyridine-3-sulfonamide, 6-(3-cyano-5-fluoro-1-phenyl-1H-pyrrolo[2,3-b]pyridin-2-yl)-N-[(2S)-1,1,1-trifluoropropan-2-yl]pyridine-3-sulfonamide, 6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide, 6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide, 6-[3-cyano-5-fluoro-1-(pyridin-2-yl)-1H-pyrrolo[2,3-b]pyridin-2-yl]-N-[(2S)-1,1,1-trifluoropropan-2-yl]pyridine-3-sulfonamide, 6-[3-cyano-1-cyclobutyl-5-(methylsulfanyl)-1H-pyrrolo[2,3-b]pyridin-2-yl]-N-[(2S)-1,1,1-trifluoropropan-2-yl]pyridine-3-sulfonamide, 5-chloro-1-cyclopentyl-2-(5-{[(2S)-1,1,1-trifluoropropan-2-yl]sulfamoyl}pyridin-2-yl)-1H-pyrrolo[2,3-b]pyridine-3-carboxamide,
5-chloro-1-cyclobutyl-2-(5-{[1-(trifluoromethyl)cyclopropyl]sulfamoyl}pyridin-2-yl)-1H-pyrrolo[2,3-b]pyridine-3-carboxamide,
5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxamide,
2[5-(tert-butylsulfamoyl)pyridin-2-yl]-5-chloro-1-cyclobutyl-1H-pyrrolo[2,3-b]pyridine-3-carboxamide,
5-chloro-1-cyclobutyl-2-(4-{[1-(trifluoromethyl)cyclopropyl]sulfamoyl}phenyl)-1H-pyrrolo[2,3-b]pyridine-3-carboxamide,
5-chloro-1-cyclobutyl-2-{4-[(1,1,1-trifluoro-2-methylpropan-2-yl)sulfamoyl]phenyl}-1H-pyrrolo[2,3-b]pyridine-3-carboxamide,
1-cyclopentyl-5-(methylsulfanyl)-2-(5-{[1-(trifluoromethyl)cyclopropyl]sulfamoyl}pyridin-2-yl)-1H-pyrrolo[2,3-b]pyridine-3-carboxylic acid,
5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxylic acid,
6-[3-cyano-1-(5-methoxypyridin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
6-[3-cyano-1-(4-methoxypyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
N-tert-butyl-4-[3-cyano-1-(pyrimidin-2-yl)-5-(trifluoromethyl)-1H-pyrrolo[2,3-b]pyridin-2-yl]benzenesulfonamide,
N-tert-butyl-4-[3-cyano-1-(pyrazin-2-yl)-5-(trifluoromethyl)-1H-pyrrolo[2,3-b]pyridin-2-yl]benzenesulfonamide,
N-tert-butyl-4-[3-cyano-1-(pyrimidin-2-yl)-5-(trifluoromethyl)-1H-pyrrolo[2,3-b]pyridin-2-yl]benzenesulfonamide,
N-tert-butyl-4-[3-cyano-1-phenyl-5-(trifluoromethyl)-1H-pyrrolo[2,3-b]pyridin-2-yl]benzenesulfonamide,
6-[3-cyano-1-cyclobutyl-5-(trifluoromethyl)-1H-pyrrolo[2,3-b]pyridin-2-yl]-2-methyl-N-[(2S)-1,1,1-trifluoropropan-2-yl]pyridine-3-sulfonamide,
6-[5-bromo-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide,
6-[5-bromo-3-cyano-1-(pyrazin-2-yl)-1H-pyrrolo[2,3-b]pyridin-2-yl]-N-[(2S)-1,1,1-trifluoropropan-2-yl]pyridine-3-sulfonamide,
1-cyclobutyl-5-methyl-2-{4-[(1,1,1-trifluoro-2-methylpropan-2-yl)sulfamoyl]phenyl}-1H-pyrrolo[2,3-b]pyridine-3-carboxamide,
1-cyclobutyl-5-methyl-2-(4-{[1-(trifluoromethyl)cyclopropyl]sulfamoyl}phenyl)-1H-pyrrolo[2,3-b]pyridine-3-carboxamide,
1-cyclobutyl-5-methyl-2-(4-{[(2S)-1,1,1-trifluoropropan-2-yl]sulfamoyl}phenyl)-1H-pyrrolo[2,3-b]pyridine-3-carboxamide,
6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyrimidin-2-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyridin-2-yl)-1H-pyrrolo[2,3-b]pyridin-2yl]-N-[(2S)-1,1,1-trifluoropropan-2-yl]pyridine-3-sulfonamide,
6-[3-cyano-5-methyl-1-(pyridin-3-yl)-1H-pyrrolo[2,3-b]pyridin-2yl]-N-[(2S)-1,1,1-trifluoropropan-2-yl]pyridine-3-sulfonamide,
6-(3-cyano-5-methyl-1-phenyl-1H-pyrrolo[2,3-b]pyridin-2-yl)-N-[(2S)-1,1,1-trifluoropropan-2-yl]pyridine-3-sulfonamide,
6-[3-cyano-5-methyl-1-(pyrazin-2-yl)-1H-pyrrolo[2,3-b]pyridin-2-yl]-N-[(2S)-1,1,1-trifluoropropan-2-yl]pyridine-3-sulfonamide,
6-{5-[benzyl(methyl)amino]-3-cyano-1-cyclobutyl-1H-pyrrolo[2,3-b]pyridin-2-yl}-N-[(2S)-1,1,1-trifluoropropan-2-yl]pyridine-3-sulfonamide,
4-{5-[benzyl(methyl)amino]-3-cyano-1-cyclobutyl-1H-pyrrolo[2,3-b]pyridin-2-yl}-N-tert-butylbenzenesulfonamide,
4-{5-[benzyl(methyl)amino]-3-cyano-1-cyclobutyl-1H-pyrrolo[2,3-b]pyridin-2-yl}-N-(1,1,1-trifluoro-2-methylpropan-2-yl)benzenesulfonamide,
6-[3-cyano-1-(5-methylpyrazin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
6-[3-cyano-1-(4-methylpyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
1-cyclobutyl-5-fluoro-2-(5-{[(2S)-1,1,1-trifluoropropan-2-yl]sulfamoyl}pyridin-2-yl)-1H-pyrrolo[2,3-b]pyridine-3-carboxamide,
1-cyclopentyl-5-methoxy-2-(5-{[(2S)-1,1,1-trifluoropropan-2-yl]sulfamoyl}pyridin-2-yl)-1H-pyrrolo[2,3-b]pyridine-3-carboxamide,
6-[3-cyano-1-cyclopropyl-5-(trifluoromethyl)-1H-pyrrolo[2,3-b]pyridin-2-yl]-N-[(2S)-1,1,1-trifluoropropan-2-yl]pyridine-3-sulfonamide,
4-[3-cyano-1-cyclopropyl-5-(trifluoromethyl)-1H-pyrrolo[2,3-b]pyridin-2-yl]-N-(1,1,1-trifluoro-2-methylpropan-2-yl)benzenesulfonamide,
[3-cyano-1-cyclobutyl-2-(5-{[(2S)-1,1,1-trifluoropropan-2-yl]sulfamoyl}pyridin-2-yl)-1H-pyrrolo[2,3-b]pyridin-5-yl](methyl)sulfoniumolate,
4-[3-cyano-1-cyclobutyl-5-(methylsulfanyl)-1H-pyrrolo[2,3-b]pyridin-2-yl]-N-[1-(trifluoromethyl)cyclopropyl]benzenesulfonamide,
6-[3-cyano-5-methoxy-1-(pyrazin-2-yl)-1H-pyrrolo[2,3-b]pyridin-2-yl]-N-[(2S)-1,1,1-trifluoropropan-2-yl]pyridine-3-sulfonamide,
5-chloro-1-cyclobutyl-2-{5-[(1-methylcyclopropyl)sulfamoyl]pyridin-2-yl}-1H-pyrrolo[2,3-b]pyridine-3-carboxamide,
1-cyclobutyl-2-(5-{[(2S)-1,1,1-trifluoropropan-2-yl]sulfamoyl}pyrimidin-2-yl)-1H-pyrrolo[2,3-b]pyridine-3-carboxamide,
6-[3-cyano-5-methyl-1-(pyridin-4-yl)-1H-pyrrolo[2,3-b]pyridin-2-yl]-N-[(2S)-1,1,1-trifluoropropan-2-yl]pyridine-3-sulfonamide,
N-tert-butyl-4-(3-cyano-1-cyclobutyl-5-fluoro-1H-pyrrolo[2,3-b]pyridin-2-yl)benzenesulfonamide,
6-[3-cyano-1-cyclobutyl-5-(methylsulfonyl)-1H-pyrrolo[2,3-b]pyridin-2-yl]-N-[(2S)-1,1,1-trifluoropropan-2-yl]pyridine-3-sulfonamide,
N-tert-butyl-4-(5-chloro-3-cyano-1-cyclobutyl-1H-pyrrolo[2,3-b]pyridin-2-yl)benzenesulfonamide,
1-cyclobutyl-5-cyclopropyl-2-{4-[(1,1,1-trifluoro-2-methylpropan-2-yl)sulfamoyl]phenyl}-1H-pyrrolo[2,3-b]pyridine-3-carboxamide,
1-cyclobutyl-5-cyclopropyl-2-(4-{[1-(trifluoromethyl)cyclopropyl]sulfamoyl}phenyl)-1H-pyrrolo[2,3-b]pyridine-3-carboxamide, 1-cyclobutyl-5-cyclopropyl-2-(5-{[1-(trifluoromethyl) cyclopropyl]sulfamoyl}pyridin-2-yl)-1H-pyrrolo[2,3-b]pyridine-3-carboxamide,
2-[4-(tert-butylsulfamoyl)phenyl]-1-cyclobutyl-5-cyclopropyl-1H-pyrrolo[2,3-b]pyridine-3-carboxamide,
2-[5-(tert-butylsulfamoyl)pyridin-2-yl]-1-cyclobutyl-5-cyclopropyl-1H-pyrrolo[2,3-b]pyridine-3-carboxamide,
1-cyclobutyl-5-ethyl-2-(5-{[(2S)-1,1,1-trifluoropropan-2-yl]sulfamoyl}pyridin-2-yl)-1H-pyrrolo[2,3-b]pyridine-3-carboxamide,
1-cyclobutyl-5-ethyl-2-{4-[(1,1,1-trifluoro-2-methylpropan-2-yl)sulfamoyl]phenyl}-1H-pyrrolo[2,3-b]pyridine-3-carboxamide,
1-cyclobutyl-5-ethyl-2-(4-{[1-(trifluoromethyl)cyclopropyl]sulfamoyl}phenyl)-1H-pyrrolo[2,3-b]pyridine-3-carboxamide,
1-cyclobutyl-5-ethyl-2-(5-{[1-(trifluoromethyl)cyclopropyl]sulfamoyl}pyridin-2-yl)-1H-pyrrolo[2,3-b]pyridine-3-carboxamide,
2[4-(tert-butylsulfamoyl)phenyl]-1-cyclobutyl-5-ethyl-1H-pyrrolo[2,3-b]pyridine-3-carboxamide,
2[5-(tert-butylsulfamoyl)pyridin-2-yl]-1-cyclobutyl-5-ethyl-1H-pyrrolo[2,3-b]pyridine-3-carboxamide,
6-[3-cyano-5-methyl-1-(pyridazin-3-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyrimidin-5-yl)-1H-pyrrolo[2,3-b]pyridin-2-yl]-N-[(2S)-1,1,1-trifluoropropan-2-yl]pyridine-3-sulfonamide,
1-cyclobutyl-5-(methylsulfanyl)-2-(5-{[(2S)-1,1,1-trifluoropropan-2-yl]sulfamoyl}pyridin-2-yl)-1H-pyrrolo[2,3-b]pyridine-3-carboxylic acid,
1-cyclobutyl-2-{4-[(1,1,1-trifluoro-2-methylpropan-2-yl)sulfamoyl]phenyl}-1H-pyrrolo[2,3-b]pyridine-3-carboxamide,
1-cyclobutyl-5-(methylsulfanyl)-2-(4-{[1-(trifluoromethyl)cyclopropyl]sulfamoyl}phenyl)-1H-pyrrolo[2,3-b]pyridine-3-carboxamide,
1-cyclobutyl-5-(methylsulfanyl)-2-(4-{[1-(trifluoromethyl)cyclopropyl]sulfamoyl}phenyl)-1H-pyrrolo[2,3-b]pyridine-3-carboxylic acid,
1-cyclobutyl-5-(methylsulfanyl)-2-{4-[(1,1,1-trifluoro-2-methylpropan-2-yl)sulfamoyl]phenyl}-1H-pyrrolo[2,3-b]pyridine-3-carboxamide,
2-[4-(tert-butylsulfamoyl)phenyl]-1-cyclobutyl-5-(methylsulfanyl)-1H-pyrrolo[2,3-b]pyridine-3-carboxamide,
2[4-(tert-butylsulfamoyl)phenyl]-5-chloro-1-cyclobutyl-1H-pyrrolo[2,3-b]pyridine-3-carboxamide,
6-[3-cyano-1-cyclobutyl-5-(methylamino)-1H-pyrrolo[2,3-b]pyridin-2-yl]-N-[(2S)-1,1,1-trifluoropropan-2-yl]pyridine-3-sulfonamide,
6-[3-cyano-1-cyclobutyl-5-(trifluoromethyl)-1H-pyrrolo[2,3-b]pyridin-2-yl]-N-(1,1,1-trifluoro-2-methylpropan-2-yl)pyridine-3-sulfonamide,
6-[3-cyano-1-cyclobutyl-5-(trifluoromethyl)-1H-pyrrolo[2,3-b]pyridin-2-yl]-N-[1-(trifluoromethyl)cyclopropyl]pyridine-3-sulfonamide,
4-[3-cyano-1-cyclobutyl-5-(trifluoromethyl)-1H-pyrrolo[2,3-b]pyridin-2-yl]-N-[1-(trifluoromethyl)cyclopropyl]benzenesulfonamide,
6-[3-cyano-1-cyclobutyl-5-(trifluoromethyl)-1H-pyrrolo[2,3-b]pyridin-2-yl]-N-(1-methylcyclopropyl)pyridine-3-sulfonamide,
1-cyclobutyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide,
1-cyclobutyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide,
1-cyclobutyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide,
1-cyclobutyl-5-(trifluoromethyl)-2-(4-{[1-(trifluoromethyl)cyclopropyl]sulfamoyl}phenyl)-1H-pyrrolo[2,3-b]pyridine-3-carboxamide,
2-[4-(tert-butylsulfamoyl)phenyl]-1-cyclobutyl-5-(trifluoromethyl)-1H-pyrrolo[2,3-b]pyridine-3-carboxamide,
6-[3-cyano-1-cyclobutyl-6-methyl-5-(trifluoromethyl)-1H-pyrrolo[2,3-b]pyridin-2-yl]-N-[(2S)-1,1,1-trifluoropropan-2-yl]pyridine-3-sulfonamide,
1-cyclopentyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide,
1-cyclopentyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide,
1-cyclopentyl-5-(trifluoromethyl)-2-(4-{[1-(trifluoromethyl)cyclopropyl]sulfamoyl}phenyl)-1H-pyrrolo[2,3-b]pyridine-3-carboxamide,
1-cyclopentyl-5-(trifluoromethyl)-2-(5-{[(2S)-1,1,1-trifluoropropan-2-yl]sulfamoyl}pyridin-2-yl)-1H-pyrrolo[2,3-b]pyridine-3-carboxamide,
1-cyclopentyl-5-methoxy-2-{5-[(1-methylcyclopropyl)sulfamoyl]pyridin-2-yl}-1H-pyrrolo[2,3-b]pyridine-3-carboxamide,
6-[3-cyano-5-ethyl-1-(pyrazin-2-yl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(4-fluoropyridin-2-yl)-1H-pyrrolo[2,3-b]pyridin-2-yl]-N-[(2S)-1,1,1-trifluoropropan-2-yl]pyridine-3-sulfonamide,
6-(3-cyano-5-ethyl-1-phenyl-1H-pyrrolo[2,3-b]pyridin-2-yl)-N-[(2S)-1,1,1-trifluoropropan-2-yl]pyridine-3-sulfonamide,
6-[3-cyano-5-ethyl-1-(pyridin-2-yl)-1H-pyrrolo[2,3-b]pyridin-2-yl]-N-[(2S)-1,1,1-trifluoropropan-2-yl]pyridine-3-sulfonamide,
6-[3-cyano-1-cyclohexyl-5-(trifluoromethyl)-1H-pyrrolo[2,3-b]pyridin-2-yl]-N-[(2S)-1,1,1-trifluoropropan-2-yl]pyridine-3-sulfonamide,
4-[3-cyano-1-cyclohexyl-5-(trifluoromethyl)-1H-pyrrolo[2,3-b]pyridin-2-yl]-N-[(2S)-1,1,1-trifluoropropan-2-yl]benzenesulfonamide,
6-[3-cyano-1-cyclohexyl-5-(trifluoromethyl)-1H-pyrrolo[2,3-b]pyridin-2-yl]-N-(1,1,1-trifluoro-2-methylpropan-2-yl)pyridine-3-sulfonamide,
4-[3-cyano-1-cyclohexyl-5-(trifluoromethyl)-1H-pyrrolo[2,3-b]pyridin-2-yl]-N-(1,1,1-trifluoro-2-methylpropan-2-yl)benzenesulfonamide,
6-[3-cyano-1-cyclohexyl-5-(trifluoromethyl)-1H-pyrrolo[2,3-b]pyridin-2-yl]-N-[1-(trifluoromethyl)cyclopropyl]pyridine-3-sulfonamide,
4-[3-cyano-1-cyclohexyl-5-(trifluoromethyl)-1H-pyrrolo[2,3-b]pyridin-2-yl]-N-[1-(trifluoromethyl)cyclopropyl]benzenesulfonamide,
4-[3-cyano-1-cyclohexyl-5-(trifluoromethyl)-1H-pyrrolo[2,3-b]pyridin-2-yl]-N-(1-methylcyclopropyl)benzenesulfonamide,
N-tert-butyl-4-[3-cyano-1-cyclohexyl-5-(trifluoromethyl)-1H-pyrrolo[2,3-b]pyridin-2-yl]benzenesulfonamide, 4-[3-cyano-1-cyclohexyl-5-(trifluoromethyl)-1H-pyrrolo[2,3-b]pyridin-2-yl]-N-[(2R)-1,1,1-trifluoropropan-2-yl]benzenesulfonamide,
6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(1,3-thiazol-5-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyrimidin-4-yl)-1H-pyrrolo[2,3-b]pyridin-2-yl]-N-[(2S)-1,1,1-trifluoropropan-2-yl]pyridine-3-sulfonamide,
6-[3-cyano-1-(5-fluoropyridin-2-yl)-5-methyl-1H-pyrrolo[2,3-b]pyridin-2--yl]-N-[(2S)-1,1,1-trifluoropropan-2-yl]pyridine-3-sulfonamide,
6-{3-cyano-5-methyl-1-[4-(trifluoromethyl)pyridin-2-yl]-1H-pyrrolo[2,3-b]pyridin-2-yl}-N-[(2S)-1,1,1-trifluoropropan-2-yl]pyridine-3-sulfonamide,
6-[1-(4-aminopyridin-2-yl)-3-cyano-5-methyl-1H-pyrrolo[2,3-b]pyridin-2-yl]-N-[(2S)-1,1,1-trifluoropropan-2-yl]pyridine-3-sulfonamide,
6-[1-(5-bromopyrimidin-2-yl)-3-cyano-5-methyl-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyridazin-4-yl)-1H-pyrrolo[2,3-b]pyridin-2-yl]-N-[(2S)-1,1,1-trifluoropropan-2-yl]pyridine-3-sulfonamide,
1-cyclohexyl-5-(trifluoromethyl)-2-(4-{[(2S)-1,1,1-trifluoropropan-2-yl]sulfamoyl}phenyl)-1H-pyrrolo[2,3-b]pyridine-3-carboxamide,
1-cyclohexyl-5-(trifluoromethyl)-2-{5-[(1,1,1-trifluoro-2-methylpropan-2-yl)sulfamoyl]pyridin-2-yl}-1H-pyrrolo[2,3-b]pyridine-3-carboxamide,
1-cyclohexyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide,
1-cyclohexyl-5-(trifluoromethyl)-2-(5-{[1-(trifluoromethyl)cyclopropyl]sulfamoyl}pyridin-2-yl)-1H-pyrrolo[2,3-b]pyridine-3-carboxamide,
1-cyclohexyl-5-(trifluoromethyl)-2-(4-{[1-(trifluoromethyl)cyclopropyl]sulfamoyl}phenyl)-1H-pyrrolo[2,3-b]pyridine-3-carboxamide,
1-cyclohexyl-2-{4-[(1-methylcyclopropyl)sulfamoyl]phenyl}-5-(trifluoromethyl)-1H-pyrrolo[2,3-b]pyridine-3-carboxamide,
2-[4-(tert-butylsulfamoyl)phenyl]-1-cyclohexyl-5-(trifluoromethyl)-1H-pyrrolo[2,3-b]pyridine-3-carboxamide,
1-cyclohexyl-5-(trifluoromethyl)-2-(4-{[(2R)-1,1,1-trifluoropropan-2-yl]sulfamoyl}phenyl)-1H-pyrrolo[2,3-b]pyridine-3-carboxamide,
6-[3-cyano-5-methyl-1-(1,3-thiazol-2-yl)-1H-pyrrolo[2,3-b]pyridin-2-yl]-N-[(2S)-1,1,1-trifluoropropan-2-yl]pyridine-3-sulfonamide,
6-[3-cyano-1-(5-isocyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide,
6-[3-cyano-1-cyclobutyl-5-(difluoromethyl)-1H-pyrrolo[2,3-b]pyridin-2-yl]-N-[(2S)-1,1,1-trifluoropropan-2-yl]pyridine-3-sulfonamide,
4-[3-cyano-1-cyclobutyl-5-(difluoromethyl)-1H-pyrrolo[2,3-b]pyridin-2-yl]-N-[(2S)-1,1,1-trifluoropropan-2-yl]benzenesulfonamide,
2-[3-cyano-1-cyclobutyl-5-(difluoromethyl)-1H-pyrrolo[2,3-b]pyridin-2-yl]-N-[(2S)-1,1,1-trifluoropropan-2-yl]pyrimidine-5-sulfonamide,
6-[3-cyano-1-cyclobutyl-5-(difluoromethyl)-1H-pyrrolo[2,3-b]pyridin-2-yl]-N-(propan-2-yl)pyridine-3-sulfonamide,
6-[3-cyano-1-cyclobutyl-5-(difluoromethyl)-1H-pyrrolo[2,3-b]pyridin-2-yl]-N-(1,1,1-trifluoro-2-methylpropan-2-yl)pyridine-3-sulfonamide,
6-[3-cyano-1-cyclobutyl-5-(difluoromethyl)-1H-pyrrolo[2,3-b]pyridin-2-yl]-N-[1-(trifluoromethyl)cyclopropyl]pyridine-3-sulfonamide,
6-[3-cyano-1-cyclobutyl-5-(difluoromethyl)-1H-pyrrolo[2,3-b]pyridin-2-yl]-N-[(1 S)-1-cyclopropylethyl]pyridine-3-sulfonamide,
6-[3-cyano-5-fluoro-1-(4-fluoropyridin-2-yl)-1H-pyrrolo[2,3-b]pyridin-2-yl]-N-[(2S)-1,1,1-trifluoropropan-2-yl]pyridine-3-sulfonamide,
6-[3-cyano-5-fluoro-1-(5-fluoropyrimidin-2-yl)-1H-pyrrolo[2,3-b]pyridin-2-yl]-N-[(2S)-1,1,1-trifluoropropan-2-yl]pyridine-3-sulfonamide,
1-cyclobutyl-5-(difluoromethyl)-2-(5-{[(2S)-1,1,1-trifluoropropan-2-yl]sulfamoyl}pyridin-2-yl)-1H-pyrrolo[2,3-b]pyridine-3-carboxamide,
1-cyclobutyl-5-(difluoromethyl)-2-(5-{[(2S)-1,1,1-trifluoropropan-2-yl]sulfamoyl}pyrimidin-2-yl)-1H-pyrrolo[2,3-b]pyridine-3-carboxamide,
1-cyclobutyl-5-(difluoromethyl)-2-{5-[(1,1,1-trifluoro-2-methylpropan-2-yl)sulfamoyl]pyridin-2-yl}-1H-pyrrolo[2,3-b]pyridine-3-carboxamide,
1-cyclobutyl-5-(difluoromethyl)-2-(5-{[1-(trifluoromethyl)cyclopropyl]sulfamoyl}pyridin-2-yl)-1H-pyrrolo[2,3-b]pyridine-3-carboxamide,
6-[3-cyano-5-ethyl-1-(5-fluoropyrimidin-2-yl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(5-fluoropyridin-2-yl)-1H-pyrrolo[2,3-b]pyridin-2-yl]-N-[(2S)-1,1,1-trifluoropropan-2-yl]pyridine-3-sulfonamide,
4-(3-cyano-1,5-dimethyl-1H-pyrrolo[2,3-b]pyridin-2-yl)-N-[(2S)-1,1,1-trifluoropropan-2-yl]benzenesulfonamide,
4-[3-cyano-1-ethyl-5-methyl-1H-pyrrolo[2,3-b]pyridin-2-yl]-N-[(2S)-1,1,1-trifluoropropan-2-yl]benzenesulfonamide,
4-[3-cyano-5-methyl-1-propyl-1H-pyrrolo[2,3-b]pyridin-2-yl]-N-[(2S)-1,1,1-trifluoropropan-2-yl]benzenesulfonamide,
4-[3-cyano-5-methyl-1-(propan-2-yl)-1H-pyrrolo[2,3-b]pyridin-2-yl]-N-[(2S)-1,1,1-trifluoropropan-2-yl]benzenesulfonamide,
4-[3-cyano-1-(cyclopropylmethyl)-5-methyl-1H-pyrrolo[2,3-b]pyridin-2-yl]-N-[(2S)-1,1,1-trifluoropropan-2-yl]benzenesulfonamide,
4-[3-cyano-5-methyl-1-(2-methylpropyl)-1H-pyrrolo[2,3-b]pyridin-2-yl]-N-[(2S)-1,1,1-trifluoropropan-2-yl]benzenesulfonamide,
4-[3-cyano-1-(cyclobutylmethyl)-5-methyl-1H-pyrrolo[2,3-b]pyridin-2-yl]-N-[(2S)-1,1,1-trifluoropropan-2-yl]benzenesulfonamide,
6-(3-cyano-1,5-dimethyl-1H-pyrrolo[2,3-b]pyridin-2-yl)-N-[(2S)-1,1,1-trifluoropropan-2-yl]pyridine-3-sulfonamide,
6-(3-cyano-1-ethyl-5-methyl-1H-pyrrolo[2,3-b]pyridin-2-yl)-N-[(2S)-1,1,1-trifluoropropan-2-yl]pyridine-3-sulfonamide,
6-(3-cyano-5-methyl-1-propyl-1H-pyrrolo[2,3-b]pyridin-2-yl)-N-[(2S)-1,1,1-trifluoropropan-2-yl]pyridine-3-sulfonamide, 6-[3-cyano-5-methyl-1-(propan-2-yl)-1H-pyrrolo[2,3-b]pyridin-2-yl]-N-[(2S)-1,1,1-trifluoropropan-2-yl]pyridine-3-sulfonamide,
6-[3-cyano-1-(cyclopropylmethyl)-5-methyl-1H-pyrrolo[2,3-b]pyridin-2-yl]-N-[(2S)-1,1,1-trifluoropropan-2-yl]pyridine-3-sulfonamide,
6-[3-cyano-5-methyl-1-(2-methylpropyl)-1H-pyrrolo[2,3-b]pyridin-2-yl]-N-[(2S)-1,1,1-trifluoropropan-2-yl]pyridine-3-sulfonamide,
6-[3-cyano-1-(cyclobutylmethyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-cyclobutyl-5-(dimethylamino)-1H-pyrrolo[2,3-b]pyridin-2-yl]-N-[(2S)-1,1,1-trifluoropropan-2-yl]pyridine-3-sulfonamide,
4-[3-cyano-1-cyclobutyl-5-(dimethylamino)-1H-pyrrolo[2,3-b]pyridin-2-yl]-N-[(2S)-1,1,1-trifluoropropan-2-yl]benzenesulfonamide,
6-[3-cyano-1-(2-fluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-(3-fluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-(4-fluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-(2,5-difluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-(3,4-difluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-1-(3,5-difluorophenyl)-5-methyl-1H-pyrrolo[2,3-b]pyridin-2-yl]-N-[(2S)-1,1,1-trifluoropropan-2-yl]pyridine-3-sulfonamide,
6-[3-cyano-5-methyl-1-(1,3-thiazol-4-yl)-1H-pyrrolo[2,3-b]pyridin-2-yl]-N-[(2S)-1,1,1-trifluoropropan-2-yl]pyridine-3-sulfonamide,
6-[3-cyano-1-(6-cyanopyrimidin-4-yl)-5-methyl-1H-pyrrolo[2,3-b]pyridin-2-yl]-N-[(2S)-1,1,1-trifluoropropan-2-yl]pyridine-3-sulfonamide,
6-[3-cyano-5-ethyl-1-(thiophen-2-yl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(4-fluorophenyl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(3-fluorophenyl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide,
6-[3-cyano-1-cyclobutyl-5-(trifluoromethyl)-1H-pyrrolo[2,3-b]pyridin-2-yl]-N-[(2-deuterium)propan-2-yl]pyridine-3-sulfonamide,
6-[3-cyano-1-(4-cyano-1,3-thiazol-2-yl)-5-methyl-1H-pyrrolo[2,3-b]pyridin-2-yl]-N-[(2S)-1,1,1-trifluoropropan-2-yl]pyridine-3-sulfonamide,
N-tert-butyl-6-[5-chloro-3-cyano-1-(1,3-thiazol-2-yl)-1H-pyrrolo[2,3-b]pyridin-2-yl]pyridine-3-sulfonamide,
N-tert-butyl-6-[3-cyano-1-phenyl-5-(trifluoromethyl)-1H-pyrrolo[2,3-b]pyridin-2-yl]pyridine-3-sulfonamide,
N-tert-butyl-6-[3-cyano-1-(4-fluorophenyl)-5-(trifluoromethyl)-1H-pyrrolo[2,3-b]pyridin-2-yl]pyridine-3-sulfonamide,
N-tert-butyl-6-[3-cyano-1-(pyridin-2-yl)-5-(trifluoromethyl)-1H-pyrrolo[2,3-b]pyridin-2-yl]pyridine-3-sulfonamide,
N-tert-butyl-6-(3-cyano-5-fluoro-1-phenyl-1H-pyrrolo[2,3-b]pyridin-2-yl)pyridine-3-sulfonamide,
N-tert-butyl-6-[3-cyano-5-fluoro-1-(4-fluorophenyl)-1H-pyrrolo[2,3-b]pyridin-2-yl]pyridine-3-sulfonamide,
N-tert-butyl-6-[3-cyano-5-fluoro-1-(pyrazin-2-yl)-1H-pyrrolo[2,3-b]pyridin-2-yl]pyridine-3-sulfonamide,
N-tert-butyl-6-[3-cyano-5-fluoro-1-(pyridin-2-yl)-1H-pyrrolo[2,3-b]pyridin-2-yl]pyridine-3-sulfonamide,
2-[5-(tert-butylsulfamoyl)pyridin-2-yl]-1-phenyl-5-(trifluoromethyl)-1H-pyrrolo[2,3-b]pyridine-3-carboxamide,
N-tert-butyl-6-(3-cyano-5-methyl-1-phenyl-1H-pyrrolo[2,3-b]pyridin-2-yl)pyridine-3-sulfonamide,
N-tert-butyl-6-[3-cyano-5-methyl-1-(pyridin-2-yl)-1H-pyrrolo[2,3-b]pyridin-2-yl]pyridine-3-sulfonamide,
N-tert-butyl-6-[3-cyano-1-(pyrazin-2-yl)-5-(trifluoromethyl)-1H-pyrrolo[2,3-b]pyridin-2-yl]pyridine-3-sulfonamide or 2-[5-(tert-butylsulfamoyl)pyridin-2-yl]-5-fluoro-1-phenyl-1H-pyrrolo[2,3-b]pyridine-3-carboxamide.

9. The compound of claim 8, wherein the compound or a salt, hydrate, solvate, racemate, enantiomer, diastereomer, or stereoisomer is selected from:
6-(5-chloro-3-cyano-1-cyclopentyl-1H-pyrrolo[2,3-b]pyridin-2-yl)-N-(1,3-difluoropropan-2-yl)pyridine-3-sulfonamide,
6-(5-chloro-3-cyano-1-cyclobutyl-1H-pyrrolo[2,3-b]pyridin-2-yl)-N-(1,3-difluoropropan-2-yl)pyridine-3-sulfonamide,
6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide,
6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide,
2-(3-cyano-1-cyclobutyl-5-fluoro-1H-pyrrolo[2,3-b]pyridin-2-yl)-N-(propan-2-yl)pyrimidine-5-sulfonamide,
2-(3-cyano-1-cyclobutyl-6-methoxy-1H-pyrrolo[2,3-b]pyridin-2-yl)-N-(1,3-difluoropropan-2-yl)pyrimidine-5-sulfonamide,
6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide,
N-tert-butyl-6-(5-chloro-3-cyano-1-cyclobutyl-1H-pyrrolo[2,3-b]pyridin-2-yl)pyridine-3-sulfonamide,
2-(5-chloro-3-cyano-1-cyclobutyl-1H-pyrrolo[2,3-b]pyridin-2-yl)-N-(propan-2-yl)pyrimidine-5-sulfonamide,
6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide,
4-(3-cyano-1-cyclobutyl-6-methyl-1H-pyrrolo[2,3-b]pyridin-2-yl)-N-[(2S)-1,1,1-trifluoropropan-2-yl]benzenesulfonamide,
6-(3-cyano-1-cyclobutyl-5-cyclopropyl-1H-pyrrolo[2,3-b]pyridin-2-yl)-N-(1-methylcyclopropyl)pyridine-3-sulfonamide,
6-(3-cyano-1-cyclobutyl-5-cyclopropyl-1H-pyrrolo[2,3-b]pyridin-2-yl)-N-(1,3-difluoropropan-2-ylpyridine-3-sulfonamide, 6-(3-cyano-1-cyclobutyl-6-methyl-1H-pyrrolo[2,3-b]
pyridin-2-yl)-N-cyclobutylpyridine-3-sulfonamide,
6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide,
6-(3-cyano-1-cyclobutyl-5-ethyl-1H-pyrrolo[2,3-b]pyridin-2-yl)-N-(1,3-difluoropropan-2-ylpyridine-3-sulfonamide,
6-[3-cyano-1-cyclobutyl-5-(difluoromethoxy)-1H-pyrrolo[2,3-b]pyridin-2-yl]-N-[(2R)-1,1,1-trifluoropropan-2-yl]pyridine-3-sulfonamide,
6-(3-cyano-1-cyclobutyl-5-methoxy-1H-pyrrolo[2,3-b]pyridin-2-yl)-N-[(2S)-1,1,1-trifluorobutan-2-yl]pyridine-3-sulfonamide,
6-[5-chloro-3-cyano-1-(pyrimidin-2-yl)-1H-pyrrolo[2,3-b]pyridin-2-yl]-N-[(2S)-1,1,1-trifluoropropan-2-yl]pyridine-3-sulfonamide,
2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide,
6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide,
6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide,
5-chloro-1-cyclobutyl-2-(5-{[1-(trifluoromethyl)cyclopropyl]sulfamoyl}pyridin-2-yl)-1H-pyrrolo[2,3-b]pyridine-3-carboxamide,
5-chloro-1-cyclobutyl-2-{5-[(1,1,1-trifluoro-2-methylpropan-2-yl)sulfamoyl]pyridin-2-yl}-1H-pyrrolo[2,3-b]pyridine-3-carboxamide,
N-tert-butyl-4-[3-cyano-1-(pyrazin-2-yl)-5-(trifluoromethyl)-1H-pyrrolo[2,3-b]pyridin-2-yl]benzenesulfonamide,
6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide,
6-[3-cyano-5-methyl-1-(pyridazin-3-yl)-1H-pyrrolo[2,3-b]pyridin-2-yl]-N-[(2S)-1,1,1-trifluoropropan-2-yl]pyridine-3-sulfonamide,
1-cyclobutyl-5-(trifluoromethyl)-2-{4-[(1,1,1-trifluoro-2-methylpropan-2-yl)sulfamoyl]phenyl}-1H-pyrrolo[2,3-b]pyridine-3-carboxamide,
6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide,
N-tert-butyl-6-[3-cyano-1-(pyridin-2-yl)-5-(trifluoromethyl)-1H-pyrrolo[2,3-b]pyridin-2-yl]pyridine-3-sulfonamide or
N-tert-butyl-6-[3-cyano-1-(pyrazin-2-yl)-5-(trifluoromethyl)-1H-pyrrolo[2,3-b]pyridin-2-yl]pyridine-3-sulfonamide.

10. The compound of claim 9, wherein the compound or a salt, hydrate, solvate, racemate, enantiomer, diastereomer, or stereoisomer is selected from:

6-(3-cyano-1-cyclobutyl-5-methoxy-1H-pyrrolo[2,3-b]pyridin-2-yl)-N-[(2S)-1,1,1-trifluoropropan-2-yl]pyridine-3-sulfonamide,
6-(5-chloro-3-cyano-1-cyclopentyl-1H-pyrrolo[2,3-b]pyridin-2-yl)-N-[(2S)-1,1,1-trifluoropropan-2-yl]pyridine-3-sulfonamide,
2-(3-cyano-1-cyclobutyl-5-fluoro-1H-pyrrolo[2,3-b]pyridin-2-yl)-N-(propan-2-yl)pyrimidine-5-sulfonamide,
6-(5-chloro-3-cyano-1-cyclobutyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-methyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-ethyl-1H-pyrrolo[2,3-b]pyridin-2-yl)-N-[(2S)-1,1,1-trifluoropropan-2-yl]pyridine-3-sulfonamide,
6-(3-cyano-1-cyclobutyl-5-ethyl-1H-pyrrolo[2,3-b]pyridin-2-yl)-N-[(2R)-1,1,1-trifluoropropan-2-yl]pyridine-3-sulfonamide,
2-(5-chloro-3-cyano-1-cyclobutyl-1H-pyrrolo[2,3-b]pyridin-2-yl)-N-[(2S)-1,1,1-trifluoropropan-2-yl]pyrimidine-5-sulfonamide,
6-[3-cyano-1-(pyrimidin-2-yl)-5-(trifluoromethyl)-1H-pyrrolo[2,3-b]pyridin-2-yl]-N-[(2S)-1,1,1-trifluoropropan-2-yl]pyridine-3-sulfonamide,
6-[3-cyano-5-fluoro-1-(pyrimidin-2-yl)-1H-pyrrolo[2,3-b]pyridin-2-yl]-N-[(2S)-1,1,1-trifluoropropan-2-yl]pyridine-3-sulfonamide,
6-[3-cyano-5-fluoro-1-(pyrazin-2-yl)-1H-pyrrolo[2,3-b]pyridin-2-yl]-N-[(2S)-1,1,1-trifluoropropan-2-yl]pyridine-3-sulfonamide,
N-tert-butyl-4-[3-cyano-1-(pyrazin-2-yl)-5-(trifluoromethyl)-1H-pyrrolo[2,3-b]pyridin-2-yl]benzenesulfonamide,
6-[3-cyano-5-cyclopropyl-1-(pyrazin-2-yl)-1H-pyrrolo[2,3-b]pyridin-2-yl]-N-[(2S)-1,1,1-trifluoropropan-2-yl]pyridine-3-sulfonamide,
6-[5-chloro-3-cyano-1-(1,3-thiazol-2-yl)-1H-pyrrolo[2,3-b]pyridin-2-yl]-N-[(2S)-1,1,1-trifluoropropan-2-yl]pyridine-3-sulfonamide,
6-[3-cyano-5-ethyl-1-(1,3-thiazol-2-yl)-1H-pyrrolo[2,3-b]pyridin-2-yl]-N-[(2S)-1,1,1-trifluoropropan-2-yl]pyridine-3-sulfonamide,
N-tert-butyl-6-[3-cyano-1-(pyridin-2-yl)-5-(trifluoromethyl)-1H-pyrrolo[2,3-b]pyridin-2-yl]pyridine-3-sulfonamide or
N-tert-butyl-6-[3-cyano-1-(pyrazin-2-yl)-5-(trifluoromethyl)-1H-pyrrolo[2,3-b]pyridin-2-yl]pyridine-3-sulfonamide.

11. A method for inhibiting HCV viral replication in cultured replicon-containing cells comprising the steps of:
1) culturing replicon-containing cells with a compound of claim 1 for a period of time sufficient to reduce the replicon RNA value, and
2) comparing the replicon RNA value in replicon-containing cells cultured with the compound of claim 1 with the replicon RNA value in replicon-containing cells that have not been cultured with the compound of claim 1; wherein the replicon is a hepatitis C virus replicon.

12. A method for treating a hepatitis C viral infection in a subject in need thereof comprising administering an effective amount of a compound of Formula (Ia):

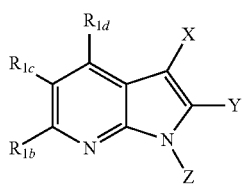

(Ia)

or a salt, hydrate, solvate, racemate, enantiomer, diastereomer, or stereoisomer thereof, wherein X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-aminocarbonyl or $C_{1-8}$alkyl-sulfonyl-;

Y is phenyl, pyridinyl or pyrimidinyl each substituted with —SO$_2$—N(R$_4$)—R$_5$, wherein phenyl, pyridinyl and pyrimidinyl are each optionally substituted with one or two additional substituents independently selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

R$_{1b}$, R$_{1c}$, and R$_{1d}$ are each selected from hydrogen, halogen, hydroxy, cyano, nitro, $C_{1-8}$alkyl, methyl, ethyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, (aryl-$C_{1-8}$alkyl)($C_{1-8}$alkyl)amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, aminocarbonyl, amino-carbonyl-amino, $C_{1-8}$alkyl-amino-carbonyl-amino, $C_{1-8}$alkyl-sulfonyl-amino, $C_{1-8}$alkylthio, $C_{1-8}$alkyl-sulfonyl, $C_{1-8}$alkyl-sulfinyl, $C_{3-14}$cycloalkyl, cyclopropyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, R$_4$ is hydrogen or $C_{1-8}$alkyl, optionally substituted on $C_{1-8}$alkyl with one or more substituents each selected from halogen, hydroxy, cyano or $C_{1-8}$alkoxy; and R$_5$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

13. A method for treating a Hepatitis C viral infection in a subject in need thereof comprising administering to said subject an effective amount of a compound of claim 1 or a salt, hydrate, solvate, racemate, enantiomer, diastereomer, or stereoisomer thereof in a range of from about 0.001 mg/Kg/day to about 500 mg/Kg/day.

14. A pharmaceutical composition comprising an effective amount of a compound of claim 1 or a salt, hydrate, solvate, racemate, enantiomer, diastereomer, or stereoisomer thereof in admixture with a pharmaceutically acceptable excipient.

15. The compound of claim 1, wherein:

halogen, when present, is selected from the group consisting of chloro and fluoro;

$C_{1-8}$alkoxy, when present, is selected from the group consisting of methoxy, ethoxy, propoxy and isopropoxy; and halo-$C_{1-8}$alkoxy, when present is difluoromethoxy.

* * * * *

UNITED STATES PATENT AND TRADEMARK OFFICE
CERTIFICATE OF CORRECTION

| | | |
|---|---|---|
| PATENT NO. | : 9,593,108 B2 | Page 1 of 1 |
| APPLICATION NO. | : 13/259283 | |
| DATED | : March 14, 2017 | |
| INVENTOR(S) | : Malcolm Maccoss et al. | |

It is certified that error appears in the above-identified patent and that said Letters Patent is hereby corrected as shown below:

In the Claims

At Column 216, Claim 5, Line 16, the printed patent should read --...wherein R1b, R1c, and R1d...--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*